US011441140B2

(12) United States Patent
Weber et al.

(10) Patent No.: US 11,441,140 B2
(45) Date of Patent: *Sep. 13, 2022

(54) DISHWASHING COMPOSITIONS COMPRISING POLYPEPTIDES HAVING BETA-GLUCANASE ACTIVITY AND USES THEREOF

(71) Applicant: Henkel AG & Co. KGaA, Duesseldorf (DE)

(72) Inventors: Thomas Weber, Dormagen (DE); Inga Kerstin Vockenroth, Duesseldorf (DE); Clarissa Maisey, Duesseldorf (DE); Astrid Spitz, Moers (DE); Lisa-Marie Schuetz, Hilden (DE); Claudia Ottow, Ratingen (DE); Daniela Herbst, Duesseldorf (DE); Iben Damager, Valby (DK); Morten Gjermansen, Greve (DK); Carsten Andersen, Vaerloese (DK); Claudia Lindner, Solingen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 239 days.

This patent is subject to a terminal disclaimer.

(21) Appl. No.: 15/782,006

(22) PCT Filed: Dec. 7, 2016

(86) PCT No.: PCT/EP2016/080150
§ 371 (c)(1),
(2) Date: Jun. 6, 2018

(87) PCT Pub. No.: WO2017/097861
PCT Pub. Date: Jun. 15, 2017

(65) Prior Publication Data
US 2019/0382691 A1 Dec. 19, 2019

(30) Foreign Application Priority Data

Dec. 7, 2015 (EP) .................................... 15198277
Dec. 7, 2015 (EP) .................................... 15198282

(51) Int. Cl.
*C12N 9/10* (2006.01)
*C11D 3/386* (2006.01)
*C12N 9/42* (2006.01)
*C12N 15/52* (2006.01)

(52) U.S. Cl.
CPC ............ *C12N 9/2448* (2013.01); *C11D 3/386* (2013.01); *C12N 15/52* (2013.01); *C11D 3/38681* (2013.01); *C12Y 302/01073* (2013.01)

(58) Field of Classification Search
CPC .... C12N 9/2488; C11D 3/38681; C11D 3/386
See application file for complete search history.

(56) References Cited

U.S. PATENT DOCUMENTS

| 4,435,307 A | 3/1984 | Barbesgaard et al. |
| 5,223,409 A | 6/1993 | Ladner et al. |
| 5,352,604 A | 10/1994 | Wilson et al. |
| 5,457,046 A | 10/1995 | Woldike et al. |
| 5,576,282 A | 11/1996 | Miracle et al. |
| 5,648,263 A | 7/1997 | Schulein et al. |
| 5,686,593 A | 11/1997 | Woldike et al. |
| 5,691,178 A | 11/1997 | Schulein et al. |
| 5,763,254 A | 6/1998 | Woldike et al. |
| 5,776,757 A | 7/1998 | Schulein et al. |
| 5,977,053 A | 11/1999 | Groth et al. |
| 6,306,812 B1 | 10/2001 | Perkins et al. |
| 6,541,233 B1 | 4/2003 | Hillen et al. |
| 7,262,042 B2 | 8/2007 | Weber et al. |
| 10,035,976 B2 * | 7/2018 | Andersen ............. C12N 9/2437 |
| 2013/0025073 A1 * | 1/2013 | Souter ................ C11D 3/38663 8/137 |

FOREIGN PATENT DOCUMENTS

| EP | 0218272 A1 | 4/1987 |
| EP | 0238216 A1 | 9/1987 |
| EP | 0258068 A2 | 3/1988 |
| EP | 0260105 A2 | 3/1988 |
| EP | 0305216 A1 | 3/1989 |
| EP | 331376 A2 | 9/1989 |
| EP | 407225 A1 | 1/1991 |
| EP | 0495257 A1 | 7/1992 |
| EP | 0531315 A1 | 3/1993 |

(Continued)

OTHER PUBLICATIONS

Yuki. W4QLD5_9BACI. UniProtKB. 2014.*
ExPASy. EC 3.2.1.73. retrieved from https://enzyme.expasy.org/EC/3.2.1.73 on Mar. 24, 2020.*
Studer. Residue mutations and their impact on protein structure and function: detecting beneficial and pathogenic changes. Biochem. J. (2013) 449, 581-594.*
Yuki. W4QVK7_BACA3. UniProtKB. 2014.*
Bishop-Lilly. A0A080UVP7_BACIU. UniProtKB. 2014.*
S B. Needleman and C.D. Wunsch, A General Method Applicable to the Search for Similarities in the Amino Acid Sequence of Two Proteins, pp. 443-453, J. Mol. Biol., Chicago, Illinois, Jul. 21, 1969.
T.K. Chose and V.S. Bisaria, Measurement of Hemicellulase Activities, Part 1: Xylanases, Pure & Appl. Chem. vol. 59, No. 12 pp. 1739-1752, New Delhi-11016, India, 1987.

(Continued)

*Primary Examiner* — Yong D Pak
(74) *Attorney, Agent, or Firm* — Lorenz & Kopf, LLP

(57) ABSTRACT

The present disclosure relates to dish washing compositions comprising polypeptides having beta-glucanase activity, catalytic domains, beta-glucan binding domains and polynucleotides encoding the polypeptides, catalytic domains or beta-glucan binding domains. The present disclosure further relates to dish washing compositions comprising polypeptides exhibiting beta-glucanase activity and one or more amylases and/or one or more proteases and uses thereof in dish wash applications and dish wash processes.

17 Claims, No Drawings

Specification includes a Sequence Listing.

(56) References Cited

FOREIGN PATENT DOCUMENTS

| | | |
|---|---|---|
| EP | 0531372 A1 | 6/1993 |
| EP | 544777 A1 | 6/1993 |
| EP | 0624154 A1 | 11/1994 |
| EP | 1867708 A1 | 12/2007 |
| EP | 1867808 A1 | 12/2007 |
| EP | 1921147 A2 | 5/2008 |
| EP | 1921148 A2 | 5/2008 |
| EP | 2361964 A1 | 8/2011 |
| GB | 1296839 A | 11/1972 |
| GB | 1372034 A | 10/1974 |
| JP | 6474992 A | 3/1989 |
| WO | 198906270 A1 | 7/1989 |
| WO | 198909259 A1 | 10/1989 |
| WO | 1991016422 A1 | 10/1991 |
| WO | 1992005249 A1 | 4/1992 |
| WO | 1992006204 A1 | 4/1992 |
| WO | 1992017577 A1 | 10/1992 |
| WO | 1992019708 A1 | 11/1992 |
| WO | 1992019709 A1 | 11/1992 |
| WO | 1992019729 A1 | 11/1992 |
| WO | 1992021760 A1 | 12/1992 |
| WO | 1993018140 A1 | 9/1993 |
| WO | 1993024618 A1 | 12/1993 |
| WO | 1994001541 A1 | 1/1994 |
| WO | 1994002597 A1 | 2/1994 |
| WO | 1994007998 A1 | 4/1994 |
| WO | 1994018314 A1 | 8/1994 |
| WO | 1994025578 A1 | 11/1994 |
| WO | 1994025583 A1 | 11/1994 |
| WO | 1995006720 A1 | 3/1995 |
| WO | 1995010602 A1 | 4/1995 |
| WO | 1995010603 A1 | 4/1995 |
| WO | 1995014783 A1 | 6/1995 |
| WO | 1995017413 A1 | 6/1995 |
| WO | 1995022615 A1 | 8/1995 |
| WO | 1995022625 A2 | 8/1995 |
| WO | 1995023221 A1 | 8/1995 |
| WO | 1995024471 A1 | 9/1995 |
| WO | 1995030744 A1 | 9/1995 |
| WO | 1995035381 A1 | 12/1995 |
| WO | 1996000292 A1 | 1/1996 |
| WO | 1996011262 A1 | 4/1996 |
| WO | 1996012012 A1 | 4/1996 |
| WO | 1996013580 A1 | 5/1996 |
| WO | 1996023873 A1 | 8/1996 |
| WO | 1996027002 A1 | 9/1996 |
| WO | 1996029397 A1 | 9/1996 |
| WO | 1996034946 A1 | 11/1996 |
| WO | 1997004079 A1 | 2/1997 |
| WO | 1997007202 A1 | 2/1997 |
| WO | 1997043424 A1 | 11/1997 |
| WO | 1998008940 A1 | 3/1998 |
| WO | 1998012307 A1 | 3/1998 |
| WO | 1998015257 A1 | 4/1998 |
| WO | 1998017767 A1 | 4/1998 |
| WO | 1998020115 A1 | 5/1998 |
| WO | 1998020116 A1 | 5/1998 |
| WO | 1999001544 A1 | 1/1999 |
| WO | 1999011768 A1 | 3/1999 |
| WO | 1999019467 A1 | 4/1999 |
| WO | 2001016285 A2 | 3/2001 |
| WO | 2001044452 A1 | 6/2001 |
| WO | 2001066712 A2 | 9/2001 |
| WO | 2002010355 A2 | 2/2002 |
| WO | 2002016547 A2 | 2/2002 |
| WO | 2002019467 A1 | 3/2002 |
| WO | 2002026024 A1 | 4/2002 |
| WO | 2003006602 A2 | 1/2003 |
| WO | 2003040279 A1 | 5/2003 |
| WO | 2004003186 A2 | 1/2004 |
| WO | 2004041979 A2 | 5/2004 |
| WO | 2005040372 A1 | 5/2005 |
| WO | 2005052146 A2 | 6/2005 |
| WO | 2005105826 A1 | 11/2005 |
| WO | 2006066594 A2 | 6/2006 |
| WO | 2006108856 A2 | 10/2006 |
| WO | 2006113314 A1 | 10/2006 |
| WO | 2006130575 A2 | 12/2006 |
| WO | 2007006305 A1 | 1/2007 |
| WO | 2007051989 A1 | 5/2007 |
| WO | 2007052004 A1 | 5/2007 |
| WO | 2007083139 A1 | 7/2007 |
| WO | 2007083141 A1 | 7/2007 |
| WO | 2007083142 A1 | 7/2007 |
| WO | 2007087242 A2 | 8/2007 |
| WO | 2007087244 A2 | 8/2007 |
| WO | 2007087258 A2 | 8/2007 |
| WO | 2007087259 A2 | 8/2007 |
| WO | 2007138054 A1 | 12/2007 |
| WO | 2008007319 A2 | 1/2008 |
| WO | 2008053191 A1 | 5/2008 |
| WO | 2008153815 A2 | 12/2008 |
| WO | 2009021867 A2 | 2/2009 |
| WO | 2009061380 A2 | 5/2009 |
| WO | 2009087523 A2 | 7/2009 |
| WO | 2009102854 A1 | 8/2009 |
| WO | 2009118375 A2 | 10/2009 |
| WO | 2011036263 A1 | 3/2011 |
| WO | 2011036264 A1 | 3/2011 |
| WO | 2011051415 A1 | 5/2011 |
| WO | 2011051416 A1 | 5/2011 |
| WO | 2011051417 A1 | 5/2011 |
| WO | 2011051418 A1 | 5/2011 |
| WO | 2011051420 A1 | 5/2011 |
| WO | 2011098531 A1 | 8/2011 |
| WO | 2011120546 A1 | 10/2011 |
| WO | 2011131260 A1 | 10/2011 |
| WO | 2013001078 A1 | 1/2013 |
| WO | 2013001087 A2 | 1/2013 |
| WO | 2014083096 A2 | 6/2014 |
| WO | WO-2015144824 A1 * | 10/2015 ..... C12Y 302/01004 |

OTHER PUBLICATIONS

Hans Neurath and Robert L. Hill, The Proteins, Third Edition, vol. IV, Academic Press, New York, San Francisco, London, 1979, A Subsidiary of Harcourt Brace Jovanovich, Publishers.

Daniele Dondi, Angelo Albini, and Nick Serpone, Interactions between different solar UVB/UVA filters contained in commercial sunscreams and consequent loss of UV protection, Photochem. Photobiol. Sci., 2006, 5, 835-843, first published as an Advance Article on the web Aug. 3, 2006.

Yang Shaoqing, et al., Purification and Characterization of a Novel Alkaline [beta]-1, 3-1, 4-glucanase (Lichenase) from Thermophilic FungusMalbranchea Cinnam, Journal of Industrial Microbiology and Biotechnology, Basingstoke, GB, vol. 41, No. 10, Aug. 12, 2014, pp. 1487-1495.

Sameh Maktouf, et al., A Laundry Detergent Compatible Lichenase: Statistical Optimization For Production Under Solid State Fermentation on Crude Millet, Industrial Crops and Products, vol. 43, May 1, 2013, pp. 349-354.

Database UniProt [Online], Oct. 1, 2000, Hybrid-Endo-Beta-1, 3-1, 4 Glucanase {ECO:0000313/EMBL:BAB06950.1}, retrieved from EBI accession No. UNIPROT:Q9K7X6.

Database UniProt [Online], Mar. 8, 2011, Glycoside Hydrolase Family 16 {ECO:0000313/EMBL:ADU30622.1}, retrieved from EBI accession No. UNIPROT:E6TRB0.

Database UniProt [Online], Mar. 19, 2014, Endo-Beta-1, 3-1, 4 Glucanase {ECO:0000313/EMBL:GAE36131.1}, retrieved from EBI accession No. UNIPROT:W4QVK7.

* cited by examiner

DISHWASHING COMPOSITIONS COMPRISING POLYPEPTIDES HAVING BETA-GLUCANASE ACTIVITY AND USES THEREOF

CROSS-REFERENCE TO RELATED APPLICATION

This application is a U.S. National-Stage entry under 35 U.S.C. § 371 based on International Application No PCT/EP2016/080150, filed Dec. 7, 2016 which was published under PCT Article 21(2) and which claims priority to European Application No. 15198282.4, filed Dec. 7, 2015 and to European Application No. 15198277.4, filed Dec. 7, 2015, each of which is hereby expressly incorporated in its entirety by reference.

REFERENCE TO A JOINT RESEARCH AGREEMENT

The embodiments claimed in the present application were made under a joint research agreement between Henkel AG & Co. KGaA and Novozymes A/S.

REFERENCE TO A SEQUENCE LISTING

This application contains a Sequence Listing in computer readable form, which is incorporated herein by reference.

TECHNICAL FIELD

The present disclosure relates to dish washing compositions comprising polypeptide(s) having beta-glucanase activity, catalytic domains, beta-glucan binding domains. The present disclosure further relates to dish washing compositions comprising polypeptides exhibiting beta-glucanase activity and one or more amylases and/or one or more proteases and uses thereof in dish wash applications and dish wash processes.

BACKGROUND

Beta-glucans are polysaccharides of glucose units linked by beta-glycosidic bonds. Cellulose is one type of beta-glucan, in which all of the glucose units are linked by beta-1,4-glucosidic bonds. This feature results in the formation of insoluble cellulose micro-fibrils. Enzymatic hydrolysis of cellulose to glucose requires the use of endo beta-glucanases (e.g. EC 3.2.1.4), cellobiohydrolases (e.g. EC 3.2.1.91) and beta-glucosidases (e.g. EC 3.2.1.21).

Beta-glucans can also be linked by beta-1,3-glucosidic bonds (e.g., as found in the cell walls of baker's yeast, *Saccharomyces cerevisiae*), beta-1,6-glucosidic bonds as well as combinations of beta-1,3-, beta-1,4- and beta-1,6-glucosidic bonds. The combination of beta-1,3- and beta-1,4-glucosidic bonds can be found, e.g. in the soluble fibre from cereals such as oats and barley. A subgroup of beta-glucanases, also known as a licheninases (or lichenases) (EC 3.2.1.73), can be used to catalyse the hydrolysis of the beta-1,4-glucosidic bonds to give beta-glucans. Licheninases (or lichenases) (e.g. EC 3.2.1.73) hydrolyse (1,4)-beta-D-glucosidic linkages in beta-D-glucans containing (1,3)- and (1,4)-bonds and can act on lichenin and cereal beta-D-glucans, but not on beta-D-glucans containing only 1,3- or 1,4-bonds. Other beta-glucanases (e.g. EC 3.2.1.4) can, for example, perform endohydrolysis of (1,4)-beta-D-glucosidic linkages in cellulose, lichenin and cereal beta-D-glucans and will also hydrolyze 1,4-linkages in beta-D-glucans containing 1,3-linkages.

The removal of cereal stains as oat and barley containing stains in dish wash is a recognised problem, and there is a considerable interest in finding enzymes that can degrade the beta-glucans found therein. Various *Bacillus* species like e.g. *B. amyloliquefaciens* express a beta-glucanase, but these enzymes are generally not very suitable for alkaline applications, e.g. at pH of about 7.5 or above.

BRIEF SUMMARY

This disclosure provides a cleaning or detergent composition, wherein the cleaning or detergent composition is a dish washing composition. The composition includes a polypeptide having beta-glucanase activity and selected from the group of:

(a) a polypeptide having at least about 89% sequence identity to the mature polypeptide of the sequence selected from the group of: SEQ ID NO: 7, SEQ ID NO: 2, SEQ ID NO: 3, SEQ ID NO: 5, SEQ ID NO: 9;

(b) a polypeptide encoded by a polynucleotide that hybridizes under low stringency conditions with (i) the mature polypeptide coding sequence of the sequence selected from the group of: SEQ ID NO: 6, SEQ ID NO: 1, SEQ ID NO: 4, SEQ ID NO: 8, or (ii) the full-length complement of (i);

(c) a polypeptide encoded by a polynucleotide having at least about 89% sequence identity to the mature polypeptide coding sequence of the sequence selected from the group of: SEQ ID NO: 6, SEQ ID NO: 1, SEQ ID NO: 4, SEQ ID NO: 8;

(d) a variant of the mature polypeptide of the sequence selected from the group of: SEQ ID NO: 7, SEQ ID NO: 2, SEQ ID NO: 3, SEQ ID NO: 5, SEQ ID NO: 9, wherein said variant comprises a substitution, deletion, and/or insertion at one or more positions; and (e) a fragment of the polypeptide of (a), (b), (c), or (d) that has beta-glucanase activity.

This disclosure also provides a cleaning or detergent composition, wherein the cleaning or detergent composition is a dish washing composition and the composition includes a polypeptide having beta-glucanase activity, selected from the group of:

(a) a polypeptide having at least about 70% sequence identity to the mature polypeptide of the sequence selected from the group of: SEQ ID NO: 7, SEQ ID NO: 2, SEQ ID NO: 3, SEQ ID NO: 5, SEQ ID NO: 9;

(b) a polypeptide encoded by a polynucleotide that hybridizes under low stringency conditions with (i) the mature polypeptide coding sequence of the sequence selected from the group of: SEQ ID NO: 6, SEQ ID NO: 1, SEQ ID NO: 4, SEQ ID NO: 8, or (ii) the full-length complement of (i);

(c) a polypeptide encoded by a polynucleotide having at least about 70% sequence identity to the mature polypeptide coding sequence of the sequence selected from the group of: SEQ ID NO: 6, SEQ ID NO: 1, SEQ ID NO: 4, SEQ ID NO: 8;

(d) a variant of the mature polypeptide of the sequence selected from the group of: SEQ ID NO: 7, SEQ ID NO: 2, SEQ ID NO: 3, SEQ ID NO: 5, SEQ ID NO: 9, wherein said variant comprising a substitution, deletion, and/or insertion at one or more positions; and (e) a fragment of the polypeptide of (a), (b), (c), or (d) that has beta-glucanase activity;

wherein the cleaning or detergent composition further comprises:
(i) one or more amylases; and/or
(ii) one or more proteases.

This disclosure even further provides a method for reducing or preventing soil redeposition using a polypeptide having beta-glucanase activity, selected from the group of:
(a) a polypeptide having at least about 70% sequence identity to the mature polypeptide of the sequence selected from the group of: SEQ ID NO: 7, SEQ ID NO: 2, SEQ ID NO: 3, SEQ ID NO: 5, SEQ ID NO: 9;
(b) a polypeptide encoded by a polynucleotide that hybridizes under low stringency conditions with (i) the mature polypeptide coding sequence of the sequence selected from the group of: SEQ ID NO: 6, SEQ ID NO: 1, SEQ ID NO: 4, SEQ ID NO: 8, or (ii) the full-length complement of (i);
(c) a polypeptide encoded by a polynucleotide having at least about 89% sequence identity to the mature polypeptide coding sequence of the sequence selected from the group of: SEQ ID NO: 6, SEQ ID NO: 1, SEQ ID NO: 4, SEQ ID NO: 8; and
(d) a variant of the mature polypeptide of the sequence selected from the group of: SEQ ID NO: 7, SEQ ID NO: 2, SEQ ID NO: 3, SEQ ID NO: 5, SEQ ID NO: 9, wherein said variant comprising a substitution, deletion, and/or insertion at one or more positions.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure provides polypeptides of glycoside hydrolase family 16 (GH16) having beta-glucanase activity (e.g. comprising or including licheninase (EC 3.2.1.73) activity) and polynucleotides encoding said polypeptides, which are highly active in degrading different types of beta-glucans (e.g. beta-D-glucans, beta-1,3-1,4 glucans, mix-linkage beta-glucans, barley beta-glucans and oatmeal beta-glucans), e.g. under alkaline conditions (e.g. at pH of about 7.5 or above), and therefore could be used in the aforementioned applications, e.g. in cleaning or detergent applications and processes such as dish washing. The existing products comprising beta-glucanases have very low effect on this type of beta-glucan as their main enzymatic substrate is cellulose. Therefore, the present disclosure provides novel beta-glucanases with improved properties (e.g. with significant improvement of performance and/or stability under alkaline conditions; beta-glucanases without cellulase activity (e.g. not having endo-cellulase activity on β-1,4 linkages between D-glucose units) (e.g. EC 3.2.1.73). A difference between use of cellulases and lichenases on textile in laundry is that the lichenases do not degrade the fibers of the textile.

Furthermore, some particular solid detergents have pH above about 10. The known beta-glucanases are not suitable for these very high pH detergents. Thus, for example, known beta-glucanases from *Bacillus amyloliquefaciens* and *Bacillus subtilis* quickly lose their activity under alkaline conditions as has been demonstrated in Example 8 herein. The present disclosure provides novel beta-glucanases with improved properties (e.g. with significant improvement of performance and/or stability under alkaline conditions).

An uncharacterized protein from *Bacillus halodurans* (uniprot:Q9K7X6) is about 88.4% identical to the beta-glucanase shown in SEQ ID NO: 7.

An uncharacterized protein from *Bacillus* cellulosilyticus (uniprot:E6TRB0) is about 80.7% identical to the beta-glucanase shown in SEQ ID NO: 3.

An uncharacterized protein from *Bacillus akibai* (uniprot: W4QVK7) is about 98.2% identical to the beta-glucanase shown in SEQ ID NO: 5.

An uncharacterized protein from *Bacillus subtilis* subsp. *niger*. (uniprot:A0A080UVP7) is about 97.9% identical to the beta-glucanase shown in SEQ ID NO: 9.

In one aspect, the present disclosure relates to a cleaning or detergent composition, wherein said cleaning or detergent composition is a dish washing composition, said composition comprising polypeptide(s) having beta-glucanase activity, selected from the group of:
(a) a polypeptide having at least about 60% sequence identity to the mature polypeptide of the sequence selected from the group of: SEQ ID NO: 2, SEQ ID NO: 3, SEQ ID NO: 5, SEQ ID NO: 7, SEQ ID NO: 9;
(b) a polypeptide encoded by a polynucleotide that hybridizes under low stringency conditions with (i) the mature polypeptide coding sequence of the sequence selected from the group of: SEQ ID NO: 1, SEQ ID NO: 4, SEQ ID NO: 6, SEQ ID NO: 8, or (ii) the full-length complement of (i);
(c) a polypeptide encoded by a polynucleotide having at least about 60% sequence identity to the mature polypeptide coding sequence of the sequence selected from the group of: SEQ ID NO: 1, SEQ ID NO: 4, SEQ ID NO: 6, SEQ ID NO: 8;
(d) a variant of the mature polypeptide of the sequence selected from the group of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
(e) a fragment of the polypeptide of (a), (b), (c), or (d) that has beta-glucanase activity;
wherein said cleaning or detergent composition further comprising:
(i) one or more amylases; and/or
(ii) one or more proteases,
preferably said polypeptide having beta-glucanase activity and said one or more amylases (e.g., SEQ ID NO: 12) (and/or said one or more proteases) have a synergistic effect; further preferably said synergistic effect is a REM synergistic effect, further most preferably said REM synergistic effect is of more than about 6.5 at about 40° C. for about 30 minutes at pH of about 7.5, further most preferably said REM synergistic effect is of more than about 6.1 at about 40° C. for about 30 minutes at pH of about 10, further most preferably said REM synergistic effect is of more than about 6.2 at about 40° C. for about 30 minutes at pH of about 10, further most preferably said beta-glucanase activity is not an endo-cellulase activity on β-1,4 linkages between D-glucose units of cellulose.

In another aspect, the present disclosure relates to a cleaning or detergent composition, wherein said cleaning or detergent composition is a dish washing composition, said composition comprising polypeptide(s) having beta-glucanase activity, selected from the group of:
(a) a polypeptide having at least about 81% sequence identity to the mature polypeptide of the sequence selected from the group of: SEQ ID NO: 2, SEQ ID NO: 3, SEQ ID NO: 5, SEQ ID NO: 7, SEQ ID NO: 9;
(b) a polypeptide encoded by a polynucleotide that hybridizes under low stringency conditions with (i) the mature polypeptide coding sequence of the sequence selected from the group of: SEQ ID NO: 1, SEQ ID NO: 4, SEQ ID NO: 6, SEQ ID NO: 8, or (ii) the full-length complement of (i);
(c) a polypeptide encoded by a polynucleotide having at least about 81% sequence identity to the mature polypeptide coding sequence of the sequence selected from the group of: SEQ ID NO: 1, SEQ ID NO: 4, SEQ ID NO: 6, SEQ ID NO: 8;
(d) a variant of the mature polypeptide of the sequence selected from the group of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
(e) a fragment of the polypeptide of (a), (b), (c), or (d) that has beta-glucanase activity;
wherein said cleaning or detergent composition further comprising:
  (i) one or more amylases; and/or
  (ii) one or more proteases,
preferably said polypeptide having beta-glucanase activity and said one or more amylases (e.g., SEQ ID NO: 12) (and/or said one or more proteases) have a synergistic effect; further preferably said synergistic effect is a REM synergistic effect, further most preferably said REM synergistic effect is of more than about 6.5 at about 40° C. for about 30 minutes at pH of about 7.5, further most preferably said REM synergistic effect is of more than about 6.1 at about 40° C. for about 30 minutes at pH of about 10, further most preferably said REM synergistic effect is of more than about 6.2 at about 40° C. for about 30 minutes at pH of about 10, further most preferably said beta-glucanase activity is not an endo-cellulase activity on β-1,4 linkages between D-glucose units of cellulose.

In another aspect, the present disclosure relates to a cleaning or detergent composition, wherein said cleaning or detergent composition is a dish washing composition, said composition comprising a composition comprising polypeptide(s) having beta-glucanase activity, selected from the group of:
(a) a polypeptide having at least about 99% sequence identity to the mature polypeptide of the sequence selected from the group of: SEQ ID NO: 2, SEQ ID NO: 3, SEQ ID NO: 5, SEQ ID NO: 7, SEQ ID NO: 9;
(b) a polypeptide encoded by a polynucleotide that hybridizes under low stringency conditions with (i) the mature polypeptide coding sequence of the sequence selected from the group of: SEQ ID NO: 1, SEQ ID NO: 4, SEQ ID NO: 6, SEQ ID NO: 8, or (ii) the full-length complement of (i);
(c) a polypeptide encoded by a polynucleotide having at least about 99% sequence identity to the mature polypeptide coding sequence of the sequence selected from the group of: SEQ ID NO: 1, SEQ ID NO: 4, SEQ ID NO: 6, SEQ ID NO: 8;
(d) a variant of the mature polypeptide of the sequence selected from the group of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
(e) a fragment of the polypeptide of (a), (b), (c), or (d) that has beta-glucanase activity;
wherein said cleaning or detergent composition further comprising:
  (i) one or more amylases; and/or
  (ii) one or more proteases,
preferably said polypeptide having beta-glucanase activity and said one or more amylases (e.g., SEQ ID NO: 12) (and/or said one or more proteases) have a synergistic effect; further preferably said synergistic effect is a REM synergistic effect, further most preferably said REM synergistic effect is of more than about 6.5 at about 40° C. for about 30 minutes at pH of about 7.5, further most preferably said REM synergistic effect is of more than about 6.1 at about 40° C. for about 30 minutes at pH of about 10, further most preferably said REM synergistic effect is of more than about 6.2 at about 40° C. for about 30 minutes at pH of about 10, further most preferably said beta-glucanase activity is not an endo-cellulase activity on β-1,4 linkages between D-glucose units of cellulose.

In another aspect, the present disclosure relates to a cleaning or detergent composition, wherein said cleaning or detergent composition is a dish washing composition, said composition comprising polypeptide(s) having beta-glucanase activity, selected from the group of:
(a) a polypeptide having at least about 89% sequence identity to the mature polypeptide of the sequence selected from the group of: SEQ ID NO: 2, SEQ ID NO: 3, SEQ ID NO: 5, SEQ ID NO: 7, SEQ ID NO: 9;
(b) a polypeptide encoded by a polynucleotide that hybridizes under low stringency conditions with (i) the mature polypeptide coding sequence of the sequence selected from the group of: SEQ ID NO: 1, SEQ ID NO: 4, SEQ ID NO: 6, SEQ ID NO: 8, or (ii) the full-length complement of (i);
(c) a polypeptide encoded by a polynucleotide having at least about 89% sequence identity to the mature polypeptide coding sequence of the sequence selected from the group of: SEQ ID NO: 1, SEQ ID NO: 4, SEQ ID NO: 6, SEQ ID NO: 8;
(d) a variant of the mature polypeptide of the sequence selected from the group of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and (e) a fragment of the polypeptide of (a), (b), (c), or (d) that has beta-glucanase activity;
wherein said cleaning or detergent composition further comprising:
  (i) one or more amylases; and/or
  (ii) one or more proteases,
preferably said polypeptide having beta-glucanase activity and said one or more amylases (e.g., SEQ ID NO: 12) (and/or said one or more proteases) have a synergistic effect; further preferably said synergistic effect is a REM synergistic effect, further most preferably said REM synergistic effect is of more than about 6.5 at about 40° C. for about 30 minutes at pH of about 7.5, further most preferably said REM synergistic effect is of more than about 6.1 at about 40° C. for about 30 minutes at pH of about 10, further most preferably said REM synergistic effect is of more than about 6.2 at about 40° C. for about 30 minutes at pH of about 10, further most preferably said beta-glucanase activity is not an endo-cellulase activity on β-1,4 linkages between D-glucose units of cellulose.

In another aspect, the present disclosure relates to a cleaning or detergent composition, wherein said cleaning or detergent composition is a dish washing composition, said composition comprising polypeptide(s) having beta-glucanase activity, selected from the group of:
(a) a polypeptide having at least about 98% sequence identity to the mature polypeptide of the sequence selected from the group of: SEQ ID NO: 2, SEQ ID NO: 3, SEQ ID NO: 5, SEQ ID NO: 7, SEQ ID NO: 9;
(b) a polypeptide encoded by a polynucleotide that hybridizes under low stringency conditions with (i) the mature polypeptide coding sequence of the sequence selected from the group of: SEQ ID NO: 1, SEQ ID NO: 4, SEQ ID NO: 6, SEQ ID NO: 8, or (ii) the full-length complement of (i); (c) a polypeptide encoded by a polynucleotide having at least about 98% sequence identity to the mature polypeptide coding sequence of the sequence selected from the group of: SEQ ID NO: 1, SEQ ID NO: 4, SEQ ID NO: 6, SEQ ID NO: 8;
(d) a variant of the mature polypeptide of the sequence selected from the group of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
(e) a fragment of the polypeptide of (a), (b), (c), or (d) that has beta-glucanase activity; wherein said cleaning or detergent composition further comprising:
 (i) one or more amylases; and/or
 (ii) one or more proteases,
preferably said polypeptide having beta-glucanase activity and said one or more amylases (e.g., SEQ ID NO: 12) (and/or said one or more proteases) have a synergistic effect; further preferably said synergistic effect is a REM synergistic effect, further most preferably said REM synergistic effect is of more than about 6.5 at about 40° C. for about 30 minutes at pH of about 7.5, further most preferably said REM synergistic effect is of more than about 6.1 at about 40° C. for about 30 minutes at pH of about 10, further most preferably said REM synergistic effect is of more than about 6.2 at about 40° C. for about 30 minutes at pH of about 10, further most preferably said beta-glucanase activity is not an endo-cellulase activity on β-1,4 linkages between D-glucose units of cellulose.

In another aspect, the present disclosure relates to a cleaning or detergent composition, wherein said cleaning or detergent composition is a dish washing composition, said composition comprising polypeptide(s) having beta-glucanase activity, selected from the group of:
(a) a polypeptide having about 100% sequence identity to the mature polypeptide of the sequence selected from the group of: SEQ ID NO: 2, SEQ ID NO: 3, SEQ ID NO: 5, SEQ ID NO: 7, SEQ ID NO: 9;
(b) a polypeptide encoded by a polynucleotide that hybridizes under low stringency conditions with (i) the mature polypeptide coding sequence of the sequence selected from the group of: SEQ ID NO: 1, SEQ ID NO: 4, SEQ ID NO: 6, SEQ ID NO: 8, or (ii) the full-length complement of (i);
(c) a polypeptide encoded by a polynucleotide having about 100% sequence identity to the mature polypeptide coding sequence of the sequence selected from the group of: SEQ ID NO: 1, SEQ ID NO: 4, SEQ ID NO: 6, SEQ ID NO: 8;
(d) a variant of the mature polypeptide of the sequence selected from the group of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
(e) a fragment of the polypeptide of (a), (b), (c), or (d) that has beta-glucanase activity; wherein said cleaning or detergent composition further comprising:
 (i) one or more amylases; and/or
 (ii) one or more proteases,
preferably said polypeptide having beta-glucanase activity and said one or more amylases (e.g., SEQ ID NO: 12) (and/or said one or more proteases) have a synergistic effect; further preferably said synergistic effect is a REM synergistic effect, further most preferably said REM synergistic effect is of more than about 6.5 at about 40° C. for about 30 minutes at pH of about 7.5, further most preferably said REM synergistic effect is of more than about 6.1 at about 40° C. for about 30 minutes at pH of about 10, further most preferably said REM synergistic effect is of more than about 6.2 at about 40° C. for about 30 minutes at pH of about 10, further most preferably said beta-glucanase activity is not an endo-cellulase activity on β-1,4 linkages between D-glucose units of cellulose.

In another aspect, the present disclosure relates to a cleaning or detergent composition, wherein said cleaning or detergent composition is a dish washing composition, said composition comprising a beta-glucanase of the present disclosure together with one or more alpha-amylases (and/or said one or more proteases). In another aspect, the present disclosure relates to a cleaning or detergent composition comprising a beta-glucanase together with one or more amylases and one or more further enzymes selected from the group comprising of proteases, lipases, cutinases, cellulases, endoglucanases, xyloglucanases, pectinases, pectin lyases, xanthanases, peroxidases, haloperoxygenases, catalases, mannanases, or any mixture thereof. In another aspect, the present disclosure relates to a cleaning or detergent composition of the present disclosure having an enzyme detergency benefit or improved wash performance in cleaning or detergent applications.

In another aspect, the present disclosure relates to use of a beta-glucanase of the present disclosure together with one or more proteases, and optionally one or more further enzymes such as proteases, lipases, cutinases, cellulases, endoglucanases, xyloglucanases, pectinases, pectin lyases, xanthanases, peroxidases, haloperoxygenases, catalases, mannanases, or any mixture thereof, for dish wash.

In another aspect, the present disclosure relates to a dishwashing composition, especially a dishwash cleaning or detergent composition, comprising one or more polypeptide(s) having beta-glucanase activity. In another aspect, the present disclosure relates to dishwashing composition, especially a dishwash cleaning or detergent composition, comprising one or more polypeptide(s) having beta-glucanase activity with improved wash performance and/or improved stability at alkaline conditions (e.g. at pH about 7.5 or above). In another aspect, the present disclosure relates to dishwashing composition, especially a dishwash cleaning or detergent composition, comprising one or more polypeptide(s) having beta-glucanase activity selected from the group of:
(a) a polypeptide having at least about 60% sequence identity to the mature polypeptide of the sequence selected from the group of: SEQ ID NO: 2, SEQ ID NO: 3, SEQ ID NO: 5, SEQ ID NO: 7, SEQ ID NO: 9;
(b) a polypeptide encoded by a polynucleotide that hybridizes under low stringency conditions with (i) the mature polypeptide coding sequence of the sequence selected from the group of: SEQ ID NO: 1, SEQ ID NO: 4, SEQ ID NO: 6, SEQ ID NO: 8, or (ii) the full-length complement of (i);
(c) a polypeptide encoded by a polynucleotide having at least about 60% sequence identity to the mature polypeptide coding sequence of the sequence selected from the group of: SEQ ID NO: 1, SEQ ID NO: 4, SEQ ID NO: 6, SEQ ID NO: 8;
(d) a variant of the mature polypeptide of the sequence selected from the group of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
(e) a fragment of the polypeptide of (a), (b), (c), or (d) that has beta-glucanase activity.

In another aspect, the present disclosure relates to dishwashing composition, especially a dishwash cleaning or detergent composition, comprising one or more polypeptide(s) having beta-glucanase activity selected from the group of:
(a) a polypeptide having at least about 81% sequence identity to the mature polypeptide of the sequence selected from the group of: SEQ ID NO: 2, SEQ ID NO: 3, SEQ ID NO: 5, SEQ ID NO: 7, SEQ ID NO: 9;
(b) a polypeptide encoded by a polynucleotide that hybridizes under low stringency conditions with (i) the mature polypeptide coding sequence of the sequence selected from the group of: SEQ ID NO: 1, SEQ ID NO: 4, SEQ ID NO: 6, SEQ ID NO: 8, or (ii) the full-length complement of (i);
(c) a polypeptide encoded by a polynucleotide having at least about 81% sequence identity to the mature polypeptide coding sequence of the sequence selected from the group of: SEQ ID NO: 1, SEQ ID NO: 4, SEQ ID NO: 6, SEQ ID NO: 8;
(d) a variant of the mature polypeptide of the sequence selected from the group of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
(e) a fragment of the polypeptide of (a), (b), (c), or (d) that has beta-glucanase activity.

In another aspect, the present disclosure relates to dishwashing composition, especially a dishwash cleaning or detergent composition, comprising one or more polypeptide(s) having beta-glucanase activity selected from the group of:
(a) a polypeptide having at least about 99% sequence identity to the mature polypeptide of the sequence selected from the group of: SEQ ID NO: 2, SEQ ID NO: 3, SEQ ID NO: 5, SEQ ID NO: 7, SEQ ID NO: 9;
(b) a polypeptide encoded by a polynucleotide that hybridizes under low stringency conditions with (i) the mature polypeptide coding sequence of the sequence selected from the group of: SEQ ID NO: 1, SEQ ID NO: 4, SEQ ID NO: 6, SEQ ID NO: 8, or (ii) the full-length complement of (i);
(c) a polypeptide encoded by a polynucleotide having at least about 99% sequence identity to the mature polypeptide coding sequence of the sequence selected from the group of: SEQ ID NO: 1, SEQ ID NO: 4, SEQ ID NO: 6, SEQ ID NO: 8;
(d) a variant of the mature polypeptide of the sequence selected from the group of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
(e) a fragment of the polypeptide of (a), (b), (c), or (d) that has beta-glucanase activity.

The present disclosure further relates to dishwashing composition, especially a dishwash cleaning or detergent composition, comprising one or more polypeptide(s) having beta-glucanase activity selected from the group of:
(a) a polypeptide having at least about 89% sequence identity to the mature polypeptide of the sequence selected from the group of: SEQ ID NO: 2, SEQ ID NO: 3, SEQ ID NO: 5, SEQ ID NO: 7, SEQ ID NO: 9;
(b) a polypeptide encoded by a polynucleotide that hybridizes under low stringency conditions with (i) the mature polypeptide coding sequence of the sequence selected from the group of: SEQ ID NO: 1, SEQ ID NO: 4, SEQ ID NO: 6, SEQ ID NO: 8, or (ii) the full-length complement of (i);
(c) a polypeptide encoded by a polynucleotide having at least about 89% sequence identity to the mature polypeptide coding sequence of the sequence selected from the group of: SEQ ID NO: 1, SEQ ID NO: 4, SEQ ID NO: 6, SEQ ID NO: 8;
(d) a variant of the mature polypeptide of the sequence selected from the group of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
(e) a fragment of the polypeptide of (a), (b), (c), or (d) that has beta-glucanase activity.

In another aspect, the present disclosure relates to dishwashing composition, especially a dishwash cleaning or detergent composition, comprising one or more polypeptide(s) having beta-glucanase activity selected from the group of:
(a) a polypeptide having at least about 98% sequence identity to the mature polypeptide of the sequence selected from the group of: SEQ ID NO: 2, SEQ ID NO: 3, SEQ ID NO: 5, SEQ ID NO: 7, SEQ ID NO: 9;
(b) a polypeptide encoded by a polynucleotide that hybridizes under low stringency conditions with (i) the mature polypeptide coding sequence of the sequence selected from the group of: SEQ ID NO: 1, SEQ ID NO: 4, SEQ ID NO: 6, SEQ ID NO: 8, or (ii) the full-length complement of (i);
(c) a polypeptide encoded by a polynucleotide having at least about 98% sequence identity to the mature polypeptide coding sequence of the sequence selected from the group of: SEQ ID NO: 1, SEQ ID NO: 4, SEQ ID NO: 6, SEQ ID NO: 8;
(d) a variant of the mature polypeptide of the sequence selected from the group of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
(e) a fragment of the polypeptide of (a), (b), (c), or (d) that has beta-glucanase activity.

In another aspect, the present disclosure relates to dishwashing composition, especially a dishwash cleaning or detergent composition, comprising one or more polypeptide(s) having beta-glucanase activity selected from the group of:
(a) a polypeptide having at least about 100% sequence identity to the mature polypeptide of the sequence selected from the group of: SEQ ID NO: 2, SEQ ID NO: 3, SEQ ID NO: 5, SEQ ID NO: 7, SEQ ID NO: 9;
(b) a polypeptide encoded by a polynucleotide that hybridizes under low stringency conditions with (i) the mature polypeptide coding sequence of the sequence selected from the group of: SEQ ID NO: 1, SEQ ID NO: 4, SEQ ID NO: 6, SEQ ID NO: 8, or (ii) the full-length complement of (i);
(c) a polypeptide encoded by a polynucleotide having at least about 100% sequence identity to the mature polypeptide coding sequence of the sequence selected from the group of: SEQ ID NO: 1, SEQ ID NO: 4, SEQ ID NO: 6, SEQ ID NO: 8;
(d) a variant of the mature polypeptide of the sequence selected from the group of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
(e) a fragment of the polypeptide of (a), (b), (c), or (d) that has beta-glucanase activity.

In another aspect, the present disclosure relates to cleaning or detergent composition, wherein said cleaning or detergent composition is a dish washing composition, said composition comprising the polypeptide of the present disclosure and the use of polypeptides of the present disclosure in degrading a beta-glucan (e.g. beta-D-glucan, beta-1,3-1,4 glucan, a mix-linkage beta-glucan, barley beta-glucan, oatmeal beta-glucan), for cleaning dishware; methods for degrading beta-glucan comprising applying a composition comprising the polypeptide of the present disclosure to the beta-glucan.

In another aspect, the present disclosure relates to a difference between the use of cellulases and lichenases of the present disclosure on textile in laundry is that the lichenases of the present disclosure do not degrade the fibers of the textile.

In another aspect, the present disclosure relates to methods of dish washing including automated dish wash (ADW) and hand dish wash (HDW) using a polypeptide or a composition (e.g. cleaning or detergent composition) of the present disclosure. In another aspect, the present disclosure relates to dish washing composition, said composition comprising polypeptide(s) of the present disclosure. In another aspect, the present disclosure relates to a cleaning or detergent composition, wherein said composition is a dish washing composition, said composition comprising said beta-glucanase polypeptide of the present disclosure and one or more amylases (and/or said one or more proteases).

In another aspect, the present disclosure relates to use of polypeptide(s) of the present disclosure in dish washing for preventing, reducing or removing a biofilm from an item. In another aspect, the present disclosure relates to use of polypeptide(s) or detergent composition of the present disclosure for reducing or preventing soil redeposition in dishwashing.

Overview of Sequence Listing

SEQ ID NO: 1 is the DNA sequence of the beta-glucanase as isolated from a strain of a *Bacillus* sp.
SEQ ID NO: 2 is the amino acid sequence of the beta-glucanase as automatically deduced from SEQ ID NO: 1.
SEQ ID NO: 3 is the amino acid sequence of the beta-glucanase as deduced from SEQ ID NO: 1 taking into account that the first amino acid (position −28) in the polypeptide shown in SEQ ID NO: 2 and encoded by the polynucleotide shown in SEQ ID NO:1 should be Met, not Val. When the first codon is gtg a Met is inserted though gtg normally codes for V.
SEQ ID NO: 4 is the DNA sequence of the beta-glucanase as isolated from a strain of a *Bacillus akibai*.
SEQ ID NO: 5 is the amino acid sequence of the beta-glucanase as deduced from SEQ ID NO: 4.
SEQ ID NO: 6 is the DNA sequence of the beta-glucanase as isolated from a strain of a *Bacillus agaradhaerens*.
SEQ ID NO: 7 is the amino acid sequence of the beta-glucanase as deduced from SEQ ID NO: 6.
SEQ ID NO: 8 is the DNA sequence of the beta-glucanase as isolated from a strain of a *Bacillus mojavensis*.
SEQ ID NO: 9 is the amino acid sequence of the beta-glucanase as deduced from SEQ ID NO: 8.
SEQ ID NO: 10 is a polypeptide secretion signal *Bacillus clausii*.
SEQ ID NO: 11 is an artificial N-terminal poly-histidine affinity purification tag sequence.
SEQ ID NO: 12 is alpha-amylase protein sequence from *Bacillus* sp. (Stainzyme).
SEQ ID NO: 13 is a polypeptide corresponding to SEQ ID NO: 2 of WO 95/10603.
SEQ ID NO: 14 is a polypeptide corresponding to SEQ ID NO: 6 in WO 02/010355.
SEQ ID NO: 15 is a polypeptide corresponding to a hybrid polypeptide comprising residues 1-33 of SEQ ID NO: 6 of WO 2006/066594 and residues 36-483 of SEQ ID NO: 4 of WO 2006/066594.
SEQ ID NO: 16 is a polypeptide corresponding to SEQ ID NO: 6 of WO 02/019467.
SEQ ID NO: 17, SEQ ID NO: 18 and SEQ ID NO: 19 are polypeptides respectively corresponding to SEQ ID NO: 1, SEQ ID NO: 2 or SEQ ID NO: 7 of WO 96/023873.
SEQ ID NO: 20 is a polypeptide corresponding to SEQ ID NO: 2 of WO 08/153815
SEQ ID NO: 21 is a polypeptide corresponding to SEQ ID NO: 10 of WO 01/66712.
SEQ ID NO: 22 is a polypeptide corresponding to SEQ ID NO: 2 of WO 09/061380.
SEQ ID NO: 23 is an amylase protein sequence from *Bacillus* sp.
SEQ ID NO: 24 is an amylase protein sequence from *Bacillus* sp.
SEQ ID NO: 25 is an amylase protein sequence from *Bacillus* sp.
SEQ ID NO: 26 is an amylase protein sequence from *Cytophaga* sp.
SEQ ID NO: 27 is an amylase protein sequence from *Bacillus* sp.
SEQ ID NO: 28 is an amylase protein sequence from *Bacillus* sp.
SEQ ID NO: 29 is an amylase protein sequence from *Bacillus halmapalus*.
SEQ ID NO: 30 is an artificial amylase protein sequence.
SEQ ID NO: 31 is an amylase protein sequence from *Bacillus* sp.
SEQ ID NO: 32 is a beta-glucanase protein sequence from *Bacillus amyloliquefaciens*.
SEQ ID NO: 33 is a beta-glucanase protein sequence from *Bacillus subtilis*.
SEQ ID NO: 34 is a protease protein sequence from *Bacillus Lentus*.
SEQ ID NO: 35 is an artificial protease protein sequence.
SEQ ID NO: 36 is an artificial protease protein sequence.
SEQ ID NO: 37 is His-tagged recombinant mature beta-glucanase protein from *Bacillus* sp-62449.
SEQ ID NO: 38 is His-tagged recombinant mature beta-glucanase protein from *Bacillus akibai*.
SEQ ID NO: 39 is His-tagged recombinant mature beta-glucanase protein from *Bacillus agaradhaerens*.
SEQ ID NO: 40 is His-tagged recombinant mature beta-glucanase protein from *Bacillus mojavensis*.

Definitions

Anti-redeposition: The term "anti-redeposition" or "anti-redeposition effect" means the reduction or prevention of soil from depositing back onto the hard surface such as dishware. The anti-redeposition effect can be determined using the Mini-LOM or Mini-TOM wash assay as described in the examples herein (e.g., as in example 14).

Synergistic effect: The term "synergistic effect" means a cooperative action of polypeptides such that a total combined effect of said polypeptides is greater than the sum of the individual enzymatic effects of said polypeptides. Non-limiting examples of synergistic effect include REM synergistic effect of a beta-glucanase polypeptide of the present disclosure and one or more alpha-amylase (and/or one or more proteases).

REM synergistic effect: REM synergistic effect of polypeptides as used herein can be measured based on the analysis of stain removal carried out by using any suitable wash performance methodology (e.g. Wascator bottle wash method). A preferred method for determining the REM synergistic effect is disclosed in examples disclosed herein, e.g. Example 7.

Beta-glucanase: The term "beta-glucanase" as used herein means an endo beta-1,4-glucanase activity (e.g. endo-1,4-β-D-glucanase) that catalyzes the hydrolyses of a beta-1,4-bonds connecting two glucosyl residues in a beta-glucan. Non-limiting examples of beta-glucanases as defined herein include cellulases (e.g. EC 3.2.1.4, e.g. having endo-cellulase activity on β-1,4 linkages between D-glucose units and licheninases (or lichenases) (e.g. EC 3.2.1.73) hydrolysing (1,4)-beta-D-glucosidic linkages in beta-D-glucans containing (1,3)- and (1,4)-bonds. Beta-glucanases (e.g. EC 3.2.1.4) can, for example, perform endohydrolysis of (1,4)-beta-D-glucosidic linkages in cellulose, lichenin and cereal beta-D-glucans and will also hydrolyze 1,4-linkages in beta-D-glucans containing 1,3-linkages. For purposes of the present disclosure, beta-glucanase activity is determined according to the procedure described in the Examples. In one aspect of the present disclosure, the polypeptides of the present disclosure have at least about 20%, e.g., at least about 40%, at least about 50%, at least about 60%, at least about 70%, at least about 80%, at least about 90%, at least about 95%, or at least about 100% of the beta-glucanase activity of the polypeptide having the sequence selected from the group of: SEQ ID NO: 7, SEQ ID NO: 2, SEQ ID NO: 3, SEQ ID NO: 5, SEQ ID NO: 9. Beta-glucanase activity can suitably be measured using barley beta-glucan as substrate. A preferred assay for determining beta-glucanase activity is disclosed in Example 1 (AZCL-Barley beta-glucan assay). A further subgroup of beta-glucanases as defined herein, also known as a licheninases (or lichenases) (e.g. EC 3.2.1.73), can also be used to catalyse the hydrolysis of the beta-1,4-glucosidic bonds to give beta-glucans. Licheninases (or lichenases) (e.g. EC 3.2.1.73) hydrolyse (1,4)-beta-D-glucosidic linkages in beta-D-glucans containing (1,3)- and (1,4)-bonds and can act on lichenin and cereal beta-D-glucans, but not on beta-D-glucans containing only 1,3- or 1,4-bonds. As used herein the term "beta-glucanase activity" comprises licheninase (or lichenases) (e.g. EC 3.2.1.73) activity.

Beta-glucan: The term "beta-glucan" as used herein means a polysaccharide that only contain glucose as structural components, and in which the glucose units are linked by beta-glycosidic bonds. Non-limiting examples of beta-glucans include beta-D-glucans, beta-1,3-1,4 glucans, mix-linkage beta-glucans, barley beta-glucans, oatmeal beta-glucans.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Biofilm: The term "biofilm" means any group of microorganisms in which cells stick to each other on a surface, such as dishware. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium.

Bacteria living in a biofilm usually have significantly different properties from free-floating bacteria of the same species, as the dense and protected environment of the film allows them to cooperate and interact in various ways. One effect of this environment is increased resistance to detergents and antibiotics, as the dense extracellular matrix and the outer layer of cells protect the interior of the community.

Carbohydrate binding module: The term "carbohydrate binding module" means the region within a carbohydrate-active enzyme that provides carbohydrate-binding activity. A majority of known carbohydrate binding modules (CBMs) are contiguous amino acid sequences with a discrete fold. The carbohydrate binding module (CBM) is typically found either at the N-terminal or at the C-terminal extremity of an enzyme. Some CBMs are known to have specificity for cellulose.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellulolytic enzyme or cellulase: The term "cellulolytic enzyme" or "cellulase" means one or more (e.g., several) enzymes that hydrolyze a cellulosic material. Such enzymes include endoglucanase(s) (e.g. EC 3.2.1.4), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases). Total cellulolytic enzyme activity can be measured using insoluble substrates, including Whatman No. 1 filter paper, microcrystalline cellulose, bacterial cellulose, algal cellulose, cotton, pretreated lignocellulose, etc. The most common total cellulolytic activity assay is the filter paper assay using Whatman No. 1 filter paper as the substrate.

Cellulolytic enzyme activity can be determined by measuring the increase in production/release of sugars during hydrolysis of a cellulosic material by cellulolytic enzyme(s) under the following conditions: from about 1 to about 50 mg of cellulolytic enzyme protein/g of cellulose in pretreated corn stover (PCS) (or other pretreated cellulosic material) for from about 3 to about 7 days at a suitable temperature such as from about 40° C. to about 80° C., e.g., about 50° C., about 55° C., about 60° C., about 65° C., or about 70° C., and a suitable pH such as from about 4 to about 9, e.g., about 5.0, about 5.5, about 6.0, about 6.5, or about 7.0, compared to a control hydrolysis without addition of cellulolytic enzyme protein. Typical conditions are about 1 ml reactions, washed or unwashed PCS, about 5% insoluble solids (dry weight), about 50 mM sodium acetate pH of about 5, about 1 mM $MnSO_4$, about 50° C., about 55° C., or about 60° C., for about 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue). It is understood herein that the cellulose may be in the form of lignocellulose, a plant cell wall material containing lignin, cellulose, and hemicellulose in a mixed matrix. In one aspect, the cellulosic material is any biomass material. In another aspect, the cellulosic material is lignocellulose, which comprises cellulose, hemicelluloses, and lignin.

In an embodiment, the cellulosic material is agricultural residue, herbaceous material (including energy crops), municipal solid waste, pulp and paper mill residue, waste paper, or wood (including forestry residue).

In another embodiment, the cellulosic material is arundo, bagasse, bamboo, corn cob, corn fiber, corn stover, miscanthus, rice straw, switchgrass, or wheat straw.

In another embodiment, the cellulosic material is aspen, eucalyptus, fir, pine, poplar, spruce, or willow.

In another embodiment, the cellulosic material is algal cellulose, bacterial cellulose, cotton linter, filter paper, microcrystalline cellulose (e.g., AVICEL®), or phosphoric-acid treated cellulose.

In another embodiment, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Detergent component: the term "detergent component" is defined herein to mean the types of chemicals which can be used in detergent compositions. Examples of detergent components are surfactants, hydrotropes, builders, co-builders, chelators or chelating agents, bleaching system or bleach components, polymers, foam boosters, suds suppressors, dispersants, perfume, bactericides, fungicides, soil suspending agents, soil release polymers, anti-redeposition agents, enzyme inhibitors or stabilizers, enzyme activators, antioxidants, and solubilizers. The detergent composition may comprise of one or more of any type of detergent component.

Detergent composition: the term "detergent composition" refers to compositions that find use in the removal of undesired compounds from items to be cleaned, such as textiles, dishes, and hard surfaces. The detergent composition may be used to e.g. clean textiles, dishes and hard surfaces for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; hard surface cleaning formulations, such as for glass, wood, plastic, ceramic and metal counter tops and windows; carpet cleaners; oven cleaners; fabric fresheners; fabric softeners; and textile and laundry pre-spotters, as well as dish wash detergents). In addition to containing a GH16 beta-glucanase of the present disclosure, the detergent formulation may contain one or more additional enzymes (such as amylases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases, transglutaminases, and combinations thereof, or any mixture thereof), and/or components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti corrosion agents, enzyme inhibitors or stabilizers, enzyme activators, transferase(s), hydrolytic enzymes, oxido reductases, bluing agents and fluorescent dyes, antioxidants, and solubilizers.

Dish wash/Dish washing: The term "dish wash"/"dish washing" refers to all forms of washing dishes, e.g. by hand dish wash (HDW) or automatic dish wash (ADW), especially household automatic dish wash, or industrial dish cleaning. Washing dishes includes, but is not limited to, the cleaning of all forms of crockery such as plates, cups, glasses, bowls, all forms of cutlery such as spoons, knives, forks and serving utensils as well as ceramics, plastics, metals, china, glass and acrylics.

Dish washing composition: The term "dish washing composition" refers to all forms of compositions for cleaning hard surfaces. The present disclosure is not restricted to any particular type of dish washing composition or any particular detergent.

Fragment: The term "fragment" means a polypeptide or a catalytic or carbohydrate binding module having one or more (e.g., several) amino acids absent from the amino and/or carboxyl terminus of a mature polypeptide or domain; wherein the fragment has beta-glucanase or carbohydrate binding activity. In one aspect, a fragment contains at least about 340 amino acid residues, or at least about 230 amino acid residues, or at least about 210 amino acid residues or at least about 200 amino acid residues, or at least about 180 amino acid residues, wherein the fragment has beta-glucanase activity.

Hard surface cleaning: The term "Hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, and cutlery such as spoons, knives, forks, serving utensils, ceramics, plastics, metals, china, glass and acrylics.

Hemicellulolytic enzyme or hemicellulase: The term "hemicellulolytic enzyme" or "hemicellulase" means one or more (e.g., several) enzymes that hydrolyze a hemicellulosic material. Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, Pure & Appl. Chem. 59: 1739-1752, at a suitable temperature such as from about 40° C. to about 80° C., e.g., about 50° C., about 55° C., about 60° C., about 65° C., or about 70° C., and a suitable pH such as from about 4 to about 9, e.g., about 5.0, about 5.5, about 6.0, about 6.5, or about 7.0.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). A fermentation broth produced by culturing a recombinant host cell expressing the polynucleotide of the present disclosure will comprise the polypeptide of the present disclosure in an isolated form.

Lichenase activity: The term "lichenase activity" means enzymes that hydrolysis beta-1,3, beta-1,4-glucans (e.g. EC 3.2.1.73).

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is selected from the group of: amino acids 1 to 222 of SEQ ID NO: 7, amino acids 1 to 351 of SEQ ID NO: 2, amino acids 1 to 351 of SEQ ID NO: 3, amino acids 1 to 245 of SEQ ID NO: 5, amino acids 1 to 214 of SEQ ID NO: 9. The amino acids −28 to −1 of SEQ ID NO: 2 are a signal peptide. The amino acids −28 to −1 of SEQ ID NO: 3 are a signal peptide. The amino acids −31 to −1 of SEQ ID NO: 5 are a signal peptide. The amino acids −15 to −1 of SEQ ID NO: 7 are a signal peptide. The amino acids −29 to −1 of SEQ ID NO: 9 are a signal peptide.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having beta-glucanase activity. In one aspect, the mature polypeptide coding sequence is selected from the group of: nucleotides 85 to 1137 of SEQ ID NO: 1, nucleotides 94 to 828 of SEQ ID NO: 4, nucleotides 46 to 711 of SEQ ID NO: 6, nucleotides 88 to 729 of SEQ ID NO: 8. The nucleotides 1 to 84 of SEQ ID NO: 1 encode a signal peptide. The nucleotides 1 to 93 of SEQ ID NO: 4 encode a signal peptide. The nucleotides 1 to 45 of SEQ ID NO: 6 encode a signal peptide. The nucleotides 1 to 87 of SEQ ID NO: 8 encode a signal peptide.

Malodor: The term "malodor" means an odor which is not desired on clean items. The cleaned item should smell fresh and clean without malodors adhered to the item. One example of malodor is compounds with an unpleasant smell, which may be produced by microorganisms. Another example of malodor can be the smell from spices, for example curry or other exotic spices adhering to an item such as a piece of textile. One way of measuring the ability of an item to adhere malodor is by using the Malodor Assay.

Pretreated corn stover: The term "Pretreated Corn Stover" or "PCS" means a cellulosic material derived from corn stover by treatment with heat and dilute sulfuric acid, alkaline pretreatment, neutral pretreatment, or any pretreatment known in the art.

Sequence identity: The relatedness between two amino acid sequences is described by the parameter "sequence identity". For purposes of the present disclosure, the sequence identity between two amino acid sequences is determined using the Needleman-Wunsch algorithm (Needleman and Wunsch, 1970, J. Mol. Biol. 48: 443-453) as implemented in the Needle program of the EMBOSS package, preferably version 5.0.0 or later. The parameters used are gap open penalty of about 10, gap extension penalty of about 0.5, and the EBLOSUM62 (EMBOSS version of BLOSUM62) substitution matrix. The output of Needle labeled "longest identity" (obtained using the −nobrief option) is used as the percent identity and is calculated as follows:

$$(\text{Identical Residues} \times 100)/(\text{Length of Alignment} - \text{Total Number of Gaps in Alignment})$$

For purposes of the present disclosure, the sequence identity between two deoxyribonucleotide sequences is determined using the Needleman-Wunsch algorithm as implemented in the Needle program of the EMBOSS package, preferably version 5.0.0 or later. The parameters used are gap open penalty of about 10, gap extension penalty of about 0.5, and the EDNAFULL (EMBOSS version of NCBI NUC4.4) substitution matrix. The output of Needle labeled "longest identity" (obtained using the –nobrief option) is used as the percent identity and is calculated as follows:

$$(\text{Identical Deoxyribonucleotides} \times 100)/(\text{Length of Alignment} - \text{Total Number of Gaps in Alignment})$$

Stringency conditions: The different stringency conditions are defined as follows.

The term "very low stringency conditions" means for probes of at least about 100 nucleotides in length, prehybridization and hybridization at about 42° C. in about 5×SSPE, about 0.3% SDS, about 200 micrograms/ml sheared and denatured salmon sperm DNA, and about 25% formamide, following standard Southern blotting procedures for from about 12 to about 24 hours. The carrier material is finally washed three times each for about 15 minutes using about 1.6×SSC, about 0.2% SDS at about 60° C.

The term "low stringency conditions" means for probes of at least about 100 nucleotides in length, prehybridization and hybridization at about 42° C. in 5×SSPE, about 0.3% SDS, about 200 micrograms/ml sheared and denatured salmon sperm DNA, and about 25% formamide, following standard Southern blotting procedures for from about 12 to about 24 hours. The carrier material is finally washed three times each for about 15 minutes using about 0.8×SSC, about 0.2% SDS at about 60° C.

The term "medium stringency conditions" means for probes of at least about 100 nucleotides in length, prehybridization and hybridization at about 42° C. in 5×SSPE, about 0.3% SDS, about 200 micrograms/ml sheared and denatured salmon sperm DNA, and about 35% formamide, following standard Southern blotting procedures for from about 12 to about 24 hours. The carrier material is finally washed three times each for about 15 minutes using about 0.8×SSC, about 0.2% SDS at about 65° C.

The term "medium-high stringency conditions" means for probes of at least about 100 nucleotides in length, prehybridization and hybridization at about 42° C. in 5×SSPE, about 0.3% SDS, about 200 micrograms/ml sheared and denatured salmon sperm DNA, and about 35% formamide, following standard Southern blotting procedures for from about 12 to about 24 hours. The carrier material is finally washed three times each for about 15 minutes using 0.4× SSC, about 0.2% SDS at about 65° C.

The term "high stringency conditions" means for probes of at least about 100 nucleotides in length, prehybridization and hybridization at about 42° C. in 5×SSPE, about 0.3% SDS, about 200 micrograms/ml sheared and denatured salmon sperm DNA, and about 50% formamide, following standard Southern blotting procedures for from about 12 to about 24 hours. The carrier material is finally washed three times each for about 15 minutes using 0.2×SSC, about 0.2% SDS at about 65° C.

The term "very high stringency conditions" means for probes of at least about 100 nucleotides in length, prehybridization and hybridization at about 42° C. in 5×SSPE, about 0.3% SDS, about 200 micrograms/ml sheared and denatured salmon sperm DNA, and about 50% formamide, following standard Southern blotting procedures for from about 12 to about 24 hours. The carrier material is finally washed three times each for about 15 minutes using 0.2× SSC, about 0.2% SDS at about 70° C.

Subsequence: The term "subsequence" means a polynucleotide having one or more (e.g., several) nucleotides absent from the 5' and/or 3' end of a mature polypeptide coding sequence; wherein the subsequence encodes a fragment having beta-glucanase activity. In one aspect, a subsequence contains at least about 1052 nucleotides of SEQ ID NO: 1 or the cDNA sequence thereof, at least about 1037 nucleotides of SEQ ID NO: 1 or the cDNA sequence thereof, or about 1022 nucleotides of SEQ ID NO: 1 or the cDNA sequence thereof).

Variant: The term "variant" means a polypeptide having beta-glucanase activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding from about 1 to about 3 amino acids adjacent to an amino acid occupying a position. The variants of the present disclosure have at least about 20%, e.g., at least about 40%, at least about 50%, at least about 60%, at least about 70%, at least about 80%, at least about 90%, at least about 95%, or at least about 100% of the beta-glucanase activity of the polypeptide of sequence selected from the group of: SEQ ID NO: 7, SEQ ID NO: 2, SEQ ID NO: 3, SEQ ID NO: 5, SEQ ID NO: 9 or the mature polypeptide of sequence selected from the group of: SEQ ID NO: 7, SEQ ID NO: 2, SEQ ID NO: 3, SEQ ID NO: 5, SEQ ID NO: 9.

Wild-type beta-glucanase: The term "wild-type" beta-glucanase means a beta-glucanase expressed by a naturally occurring microorganism, such as a bacterium, yeast, or filamentous fungus found in nature.

Wash performance: The term "wash performance" is defined herein as the ability of an enzyme or a blend of enzymes to remove stains present on an object to be cleaned during e.g. wash or hard surface cleaning, such as dish washing, relative to the wash performance without one or more on the enzymes present.

DETAILED DESCRIPTION OF THE PRESENT DISCLOSURE

Dishwashing Compositions Comprising One or More Polypeptide(s) Having Beta-Glucanase Activity This present disclosure provides the use of novel beta-glucanases and one or more amylases (and/or one or more proteases) for cleaning or detergent compositions which have a benefit in removing stains and which can be used in cleaning or detergent applications, such as dishwashing or for processes such as dish wash. The present disclosure also provides the use of beta-glucanases that are wash stable in detergent formulations in the presence of amylases. The beta-glucanases of the present disclosure may show synergistic effect with one or more amylases (and/or one or more proteases) (e.g. wherein a preferred method for determining the REM synergistic effect is disclosed in examples disclosed herein, e.g. Example 7).

In an embodiment, the present disclosure relates to a cleaning or detergent composition, wherein said cleaning or detergent composition is a dish washing composition, the composition comprising polypeptide(s) having beta-glucanase activity, wherein said polypeptides having a sequence identity to the mature polypeptide of the sequence selected from the group of: SEQ ID NO: 2, SEQ ID NO: 3, SEQ ID NO: 5, SEQ ID NO: 7, SEQ ID NO: 9; at least about 60%, e.g., at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%, which have beta-glucanase activity; and one or more amylases (and/or one or more proteases), preferably said polypeptide having beta-glucanase activity and said one or more amylases (and/or one or more proteases) have a synergistic effect; further preferably said synergistic effect is a REM synergistic effect, further most preferably said REM synergistic effect is of more than about 6.5 at about 40° C. for about 30 minutes at pH of about 7.5, further most preferably said REM synergistic effect is of more than about 6.1 at about 40° C. for about 30 minutes at pH of about 10, further most preferably said REM synergistic effect is of more than about 6.2 at about 40° C. for about 30 minutes at pH of about 10, further most preferably said beta-glucanase activity is not an endo-cellulase activity on β-1,4 linkages between D-glucose units of cellulose.

In an embodiment, the present disclosure relates to cleaning or detergent composition wherein said cleaning or detergent composition is a dish washing composition, said composition comprise polypeptide(s) having a sequence identity to the mature polypeptide of the sequence selected from the group of: SEQ ID NO: 2, SEQ ID NO: 3, SEQ ID NO: 5, SEQ ID NO: 7, SEQ ID NO: 9; at least about 60%, e.g., at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%, which have beta-glucanase activity. An embodiment of the present disclosure is a cleaning or detergent composition wherein said cleaning or detergent composition is a dish washing composition, said composition comprising said beta-glucanase polypeptide and one or more amylases (and/or one or more proteases).

In one aspect, the polypeptide(s) differ by up to about 10 amino acids, e.g., 1, 2, 3, 4, 5, 6, 7, 8, 9, or 10, from the mature polypeptide of sequence selected from the group of: SEQ ID NO: 2, SEQ ID NO: 3, SEQ ID NO: 5, SEQ ID NO: 7, SEQ ID NO: 9. An embodiment of the present disclosure is a cleaning or detergent composition wherein said cleaning or detergent composition is a dish washing composition, said composition comprising said beta-glucanase polypeptide and one or more amylases (and/or one or more proteases).

In one embodiment, the present disclosure relates to a cleaning or detergent composition wherein said cleaning or detergent composition is a dish washing composition, said composition comprising a beta-glucanase having at least about 81% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 82% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 83% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 84% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 85% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 86% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 87% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 88% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 89% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 90% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 91% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 92% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 93% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 94% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 95% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 96% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 97% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 98% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having at least about 99% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In one embodiment, the present disclosure relates to a cleaning or detergent composition wherein said cleaning or detergent composition is a dish washing composition, said composition comprising a beta-glucanase having about 100% identity to the mature polypeptide of sequence selected from the group of: SEQ ID NO: 2, SEQ ID NO: 3, SEQ ID NO: 5, SEQ ID NO: 7, SEQ ID NO: 9 and one or more amylases (and/or one or more proteases).

In another embodiment of the present disclosure the polypeptide having beta-glucanase activity and one or more amylases (and/or one or more proteases) have a synergistic effect; preferably said synergistic effect is a REM synergistic effect, further preferably said REM synergistic effect is of more than about 6.5 at about 40° C. for about 30 minutes at pH of about 7.5, further preferably said REM synergistic effect is of more than about 6.1 at about 40° C. for about 30 minutes at pH of about 10, further preferably said REM synergistic effect is of more than about 6.2 at about 40° C. for about 30 minutes at pH of about 10, further preferably said beta-glucanase activity is not an endo-cellulase activity on β-1,4 linkages between D-glucose units of cellulose.

In another embodiment REM synergistic effect is of more than about 1.4 (such as about any of the following: about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9.0) at about 40° C. (or about 35° C., about 45° C., about 50° C., about 55° C., about 60° C.) for about 30 minutes (or about 15 min, about 20 min, about 25 min, about 35 min, about 40 min) at pH of about 7.0 (or about 7.5, about 8.0, about 8.5, about 9.0, about 9.5, about 10.0, about 10.5, about 11.0, about 11.5, about 12.0, about 12.5, about 13.0, about 13.5), e.g. in Wascator bottle wash in Model detergent A1 at about 40° C., for about 30 min (pH about 7.7), or Wascator bottle wash in Model detergent X1 at about 40° C., for about 30 min (pH about 10.1), or Wascator bottle wash in ADW Model detergent A1 at about 40° C., for about 30 min (pH about 10.2) (e.g. see Example 7).

In another embodiment a pH optimum of a polypeptide of the present disclosure is selected in the range from about 6 to about 9. In another embodiment a pH optimum of a polypeptide of the present disclosure is selected from the group of: about 6, about 6.5, about 7, about 7.5, about 8, about 8.5, about 9. In another embodiment a pH optimum of a polypeptide of the present disclosure is at least about 6 (or at least about 6.5, or at least about 7, or at least about 7.5, or at least about 8, or at least about 8.5, or at least about 9). In another embodiment a pH optimum of a polypeptide of the present disclosure is more than about 6 (or more than about 6.5, or more than about 7, or more than about 7.5, or more than about 8, or more than about 8.5, or more than about 9).

In another embodiment a pH optimum of a polypeptide of the present disclosure is selected in the range from about 6 to about 9, wherein said polypeptide has a significantly higher relative activity at pH of about 10 ranging from about 23 to about 90% compared to a beta-glucanase from *Bacillus subtilis* or *Bacillus amyloliquefaciens*. In another embodiment a pH optimum of a polypeptide of the present disclosure is selected from the group of: about any of the following about 6, about 6.5, about 7, about 7.5, about 8, about 8.5, about 9, wherein said polypeptide has a significantly higher relative activity at pH of about 10 ranging from about 23 to about 90% compared to a beta-glucanase from *Bacillus subtilis* or *Bacillus amyloliquefaciens*. In another embodiment a pH optimum of a polypeptide of the present disclosure is at least about 6 (or at least about 6.5, or at least about 7, or at least about 7.5, or at least about 8, or at least about 8.5, or at least about 9), wherein said polypeptide has a significantly higher relative activity at pH of about 10 ranging from about 23 to about 90% compared to a beta-glucanase from *Bacillus subtilis* or *Bacillus amyloliquefaciens*. In another embodiment a pH optimum of a polypeptide of the present disclosure is more than about 6 (or more than about 6.5, or more than about 7, or more than about 7.5, or more than about 8, or more than about 8.5, or more than about 9), wherein said polypeptide has a significantly higher relative activity at pH of about 10 ranging from about 23 to about 90% compared to a beta-glucanase from *Bacillus subtilis* or *Bacillus amyloliquefaciens*.

In one aspect, the polypeptides differ by no more than thirty amino acids, e.g., by twenty five amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the polypeptide of sequence selected from the group of: SEQ ID NO: 2, SEQ ID NO: 3, SEQ ID NO: 5, SEQ ID NO: 7, SEQ ID NO: 9. An embodiment is a composition (e.g. a cleaning or detergent composition) comprising said beta-glucanase polypeptide and one or more amylases (and/or one or more proteases).

In an embodiment, the polypeptide has been isolated. A polypeptide of the present disclosure preferably comprises or of the amino acid sequence selected from the group of: SEQ ID NO: 2, SEQ ID NO: 3, SEQ ID NO: 5, SEQ ID NO: 7, SEQ ID NO: 9 or an allelic variant thereof; or is a fragment thereof having beta-glucanase activity. In another aspect, the polypeptide comprises or of the mature polypeptide of sequence selected from the group of: SEQ ID NO: 2, SEQ ID NO: 3, SEQ ID NO: 5, SEQ ID NO: 7, SEQ ID NO: 9. An embodiment of the present disclosure is a cleaning or detergent composition wherein said cleaning or detergent composition is a dish washing composition, said composition comprise said beta-glucanase polypeptide and one or more amylases (and/or one or more proteases).

In another aspect, the polypeptide comprises of amino acids amino acids 1 to 351 of SEQ ID NO: 2, amino acids 1 to 351 of SEQ ID NO: 3, amino acids 1 to 245 of SEQ ID NO: 5, amino acids 1 to 222 of SEQ ID NO: 7, amino acids 1 to 214 of SEQ ID NO: 9. An embodiment of the present disclosure is a composition (e.g. a cleaning or detergent composition) comprising wherein said cleaning or detergent composition is a dish washing composition, said composition said beta-glucanase polypeptide and one or more amylases (and/or one or more proteases).

In another embodiment beta-glucanase of the present disclosure is not an endo-cellulase having activity on β-1,4 linkages between D-glucose units of cellulose. In another embodiment beta-glucanase of the present disclosure have licheninase (EC 3.2.1.73) enzymatic activity having activity on β-1,3 β-1,4 glucans. An embodiment of the present disclosure is a composition (e.g. a cleaning or detergent composition) wherein said cleaning or detergent composition is a dish washing composition, said composition comprising said beta-glucanase polypeptide and one or more amylases (and/or one or more proteases).

In another embodiment beta-glucanase of the present disclosure comprises alkaline beta-glucanase activity (e.g. beta-glucanase activity in an aqueous solution at pH of about 7.5 or above, e.g. beta-glucanase activity at pH selected from the group of 7.5, 8, 9, 10, 11, 12, 13, 13.5, e.g. beta-glucanase activity at pH in the range from about 7.5 to about 13.5, wherein said aqueous solution optionally comprises a bleaching agent, preferably said pH is selected in the range from about 7.5 to about 12.5, further preferably said pH is selected in the range from about 8.5 to about 11.5, most preferably said pH is selected in the range from about 9.5 to about 10.5). An embodiment of the present disclosure is a cleaning or detergent composition wherein said cleaning or detergent composition is a dish washing composition, said composition comprising said beta-glucanase polypeptide and one or more amylases (and/or one or more proteases).

In another embodiment a beta-glucanase of the present disclosure is capable of:
i) having beta-glucanase activity for at least about 15 minutes in an aqueous solution with a pH selected in the range from about 7.5 to about 13.5, wherein said aqueous solution optionally comprises a bleaching agent, preferably said pH is selected in the range from about 7.5 to about 12.5, further preferably said pH is selected in the range from about 8.5 to about 11.5, most preferably said pH is selected in the range from about 9.5 to about 10.5; and/or
ii) having beta-glucanase activity for at least about 15 minutes in an aqueous solution at a temperature selected in the range from about 20° C. to about 75° C., wherein said aqueous solution optionally comprises a bleaching agent.

An embodiment of the present disclosure is a composition (e.g. a cleaning or detergent composition) wherein said cleaning or detergent composition is a dish washing composition, said composition comprising said beta-glucanase polypeptide and one or more amylases (and/or one or more proteases).

In another embodiment a beta-glucanase of the present disclosure is capable of having beta-glucanase activity in an aqueous solution at a temperature selected in the range from about 20° C. to about 75° C., wherein said aqueous solution optionally comprises a bleaching agent, preferably said temperature is selected in the range from about 40° C. to about 60° C. In another embodiment a beta-glucanase of the present disclosure is capable of having beta-glucanase activity in an aqueous solution at a temperature selected from the group of: about any of the following about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C.

An embodiment of the present disclosure is a composition (e.g. a cleaning or detergent composition) comprising said beta-glucanase polypeptide and one or more amylases (and/or one or more proteases).

In another embodiment a beta-glucanase of the present disclosure is capable of having beta-glucanase activity for at least about 15 minutes, preferably at least about 30 minutes. In another embodiment a beta-glucanase of the present disclosure is capable of having beta-glucanase activity for a period of time selected from the group of: at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30 minutes, e.g. in combination with any single or multiple embodiments as disclosed herein. An embodiment of the present disclosure is a composition (e.g. a cleaning or detergent composition) comprising said beta-glucanase polypeptide and one or more amylases (and/or one or more proteases).

In another embodiment, a cleaning or detergent composition wherein said cleaning or detergent composition is a dish washing composition, said composition comprises a beta-glucanase polypeptide and one or more amylases, wherein said amylase is an alpha-amylase.

In another embodiment, a cleaning or detergent composition of the present disclosure wherein said cleaning or detergent composition is a dish washing composition, said composition comprising a beta-glucanase polypeptide and one or more amylases, wherein said alpha-amylase is selected from the group of:
(a) a polypeptide having at least about 90% sequence identity to SEQ ID NO: 13 (corresponding to SEQ ID NO: 2 of WO 95/10603);
(b) a polypeptide having at least about 90% sequence identity to SEQ ID NO: 13 (corresponding to SEQ ID NO: 2 in WO 95/10603) wherein the polypeptide comprises a substitution in one or more of positions: 15, 23, 105, 106, 124, 128, 133, 154, 156, 178, 179, 181, 188, 190, 197, 201, 202, 207, 208, 209, 211, 243, 264, 304, 305, 391, 408, and/or 444;
(c) a polypeptide having at least about 90% sequence identity to SEQ ID NO: 14 (corresponding to SEQ ID NO: 6 in WO 02/010355);
(d) a polypeptide having at least about 90% sequence identity to the hybrid polypeptide of SEQ ID NO: 15 (comprising residues from about 1 to about 33 of SEQ ID NO: 6 of WO 2006/066594 and residues from about 36 to about 483 of SEQ ID NO: 4 of WO 2006/066594);
(e) a polypeptide having at least about 90% sequence identity to the hybrid polypeptide of SEQ ID NO: 15 (comprising residues from about 1 to about 33 of SEQ ID NO: 6 of WO 2006/066594 and residues from about 36 to about 483 of SEQ ID NO: 4 of WO 2006/066594), wherein the hybrid polypeptide comprises a substitution, a deletion or an insertion in one of more of positions: 48, 49, 107, 156, 181, 190, 197, 201, 209 and/or 264;
(f) a polypeptide having at least about 90% sequence identity to SEQ ID NO: 16 (corresponding to SEQ ID NO: 6 of WO 02/019467);
(g) a polypeptide having at least about 90% sequence identity to SEQ ID NO: 16 (corresponding to SEQ ID NO: 6 of WO 02/019467), wherein the polypeptide comprises a substitution, a deletion or an insertion in one of more of positions: 181, 182, 183, 184, 195, 206, 212, 216 and/or 269;
(h) a polypeptide having at least about 90% sequence identity to SEQ ID NO: 17, SEQ ID NO: 18 or SEQ ID NO: 19 (corresponding to SEQ ID NO: 1, SEQ ID NO: 2 or SEQ ID NO: 7 of WO 96/023873)
(i) a polypeptide having at least about 90% sequence identity to SEQ ID NO: 17, SEQ ID NO: 18 or SEQ ID NO: 19 (corresponding to SEQ ID NO: 1, SEQ ID NO: 2 or SEQ ID NO: 7 of WO 96/023873), wherein the polypeptide comprises a substitution, a deletion or an insertion in one of more of positions: 140, 183, 184 195, 206, 243, 260, 304 and/or 476;
(j) a polypeptide having at least about 90% sequence identity to SEQ ID NO: 20 (corresponding to SEQ ID NO: 2 of WO 08/153815);
(k) a polypeptide having at least about 90% sequence identity to SEQ ID NO: 21 (corresponding to SEQ ID NO: 10 of WO 01/66712);
(l) a polypeptide having at least about 90% sequence identity to SEQ ID NO: 21 (corresponding to SEQ ID NO: 10 of WO 01/66712), wherein the polypeptide comprises a substitution, a deletion or an insertion in one of more of positions: 176, 177, 178, 179, 190, 201, 207, 211 and/or 264;
(m) a polypeptide having at least about 90% sequence identity to SEQ ID NO: 22 (corresponding to SEQ ID NO: 2 of WO 09/061380);
(n) a polypeptide having at least about 90% sequence identity to SEQ ID NO: 22 (corresponding to SEQ ID NO: 2 of WO 09/061380), wherein the polypeptide comprises a substitution, a deletion or an insertion in one of more of positions: 87, 98, 125, 128, 131, 165, 178, 180, 181, 182, 183, 201, 202, 225, 243, 272, 282, 305, 309, 319, 320, 359, 444 and/or 475;
(o) a polypeptide having at least about 90% sequence identity to SEQ ID NO: 21, wherein the polypeptide comprises a substitution, a deletion or an insertion in one of more of positions: 28, 118, 174; 181, 182, 183, 184, 186, 189, 195, 202, 298, 299, 302, 303, 306, 310, 314; 320, 324, 345, 396, 400, 439, 444, 445, 446, 449, 458, 471 and/or 484;
(p) a polypeptide having at least about 90% sequence identity to SEQ ID NO: 12;
(q) a polypeptide having at least about 90% sequence identity (e.g., at least about 95% or about 100% sequence identity) to a variant of SEQ ID NO:23 having alterations G182*+D183*;
(r) a polypeptide having at least about 90% sequence identity (e.g., at least about 95% or about 100% sequence identity) to a variant of SEQ ID NO:24 having alterations H183*+G184*+I405L+A421H+A422P+A428T;
(s) a polypeptide having at least about 90% sequence identity (e.g., at least about 95% or about 100% sequence identity) to a variant of SEQ ID NO:24 having alterations M9L+R118K+G149A+G182T+G186A+D183*+G184*+N195F+M202L+T257I+Y295F+N299Y+R320K+M323T+A339S+E345R+R458K;
(t) a polypeptide having at least about 90% sequence identity (e.g., at least about 95% or about 100% sequence identity) to a variant of SEQ ID NO: 24 having alterations R178*+G179*+E187P+I203Y+R458N+T459S+D460T+G476K
(u) a polypeptide having at least about 90% sequence identity (e.g., at least about 95% or about 100% sequence identity) to a variant of SEQ ID NO: 27 having alteration M202L;

(v) a polypeptide having at least about 90% sequence identity (e.g., at least about 95% or about 100% sequence identity) to a variant of SEQ ID NO: 28 having alterations R180*+S181*+S243Q+G475K;
(w) a polypeptide having at least about 90% sequence identity (e.g., at least about 95% or about 100% sequence identity) to a variant of SEQ ID NO: 29 having alterations D183*+G184*+W140Y+N195F+I206Y+Y243F+E260G+ G304R+G476K;
(x) a polypeptide having at least about 90% sequence identity (e.g., at least about 95% or about 100% sequence identity) to a variant of SEQ ID NO: 30 having alterations H1*+N54S+V56T+K72R+G109A+F113Q+R116Q+ W167F+Q172G+A174S+G184T+N195F+V206L+K391A+ P473R+G476K;
(y) a polypeptide having at least about 90% sequence identity (e.g., at least about 95% or about 100% sequence identity) to a variant of SEQ ID NO: 31 having alterations M9L+R118K+G149A+G182T+G186A+D183*+G184*+ N195F+T246V+T257I+Y295F+N299Y+R320K+M323T+ A339S+E345R+R458K.

In another embodiment, a cleaning or detergent composition of the present disclosure wherein said cleaning or detergent composition is a dish washing composition, said composition comprises a beta-glucanase polypeptide and one or more proteases, wherein said protease is selected from the group of:
a) a polypeptide having protease activity, which has at least about 60% sequence identity (e.g., at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% sequence identity) to SEQ ID NO: 34;
b) a polypeptide having protease activity, which has at least about 60% sequence identity (e.g., at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% sequence identity) to SEQ ID NO: 35;
c) a polypeptide having protease activity, which has at least about 60% sequence identity (e.g., at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% sequence identity) to SEQ ID NO: 36.

In another embodiment, the present disclosure relates to polypeptide(s) having beta-glucanase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence selected from the group of: SEQ ID NO: 1, SEQ ID NO: 4, SEQ ID NO: 6, SEQ ID NO: 8, (ii) the cDNA sequence thereof, or (iii) the full-length complement of (i) or (ii) (In an embodiment, the polypeptide has been isolated. An embodiment of the present disclosure is a composition (e.g. a cleaning or detergent composition) wherein said cleaning or detergent composition is a dish washing composition, said composition comprising said beta-glucanase polypeptide and one or more amylases (and/or one or more proteases).

The polynucleotide of sequence selected from the group of: SEQ ID NO: 1, SEQ ID NO: 4, SEQ ID NO: 6, SEQ ID NO: 8 or a subsequence thereof, as well as the polypeptide of sequence selected from the group of: SEQ ID NO: 2, SEQ ID NO: 3, SEQ ID NO: 5, SEQ ID NO: 7, SEQ ID NO: 9 or a fragment thereof may be used to design nucleic acid probes to identify and clone DNA encoding polypeptides having beta-glucanase activity from strains of different genera or species according to methods well known in the art. An embodiment of the present disclosure is a composition (e.g. a cleaning or detergent composition) comprising said beta-glucanase polypeptide and one or more amylases (and/or one or more proteases). In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least about 15, e.g., at least about 25, at least about 35, or at least about 70 nucleotides in length. Preferably, the nucleic acid probe is at least about 100 nucleotides in length, e.g., at least about 200 nucleotides, at least about 300 nucleotides, at least about 400 nucleotides, at least about 500 nucleotides, at least about 600 nucleotides, at least about 700 nucleotides, at least about 800 nucleotides, or at least about 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present disclosure. An embodiment of the present disclosure is a composition (e.g. a cleaning or detergent composition) wherein said cleaning or detergent composition is a dish washing composition, said composition comprising said beta-glucanase polypeptide and one or more amylases (and/or one or more proteases).

A genomic DNA or cDNA library prepared from such other strains may be screened for DNA that hybridizes with the probes described above and encodes a polypeptide having beta-glucanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with sequence selected from the group of: SEQ ID NO: 1, SEQ ID NO: 4, SEQ ID NO: 6, SEQ ID NO: 8 or a subsequence thereof, the carrier material is used in a Southern blot. An embodiment of the present disclosure is a composition (e.g. a cleaning or detergent composition) wherein said cleaning or detergent composition is a dish washing composition, said composition comprising said beta-glucanase polypeptide and one or more amylases (and/or one or more proteases).

For purposes of the present disclosure, hybridization indicates that the polynucleotide hybridizes to a labeled nucleic acid probe corresponding to (i) sequence selected from the group of: SEQ ID NO: 1, SEQ ID NO: 4, SEQ ID NO: 6, SEQ ID NO: 8; (ii) the mature polypeptide coding sequence selected from the group of: SEQ ID NO: 1, SEQ ID NO: 4, SEQ ID NO: 6, SEQ ID NO: 8; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection techniques known in the art. An embodiment of the present disclosure is a composition (e.g. a cleaning or detergent composition) wherein said cleaning or detergent composition is a dish washing composition, said composition comprising said beta-glucanase polypeptide and one or more amylases (and/or one or more proteases).

In one aspect, the nucleic acid probe is nucleotides 85 to 1137 or nucleotides 1 to 1137 of SEQ ID NO: 1. In one aspect, the nucleic acid probe is nucleotides 1 to 828 or nucleotides 94 to 828 of SEQ ID NO: 4. In one aspect, the nucleic acid probe is nucleotides 1 to 711 or nucleotides 46 to 711 of SEQ ID NO: 6. In one aspect, the nucleic acid probe is nucleotides 1 to 729 or nucleotides 88 to 729 of SEQ ID NO: 8. An embodiment of the present disclosure is a composition (e.g. a cleaning or detergent composition) wherein said cleaning or detergent composition is a dish washing composition, said composition comprising said beta-glucanase polypeptide and one or more amylases (and/or one or more proteases).

In another aspect, the nucleic acid probe is a polynucleotide that encodes the polypeptide of sequence selected from the group of: SEQ ID NO: 2, SEQ ID NO: 3, SEQ ID NO: 5, SEQ ID NO: 7, SEQ ID NO: 9; the mature polypeptide thereof; or a fragment thereof. An embodiment of the present disclosure is a composition (e.g. a cleaning or detergent composition) wherein said cleaning or detergent composition is a dish washing composition, said composition comprising said beta-glucanase polypeptide and one or more amylases (and/or one or more proteases).

In another aspect, the nucleic acid probe is a sequence selected from the group of: SEQ ID NO: 1, SEQ ID NO: 4, SEQ ID NO: 6, SEQ ID NO: 8. An embodiment of the present disclosure is a composition (e.g. a cleaning or detergent composition) wherein said cleaning or detergent composition is a dish washing composition, said composition comprising said beta-glucanase polypeptide and one or more amylases (and/or one or more proteases).

In another embodiment, the present disclosure relates to an polypeptide having beta-glucanase activity encoded by a polynucleotide having a sequence identity to the mature polypeptide coding sequence of the sequence selected from the group of: SEQ ID NO: 2, SEQ ID NO: 3, SEQ ID NO: 5, SEQ ID NO: 7, SEQ ID NO: 9 of at least about 60%, e.g., at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%. An embodiment of the present disclosure is a composition (e.g. a cleaning or detergent composition) wherein said cleaning or detergent composition is a dish washing composition, said composition comprising said beta-glucanase polypeptide and one or more amylases (and/or one or more proteases). In a further embodiment, the polypeptide has been isolated.

In another embodiment, the present disclosure relates to variants of the mature polypeptide of sequence selected from the group of: SEQ ID NO: 2, SEQ ID NO: 3, SEQ ID NO: 5, SEQ ID NO: 7, SEQ ID NO: 9 comprising a substitution, deletion, and/or insertion at one or more (e.g., several) positions. An embodiment of the present disclosure is a composition (e.g. a cleaning or detergent composition) comprising said beta-glucanase polypeptide and one or more amylases (and/or one or more proteases). In an embodiment, the number of amino acid substitutions, deletions and/or insertions introduced into the mature polypeptide of sequence selected from the group of: SEQ ID NO: 2, SEQ ID NO: 3, SEQ ID NO: 5, SEQ ID NO: 7, SEQ ID NO: 9 is up to about 10, e.g., 1, 2, 3, 4, 5, 6, 7, 8, 9, or 10.

An embodiment of the present disclosure is a composition (e.g. a cleaning or detergent composition) comprising said beta-glucanase polypeptide and one or more amylases (and/or one or more proteases). The amino acid changes may be of a minor nature, that is conservative amino acid substitutions or insertions that do not significantly affect the folding and/or activity of the protein; small deletions, typically of from about 1 to about 30 amino acids; small amino- or carboxyl-terminal extensions, such as an amino-terminal methionine residue; a small linker peptide of up to from about 20 to about 25 residues; or a small extension that facilitates purification by changing net charge or another function, such as a poly-histidine tract, an antigenic epitope or a binding domain. An embodiment of the present disclosure is a composition (e.g. a cleaning or detergent composition) wherein said cleaning or detergent composition is a dish washing composition, said composition comprising said beta-glucanase polypeptide and one or more amylases (and/or one or more proteases).

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis. In the latter technique, single alanine mutations are introduced at every residue in the molecule, and the resultant molecules are tested for beta-glucanase activity to identify amino acid residues that are critical to the activity of the molecule. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed in WO 95/17413; or WO 95/22625. Other methods that can be used include error-prone PCR, phage display (e.g., U.S. Pat. No. 5,223,409; WO 92/06204), and region-directed mutagenesis ( ).

Mutagenesis/shuffling methods can be combined with high-throughput, automated screening methods to detect activity of cloned, mutagenized polypeptides expressed by host cells ( ). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present disclosure. A fusion polypeptide is produced by fusing a polynucleotide encoding another polypeptide to a polynucleotide of the present disclosure. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally ( ).

A fusion polypeptide can further comprise a cleavage site between the two polypeptides. Upon secretion of the fusion protein, the site is cleaved releasing the two polypeptides.
Sources of Polypeptides Having Beta-Glucanase Activity A polypeptide having beta-glucanase activity of the present disclosure may be obtained from microorganisms of any genus (e.g. genus *Bacillus*). For purposes of the present disclosure, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a Gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* polypeptide having beta-glucanase activity, or a Gram-negative bacterial polypeptide such as a *Campylobacter, E. coli, Flavobacterium, Fusobacterium, Helicobacter, Ilyobacter, Neisseria, Pseudomonas, Salmonella,* or *Ureaplasma* polypeptide.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, Bacillus* sp., *Bacillus* akibai, *Bacillus agaradhaerens, Bacillus mojavensis* or *Bacillus thuringiensis* polypeptide.

In another aspect, the polypeptide is not a fungal polypeptide (e.g. a polypeptide of the present disclosure excludes fungal polypeptides). An embodiment of the present disclosure is a composition (e.g. a cleaning or detergent composition) comprising said beta-glucanase polypeptide and one or more amylases (and/or one or more proteases).

It will be understood that for the aforementioned species, the present disclosure encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art.

In preferred embodiments a polypeptide of the present disclosure is a bacterial polypeptide (preferably isolated from a bacterium/bacteria from genus *Bacillus*). In further preferred embodiments a polypeptide of the present disclosure belongs to Glycoside Hydrolase Family 16 (GH16) (e.g. has Glycoside hydrolases (EC 3.2.1.-) activity). For example, the polypeptide may be a polypeptide having beta-glucanase activity from within a genus *Bacillus*, e.g. from *Bacillus* sp-62449, *Bacillus* akibai, *Bacillus agaradhaerens, Bacillus mojavensis*. An embodiment of the present disclosure is a composition (e.g. a cleaning or detergent composition) comprising said beta-glucanase polypeptide and one or more amylases (and/or one or more proteases).
Catalytic Domains In one embodiment, the present disclosure also relates to cleaning or detergent compositions, wherein said cleaning or detergent composition is a dish washing composition, said composition comprising catalytic domains having a sequence identity to amino acids from about 33 to about 249 of SEQ ID NO: 2 of at least about 60%, e.g., at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%. In one aspect, the catalytic domains comprise amino acid sequences that differ by up to about 10 amino acids, e.g., 1, 2, 3, 4, 5, 6, 7, 8, 9, or 10, from amino acids from about 33 to about 249 of SEQ ID NO: 2. The catalytic domain preferably comprises or of amino acids from about 33 to about 249 of SEQ ID NO: 2 or an allelic variant thereof; or is a fragment thereof having beta-glucanase activity. An embodiment of the present disclosure is a cleaning or detergent compositions, wherein said cleaning or detergent composition is a dish washing composition, said composition comprising said beta-glucanase polypeptide and one or more amylases (and/or one or more proteases).

In one embodiment, the present disclosure also relates to catalytic domains having a sequence identity to amino acids from about 62 to about 245 of SEQ ID NO: 2 of at least about 60%, e.g., at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%. In one aspect, the catalytic domains comprise amino acid sequences that differ by up to about 10 amino acids, e.g., 1, 2, 3, 4, 5, 6, 7, 8, 9, or 10, from amino acids 62 to 245 of SEQ ID NO: 2. The catalytic domain preferably comprises or of amino acids 62 to 245 of SEQ ID NO: 2 or an allelic variant thereof; or is a fragment thereof having beta-glucanase activity. An embodiment of the present disclosure is a cleaning or detergent compositions, wherein said cleaning or detergent composition is a dish washing composition, said composition comprising said beta-glucanase polypeptide and one or more amylases (and/or one or more proteases).

In one embodiment, the present disclosure also relates to catalytic domains having a sequence identity to amino acids 33 to 249 of SEQ ID NO: 3 of at least about 60%, e.g., at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%. In one aspect, the catalytic domains comprise amino acid sequences that differ by up to about 10 amino acids, e.g., 1, 2, 3, 4, 5, 6, 7, 8, 9, or 10, from amino acids from about 33 to about 249 of SEQ ID NO: 3. The catalytic domain preferably comprises or of amino acids from about 33 to about 249 of SEQ ID NO: 3 or an allelic variant thereof; or is a fragment thereof having beta-glucanase activity. An embodiment of the present disclosure is a cleaning or detergent compositions, wherein said cleaning or detergent composition is a dish washing composition, said composition comprising said beta-glucanase polypeptide and one or more amylases (and/or one or more proteases).

In one embodiment, the present disclosure also relates to catalytic domains having a sequence identity to amino acids from about 62 to about 245 of SEQ ID NO: 3 of at least about 60%, e.g., at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%. In one aspect, the catalytic domains comprise amino acid sequences that differ by up to about 10 amino acids, e.g., 1, 2, 3, 4, 5, 6, 7, 8, 9, or 10, from amino acids 62 to 245 of SEQ ID NO: 3. The catalytic domain preferably comprises or of amino acids 62 to 245 of SEQ ID NO: 3 or an allelic variant thereof; or is a fragment thereof having beta-glucanase activity. An embodiment of the present disclosure is a cleaning or detergent compositions, wherein said cleaning or detergent composition is a dish washing composition, said composition comprising said beta-glucanase polypeptide and one or more amylases (and/or one or more proteases).

In one embodiment, the present disclosure also relates to catalytic domains having a sequence identity to amino acids 32 to 254 of SEQ ID NO: 5 of at least about 60%, e.g., at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%. In one aspect, the catalytic domains comprise amino acid sequences that differ by up to about 10 amino acids, e.g., 1, 2, 3, 4, 5, 6, 7, 8, 9, or 10, from amino acids 32 to 254 of SEQ ID NO: 5. The catalytic domain preferably comprises or of amino acids from about 32 to about 254 of SEQ ID NO: 5 or an allelic variant thereof; or is a fragment thereof having beta-glucanase activity. An embodiment of the present disclosure is a cleaning or detergent compositions, wherein said cleaning or detergent composition is a dish washing composition, said composition comprising said beta-glucanase polypeptide and one or more amylases (and/or one or more proteases).

In one embodiment, the present disclosure also relates to catalytic domains having a sequence identity to amino acids from about 60 to about 249 of SEQ ID NO: 5 of at least about 60%, e.g., at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%. In one aspect, the catalytic domains comprise amino acid sequences that differ by up to about 10 amino acids, e.g., 1, 2, 3, 4, 5, 6, 7, 8, 9, or 10, from amino acids from about 60 to about 249 of SEQ ID NO: 5. The catalytic domain preferably comprises or of amino acids 60 to 249 of SEQ ID NO: 5 or an allelic variant thereof; or is a fragment thereof having beta-glucanase activity. An embodiment of the present disclosure is a cleaning or detergent compositions, wherein said cleaning or detergent composition is a dish washing composition, said composition comprising said beta-glucanase polypeptide and one or more amylases (and/or one or more proteases).

In one embodiment, the present disclosure also relates to catalytic domains having a sequence identity to amino acids from about 20 to about 236 of SEQ ID NO: 7 of at least about 60%, e.g., at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%. An embodiment of the present disclosure is a composition (e.g. a cleaning or detergent composition) comprising said beta-glucanase polypeptide and one or more amylases (and/or one or more proteases). In one aspect, the catalytic domains comprise amino acid sequences that differ by up to about 10 amino acids, e.g., 1, 2, 3, 4, 5, 6, 7, 8, 9, or 10, from amino acids 20 to 236 of SEQ ID NO: 7. The catalytic domain preferably comprises or of amino acids 20 to 236 of SEQ ID NO: 7 or an allelic variant thereof; or is a fragment thereof having beta-glucanase activity. An embodiment of the present disclosure is a cleaning or detergent compositions, wherein said cleaning or detergent composition is a dish washing composition, said composition comprising said beta-glucanase polypeptide and one or more amylases (and/or one or more proteases).

In one embodiment, the present disclosure also relates to catalytic domains having a sequence identity to amino acids 49 to 230 of SEQ ID NO: 7 of at least about 60%, e.g., at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%. An embodiment of the present disclosure is a cleaning or detergent compositions, wherein said cleaning or detergent composition is a dish washing composition, said composition comprising said beta-glucanase polypeptide and one or more amylases (and/or one or more proteases). In one aspect, the catalytic domains comprise amino acid sequences that differ by up to about 10 amino acids, e.g., 1, 2, 3, 4, 5, 6, 7, 8, 9, or 10, from amino acids 49 to 230 of SEQ ID NO: 7. The catalytic domain preferably comprises or of amino acids 49 to 230 of SEQ ID NO: 7 or an allelic variant thereof; or is a fragment thereof having beta-glucanase activity. An embodiment of the present disclosure is a cleaning or detergent compositions, wherein said cleaning or detergent composition is a dish washing composition, said composition comprising said beta-glucanase polypeptide and one or more amylases (and/or one or more proteases).

In one embodiment, the present disclosure also relates to catalytic domains having a sequence identity to amino acids 30 to 243 of SEQ ID NO: 9 of at least about 60%, e.g., at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%. An embodiment of the present disclosure is a composition (e.g. a cleaning or detergent composition) comprising said beta-glucanase polypeptide and one or more amylases (and/or one or more proteases). In one aspect, the catalytic domains comprise amino acid sequences that differ by up to about 10 amino acids, e.g., 1, 2, 3, 4, 5, 6, 7, 8, 9, or 10, from amino acids 30 to 243 of SEQ ID NO: 9. The catalytic domain preferably comprises or of amino acids 30 to 243 of SEQ ID NO: 9 or an allelic variant thereof; or is a fragment thereof having beta-glucanase activity. An embodiment of the present disclosure is a cleaning or detergent compositions, wherein said cleaning or detergent composition is a dish washing composition, said composition comprising said beta-glucanase polypeptide and one or more amylases (and/or one or more proteases).

In one embodiment, the present disclosure also relates to catalytic domains having a sequence identity to amino acids 55 to 239 of SEQ ID NO: 9 of at least about 60%, e.g., at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%. An embodiment of the present disclosure is a cleaning or detergent compositions, wherein said cleaning or detergent composition is a dish washing composition, said composition comprising said beta-glucanase polypeptide and one or more amylases (and/or one or more proteases). In one aspect, the catalytic domains comprise amino acid sequences that differ by up to about 10 amino acids, e.g., 1, 2, 3, 4, 5, 6, 7, 8, 9, or 10, from amino acids 55 to 239 of SEQ ID NO: 9. The catalytic domain preferably comprises or of amino acids 55 to 239 of SEQ ID NO: 9 or an allelic variant thereof; or is a fragment thereof having beta-glucanase activity. An embodiment of the present disclosure is a cleaning or detergent compositions, wherein said cleaning or detergent composition is a dish washing composition, said composition comprising said beta-glucanase polypeptide and one or more amylases (and/or one or more proteases).

Binding Domains

The GH16 beta-glucanase of the present disclosure may comprise a carbohydrate binding module (or CBM). In one embodiment a CBM is in amino acids 264-377 of SEQ ID NO: 2. An embodiment of the present disclosure is a composition (e.g. a cleaning or detergent composition) comprising said beta-glucanase polypeptide and one or more amylases (and/or one or more proteases). In another embodiment a CBM is in amino acids 264-377 of SEQ ID NO: 3. An embodiment of the present disclosure is a cleaning or detergent compositions, wherein said cleaning or detergent composition is a dish washing composition, said composition comprising said beta-glucanase polypeptide and one or more amylases (and/or one or more proteases).

In one embodiment, the present disclosure also relates to carbohydrate binding module having a sequence identity to amino acids 264 to 377 of SEQ ID NO: 2 of at least about 60%, e.g., at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%. An embodiment of the present disclosure is a cleaning or detergent compositions, wherein said cleaning or detergent composition is a dish washing composition, said composition comprising said beta-glucanase polypeptide and one or more amylases (and/or one or more proteases). In one aspect, the carbohydrate binding module comprise amino acid sequences that differ by up to about 10 amino acids, e.g., 1, 2, 3, 4, 5, 6, 7, 8, 9, or 10, from amino acids 264 to 377 of SEQ ID NO: 2. An embodiment of the present disclosure is cleaning or detergent compositions, wherein said cleaning or detergent composition is a dish washing composition, said composition comprising said beta-glucanase polypeptide and one or more amylases (and/or one or more proteases).

In one embodiment, the present disclosure also relates to carbohydrate binding module having a sequence identity to amino acids 264 to 377 of SEQ ID NO: 3 of at least about 60%, e.g., at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%. An embodiment of the present disclosure is a cleaning or detergent compositions, wherein said cleaning or detergent composition is a dish washing composition, said composition comprising said beta-glucanase polypeptide and one or more amylases (and/or one or more proteases). In one aspect, the carbohydrate binding module comprise amino acid sequences that differ by up to about 10 amino acids, e.g., 1, 2, 3, 4, 5, 6, 7, 8, 9, or 10, from amino acids 264 to 377 of SEQ ID NO: 3. An embodiment of the present disclosure is a cleaning or detergent compositions, wherein said cleaning or detergent composition is a dish washing composition, said composition comprising said beta-glucanase polypeptide and one or more amylases (and/or one or more proteases).

The carbohydrate binding module preferably comprises or of amino acids 264 to 377 of SEQ ID NO: 2 or an allelic variant thereof; or is a fragment thereof having carbohydrate binding activity. An embodiment of the present disclosure is a cleaning or detergent compositions, wherein said cleaning or detergent composition is a dish washing composition, said composition comprising said beta-glucanase polypeptide and one or more amylases (and/or one or more proteases). The carbohydrate binding module preferably comprises or of amino acids 264 to 377 of SEQ ID NO: 3 or an allelic variant thereof; or is a fragment thereof having carbohydrate binding activity. An embodiment of the present disclosure is a cleaning or detergent compositions, wherein said cleaning or detergent composition is a dish washing composition, said composition comprising said beta-glucanase polypeptide and one or more amylases (and/or one or more proteases).

In another embodiment, the present disclosure also relates to carbohydrate binding module variants of amino acids 264 to 377 of SEQ ID NO: 2 (or SEQ ID NO: 3) comprising a substitution, deletion, and/or insertion at one or more (e.g., several) positions. In one aspect, the number of amino acid substitutions, deletions and/or insertions introduced into the sequence of amino acids 264 to 377 of SEQ ID NO: 2 (or SEQ ID NO: 3) is up to about 10, e.g., 1, 2, 3, 4, 5, 6, 8, 9, or 10. An embodiment of the present disclosure is a cleaning or detergent compositions, wherein said cleaning or detergent composition is a dish washing composition, said composition comprising said beta-glucanase polypeptide and one or more amylases (and/or one or more proteases).

A carbohydrate binding module of the present disclosure may be applied in a fusion protein comprising at least one carbohydrate binding module operably linked to a catalytic domain. The catalytic domain may be from a hydrolase, isomerase, ligase, lyase, oxidoreductase, or transferase, aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase. The polynucleotide encoding the catalytic domain may be obtained from any prokaryotic, eukaryotic, or other source.

Polynucleotides

The present disclosure also relates to polynucleotides encoding a polypeptide, a catalytic domain, or carbohydrate binding module of the present disclosure, as described herein. In an embodiment, the polynucleotide encoding the polypeptide, catalytic domain, or carbohydrate binding module of the present disclosure has been isolated.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. Other nucleic acid amplification procedures such as ligase chain reaction (LCR), ligation activated transcription (LAT) and polynucleotide-based amplification (NASBA) may be used. The polynucleotides may be cloned from a strain of *Bacillus*, or a related organism and thus, for example, may be an allelic or species variant of the polypeptide encoding region of the polynucleotide.

Modification of a polynucleotide encoding a polypeptide of the present disclosure may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of sequence selected from the group of: SEQ ID NO: 1, SEQ ID NO: 4, SEQ ID NO: 6, SEQ ID NO: 8 or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence.

Compositions

The present disclosure also relates to cleaning or detergent compositions, wherein said cleaning or detergent composition is a dish washing composition, said composition comprising polypeptide(s) of the present disclosure. An embodiment is a cleaning or detergent composition, wherein said composition is a dishwashing composition, said composition comprising a beta-glucanase polypeptide of the present disclosure and one or more amylases (and/or one or more proteases). Preferably, the compositions are enriched in such a polypeptide. The term "enriched" indicates that the beta-glucanase activity of the composition has been increased, e.g., with an enrichment factor of at least about 1.1.

The compositions may comprise polypeptide(s) of the present disclosure as the major enzymatic component, e.g., a mono-component composition. Alternatively, the compositions may comprise multiple enzymatic activities, such as one or more (e.g., several) enzymes selected from the group of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase. An embodiment is a cleaning or detergent compositions, wherein said cleaning or detergent composition is a dish washing composition, said composition comprising a beta-glucanase polypeptide of the present disclosure and one or more amylases (and/or one or more proteases).

The compositions may be prepared in accordance with methods known in the art and may be in the form of a liquid or a dry composition. The compositions may be stabilized in accordance with methods known in the art. An embodiment is a cleaning or detergent compositions, wherein said cleaning or detergent composition is a dish washing composition, said composition comprising a beta-glucanase polypeptide of the present disclosure and one or more amylases (and/or one or more proteases).

Examples are given below of preferred uses of the compositions of the present disclosure. The dosage of the composition and other conditions under which the composition is used may be determined on the basis of methods known in the art.

Uses

The beta-glucanases of the present disclosure may be used in applications where beta-glucan (e.g. beta-D-glucan, beta-1,3-1,4 glucan, mix-linkage beta-glucan, barley beta-glucan, oatmeal beta-glucan) needs to be degraded (e.g. under alkaline conditions). An embodiment is a cleaning or detergent composition comprising a beta-glucanase polypeptide of the present disclosure and one or more amylases (and/or one or more proteases). Examples of where beta-glucanases could be used include detergent applications, paper and pulp productions. In one aspect, beta-glucanases of the present disclosure may be used for cleaning dish ware, dish wash including Automatic Dish Wash (ADW) especially household automatic dish wash, Hand Dish Wash (HDW), and/or in a cleaning process such as dish wash including Automatic Dish Wash (ADW), especially household automatic dish wash, and industrial dish cleaning, dish wash including Automatic Dish Wash (ADW), and/or for at least one of the following: preventing, reducing or removing a biofilm and/or malodor from an item, and/or for anti-redeposition. An embodiment is a cleaning or detergent compositions, wherein said cleaning or detergent composition is a dish washing composition, said composition comprising a beta-glucanase polypeptide of the present disclosure and one or more amylases (and/or one or more proteases).

Such beta-glucanases preferably have at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% sequence identity to the mature polypeptide of the sequence selected from the group of: SEQ ID NO: 7, SEQ ID NO: 2, SEQ ID NO: 3, SEQ ID NO: 5, SEQ ID NO: 9. An embodiment of the present disclosure is a cleaning or detergent compositions, wherein said cleaning or detergent composition is a dish washing composition, said composition comprising said beta-glucanase polypeptide and one or more amylases (and/or one or more proteases).

Biofilm can develop when microorganisms are present on an item and stick together on the item. Some microorganisms tend to adhere to the surface of items such as textiles. Some microorganisms adhere to such surfaces and form a biofilm on the surface. The biofilm may be sticky and the adhered microorganisms and/or the biofilm may be difficult to remove. Furthermore the biofilm adhere soil due to the sticky nature of the biofilm.

The present disclosure concerns the use of polypeptide(s) having beta-glucanase activity for preventing, reducing or removing a biofilm from an item, wherein the polypeptide is obtained from a bacterial source and wherein the item is dishware. An embodiment is a cleaning or detergent compositions, wherein said cleaning or detergent composition is a dish washing composition, said composition comprising a beta-glucanase polypeptide of the present disclosure and one or more amylases (and/or one or more proteases). In one embodiment as contemplated herein the polypeptide having beta-glucanase activity is used for preventing, reducing or removing the stickiness of an item. An embodiment is a cleaning or detergent compositions, wherein said cleaning or detergent composition is a dish washing composition, said composition comprising a beta-glucanase polypeptide of the present disclosure and one or more amylases (and/or one or more proteases).

The present disclosure also relates to cleaning or detergent compositions, wherein said cleaning or detergent composition is a dish washing composition, said composition comprising a beta-glucanase of the present disclosure (e.g., polypeptide(s) of the present disclosure). The present disclosure also relates to said compositions comprising a beta-glucanase of the present disclosure (e.g., polypeptide(s) of the present disclosure) and one or more additional enzymes. The present disclosure also relates to cleaning or detergent compositions, wherein said cleaning or detergent composition is a dish washing composition, said composition comprising a beta-glucanase of the present disclosure (e.g., polypeptide(s) of the present disclosure) and one or more amylases (and/or one or more proteases), preferably said one or more amylases is one or more alpha-amylases. An embodiment is a cleaning or detergent composition wherein said composition is a dishwashing composition, said composition comprising a beta-glucanase polypeptide of the present disclosure and one or more amylases (and/or one or more proteases).

In one embodiment, the present disclosure relates to cleaning or detergent compositions, wherein said cleaning or detergent composition is a dish washing composition, said composition comprising a beta-glucanase of the present disclosure and a suitable surfactant. An embodiment is a cleaning or detergent compositions, wherein said cleaning or detergent composition is a dish washing composition, said composition comprising a beta-glucanase polypeptide of the present disclosure and one or more amylases (and/or one or more proteases).

The present disclosure also relates to cleaning or detergent compositions, wherein said cleaning or detergent composition is a dish washing composition, said composition comprising an isolated polypeptide having beta-glucanase activity selected from the group of: a) a polypeptide having at least about 75% sequence identity, at least about 80% sequence identity, at least about 81% sequence identity, at least about 82% sequence identity, at least about 83% sequence identity, at least about 84% sequence identity, at least about 85% sequence identity, at least about 86% sequence identity, at least about 87% sequence identity, at least about 88% sequence identity, at least about 89% sequence identity, at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, at least about 99% sequence identity or even about 100% sequence identity to the mature polypeptide of the sequence selected from the group of: SEQ ID NO: 2, SEQ ID NO: 3, SEQ ID NO: 5, SEQ ID NO: 7, SEQ ID NO: 9; b) a polypeptide encoded by a polynucleotide that hybridizes under medium stringency conditions with (i) the mature polypeptide coding sequence of the sequence selected from the group of: SEQ ID NO: 1, SEQ ID NO: 4, SEQ ID NO: 6, SEQ ID NO: 8 or (ii) the full-length complementary strand of (i); c) a polypeptide encoded by a polynucleotide having at least about 75% sequence identity, at least about 80% sequence identity, at least about 81% sequence identity, at least about 82% sequence identity, at least about 83% sequence identity, at least about 84% sequence identity, at least about 85% sequence identity, at least about 86% sequence identity, at least about 87% sequence identity, at least about 88% sequence identity, at least about 89% sequence identity, at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, at least about 99% sequence identity or even about 100% sequence identity to the mature polypeptide coding sequence of the sequence selected from the group of: SEQ ID NO: 1, SEQ ID NO: 4, SEQ ID NO: 6, SEQ ID NO: 8; e) a variant comprising a substitution, deletion, and/or insertion of one or more (e.g. several) amino acids of the mature polypeptide of the sequence selected from the group of: SEQ ID NO: 2, SEQ ID NO: 3, SEQ ID NO: 5, SEQ ID NO: 7, SEQ ID NO: 9; and f) a fragment of a polypeptide of (a), (b), (c), or (d) that has beta-glucanase activity. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the cleaning or detergent compositions, wherein said cleaning or detergent composition is a dish washing composition, said composition of the present disclosure comprises an isolated polypeptide having beta-glucanase activity and having at least about 60% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 75% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 81% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 82% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 83% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 84% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 85% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 86% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 87% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 88% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 89% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 90% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 91% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 92% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 93% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 94% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 95% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 96% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 97% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 98% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 99% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment the compositions of the present disclosure comprises an isolated polypeptide having beta-glucanase activity and having at least about 100% sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

In one embodiment, the detergent composition may be adapted for specific uses such as dish washing.

In another embodiment a composition of the present disclosure is a cleaning or a detergent composition. An embodiment is a cleaning or detergent compositions, wherein said cleaning or detergent composition is a dish washing composition, said composition a beta-glucanase polypeptide of the present disclosure and one or more amylases (and/or one or more proteases).

Alkaline Liquid detergents having high pH are widely used in cleaning, such dish wash cleaning. Liquid detergents with elevated pH are especially commonly used by consumers in North America. The high pH cleaning compositions are also used in industrial cleaning processes. Alkaline detergents include liquids having detergent properties. The pH of such detergents usually ranges in pH from about 9 to about 12.5. The high pH detergents typically comprise components such as surfactants, builders and bleach components and additionally they may also contain a significant amount of water and alkalis such as NaOH, TSP (Trisodium phosphate), ammonia, Sodium carbonate, Potassium hydroxide (KOH) these alkalis are usually added in amount corresponding to from about 0.1 to about 30 percent weight (wt). Adding enzymes to detergents is highly advantageous as the specific activities of these enzymes effectively removes specific stains from surfaces such as dishes and cutlery. However, the difficulty of maintaining acceptable enzyme stability in the high pH liquid detergents has for many years prohibited inclusion of enzymes into these detergents. In another embodiment the present disclosure relates high pH liquid cleaning compositions comprising an alkaline stable beta-glucanase of the present disclosure suitable for use in such compositions.

In another embodiment a composition of the present disclosure preferably contains alkaline buffer system to provide a pH of at least about 7.5, at least about 8, at least about 9, preferably pH of about 10 or above. Preferably the pH is from about 9 to about 13. In order to achieve the high pH it is necessary to have present an alkali metal hydroxide especially sodium or potassium hydroxide, normally in an amount of from about 0.1 to about 30% by weight (percentage by weight, abbreviated wt %) of the composition, and preferably from about 1.0 to about 2.5%, or higher amounts of a suitable alkali metal silicate such as metal silicate, according to the desired pH for the product.

In another embodiment a composition of the present disclosure has pH of about 6.5 or above, preferably pH of about 7.0 or above, more preferably pH of about 7.5 or above, and optionally comprises a bleaching agent; preferably said pH is selected in the range from about 7.5 to about 13.5, further preferably said pH is selected in the range from about 7.5 to about 12.5, most preferably said pH is selected in the range from about 8.5 to about 11.5. In a preferred embodiment, dish washing compositions with such preferred pH-ranges are solid.

In another embodiment a dish washing composition of the present disclosure more preferably a automatic dish washing or hand dish washing composition in form of a liquid or a gel, has a pH of about 6.5 or above; preferably said pH is selected in the range from about 6.5 to about 9.5, more preferably from about 7.0 to about 9.0, more preferably from about 7.5 to about 8.5.

In another embodiment the present disclosure relates to a liquid cleaning composition having pH of about 6.5 or above, pH of about 6.5 or above, preferably pH of about 7.5 or above, comprising at least about 0.001 wt % beta-glucanase, (e.g. at least about 0.01 wt % beta-glucanase), wherein said beta-glucanase has an amino acid sequence which has at least about 81% sequence identity to the mature polypeptide of the sequence selected from the group of: SEQ ID NO: 2, SEQ ID NO: 3, SEQ ID NO: 5, SEQ ID NO: 7, SEQ ID NO: 9. In further related embodiments beta-glucanase has an amino acid sequence which has at least about 82% (or at least about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98% or about 99% or about 100%) sequence identity to the mature polypeptide of the sequence selected from the group of: SEQ ID NO: 2, SEQ ID NO: 3, SEQ ID NO: 5, SEQ ID NO: 7, SEQ ID NO: 9. An embodiment is a cleaning or detergent compositions, wherein said cleaning or detergent composition is a dish washing composition, said composition comprising a beta-glucanase polypeptide of the present disclosure and one or more amylases (and/or one or more proteases).

The cleaning or detergent compositions of the present disclosure, especially the dish washing compositions, are formulated for hand or machine dishwashing operations, especially in household dishwashing machines, preferably for cleaning purposes added in the main wash or with the rinse aid. It can also be used to clean the parts of the dishwasher interior during dish washing process, especially the hidden parts, like the water pipelines inside the machine, especially these in the rotatable arms, and the sieve/filter. The detergent compositions of the present disclosure may find use in automatic dishwashing applications. An embodiment is a cleaning or detergent composition wherein said cleaning or detergent composition is a dish washing composition, said composition comprising a beta-glucanase polypeptide of the present disclosure and one or more amylases (and/or one or more proteases).

The detergent composition of the present disclosure may be in any convenient form, e.g., a bar, a tablet, a powder, a granule, a paste or a liquid. A liquid detergent may be aqueous, typically containing up to about 70% water and from about 0 to about 30% organic solvent, or non-aqueous. An embodiment is a cleaning or detergent composition wherein said composition is a dishwashing composition, said composition comprising a beta-glucanase polypeptide of the present disclosure and one or more amylases (and/or one or more proteases).

Unless otherwise noted, all component or composition levels provided herein are made in reference to the active level of that component or composition, and are exclusive of impurities, for example, residual solvents or by-products, which may be present in commercially available sources. An embodiment is a cleaning or detergent compositions, wherein said cleaning or detergent composition is a dish washing composition, said composition comprising a beta-glucanase polypeptide of the present disclosure and one or more amylases (and/or one or more proteases).

The beta-glucanase of the present disclosure is normally incorporated in the cleaning or detergent compositions, wherein said cleaning or detergent composition is a dish washing composition, at a level of from about 0.000001% to about 2% of enzyme protein by weight of the composition, preferably at a level of from about 0.00001% to about 1% of enzyme protein by weight of the composition, more preferably at a level of from about 0.0001% to about 0.75% of enzyme protein by weight of the composition, even more preferably at a level of from about 0.001% to about 0.5% of enzyme protein by weight of the composition. An embodiment is a cleaning or detergent composition wherein said cleaning or detergent composition is a dish washing composition, said composition comprising a beta-glucanase polypeptide of the present disclosure and one or more amylases (and/or one or more proteases).

Furthermore, the beta-glucanase of the present disclosure is normally incorporated in the cleaning or detergent compositions, wherein said cleaning or detergent composition is a dish washing composition, in such amounts that their concentration in the wash water is at a level of from about 0.0000001% to about 1% enzyme protein, preferably at a level of from about 0.000005% to about 0.01% of enzyme protein, more preferably at a level of from about 0.000001% to about 0.005% of enzyme protein, even more preferably at a level of from about 0.00001% to about 0.001% of enzyme protein in wash water. An embodiment is a cleaning or detergent composition comprising a beta-glucanase polypeptide of the present disclosure and one or more amylases (and/or one or more proteases).

As is well known, the amount of enzyme will also vary according to the particular application and/or as a result of the other components included in the compositions.

A composition for use in automatic dishwash (ADW), for example, may include from about 0.0001% to about 50%, from about 0.001% to about 50%, such as from about 0.01% to about 25%, such as from about 0.02% to about 20%, such as from about 0.1 to about 15% of enzyme protein by weight of the composition. An embodiment is a cleaning or detergent composition wherein said cleaning or detergent composition is a dish washing composition, said composition comprising a beta-glucanase polypeptide of the present disclosure and one or more amylases (and/or one or more proteases).

A preferred dish washing composition, preferably automatic dish washing composition comprises the polypeptide of the present disclosure in concentrations of from about 0.00001 mg enzyme protein/g composition to about 100 mg enzyme protein/g composition, preferred from about 0.0001 mg enzyme protein/g composition to about 50 mg enzyme protein/g composition, more preferred from about 0.001 mg enzyme protein/g composition to about 20 mg enzyme protein/g composition, especially preferred from about 0.01 mg enzyme protein/g composition to about 10 mg enzyme protein/g composition.

A preferred dish washing composition, preferably automatic dish washing composition, especially a composition formulated as unit dose product, comprises the polypeptide of the invention in amounts from about 0.01 mg/job to about 100 mg enzyme protein/job, preferred from about 0.1 mg enzyme protein/job to about 20 mg/job, more preferred from about 0.2 to about 10 mg enzyme protein/job, especially preferred from about 0.3 to about 5 mg enzyme protein/job. For example, amounts of about 0.5 mg, about 1 mg, about 1.5 mg, about 2 mg or about 2.5 mg enzyme protein/job can be used. The expression mg per job (mg/job) or mg/application refers to the amount of active substance used in relation to the total weight of the composition used for a complete cleaning cycle (which is to say in the case of automatic dishwashing agents, the total amount of the cleaning agent used in a complete cleaning cycle of a dishwasher). In the case of proportioned cleaning agents (preferably automatic dishwashing agents), this information is the amount of the active substance in mg based on the total weight of the proportioned cleaning composition.

Said amounts are also applicable for each of the other individual enzyme proteins (e.g. amylase or protease) used in the dishwashing composition of the present disclosure. In some preferred embodiments, the detergent compositions provided herein are typically formulated such that, during use in aqueous cleaning operations, the wash water has a pH of from about 5.0 to about 13.5, or in alternative embodiments, even from about 6.0 to about 10.5, such as from about 5 to about 11, from about 5 to about 10, from about 5 to about 9, from about 5 to about 8, from about 5 to about 7, from about 6 to about 11, from about 6 to about 10, from about 6 to about 9, from about 6 to about 8, from about 6 to about 7, from about 7 to about 11, from about 7 to about 10, from about 7 to about 9, or from about 7 to about 8. Preferably, the detergent compositions provided herein are typically formulated such that, during use in aqueous cleaning operations, the wash water has a pH selected in the range from about 7.5 to about 13.5, further preferably said pH is selected in the range from about 8.5 to about 11.5, most preferably said pH is selected in the range from about 9.5 to about 10.5; further most preferably pH of about 7.5 or above. An embodiment is a cleaning or detergent composition comprising a beta-glucanase polypeptide of the present disclosure and one or more amylases (and/or one or more proteases).

In one embodiment, the beta-glucanase in the compositions of the present disclosure has improved stability, in particular improved storage stability in a high pH liquid cleaning composition, compared to known beta-glucanases. In a preferred embodiment, the beta-glucanase of the present disclosure has improved stability, in particular improved storage stability, and on par or improved wash performance compared to the known beta-glucanases. An embodiment is a cleaning or detergent compositions, wherein said cleaning or detergent composition is a dish washing composition, said composition comprising a beta-glucanase polypeptide of the present disclosure and one or more amylases (and/or one or more proteases).

Techniques for controlling pH at recommended usage levels include the use of buffers, alkalis, acids, etc., and are well known to those skilled in the art. An embodiment is a cleaning or detergent composition comprising a beta-glucanase polypeptide of the present disclosure and one or more amylases (and/or one or more proteases).

Enzyme components weights are based on total protein. All percentages and ratios are calculated by weight unless otherwise indicated. All percentages and ratios are calculated based on the total composition unless otherwise indicated. In the exemplified detergent composition, the enzymes levels are expressed by pure enzyme by weight of the total composition and unless otherwise specified, the detergent ingredients are expressed by weight of the total composition.

The enzymes of the present disclosure also find use in dishwashing detergent additive products. A detergent additive product comprising a beta-glucanase of the present disclosure is suited for inclusion in a wash process when, e.g., temperature is low, such as at temperatures about 40° C. or below, the pH is between from about 6 and about 8 and the washing time short, e.g., below about 30 min. A detergent additive product comprising a beta-glucanase of the present disclosure is further ideally suited for inclusion in a alkaline wash process when, e.g., a pH selected in the range from about 7.5 to about 13.5, a temperature selected in the range from about 20° C. to about 75° C., and the washing time short, e.g., below about 30 min, e.g. at least about 15 minutes. An embodiment is a cleaning or detergent composition comprising a beta-glucanase polypeptide of the present disclosure and one or more amylases (and/or one or more proteases). Alternatively, a detergent additive product comprising a beta-glucanase of the present disclosure is suited for cleaning of a household dishwasher, e.g. from built-up residues on the filter and in the sump of the machines, preferably from residues containing beta-glucan-containing fibres. Such a machine-cleaning additive product may be suitable to clean the machine at the same time from other residues like fat or limescale.

The dishwashing detergent additive product may be a beta-glucanase of the present disclosure and preferably an additional enzyme. In one embodiment, the additive is packaged in dosage form for addition to a cleaning process. The single dosage may comprise a pill, tablet, gelcap or other single dosage unit including powders and/or liquids. In some embodiments, filler and/or carrier material(s) are included, suitable filler or carrier materials include, but are not limited to, various salts of sulfate, carbonate and silicate as well as talc, clay and the like. In some embodiments filler and/or carrier materials for liquid compositions include water and/or low molecular weight primary and secondary alcohols including polyols and diols. Examples of such alcohols include, but are not limited to, methanol, ethanol, propanol and isopropanol.

In one particularly preferred embodiment of the dish washing composition or dishwashing detergent additives the beta-glucanase as contemplated herein is employed in a granular composition or liquid, the beta-glucanase may be in form of an encapsulated particle. In one embodiment, the encapsulating material is selected from the group of carbohydrates, natural or synthetic gums, chitin and chitosan, cellulose and cellulose derivatives, silicates, phosphates, borates, polyvinyl alcohol, polyethylene glycol, paraffin waxes and combinations thereof.

The compositions as contemplated herein typically comprise one or more detergent ingredients. The term detergent compositions include articles and cleaning and treatment compositions. The term cleaning composition includes, unless otherwise indicated, tablet, granular or powder form; liquid, gel- or paste-form, Hand dishwashing agents or light duty dishwashing agents, especially those of the high-foaming type; machine dishwashing agents (or automatic dishwashing compositions), including the various tablet, granular, gel-form, liquid and rinse-aid types for household and institutional use are possible. The composition is preferably in unit dose packages, including those known in the art and those that are water soluble, water insoluble and/or water permeable. These may encompass single chamber and multichamber pouches.

In embodiments in which cleaning and/or detergent components may not be compatible with the beta-glucanase of the present disclosure, suitable methods may be used for keeping the cleaning and/or detergent components and the beta-glucanase separated (i.e., not in contact with each other) until combination of the two components is appropriate. Such separation methods include any suitable method known in the art (e.g., gelcaps, encapsulation, tablets, and physical separation e.g., by use of a water dissolvable pouch having one or more compartments).

As mentioned when the beta-glucanase of the present disclosure is employed as a component of a detergent composition (e.g. a dishwashing detergent composition), it may, for example, be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are polyethyleneglycol (PEG) products with mean molecular weights of from about 1000 to about 20000; ethoxylated nonylphenols having from about 16 to about 50 ethylene oxide units; ethoxylated fatty alcohols in which the alcohol contains from about 12 to about 20 carbon atoms and in which there are from about 15 to about 80 ethylene oxide units; fatty alcohols; fatty acids; and mono- and di- and triglycerides of fatty acids. Examples of film-forming coating materials suitable for application by fluid bed techniques are given in GB 1483591.

In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), tin (II), cobalt (II), copper (II), nickel (II), and oxovanadium (IV)). The enzymes of the detergent compositions of the present disclosure may also be stabilized using conventional stabilizing agents such as polyol, e.g., propylene glycol or glycerol, a sugar or sugar alcohol, lactic acid, and the composition may be formulated as described in, e.g., WO 92/19709 and WO 92/19708. The enzymes of the present disclosure may also be stabilized by adding reversible enzyme inhibitors, e.g., of the protein type (as described in EP 544 777) or the boronic acid type. In a preferred embodiment the enzyme stabilizers are of the boronic acid type, more preferably 4-formyl phenyl boronic acid. The dishwashing composition of the present disclosure is preferably free of boric acid and/or borate, which is to say in particular comprises boric acid and borate in amounts of less than about 0.1 wt. %, preferably less than about 0.01 wt. %, based on the total composition.

Other enzyme stabilizers are well known in the art, such as peptide aldehydes and protein hydrolysate, e.g. the beta-glucanase as contemplated herein may be stabilized using peptide aldehydes or ketones such as described in WO2005/105826 and WO2009/118375.

Protected enzymes for inclusion in a detergent composition of the present disclosure may be prepared, as mentioned above, according to the method disclosed in EP 238 216.

The composition may be augmented with one or more agents for preventing or removing the formation of the biofilm. These agents may include, but are not limited to, dispersants, surfactants, detergents, other enzymes, antimicrobials, and biocides.

The compositions of the present disclosure may be applied in dosing elements to be used in an auto-dosing device. The dosing elements comprising the composition of the present disclosure can be placed into a delivery cartridge as that described in WO 2007/052004 and WO 2007/0833141 or WO 2011/051420, WO 2011/051415, WO 2011/051416, WO 2011/051417, WO 2011/051418, WO 2011/120546 and WO 2011/131260. The dosing elements can have an elongated shape and set into an array forming a delivery cartridge which is the refill for an auto-dosing dispensing device as described in case WO 2007/051989. The delivery cartridge is to be placed in an auto-dosing delivery device, such as that described in WO 2008/053191.

Suitable disclosure of auto-dosing devices can be found in WO 2007/083139, WO 2007/051989, WO 2007/083141, WO 2007/083142 and EP2361964.

Other Enzymes

In one embodiment of the dish washing composition, a beta-glucanase of the present disclosure is combined with one or more enzymes, such as at least two enzymes, more preferred at least three, four or five enzymes. Preferably, the enzymes have different substrate specificity, e.g., proteolytic activity, amylolytic activity, lipolytic activity, hemicellulytic activity or pectolytic activity. An embodiment is a cleaning or detergent composition comprising a beta-glucanase polypeptide of the present disclosure and one or more amylases (and/or one or more proteases).

The detergent additive as well as the detergent composition as contemplated herein may comprise one or more enzymes such as a protease, lipase, cutinase, an amylase, carbohydrase, cellulase, pectinase, mannanase, arabinase, galactanase, xylanase, oxidase, e.g., a laccase and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases: Suitable cellulases include those of animal, vegetable or microbial origin. Particularly suitable cellulases include those of bacterial or fungal origin. Chemically modified or protein engineered variants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 1999/001544.

Commercially available cellulases include Celluzyme®, and Carezyme® (Novozymes A/S), Clazinase®, and Puradax HA® (Genencor International Inc.), and KAC-500 (B)® (Kao Corporation).

Proteases: Suitable proteases include those of bacterial, fungal, plant, viral or animal origin e.g. microbial or vegetable origin. Microbial origin is preferred. Chemically modified or protein engineered variants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease. Serine proteases are a subgroup of proteases exemplified by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin lentus, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from Cellulomonas described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the protease variants may comprise the mutations: S3T, V4I, S9R, A15T, K27R, *36D, V68A, N76D, N87S,R, *97E, A98S, S99G,D,A, S99AD, S101G,M,R S103A, V104I,Y,N, S106A, G118V,R,H120D,N,N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases: Suitable lipases include those of animal, vegetable or microbial origin. Particularly suitable lipases include those of bacterial or fungal origin. Chemically modified or protein engineered variants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis, B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™, Lipolase Ultra™, and Lipex™ (Novozymes A/S).

Amylases: Suitable amylases which can be used together with beta-glucanase of the present disclosure may be an alpha-amylase or a glucoamylase and may be of bacterial or fungal origin. Chemically modified or protein engineered variants are included. Amylases include, for example, alpha-amylases obtained from *Bacillus*, e.g., a special strain of *Bacillus licheniformis*, described in more detail in GB 1,296,839. Suitable amylases include amylases having SEQ ID NO: 3 in WO 95/10603 or variants having about 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444. Different suitable amylases include amylases having SEQ ID NO: 6 in WO 02/010355 or variants thereof having about 90% sequence identity to SEQ ID NO: 6. Preferred variants of SEQ ID NO: 6 are those having a deletion in positions 181 and 182 and a substitution in position 193. Other amylases which are suitable are hybrid alpha-amylase comprising residues from about 1 to about 33 of the alpha-amylase derived from *B. amyloliquefaciens* shown in SEQ ID NO: 6 of WO 2006/066594 and residues from about 36 to about 483 of the *B. licheniformis* alpha-amylase shown in SEQ ID NO: 4 of WO 2006/066594 or variants having about 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues from about 1 to about 33 of the alpha-amylase derived from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having about 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184. Additional amylases which can be used are those having SEQ ID NO: 1, SEQ ID NO: 3, SEQ ID NO: 2 or SEQ ID NO: 7 of WO 96/023873 or variants thereof having about 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476. More preferred variants are those having a deletion in positions 181 and 182 or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476. Other amylases which can be used are amylases having SEQ ID NO: 2 of WO 08/153815, SEQ ID NO: 10 in WO 01/66712 or variants thereof having about 90% sequence identity to SEQ ID NO: 2 of WO 08/153815 or about 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264. Further suitable amylases are amylases having SEQ ID NO: 2 of WO 09/061380 or variants having about 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:
N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181. Other suitable amylases are the alpha-amylase having SEQ ID NO: 12 in WO01/66712 or a variant having at least about 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions. Other examples are amylase variants such as those described in WO2011/098531, WO2013/001078 and WO2013/001087. Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

Peroxidases/Oxidases: Suitable peroxidases/oxidases include those of plant, bacterial or fungal origin. Chemically modified or protein engineered variants are included. Examples of useful peroxidases include peroxidases from Coprinus, e.g., from C. cinereus, and variants thereof as those described in WO 93/24618, WO 95/10602, and WO 98/15257.

Commercially available peroxidases include Guardzyme® (Novozymes A/S).

The detergent enzyme(s) may be included in a detergent composition by adding separate additives containing one or more enzymes, or by adding a combined additive comprising all of these enzymes. A detergent additive of the present disclosure, i.e., a separate additive or a combined additive, can be formulated, for example, as a granulate, liquid, slurry, etc. Preferred detergent additive formulations are granulates, in particular non-dusting granulates as described above, liquids, in particular stabilized liquids, or slurries.

Surfactants Typically, the cleaning or detergent compositions, wherein said cleaning or detergent composition is a dish washing composition, said composition comprises (by weight of the composition, total amount of surfactant by weight of the composition) one or more surfactants in the range of from about 0% to about 50%, preferably from about 2% to about 40%, more preferably from about 5% to about 35%, more preferably from about 7% to about 30%, most preferably from about 10% to about 25%, even most preferably from about 15% to about 20%. In a preferred embodiment the detergent is a liquid or powder detergent comprising less than about 40%, preferably less than about 30%, more preferably less than about 25%, even more preferably less than about 20% by weight of surfactant. The composition may comprise from about 0.1% to about 15%, preferably from about 0.2% to about 12%, from about 0.5% to about 10%, most preferably from about 1.0% to about 8.0%, of one or more surfactants (total amount of surfactant by weight of the composition). Preferred surfactants are anionic surfactants, non-ionic surfactants, cationic surfactants, zwitterionic surfactants, amphoteric surfactants, and mixtures thereof.

All nonionic surfactants known to a person skilled in the art may be used as nonionic surfactants. Suitable nonionic surfactants are, for example, alkyl glycosides of the general formula RO(G)x, where R corresponds to a primary straight-chain or methyl-branched, in particular methyl-branched at the 2-position, aliphatic group having 8 to 22, preferably 12 to 18 carbon atoms, and G is the symbol that denotes a glycose unit having 5 or 6 carbon atoms, preferably glucose. The degree of oligomerization x, which indicates the distribution of monoglycosides and oligoglycosides, is any number between from about 1 and about 10; x is preferably from about 1.2 to about 1.4.

Another class of nonionic surfactants that can preferably be used, which can be used either as the sole nonionic surfactant or in combination with other nonionic surfactants, is alkoxylated, preferably ethoxylated or ethoxylated and propoxylated fatty acid alkyl esters, preferably having 1 to 4 carbon atoms in the alkyl chain.

Nonionic surfactants of the amine oxide type, for example N-cocoalkyl-N,N-dimethylamine oxide and N-tallowalkyl-N,N-dihydroxyethylamine oxide, and of the fatty acid alkanolamide type may also be suitable. The quantity of these nonionic surfactants is preferably no more than that of the ethoxylated fatty alcohols, in particular no more than half thereof. Further suitable surfactants are polyhydroxyfatty acid amides, also known as PHFA.

Low-foaming nonionic surfactants can be used as preferred surfactants. With particular preference, the cleaning agents, preferably dishwashing agents, in particular machine dishwashing agents contain nonionic surfactants from the group of alkoxylated alcohols. Alkoxylated, advantageously ethoxylated, in particular primary alcohols having preferably 8 to 18 carbon atoms and on average from about 1 to about 12 mol ethylene oxide (EO) per mol of alcohol, in which the alcohol residue can be linear or preferably methyl-branched at the 2-position, or can contain linear and methyl-branched residues in the mixture, such as those usually present in oxo alcohol groups, are preferably used as nonionic surfactants. However, alcohol ethoxylates having linear groups of alcohols of native origin having from about 12 to about 18 carbon atoms, for example of coconut, palm, tallow fatty or oleyl alcohol, and an average of from about 2 to about 8 mol EO per mol of alcohol are particularly preferred. The preferred ethoxylated alcohols include, for example, $C_{12-14}$ alcohols having about 3 EO or about 4 EO, $C_{9-11}$ alcohol having about 7 EO, $C_{13-15}$ alcohols having about 3 EO, about 5 EO, about 7 EO, or about 8 EO, $C_{12-18}$ alcohols having about 3 EO, about 5 EO, or about 7 EO, and mixtures thereof, such as mixtures of $C_{12-14}$ alcohol having about 3 EO and $C_{12-18}$ alcohol having about 5 EO. The degrees of ethoxylation indicated represent statistical averages that can correspond to an integer or a fractional number for a specific product. Preferred alcohol ethoxylates exhibit a restricted distribution of homologs (narrow range ethoxylates, NRE). In addition to these nonionic surfactants, fatty alcohols having more than 12 EO can also be used. Examples of these are tallow fatty alcohol having about 14 EO, about 25 EO, about 30 EO, or about 40 EO.

Nonionic surfactants that have a melting point above room temperature are particularly preferred. Nonionic surfactant(s) having a melting point above about 20° C., preferably above about 25° C., particularly preferably between from about 25 and about 60° C., and in particular between from about 26.6 and about 43.3° C., is/are particularly preferred.

Surfactants that are preferably to be used come from the groups of alkoxylated nonionic surfactants, in particular ethoxylated primary alcohols. It has been found that dishwashing compositions comprising polypeptide(s) as contemplated herein in combination with nonionic surfactants are surprisingly capable of reducing the built up of soils in the interior of the dish washing machine, especially on the sieve/filter.

Builders and Co-Builders

The main role of builder is to sequester divalent metal ions (such as calcium and magnesium ions) from the wash solution that would otherwise interact negatively with the surfactant system. Builders are also effective at removing metal ions and inorganic soils from the fabric surface, leading to improved removal of particulate and beverage stains. Builders are also a source of alkalinity and can buffer the pH of the wash water to a level above about 7.5, e.g. from about 9.5 to about 11. The buffering capacity is also termed reserve alkalinity, and should preferably be greater than about 4 (e.g. for solid automatic dishwashing compositions).

The detergent compositions of the present disclosure may comprise one or more detergent builders or builder systems. Many suitable builder systems are described in the literature. The detergent composition may contain from about 0 to about 65% by weight, such as from about 5% to about 50% of a detergent builder or co-builder, or a mixture thereof. In a dish washing detergent, the level of builder is typically from about 40 to about 65%, particularly from about 50 to about 65%. The builder and/or co-builder may particularly be a chelating agent that forms water-soluble complexes with Ca and Mg.

The builders include in particular silicates, carbonates and organic cobuilders, especially polycarboxylate(s) and/or aminocarboxylate(s).

Crystalline layered silicates may be used in the agents described herein. Such cleaning agents, preferably dishwashing agents, in particular machine dishwashing agents, preferably contain a weight fraction of crystalline layered silicate from about 0.1 to about 20 wt %, preferably from about 0.2 to about 15 wt %, and in particular from about 0.4 to about 10 wt %, in each case based on the total weight of these agents.

Other builders are the alkali carriers. Valid examples of alkali carriers include alkali metal hydroxides, alkali metal carbonates, alkali metal hydrogen carbonates, alkali metal sesquicarbonates, the described alkali silicates, alkali metal silicates and mixtures of the above-mentioned substances, wherein within the meaning of the present disclosure preferably the alkali carbonates, in particular sodium or potassium carbonate, sodium hydrogen carbonate or sodium sesquicarbonate may be used. However, also the corresponding potassium analogs may be useful in addition to or in complete replacement of the sodium salts. Due to the low chemical compatibility of the optional alkali metal hydroxides with the remaining ingredients of cleaning agents, in particular dishwashing agents, preferably machine dishwashing agents, compared to other builder substances, they are preferably used only in small quantities or not at all.

Builders include, but are not limited to, alkali metal silicates, alkaline earth and alkali metal carbonates, aluminosilicate builders (e.g., zeolite) and polycarboxylate compounds, ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Ethanole amines (MEA, DEA, and TEA) may also contribute to the buffering capacity in liquid detergents.

Any builder and/or co-builder known in the art for use in dish washing compositions, especially ADW or HDW cleaning detergents may be utilized. Non-limiting examples of builders include zeolites, carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

Preferred dishwash compositions of the present disclosure are "phosphate-free". "Phosphate-free," as used herein, means that the composition in question is essentially free of phosphates, which is to say in particular comprises phosphates in amounts of less than about 0.1 wt. %, preferably less than about 0.01 wt. %, based on the total composition. The expression "phosphates", as used in this context, does not include the phosphonates described hereafter.

The use of carbonate(s) and/or hydrogen carbonate(s), preferably alkali carbonate(s), particularly preferably sodium carbonate, in quantities from about 2 to about 50 wt %, preferably from about 5 to about 40 wt %, and in particular from about 7.5 to about 30 wt %, in each case based on the weight of the agent, preferably machine dishwashing agent, is particularly preferred. Agents that, based on the weight of the machine dishwashing agent, contain less than about 20 wt %, especially less than about 17 wt %, preferably less than about 13 wt %, and in particular less than about 9 wt % carbonate(s) and/or hydrogen carbonate(s), preferably alkali carbonate(s), particularly preferably sodium or potassium carbonate, are particularly preferred.

In particular, polycarboxylates/polycarboxylic acids, polymeric polycarboxylates, aspartic acid, polyacetals, dextrins, further organic cobuilders, and phosphonates should be mentioned as organic cobuilders. These substance classes are described hereafter.

Usable organic builder substances are, for example, the polycarboxylic acids that can be used in the form of the free acid and/or of the sodium salts thereof, wherein polycarboxylic acids shall be understood to mean those carboxylic acids that carry more than one acid function. These include, for example, citric acid, adipic acid, succinic acid, glutaric acid, malic acid, tartaric acid, maleic acid, fumaric acid, saccharic acids, nitrilotriacetic acid (NTA), provided that such use is not objectionable for ecological reasons, and mixtures thereof. In addition to the builder effect, the free acids typically also have the property of being an acidifying component and are thus also used as agents to set a lower and milder pH value. In particular, citric acid, succinic acid, glutaric acid, adipic acid, gluconic acid and arbitrary mixtures of these should be mentioned here.

The use of citric acid and/or citrates in these agents has proven to be particularly advantageous for the cleaning and rinsing power of agents described herein. Preferred are therefore cleaning agents, preferably dishwashing agents, particularly preferably machine dishwashing agents, exemplified in that the agent contains citric acid or a salt of citric acid, and the weight fraction of the citric acid or of the salt of citric acid especially is more than about 10 wt %, preferably more than about 15 wt %, and in particular between about 20 and about 40 wt %.

Further preferred examples include chelators such as aminocarboxylates, aminopolycarboxylates and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), and combinations and salts thereof. Further exemplary builders and/or co-builders are described in, e.g., WO 09/102854, U.S. Pat. No. 5,977,053.

Aminocarboxylic acids and/or the salts thereof are another significant class of phosphate-free builders. Particularly preferred representatives of this class are methylglycine diacetic acid (MGDA) or the salts thereof, and glutamine diacetic acid (GLDA) or the salts thereof, or ethylenediamine diacetic acid (EDDS) or the salts thereof. The content of these amino carboxylic acids or of the salts thereof can amount to, for example, between about 0.1 and about 15 wt %, preferably between about 0.5 and about 10 wt %, and in particular between about 0.5 and about 6 wt %. Aminocarboxylic acids and the salts thereof can be used together with the above-mentioned builders, in particular also with the phosphate-free builders.

The detergent composition may also contain from about 0 to about 50% by weight, such as from about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA).

Suitable builders moreover include polymeric polycarboxylates; for example, these are the alkali metal salts of polyacrylic acid or of polymethacrylic acid, for example those having a relative molar mass from about 500 to about 70,000 g/mol. Suitable polymers are in particular polyacrylates, which preferably have a molar mass from about 2000 to about 20,000 g/mol. Due to the superior solubility thereof, short-chain polyacrylates having molar masses from about 2000 to about 10,000 g/mol, and particularly preferably from about 3000 to about 5000 g/mol, may in turn be preferred from this group.

In a preferred embodiment the dish washing composition of the present disclosure may comprise, if allowed according to the jurisdiction of the country where the dishwashing composition is used, phosphonates, preferable 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), diethylenetriamine penta(methylenephosphonic acid) (DTPMP), aminotris(methylenephosphonic acid) (ATMP).

In an alternative embodiment the dish washing composition of the present disclosure are phosphate-free as defined above and comprise no ore only small amounts of phosphonates. In a preferred embodiment the dish washing composition contains less than about 15 mg/job phosphorus, more preferred less than about 10 mg/job phosphorus, most preferred less than about 1 mg/job phosphorus.

Bleaches

The detergent compositions of the present disclosure may comprise one or more bleaching agents. In particular powdered detergents may comprise one or more bleaching agents. Suitable bleaching agents include other photobleaches, pre-formed peracids, sources of hydrogen peroxide, bleach activators, hydrogen peroxide, bleach catalysts and mixtures thereof. In general, when a bleaching agent is used, the compositions of the present disclosure may comprise from about 0.1% to about 50% or even from about 0.1% to about 25% bleaching agent by weight of the subject cleaning composition. Examples of suitable bleaching agents include:

(1) other photobleaches for example Vitamin K3;
(2) preformed peracids: Suitable preformed peracids include, but are not limited to, compounds selected from the group of percarboxylic acids and salts, percarbonic acids and salts, perimidic acids and salts, peroxymonosulfuric acids and salts, for example, Oxone, and mixtures thereof. Suitable percarboxylic acids include hydrophobic and hydrophilic peracids having the formula R—(C=O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen;
(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the present disclosure the inorganic perhydrate salts are selected from the group of sodium salts of perborate, percarbonate and mixtures thereof. When employed, inorganic perhydrate salts are typically present in amounts of from about 0.05 to about 40 wt %, or from about 1 to about 30 wt % of the overall composition and are typically incorporated into such compositions as a crystalline solid that may be coated. Suitable coatings include inorganic salts such as alkali metal silicate, carbonate or borate salts or mixtures thereof, or organic materials such as water-soluble or dispersible polymers, waxes, oils or fatty soaps. Useful bleaching compositions are described in U.S. Pat. Nos. 5,576,282, and 6,306,812;
(4) bleach activators having R—(C=O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the present disclosure the subject cleaning composition may comprise NOBS, TAED or mixtures thereof; and
(5) bleach catalysts that are capable of accepting an oxygen atom from peroxyacid and transferring the oxygen atom to an oxidizable substrate are described in WO 2008/007319. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof. The bleach catalyst will typically be comprised in the detergent composition at a level of from about 0.0005% to about 0.2%, from about 0.001% to about 0.1%, or even from about 0.005% to about 0.05% by weight.

When present, the peracid and/or bleach activator is generally present in the composition in an amount of from about 0.1 to about 60 wt %, from about 0.5 to about 40 wt % or even from about 0.6 to about 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from about 1:1 to about 35:1, or even from about 2:1 to about 10:1.

Adjunct Materials

Dispersants—The detergent compositions of the present disclosure can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms.

Soil release polymers—The dishwashing compositions of the present disclosure may also include one or more soil release polymers which aid the removal of soils from fabrics such as cotton and polyester based fabrics, in particular the removal of hydrophobic soils from polyester based fabrics. The soil release polymers may for example be nonionic or anionic terephthalate based polymers, polyvinyl caprolactam and related copolymers, vinyl graft copolymers, polyester polyamides. Another type of soil release polymers are amphiphilic alkoxylated grease cleaning polymers comprising a core structure and a plurality of alkoxylate groups attached to that core structure. The core structure may comprise a polyalkyleneamine structure or a polyalkanolamine structure as described in detail in WO 2009/087523. Furthermore random graft co-polymers are suitable soil release polymers Suitable graft co-polymers are described in more detail in WO 2007/138054, WO 2006/108856 and WO 2006/113314. Other soil release polymers are substituted polysaccharide structures especially substituted cellulosic structures such as modified cellulose derivatives such as those described in EP 1 867 808 or WO 2003/040279. Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-redeposition agents—The dishwashing compositions of the present disclosure may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to bactericides, binders, carriers, dyes, enzyme stabilizers, fillers, foam regulators, hydrotropes, perfumes, pigments, sod suppressors, solvents, structurants for liquid detergents and/or structure elasticizing agents.

A typical basic formulation for a machine dishwashing composition, that can preferably be used, for example, for solid powders or preferably in tablet form, comprises the following materials:

One or more polypeptide(s) as contemplated herein from about 0.001 to about 5 wt % (enzyme protein) and

| | |
|---|---|
| Sodium citrate | from about 10 to about 50 wt % |
| MGDA or GLDA, sodium salt | from about 0 to about 40 wt % |
| sodium carbonate | from about 10 to about 30 wt % |
| sodium disilicate | from about 0 to about 40 wt % |
| sodium percarbonate | from about 5 to about 20 wt % |
| bleach activator | from about 1 to about 4 wt % |
| bleach catalyst | from about 0.001 to about 1 wt % |
| sulfopolymer | from about 2.5 to about 15 wt % |
| polycarboxylate | from about 0.5 to about 15 wt % |
| nonionic surfactant(s) | from about 1.5 to about 15 wt % |
| phosphonate | from about 0 to about 10 wt % |
| proteases (enzyme protein) | from about 0.0001 to about 5 wt % |
| amylase (enzyme protein) | from about 0.0001 to about 5 wt % |
| Glass corrosion inhibitor | from about 0 to about 1 wt % | wherein the information in wt % in each case is based on the total composition.

Additionally the composition may contain additives as disintegrants, silver protection agents, filling agents, processing aids, pH adjusting agents, perfume, dyes etc.

A typical basic formulation for a automatic dishwashing composition, especially useful in household dishwashers, that can preferably be used, for example, in gel-form or preferably in liquid form, comprises the following materials:

One or more polypeptide as contemplated herein (enzyme protein) from about 0.001 to about 5 wt % and

| | |
|---|---|
| Sodium citrate | from about 5 to about 50 wt % |
| MGDA or GLDA, tetrasodium salt | from about 0 to about 20 wt % |
| Sulfopolymer | from about 2.5 to about 15 wt % |
| polycarboxylate | from about 0 to about 10 wt % |
| nonionic surfactant(s) | from about 0.5 to about 10 wt % |
| Phosphonate | from about 0 to about 10 wt % |
| proteases (enzyme protein) | from about 0.0001 to about 5 wt % |
| amylase (enzyme protein) | from about 0.0001 to about 5 wt % | wherein the information in wt % in each case is based on the total composition.

Additionally the composition may contain additives as rheology modifiers, filling agents, processing aids, pH adjusting agents, perfume, dyes etc.

The soils and stains that are important for detergent formulators are composed of many different substances, and a range of different enzymes, all with different substrate specificities have been developed for use in detergents both in relation to laundry and hard surface cleaning, such as dishwashing. These enzymes are considered to provide an enzyme detergency benefit, since they specifically improve stain removal in the cleaning process they are applied in as compared to the same process without enzymes. Stain removing enzymes that are known in the art include enzymes such as carbohydrases, amylases, proteases, lipases, cellulases, hemicellulases, xylanases, cutinases, and pectinase.

In a preferred aspect of the present disclosure the beta-glucanase of the present disclosure may be combined with at least two enzymes. These additional enzymes are described in details in the section "other enzymes", more preferred at least three, four or five enzymes. Preferably, the enzymes have different substrate specificity, e.g., carbolytic activity, proteolytic activity, amylolytic activity, lipolytic activity, hemicellulytic activity or pectolytic activity. The enzyme combination may for example be a beta-glucanase of the present disclosure with another stain removing enzyme, e.g., a beta-glucanase of the present disclosure and a protease, a beta-glucanase of the present disclosure and a serine protease, a beta-glucanase of the present disclosure and an amylase, a beta-glucanase of the present disclosure and a cellulase, beta-glucanase of the present disclosure and a lipase, a beta-glucanase of the present disclosure and a cutinase, a beta-glucanase of the present disclosure and a pectinase or a beta-glucanase of the present disclosure and an anti-redeposition enzyme. More preferably, the beta-glucanase of the present disclosure is combined with at least two other stain removing enzymes, e.g., a beta-glucanase of the present disclosure, a lipase and an amylase; or a beta-glucanase of the present disclosure, a protease and an amylase; or a beta-glucanase of the present disclosure, a protease and a lipase; or a beta-glucanase of the present disclosure, a protease and a pectinase; or a beta-glucanase of the present disclosure, a protease and a cellulase; or a beta-glucanase of the present disclosure, a protease and a hemicellulase; or a beta-glucanase of the present disclosure, a protease and a cutinase; or a beta-glucanase of the present disclosure, an amylase and a pectinase; or a beta-glucanase of the present disclosure, an amylase and a cutinase; or a beta-glucanase of the present disclosure, an amylase and a cellulase; or a beta-glucanase of the present disclosure, an amylase and a hemicellulase; or a beta-glucanase of the present disclosure, a lipase and a pectinase; or a beta-glucanase of the present disclosure, a lipase and a cutinase; or a beta-glucanase of the present disclosure, a lipase and a cellulase; or a beta-glucanase of the present disclosure, a lipase and a hemicellulase. Even more preferably, a beta-glucanase of the present disclosure may be combined with at least three other stain removing enzymes, e.g., a beta-glucanase of the present disclosure, a protease, a lipase and an amylase; or a beta-glucanase of the present disclosure, a protease, an amylase and a pectinase; or a beta-glucanase of the present disclosure, a protease, an amylase and a cutinase; or a beta-glucanase of the present disclosure, a protease, an amylase and a cellulase; or a beta-glucanase of the present disclosure, a protease, an amylase and a hemicellulase; or a beta-glucanase of the present disclosure, an amylase, a lipase and a pectinase; or a beta-glucanase of the present disclosure, an amylase, a lipase and a cutinase; or a beta-glucanase of the present disclosure, an amylase, a lipase and a cellulase; or a beta-glucanase of the present disclosure, an amylase, a lipase and a hemicellulase; or a beta-glucanase of the present disclosure, a protease, a lipase and a pectinase; or a beta-glucanase of the present disclosure, a protease, a lipase and a cutinase; or a beta-glucanase of the present disclosure, a protease, a lipase and a cellulase; or a beta-glucanase of the present disclosure, a protease, a lipase and a hemicellulase. A beta-glucanase according to the present disclosure may be combined with any of the enzymes selected from the non-exhaustive list comprising: carbohydrases, such as an amylase, a hemicellulase, a pectinase, a cellulase, a xanthanase or a pullulanase, a peptidase, a protease or a lipase.

In a preferred embodiment, a beta-glucanase of the present disclosure is combined with a serine protease, e.g., an S8 family protease such as Savinase®.

In another embodiment of the present disclosure, a beta-glucanase of the present disclosure may be combined with one or more metalloproteases, such as an M4 metalloprotease, including Neutrase® or Thermolysin. Such combinations may further comprise combinations of the other detergent enzymes as outlined above.

The cleaning process is a dishwashing process. The cleaning process can for example be carried out in a machine washing process or in a manual washing process. The washing solution can for example be an aqueous washing solution containing a detergent composition.

The last few years there have been an increasing interest in replacing components in detergents, which is derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases is needed to achieve a similar or improved wash performance when compared to the traditional detergent compositions.

Typical detergent compositions includes various components in addition to the enzymes, these components have different effects, some components like the surfactants lower the surface tension in the detergent, which allows the stain being cleaned to be lifted and dispersed and then washed away, other components like bleach systems removes discolor often by oxidation and many bleaches also have strong bactericidal properties, and are used for disinfecting and sterilizing. Yet other components like builder and chelator softens, e.g., the wash water by removing the metal ions from the liquid.

In a particular embodiment, the present disclosure concerns the use of a composition comprising a beta-glucanase of the present disclosure, wherein said composition further comprises at least one or more of the following a surfactant, a builder, a chelator or chelating agent, bleach system or bleach component in dish wash.

In a preferred embodiment of the present disclosure the amount of a surfactant, a builder, a chelator or chelating agent, bleach system and/or bleach component are reduced compared to amount of surfactant, builder, chelator or chelating agent, bleach system and/or bleach component used without the added beta-glucanase of the present disclosure. Preferably the at least one component which is a surfactant, a builder, a chelator or chelating agent, bleach system and/or bleach component is present in an amount that is about 1% less, such as about 2% less, such as about 3% less, such as about 4% less, such as about 5% less, such as about 6% less, such as about 7% less, such as about 8% less, such as about 9% less, such as about 10% less, such as about 15% less, such as about 20% less, such as about 25% less, such as about 30% less, such as about 35% less, such as about 40% less, such as about 45% less, such as about 50% less than the amount of the component in the system without the addition of beta-glucanase of the present disclosure, such as a conventional amount of such component. In one aspect, the beta-glucanase of the present disclosure is used in detergent compositions wherein said composition is free of at least one component which is a surfactant, a builder, a chelator or chelating agent, bleach system or bleach component and/or polymer.

Detergent Compositions

In one embodiment, the present disclosure is directed to detergent compositions comprising an enzyme of the present disclosure in combination with one or more additional cleaning composition components. The choice of additional components is within the skill of the artisan and includes conventional ingredients, including the exemplary non-limiting components set forth below.

In one embodiment, the present disclosure is directed to an ADW (Automatic Dish Wash) compositions comprising an enzyme of the present disclosure in combination with one or more additional ADW composition components. The choice of additional components is within the skill of the artisan and includes conventional ingredients, including the exemplary non-limiting components set forth below.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to about 60% by weight, such as from about 1% to about 40%, or from about 3% to about 20%, or from about 3% to about 10%. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0% to about 40% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0% to about 40% by weight of a zwitterionic surfactant. Non-limiting examples of zwitterionic surfactants include betaines such as alkyldimethylbetaines, sulfobetaines, and combinations thereof.

Hydrotropes

A hydrotrope is a compound that solubilizes hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain from about 0 to about 10% by weight, for example from about 0 to about 5% by weight, such as from about 0.5 to about 5%, or from about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Bleaching Systems

The detergent may contain from about 0 to about 30% by weight, such as from about 1% to about 20%, of a bleaching system. Any bleaching system known in the art for use in dish wash, especially automatic dish washing (ADW) cleaning detergents may be utilized. Suitable bleaching system components include bleaching catalysts, photobleaches, bleach activators, sources of hydrogen peroxide such as sodium percarbonate, sodium perborates and hydrogen peroxide—urea (1:1), preformed peracids and mixtures thereof. Suitable preformed peracids include, but are not limited to, peroxycarboxylic acids and salts, diperoxydicarboxylic acids, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable examples are tetraacetylethylenediamine (TAED), sodium 4-[(3,5,5-trimethylhexanoyl)oxy] benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), and/or those disclosed in WO98/17767.

It is also possible to use combinations of conventional bleach activators. These bleach activators are preferably used in quantities of up to about 10 wt %, in particular from about 0.1 wt % to about 8 wt %, particularly from about 2 to about 8 wt %, and particularly preferably from about 2 to about 6 wt %, based in each case on the total weight of the bleach activator-containing agent.

A particular family of bleach activators of interest was disclosed in EP624154 and particularly preferred in that family is acetyl triethyl citrate (ATC). ATC or a short chain triglyceride like triacetin has the advantage that it is environmentally friendly Furthermore acetyl triethyl citrate and triacetin have good hydrolytical stability in the product upon storage and are efficient bleach activators. Finally ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido)peroxy-hexanoic acid (PAP). The bleaching system may also include a bleach catalyst. In some embodiments the bleach component may be an organic catalyst selected from the group of organic catalysts having the following formulae:

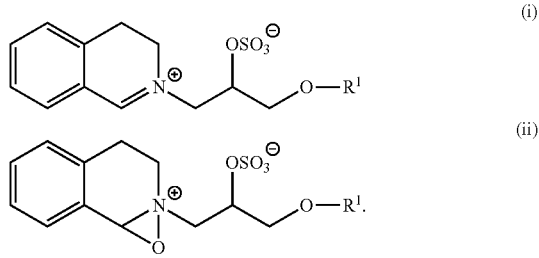

(iii) and mixtures thereof;
wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl. Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Preferably the bleach component comprises a source of peracid in addition to bleach catalyst, particularly organic bleach catalyst.

In a preferred embodiment the dishwashing compositions, in particular machine dishwashing compositions, especially solid automatic dishwashing compositions can furthermore contain bleach catalysts. The usable bleach catalysts include, but are not limited to, the group of the bleach-boosting transition metal salts and transition metal complexes, preferably the Mn, Fe, Co, Ru or Mo complexes, particularly preferably from the group of the manganese and/or cobalt salts and/or complexes, in particular the cobalt (amine) complexes, the cobalt (acetate) complexes, the cobalt (carbonyl) complexes, the chlorides of cobalt or manganese, manganese sulfate and the complexes of manganese with 1,4,7-trimethyl-1,4,7-triazacyclononane ($Mn_3$-TACN) or 1,2,4,7-tetramethyl-1,4,7-triazacyclononane ($Mn_4$-TACN).

Cleaning compositions, preferably dishwashing compositions, in particular machine dishwashing compositions that contain from about 0.001 to about 1 wt %, preferably from about 0.01 to about 0.1 wt % bleach catalyst, preferably an Mn complex, in particular a complex of manganese with 1,4,7-trimethyl-1,4,7-triazacyclononane ($Mn_3$-TACN) or 1,2,4,7-tetramethyl-1,4,7-triazacyclononane ($Mn_4$-TACN) are preferred.

The source of peracid may be selected from (a) preformed peracid; (b) percarbonate, perborate or persulfate salt (hydrogen peroxide source) preferably in combination with a bleach activator; and (c) perhydrolase enzyme and an ester for forming peracid in situ in the presence of water in a dish wash treatment step.

Polymers

The detergent may contain from about 0 to about 10% by weight, such as from about 0.5 to about 5%, from about 2 to about 5%, from about 0.5 to about 2% or from about 0.2 to about 1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly (vinylpyrrolidone) (PVP), poly(ethyleneglycol) or poly (ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

In a preferred embodiment the composition of the present disclosure also comprises one or more copolymeric polycarboxylates, in particular those of acrylic acid with methacrylic acid, and of acrylic acid or methacrylic acid with maleic acid.

The (co)polymeric polycarboxylates can be used either as a powder or as an aqueous solution. The content of (co)

polymeric polycarboxylates in the cleaning agents, preferably dishwashing agents, in particular machine dishwashing agents, is preferably from about 0.5 to about 20 wt %, and in particular from about 3 to about 10 wt %.

To improve water solubility, the polymers can also contain allyl sulfonic acids, such as allyloxybenzene sulfonic acid and methallyl sulfonic acid, as a monomer. Further preferred copolymers are those that contain acrolein and acrylic acid/acrylic acid salts or acrolein and vinylacetate as monomers.

Moreover, all compounds that are able to form complexes with alkaline earth ions can be used as builders.

In a most preferred embodiment of the present disclosure the dishwash detergent and cleaning composition of the present disclosure additionally comprises a copolymer that contains at least one sulfonic acid containing monomer, a so-called sulfo polymer.

The amount by weight of the sulfo polymer in the total weight of the detergent or cleaning agent produced as contemplated herein is preferably from about 0.1 to about 20% by weight, in particular from about 0.5 to about 18% by weight, particularly preferably from about 1.0 to about 15% by weight, in particular from about 4 to about 14% by weight, particularly from about 6 to about 12% by weight.

The aqueous solutions of the at least one sulfo polymer typically contain from about 20 to about 70% by weight, in particular from about 30 to about 50% by weight, preferably approx. 35 to about 40% by weight sulfo polymer(s).

A polysulfonate copolymer, optionally a hydrophobically modified polysulfonate copolymer, is preferably used as the sulfo polymer. The copolymers may contain two, three, four or more different monomer units.

Preferred polysulfonate copolymers contain at least one monomer from the group of unsaturated carboxylic acids in addition to monomer(s) containing sulfonic acid groups.

Unsaturated carboxylic acids of the formula $R^1(R^2)C=C(R^3)COOH$, in which $R^1$ to $R^3$ independently of one another stand for —H, —$CH_3$, a linear or branched saturated alkyl radical with 2 to 12 carbon atoms, a linear or branched mono- or polyunsaturated alkenyl radical with 2 to 12 carbon atoms, —$NH_2$, —OH or —COOH-substituted alkyl or alkenyl radicals as defined above, or standing for —COOH or —$COOR^4$, where $R^4$ is a saturated or unsaturated linear or branched hydrocarbon radical with 1 to 12 carbon atoms are particularly preferably used as unsaturated carboxylic acid(s).

Particularly preferred unsaturated carboxylic acids include acrylic acid, methacrylic acid, ethacrylic acid, α-chloroacrylic acid, α-cyanoacrylic acid, crotonic acid, α-phenylacrylic acid, maleic acid, maleic anhydride, fumaric acid, itaconic acid, citraconic acid, methylene malonic acid, sorbic acid, cinnamic acid or mixtures thereof. The unsaturated dicarboxylic acids may of course also be used.

Preferred monomers containing sulfonic acid groups are those of the formula

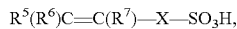

where $R^5$ to $R^7$ independently of one another stand for —H, —$CH_3$, a linear or branched saturated alkyl radical with 2 to 12 carbon atoms, a linear or branched mono- or polyunsaturated alkenyl radical with 2 to 12 carbon atoms, —$NH_2$, —OH or —COOH-substituted alkyl or alkenyl radicals or —COOH or —$COOR^4$, where $R^4$ is a saturated or unsaturated linear or branched hydrocarbon radical with 1 to 12 carbon atoms, and X stands for a spacer group, which is optionally present and is selected from —$(CH_2)_n$— where n=0 to 4, —COO—$(CH_2)_k$— where k=1 to 6, —C(O)—NH—C($CH_3)_2$—, —C(O)—NH—C($CH_3)_2$—$CH_2$— and —C(O)—NH—CH($CH_3$)—$CH_2$—.

Among these monomers, the preferred ones are those of the formulas

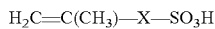

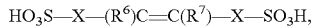

where $R^6$ and $R^7$, independently of one another, are selected from —H, —$CH_3$, —$CH_2CH_3$, —$CH_2CH_2CH_3$ and —CH($CH_3)_2$, and X stands for a spacer group, which is optionally present and is selected from —$(CH_2)_n$— where n=0 to 4, —COO—$(CH_2)_k$— where k=1 to 6, —C(O)—NH—C($CH_3)_2$—, —C(O)—NH—C($CH_3)_2$—$CH_2$— and —C(O)—NH—CH($CH_3$)—$CH_2$—.

Particularly preferred monomers that contain sulfonic acid groups include 1-acrylamido-1-propanesulfonic acid, 2-acrylamido-2-propanesulfonic acid, 2-acrylamido-2-methyl-1-propanesulfonic acid, 2-methacrylamido-2-methyl-1-propanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy) propanesulfonic acid, 2-methyl-2-propene-1-sulfonic acid, styrenesulfonic acid, vinylsulfonic acid, 3-sulfopropyl acrylate, 3-sulfopropyl methacrylate, sulfomethacrylamide, sulfomethyl methacrylamide as well as mixtures of the aforementioned acids or their water-soluble salts.

The sulfonic acid groups in the polymers may be present entirely or partially in neutralized form, i.e., in some or all of the sulfonic acid groups, the acidic hydrogen atom in the sulfonic acid group may be replaced by metal ions, preferably alkali metal ions and in particular sodium ions. The use of copolymers containing partially or fully neutralized sulfonic acid groups is preferred as contemplated herein.

The monomer distribution in the copolymers preferred for use as contemplated herein is preferably from about 5% to about 95% by weight in copolymers that contain only monomers containing carboxylic acid groups and monomers containing sulfonic acid groups, particularly preferably the amount of the monomer containing sulfonic acid groups is from about 50% to about 90% by weight and the amount of the monomer containing carboxylic acid groups is from about 10% to about 50% by weight and the monomers here are preferably selected from those listed above.

The molecular weight of the sulfo copolymers preferred for use as contemplated herein may be varied to adjust the properties of the polymers to the desired intended purpose. Preferred cleaning compositions are exemplified in that the copolymers have molecular weights of from about 2000 to about 200,000 gmol-$^1$, preferably from about 4000 to about 25,000 gmol-$^1$ and in particular from about 5000 to about 15,000 gmol-$^1$.

In another preferred embodiment, the copolymers also comprise at least one nonionic, preferably hydrophobic, monomer in addition to the monomer that contains carboxyl groups and the monomer that contains sulfonic acid groups. The clear rinsing performance of automatic dishwasher detergents as contemplated herein has been improved by using these polymers in particular.

Anionic copolymers comprising monomers that contain carboxylic acid groups, monomers that contain sulfonic acid groups and nonionic monomers, in particular hydrophobic monomers, are therefore preferred as contemplated herein.

Preferably monomers of the general formula $R^1(R^2)C=C(R^3)$—X—$R^4$, in which $R^1$ to $R^3$ independently of one another stand for —H, —$CH_3$ or —$C_2H_5$, X stands for a spacer group that is optionally present and is selected from —$CH_2$—, —C(O)O— and —C(O)—NH—, and $R^4$ stands for a linear or branched saturated alkyl radical with 2 to 22 carbon atoms or for an unsaturated, preferably aromatic radical with 6 to 22 carbon atoms, are preferably used as the nonionic monomers.

Particularly preferred nonionic monomers include butene, isobutene, pentene, 3-methylbutene, 2-methylbutene, cyclopentene, hexene, 1-hexene, 2-methyl-1-pentene, 3-methyl-1-pentene, cyclohexene, methyl cyclopentene, cycloheptene, methyl cyclohexene, 2,4,4-trimethyl-1-pentene, 2,4,4-trimethyl-2-pentene, 2,3-dimethyl-1-hexene, 2,4-dimethyl-1-hexene, 2,5-dimethyl-1-hexene, 3,5-dimethyl-1-hexene, 4,4-dimethyl-1-hexane, ethyl cyclohexyne, 1-octene, α-olefins with 10 or more carbon atoms such as, for example, 1-decene, 1-dodecene, 1-hexadecene, 1-octadecene and $C_{22}$ α-olefin, 2-styrene, α-methylstyrene, 3-methylstyrene, 4-propylstyrene, 4-cyclohexylstyrene, 4-dodecylstyrene, 2-ethyl-4-benzylstyrene, 1-vinylnaphthalene, 2-vinylnaphthalene, acrylic acid methyl ester, acrylic acid ethyl ester, acrylic acid propyl ester, acrylic acid butyl ester, acrylic acid pentyl ester, acrylic acid hexyl ester, methacrylic acid methyl ester, N-(methyl)acrylamide, acrylic acid 2-ethylhexyl ester, methacrylic acid 2-ethylhexyl ester, N-(2-ethylhexyl)acrylamide, acrylic acid octyl ester, methacrylic acid octyl ester, N-(octyl)acrylamide, acrylic acid lauryl ester, methacrylic acid lauryl ester, N-(lauryl)acrylamide, acrylic acid stearyl ester, methacrylic acid stearyl ester, N-(stearyl)acrylamide, acrylic acid behenyl ester, methacrylic acid behenyl ester and N-(behenyl)acrylamide or mixtures thereof.

The monomer distribution of the hydrophobically modified copolymers preferred for use as contemplated herein preferably amounts to from about 5% to about 80% by weight, with respect to the monomers that contain sulfonic acid groups, the hydrophobic monomer and the monomer that contains carboxylic acid groups; the amount of the monomer that contains sulfonic acid groups and of the hydrophobic monomer is particularly preferably from about 5% to about 30% by weight each, and the amount of the monomer that contains carboxylic acid groups is from about 60% to about 80% by weight; the monomers here are preferably selected from those listed above.

Surprisingly, it has been found that polypeptide(s) of the present disclosure in combination with a copolymer that comprises monomers that contain sulfonic acid groups (Sulfopolymer) in a dish washing composition, preferably an automatic dish washing composition has several advantages.

Firstly, the compositions do not only clean the dishes surprisingly better, show less filming on glasses, show less limescale accumulation, exhibit excellent shine after rinsing and show less deposits on the dish ware. These compositions also reduce the built up of mixed dirt in the interior of the dishwashing machine, especially the sieve.

Furthermore, the compositions contain specific enzyme stabilizing agents. It has been found that these combinations comprising polypeptide(s) of the present disclosure in combination with a copolymer that comprises monomers that contain sulfonic acid groups (Sulfopolymer) show a better cleaning performance on enzyme related soil. This is due without being bound to the theory due to a better stabilization of the enzymes in the composition. This can be observed especially in dish washing composition that are in form of a liquid or a gel.

Adjunct Materials

Any detergent components known in the art for use in dish wash, especially ADW cleaning detergents may also be utilized. Other optional detergent components include anti-corrosion agents, anti-soil redeposition agents, bactericides, binders, corrosion inhibitors and glass corrosion inhibitors, disintegrants/disintegration agents, dyes, enzyme stabilizers (including boric acid, borates, CMC, and/or polyols such as propylene glycol), fillers/processing aids, foam boosters, foam (suds) regulators, perfumes, soil-suspending agents, suds suppressors, tarnish inhibitors, either alone or in combination. Any ingredient known in the art for use in laundry/ADW/hard surface cleaning detergents may be utilized. The choice of such ingredients is well within the skill of the artisan.

Soil Release Polymers

The detergent compositions of the present disclosure may also include one or more soil release polymers which aid the removal of soils from fabrics such as cotton and polyester based fabrics, in particular the removal of hydrophobic soils from polyester based fabrics. The soil release polymers may for example be nonionic or anionic terephthalate based polymers, polyvinyl caprolactam and related copolymers, vinyl graft copolymers, polyester polyamides. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose derivatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present disclosure may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present disclosure may also include one or more rheology modifiers, structurants or thickeners, as distinct from viscosity reducing agents. The rheology modifiers are selected from the group of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, bactericides, binders, carriers, dyes, enzyme stabilizers, fillers, foam regulators, hydrotropes, perfumes, pigments, sud suppressors, solvents, and structurants for liquid detergents and/or structure elasticizing agents.

Washing Method

The detergent compositions of the present disclosure are ideally suited for dish washing processes. The solution preferably has a pH of from about 5.5 to about 8, further preferably pH selected in the range from about 7.5 to about 13.5, or in the range from about 7.5 to about 12.5, or in the range from about 8.5 to about 11.5, or in the range from about 9.5 to about 10.5, or pH of about 7.5 or above.

A preferred embodiment concerns a method of cleaning, the method comprising the steps of: contacting an object with a high pH cleaning composition (e.g. pH of about 7.5 or above) comprising a beta-glucanase of the present disclosure under conditions suitable for cleaning the object. In a preferred embodiment the cleaning composition is used in a dish wash process.

Still another embodiment relates to a method for removing stains from fabric or dishware which comprises contacting the dishware with a cleaning composition (e.g. pH of about 6.0 or above), preferably a high pH cleaning composition (e.g. pH of about 7.5 or above) comprising a beta-glucanase of the present disclosure under conditions suitable for cleaning the object.

In another embodiment the cleaning composition, preferably the high pH cleaning composition of the present disclosure is suited for use in liquid dish wash applications. Accordingly, the present disclosure includes a method for washing a hard surface such as dishware. The method comprises the steps of contacting the dishware to be cleaned with a solution comprising the dishwashing composition, preferably high pH cleaning composition as contemplated herein. The hard surface may comprise any dishware such as crockery, cutlery, ceramics, plastics such as melamine, metals, china, glass, acrylics. The solution preferably has a pH of about 6.5, e.g. from about 7.5 or above, e.g. from about 9 to about 13.5.

The compositions may be employed at concentrations of from about 100 ppm, preferably about 500 ppm to about 15,000 ppm in solution. The water temperatures typically range from about 5° C. to about 90° C., including about 10° C., about 15° C., about 20° C., about 25° C., about 30° C., about 35° C., about 40° C., about 45° C., about 50° C., about 55° C., about 60° C., about 65° C., about 70° C. and about 75° C., In particular embodiments, the washing method is conducted at a pH of from about 5.0 to about 11.5, or in alternative embodiments, even from about 6 to about 10.5, such as from about 5 to about 11, from about 5 to about 10, from about 5 to about 9, from about 5 to about 8, from about 5 to about 7, from about 5.5 to about 11, from about 5.5 to about 10, from about 5.5 to about 9, from about 5.5 to about 8, from about 5.5. to about 7, from about 6 to about 11, from about 6 to about 10, from about 6 to about 9, from about 6 to about 8, from about 6 to about 7, from about 6.5 to about 11, from about 6.5 to about 10, from about 6.5 to about 9, from about 6.5 to about 8, from about 6.5 to about 7, from about 7 to about 11, from about 7 to about 10, from about 7 to about 9, or from about 7 to about 8, preferably from about 5.5 to about 9, and more preferably from about 6 to about 8. In preferred embodiments the washing method is conducted at a pH selected in the range from about 7.5 to about 13.5, or in the range from about 7.5 to about 12.5, or in the range from about 8.5 to about 11.5, or in the range from about 9.5 to about 10.5, or pH of about 7.5 or above.

In some preferred embodiments, the high pH cleaning compositions provided herein are typically formulated such that, during use in aqueous cleaning operations, the wash water has a pH of from about 9 to about 13.5, or in alternative embodiments, or from about 10 to about 13.5 even from about 11 to about 13.5. In some preferred embodiments the liquid laundry products are formulated to have a pH from about 12 to about 13.5. Techniques for controlling pH at recommended usage levels include the use of buffers, acids, alkalis, etc., and are well known to those skilled in the art. In the context of the present disclosure alkalis are used to adjust pH to from about 9 to about 13.5 preferably from about 10 to about 13.5.

In particular embodiments, the washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

The present disclosure relates to a method of cleaning a dishware or with a detergent composition comprising a beta-glucanase of the present disclosure.

A preferred embodiment concerns a method of cleaning, said method comprising the steps of: contacting an object with a cleaning composition comprising a beta-glucanase of the present disclosure under conditions suitable for cleaning said object. In a preferred embodiment the cleaning composition is a detergent composition and the process is a dish wash process.

Low Temperature Uses

One embodiment of the present disclosure concerns a method of doing dish wash or industrial dish cleaning comprising contacting a surface to be cleaned with a beta-glucanase of the present disclosure, and wherein said dish wash, industrial or institutional dish cleaning is performed at a temperature of about 40° C. or below. One embodiment of the present disclosure relates to the use of a beta-glucanase in dish wash or a cleaning process wherein the temperature in, dish wash, industrial dish cleaning is about 40° C. or below In another embodiment, the present disclosure concerns the use of a beta-glucanase as contemplated herein in a beta-glucan removing process, wherein the temperature in the beta-glucan removing process is about 40° C. or below.

In each of the above-identified methods and uses, the wash temperature is about 40° C. or below, such as about 39° C. or below, such as about 38° C. or below, such as about 37° C. or below, such as about 36° C. or below, such as about 35° C. or below, such as about 34° C. or below, such as about 33° C. or below, such as about 32° C. or below, such as about 31° C. or below, such as about 30° C. or below, such as about 29° C. or below, such as about 28° C. or below, such as about 27° C. or below, such as about 26° C. or below, such as about 25° C. or below, such as about 24° C. or below, such as about 23°

C. or below, such as about 22° C. or below, such as about 21° C. or below, such as about 20° C. or below, such as about 19° C. or below, such as about 18° C. or below, such as about 17° C. or below, such as about 16° C. or below, such as about 15° C. or below, such as about 14° C. or below, such as about 13° C. or below, such as about 12° C. or below, such as about 11° C. or below, such as about 10° C. or below, such as about 9° C. or below, such as about 8° C. or below, such as about 7° C. or below, such as about 6° C. or below, such as about 5° C. or below, such as about 4° C. or below, such as about 3° C. or below, such as about 2° C. or below, such as about 1° C. or below.

In another preferred embodiment, the wash temperature is in the range of from about 5 to about 40° C., such as from about 5 to about 30° C., from about 5 to about 20° C., from about 5 to about 10° C., from about 10 to about 40° C., from about 10 to about 30° C., from about 10 to about 20° C., from about 15 to about 40° C., from about 15 to about 30° C., from about 15 to about 20° C., from about 20 to about 40° C., from about 20 to about 30° C., from about 25 to about 40° C., from about 25 to about 30° C., or from about 30 to about 40° C. In particular preferred embodiments the wash temperature is about 20° C., about 30° C., or about 40° C.

High Temperature Uses

One embodiment of the present disclosure concerns a method of doing dish wash or industrial dish cleaning comprising contacting a surface to be cleaned with a beta-glucanase of the present disclosure, and wherein said dish wash, industrial or institutional dish cleaning is performed at a temperature of about 75° C. or below. One embodiment of the present disclosure relates to the use of a beta-glucanase in dish wash or a industrial dish cleaning process wherein the temperature in dish wash, industrial dish cleaning is about 70° C. or below.

In another embodiment, the present disclosure concerns the use of a beta-glucanase as contemplated herein in a beta-glucan removing process, wherein the temperature in the beta-glucan removing process is about 65° C. or below.

In each of the above-identified methods and uses, the wash temperature is about 60° C. or below, such as about 59° C. or below, such as about 58° C. or below, such as about 57° C. or below, such as about 56° C. or below, such as about 55° C. or below, such as about 54° C. or below, such as about 53° C. or below, such as about 52° C. or below, such as about 51° C. or below, such as about 50° C. or below, such as about 49° C. or below, such as about 48° C. or below, such as about 47° C. or below, such as about 46° C. or below, such as about 45° C. or below, such as about 44° C. or below, such as about 43° C. or below, such as about 42° C. or below, such as about 41° C. or below.

In another preferred embodiment, the wash temperature is in the range of from about 41 to about 90° C., such as from about 41 to about 80° C., from about 41 to about 85° C., from about 41 to about 80° C., from about 41 to about 75° C., from about 41 to about 70° C., from about 41 to about 65° C., from about 41 to about 60° C.

Methods for reducing or preventing soil redeposition using polypeptide(s) or detergent composition comprising polypeptide(s) of the present disclosure An embodiment of the present disclosure is a method for reducing or preventing soil redeposition using a detergent composition comprising polypeptide(s) of the present disclosure.

In one embodiment, the detergent composition further comprises one or more detergent components selected from the group comprising surfactants, builders, hydrotopes, bleaching systems, polymers, adjunct materials, dispersants, soil release polymers, or any mixture thereof. The detergent composition wherein said cleaning or detergent composition is a dish washing composition, said composition may be in the form of a bar, a homogenous tablet, a tablet having two or more layers, a pouch having one or more compartments, the compartment(s) containing one or more different phases, a regular or compact powder, a granulate, a paste, a gel, or a regular, compact or concentrated liquid, two or more liquids and/or gels in a multichamber-bottle and may be used for dish wash.

In another embodiment, the detergent composition wherein said cleaning or detergent composition is a dish washing composition, said composition) comprises one or more additional enzymes selected from the group comprising proteases, amylases, lipases, cutinases, cellulases, endoglucanases, xyloglucanases, pectinases, pectin lyases, xanthanases, peroxidaes, haloperoxygenases, catalases and mannanases, or any mixture thereof.

In a further embodiment, the detergent composition wherein said cleaning or detergent composition is a dish washing composition, said composition comprises one or more detergent components selected from the group comprising surfactants, builders, hydrotopes, bleaching systems, polymers, adjunct materials, dispersants and soil release polymers, or any mixture thereof and one or more additional enzymes selected from the group comprising proteases, amylases, lipases, cutinases, cellulases, endoglucanases, xyloglucanases, pectinases, pectin lyases, xanthanases, peroxidaes, haloperoxygenases, catalases and mannanases, or any mixture thereof.

The method may comprise the following steps:
(a) providing a wash liquor by dissolving/mixing the detergent composition in water;
(b) washing the objects/in the wash liquor;
(c) draining the wash liquor and optionally repeating the wash cycle; and
(d) rinsing and optionally drying the objects.

In a preferred embodiment the method may comprise the following steps:
providing water and rinsing the objects
optionally, draining the water and providing fresh water
dosing the detergent composition into the water to form a wash liquor
agitating the wash liquor, thereby washing the objects, optionally heating the liquor
draining the wash liquor
optionally providing fresh water, rinsing the objects, and draining the liquid
optionally providing fresh water, rinsing the objects, and during this step dosing an optional additional agent into the liquor, e.g. a rinse-aid, optionally heating the liquor, and afterwards draining the liquor.
optionally letting remaining liquid evaporate from the objects.

A preferred embodiment of the present disclosure is a method for reducing soil redeposition using a detergent composition wherein said cleaning or detergent composition is a dish washing composition, said composition comprising: a polypeptide having beta-glucanase activity, selected from the group of:
(a) a polypeptide having at least about 60% sequence identity to the mature polypeptide of the sequence selected from the group of: SEQ ID NO: 2, SEQ ID NO: 3, SEQ ID NO: 5, SEQ ID NO: 7, SEQ ID NO: 9;
(b) a polypeptide encoded by a polynucleotide that hybridizes under low stringency conditions with (i) the mature polypeptide coding sequence of the sequence selected from the group of: SEQ ID NO: 1, SEQ ID NO: 4, SEQ ID NO: 6, SEQ ID NO: 8, or (ii) the full-length complement of (i);
(c) a polypeptide encoded by a polynucleotide having at least about 60% sequence identity to the mature polypeptide coding sequence of the sequence selected from the group of: SEQ ID NO: 1, SEQ ID NO: 4, SEQ ID NO: 6, SEQ ID NO: 8;
(d) a variant of the mature polypeptide of the sequence selected from the group of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
(e) a fragment of the polypeptide of (a), (b), (c), or (d) that has beta-glucanase activity A preferred embodiment of the present disclosure is a method for reducing soil redeposition using a detergent wherein said cleaning or detergent composition is a dish washing composition, said composition comprising: a polypeptide having beta-glucanase activity, selected from the group of:
(a) a polypeptide having at least about 60% sequence identity to the mature polypeptide of the sequence selected from the group of: SEQ ID NO: 2, SEQ ID NO: 3, SEQ ID NO: 5, SEQ ID NO: 7, SEQ ID NO: 9;
(b) a polypeptide encoded by a polynucleotide that hybridizes under low stringency conditions with (i) the mature polypeptide coding sequence of the sequence selected from the group of: SEQ ID NO: 1, SEQ ID NO: 4, SEQ ID NO: 6, SEQ ID NO: 8, or (ii) the full-length complement of (i);
(c) a polypeptide encoded by a polynucleotide having at least about 60% sequence identity to the mature polypeptide coding sequence of the sequence selected from the group of: SEQ ID NO: 1, SEQ ID NO: 4, SEQ ID NO: 6, SEQ ID NO: 8;
(d) a variant of the mature polypeptide of the sequence selected from the group of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
(e) a fragment of the polypeptide of (a), (b), (c), or (d) that has beta-glucanase activity; wherein said cleaning or detergent composition, wherein said cleaning or detergent composition is a dish washing composition, further comprising:
(i) one or more amylases; and/or
(ii) one or more proteases.

The dishwashing compositions of the present disclosure further relate to the following paragraphs:

A polypeptide having beta-glucanase activity, selected from the group of:
(a) a polypeptide having at least about 60% sequence identity to the mature polypeptide of the sequence selected from the group of: SEQ ID NO: 2, SEQ ID NO: 3, SEQ ID NO: 5, SEQ ID NO: 7, SEQ ID NO: 9;
(b) a polypeptide encoded by a polynucleotide that hybridizes under low stringency conditions with (i) the mature polypeptide coding sequence of the sequence selected from the group of: SEQ ID NO: 1, SEQ ID NO: 4, SEQ ID NO: 6, SEQ ID NO: 8, or (ii) the full-length complement of (i);
(c) a polypeptide encoded by a polynucleotide having at least about 60% sequence identity to the mature polypeptide coding sequence of the sequence selected from the group of: SEQ ID NO: 1, SEQ ID NO: 4, SEQ ID NO: 6, SEQ ID NO: 8;
(d) a variant of the mature polypeptide of the sequence selected from the group of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
(e) a fragment of the polypeptide of (a), (b), (c), or (d) that has beta-glucanase activity; preferably said beta-glucanase activity is not an endo-cellulase activity on β-1,4 linkages between D-glucose units of cellulose.

The polypeptide of paragraph 1, having at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% sequence identity to the mature polypeptide of the sequence selected from the group of: SEQ ID NO: 2, SEQ ID NO: 3, SEQ ID NO: 5, SEQ ID NO: 7, SEQ ID NO: 9.

3. The polypeptide of paragraph 1 or 2, which is encoded by a polynucleotide that hybridizes under low stringency conditions, low-medium stringency conditions, medium stringency conditions, medium-high stringency conditions, high stringency conditions, or very high stringency conditions with (i) the mature polypeptide coding sequence of the sequence selected from the group of: SEQ ID NO: 1, SEQ ID NO: 4, SEQ ID NO: 6, SEQ ID NO: 8; or (ii) the full-length complement of (i).

4. The polypeptide of any of paragraphs 1-3, which is encoded by a polynucleotide having at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% sequence identity to the mature polypeptide coding sequence of the sequence selected from the group of: SEQ ID NO: 1, SEQ ID NO: 4, SEQ ID NO: 6, SEQ ID NO: 8.

5. The polypeptide of any of paragraphs 1-4, comprising or of: i) the sequence selected from the group of: SEQ ID NO: 2, SEQ ID NO: 3, SEQ ID NO: 5, SEQ ID NO: 7, SEQ ID NO: 9; or ii) the mature polypeptide of the sequence selected from the group of: SEQ ID NO: 2, SEQ ID NO: 3, SEQ ID NO: 5, SEQ ID NO: 7, SEQ ID NO: 9.

6. The polypeptide of paragraph 5, wherein the mature polypeptide is selected from the group of: amino acids 1 to 351 of SEQ ID NO: 2, amino acids 1 to 351 of SEQ ID NO: 3, amino acids 1 to 245 of SEQ ID NO: 5, amino acids 1 to 222 of SEQ ID NO: 7, amino acids 1 to 214 of SEQ ID NO: 9.

7. The polypeptide of any of paragraphs 1-4, which is a variant of the mature polypeptide of the sequence selected from the group of: i) SEQ ID NO: 2, ii) SEQ ID NO: 3, iii)

SEQ ID NO: 5, iv) SEQ ID NO: 7, v) SEQ ID NO: 9; wherein said variant comprising a substitution, deletion, and/or insertion at one or more positions.

8. The polypeptide of paragraph 1, which is a fragment of the sequence selected from the group of: SEQ ID NO: 2, SEQ ID NO: 3, SEQ ID NO: 5, SEQ ID NO: 7, SEQ ID NO: 9, wherein the fragment has beta-glucanase activity.

9. The polypeptide of any of paragraphs 1-8, wherein said polypeptide is capable of having beta-glucanase activity in an aqueous solution with a pH selected in the range from about 7.5 to about 13.5, wherein said aqueous solution optionally comprises a bleaching agent, preferably said pH is selected in the range from about 7.5 to about 12.5, further preferably said pH is selected in the range from about 8.5 to about 11.5, most preferably said pH is selected in the range from about 9.5 to about 10.5.

10. The polypeptide of any of paragraphs 1-9, wherein said polypeptide is capable of having beta-glucanase activity in an aqueous solution at a temperature selected in the range from about 20° C. to about 75° C., wherein said aqueous solution optionally comprises a bleaching agent, preferably said temperature is selected in the range from about 40° C. to about 60° C.

11. The polypeptide of any of paragraphs 9-10, wherein said polypeptide is capable of having beta-glucanase activity for at least about 15 minutes, preferably for about 30 minutes.

12. The polypeptide of any of paragraphs 1-11, wherein said beta-glucanase activity comprises alkaline beta-glucanase activity, wherein said alkaline beta-glucanase activity is beta-glucanase activity at pH of about 7.5 or above.

13. The polypeptide of any of paragraphs 1-12, wherein said beta-glucanase activity comprises licheninase EC 3.2.1.73 activity, preferably said beta-glucanase activity is licheninase EC 3.2.1.73 activity.

14. A composition comprising one or more polypeptide(s) of any of paragraphs 1-13, said composition is a dish washing composition.

15. The composition of paragraph 14, further comprising one or more detergent components.

16. The composition of paragraph 15, wherein the detergent component is selected from the group of: surfactants, hydrotropes, builders, co-builders, chelators, bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors, enzyme stabilizers, enzyme activators, antioxidants, and solubilizers.

17. The composition of any of paragraphs 14-16, further comprising one or more additional enzymes, preferably said one or more additional enzymes is:
i) one or more amylases, further preferably said one or more amylases is one or more alpha-amylases; or
ii) one or more proteases; or
iii) one or more amylases as in (i) and one or more proteases.

18. The composition of any of paragraphs 14-17, further comprising an enzyme selected from the group of: DNases, perhydrolases, amylases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases, transglutaminases, and combinations thereof.

19. The composition of any of paragraphs 14-18, wherein said composition has pH of about 7.5 or above and optionally, comprises a bleaching agent; preferably said pH is selected in the range from about 7.5 to about 13.5, further preferably said pH is selected in the range from about 7.5 to about 12.5, most preferably said pH is selected in the range from about 8.5 to about 11.5, further most preferably said pH is selected in the range from about 9.5 to about 10.5.

20. The composition of any of paragraphs 14-19, wherein said composition has improved stability and/or performance under alkaline conditions, preferably said alkaline conditions have pH of about 7.5 or above.

21. The composition of any of paragraphs 14-20, wherein said composition is a cleaning or detergent composition, said cleaning or detergent composition is a dish washing composition.

22. Use of one or more polypeptide(s) of any of paragraphs 1-13 or the composition of any of paragraphs 14-21 for degrading a beta-glucan, preferably said beta-glucan is a beta-D-glucan, further preferably said beta-glucan is a beta-1,3-1,4 glucan, most preferably said beta-glucan is a mix-linkage beta-glucan, further most preferably said beta-glucan is a barley beta-glucan or oatmeal beta-glucan (e.g., from cooked oats and/or from cooked and burned-in oats and/or from uncooked oats); optionally said use is carried out under alkaline conditions having pH of about 7.5 or above.

23. Use of one or more polypeptide(s) of any of paragraphs 1-13 or the composition of any of paragraphs 14-21 for washing or cleaning a textile and/or a hard surface such as dish wash including Automatic Dish Wash (ADW), preferably said washing or cleaning is washing or cleaning of cooked oats and/or cooked and burned-in oats and/or uncooked oats; optionally said use is carried out under alkaline conditions having pH of about 7.5 or above.

24. Use of one or more polypeptide(s) of any of paragraphs 1-13 or the composition of any of paragraphs 14-21 in a cleaning process such as laundry or hard surface cleaning including dish wash including Automatic Dish Wash (ADW) and industrial cleaning; optionally said use is carried out under alkaline conditions having pH of about 7.5 or above.

25. Use of one or more polypeptide(s) of any of paragraphs 1-13 or the composition of any of paragraphs 14-21 for laundering and/or hard surface cleaning including dish wash including Automatic Dish Wash (ADW), wherein said polypeptide or said composition has an enzyme detergency benefit; optionally said use is carried out under alkaline conditions having pH of about 7.5 or above.

26. Use of one or more polypeptide(s) of any of paragraphs 1-13 or the composition of any of paragraphs 14-21 for at least one of the following: preventing, reducing or removing a biofilm from an item, preferably a malodor is reduced or removed from said item; optionally said use is carried out under alkaline conditions having pH of about 7.5 or above.

27. A process of degrading a beta-glucan comprising applying one or more polypeptide(s) of any of paragraphs 1-13 or a composition of any of paragraphs 14-21 to said beta-glucan, preferably said beta-glucan is a beta-D-glucan, further preferably said beta-glucan is a beta-1,3-1,4 glucan, most preferably said beta-glucan is a mix-linkage beta-glucan, further most preferably said beta-glucan is a barley beta-glucan or oatmeal beta-glucan (e.g., from cooked oats and/or from cooked and burned-in oats and/or from uncooked oats); optionally, said process is carried out under alkaline conditions having pH of about 7.5 or above.

28. The process of paragraph 27, wherein said beta-glucan is on the surface of a textile or hard surface, such as dish wash, preferably said beta-glucan is from cooked oats and/or from cooked and burned-in oats and/or from uncooked oats.

29. A fermentation broth formulation or cell culture composition comprising the polypeptide of any of paragraphs 1-13.

30. A polynucleotide encoding the polypeptide of any of paragraphs 1-13.

31. A nucleic acid construct or expression vector capable of expressing a polynucleotide of paragraph 30, preferably said nucleic acid construct or said expression vector comprising the polynucleotide of paragraph 30 operably linked to one or more control sequences that direct the production of the polypeptide in an expression host.

32. A recombinant host cell comprising the polynucleotide of paragraph 30, preferably said polynucleotide is operably linked to one or more control sequences that direct the production of the polypeptide, further preferably said recombinant host cell is an isolated recombinant host cell, further most preferably said recombinant host cell is a heterologous host cell (e.g., a host cell that is not a *Bacillus agaradhaerens* host cell or a host cell that is not a *Bacillus* sp-62449 host cell or a host cell that is not a *Bacillus akibai* host cell or a host cell that is not a *Bacillus mojavensis* host cell).

33. A composition comprising at least one of the following: i) a polynucleotide of paragraph 30; or ii) a nucleic acid construct of paragraph 31; or iii) an expression vector of paragraph 31.

34. A method for producing the polypeptide of any of paragraphs 1-13, comprising cultivating a cell, which in its wild-type form produces the polypeptide, under conditions conducive for production of the polypeptide.

35. The method of paragraph 34, further comprising recovering the polypeptide.

36. A method for producing a polypeptide having beta-glucanase activity, comprising cultivating the host cell of paragraph 32 under conditions conducive for production of the polypeptide.

37. The method of paragraph 36, further comprising recovering the polypeptide.

38. A transgenic plant, plant part or plant cell transformed with a polynucleotide encoding the polypeptide of any of paragraphs 1-13.

39. A method for producing a polypeptide having beta-glucanase activity, comprising cultivating the transgenic plant or plant cell of paragraph 38 under conditions conducive for production of the polypeptide.

40. The method of paragraph 39, further comprising recovering the polypeptide.

41. A polypeptide having beta-glucanase activity, wherein said polypeptide is selected from the group of:
(a) a polypeptide having at least about 89% sequence identity to the mature polypeptide of the sequence selected from the group of: SEQ ID NO: 7, SEQ ID NO: 2, SEQ ID NO: 3, SEQ ID NO: 5, SEQ ID NO: 9;
(b) a polypeptide encoded by a polynucleotide having at least about 89% sequence identity to the mature polypeptide coding sequence of the sequence selected from the group of: SEQ ID NO: 6, SEQ ID NO: 1, SEQ ID NO: 4, SEQ ID NO: 8.

42. The polypeptide of paragraph 41, having at least about 90%, at least about 91%, at least about 92%, at least about 93%, at least about 94%, at least about 95%, at least about 96%, at least about 97%, at least about 98%, at least about 99% or about 100% sequence identity to the mature polypeptide of the sequence selected from the group of: SEQ ID NO: 7, SEQ ID NO: 2, SEQ ID NO: 3, SEQ ID NO: 5, SEQ ID NO: 9.

43. The polypeptide of any of paragraphs 41-42, wherein the mature polypeptide is selected from the group of: amino acids 1 to 222 of SEQ ID NO: 7, amino acids 1 to 351 of SEQ ID NO: 2, amino acids 1 to 351 of SEQ ID NO: 3, amino acids 1 to 245 of SEQ ID NO: 5, amino acids 1 to 214 of SEQ ID NO: 9.

44. The polypeptide of any of paragraphs 41-43, wherein said polypeptide is capable of:
i) having beta-glucanase activity for at least about 15 minutes in an aqueous solution with a pH selected in the range from about 7.5 to about 13.5, wherein said aqueous solution optionally comprises a bleaching agent, preferably said pH is selected in the range from about 7.5 to about 12.5, further preferably said pH is selected in the range from about 8.5 to about 11.5, most preferably said pH is selected in the range from about 9.5 to about 10.5; and/or
ii) having beta-glucanase activity for at least about 15 minutes in an aqueous solution at a temperature selected in the range from about 20° C. to about 75° C., wherein said aqueous solution optionally comprises a bleaching agent.

45. The polypeptide of any of paragraphs 41-44, wherein said beta-glucanase activity comprises licheninase EC 3.2.1.73 activity.

46. The polypeptide of paragraph 45, wherein said beta-glucanase activity is licheninase EC 3.2.1.73 activity.

47. A composition comprising one or more polypeptide(s) of any of paragraphs 41-46, said composition is a dish washing composition.

48. The composition of paragraph 47, further comprising:
i) one or more detergent components; and/or
ii) one or more additional enzymes, preferably said one or more additional enzymes is:
a) one or more amylases, further preferably said one or more amylases is one or more alpha-amylases; or
b) one or more proteases; or
c) one or more amylases as in (a) and one or more proteases.

49. The composition of any of paragraphs 47-48, wherein said composition has pH of about 7.5 or above and optionally comprises a bleaching agent; preferably said pH is selected in the range from about 7.5 to about 13.5, further preferably said pH is selected in the range from about 7.5 to about 12.5, most preferably said pH is selected in the range from about 8.5 to about 11.5, further most preferably said pH is selected in the range from about 9.5 to about 10.5.

50. The composition of any of paragraphs 47-49, wherein said composition is a cleaning or a detergent composition, said cleaning or detergent composition is a dish washing composition.

51. Use of one or more polypeptide(s) of any of paragraphs 41-46 or the composition of any of paragraphs 47-50 in a cleaning process such as laundry or hard surface cleaning including dish wash; optionally said use is carried out under alkaline conditions having pH of about 7.5 or above.

52. A fermentation broth formulation or cell culture composition comprising the polypeptide of any of paragraphs 41-46.

53. A polynucleotide encoding the polypeptide of any of paragraphs 41-46.

54. A nucleic acid construct or expression vector capable of expressing a polynucleotide of paragraph 53, preferably said nucleic acid construct or said expression vector comprising the polynucleotide of paragraph 53 operably linked to one or more control sequences that direct the production of the polypeptide in an expression host.

55. A recombinant host cell comprising the polynucleotide of paragraph 53, preferably said polynucleotide is operably linked to one or more control sequences that direct the production of the polypeptide, further preferably said recombinant host cell is an isolated recombinant host cell, further most preferably said recombinant host cell is a heterologous host cell (e.g., a host cell that is not a *Bacillus agaradhaerens* host cell or a host cell that is not a *Bacillus* sp-62449 host cell or a host cell that is not a *Bacillus* akibai host cell or a host cell that is not a *Bacillus mojavensis* host cell).

56. A cleaning or detergent composition comprising one or more polypeptide(s) having beta-glucanase activity, selected from the group of:
(a) a polypeptide having at least about 60% sequence identity to the mature polypeptide of the sequence selected from the group of: SEQ ID NO: 2, SEQ ID NO: 3, SEQ ID NO: 5, SEQ ID NO: 7, SEQ ID NO: 9;
(b) a polypeptide encoded by a polynucleotide that hybridizes under low stringency conditions with (i) the mature polypeptide coding sequence of the sequence selected from the group of: SEQ ID NO: 1, SEQ ID NO: 4, SEQ ID NO: 6, SEQ ID NO: 8, or (ii) the full-length complement of (i);
(c) a polypeptide encoded by a polynucleotide having at least about 60% sequence identity to the mature polypeptide coding sequence of the sequence selected from the group of: SEQ ID NO: 1, SEQ ID NO: 4, SEQ ID NO: 6, SEQ ID NO: 8;
(d) a variant of the mature polypeptide of the sequence selected from the group of: SEQ ID NO: 2, SEQ ID NO: 3, SEQ ID NO: 5, SEQ ID NO: 7, SEQ ID NO: 9, wherein said variant comprising a substitution, deletion, and/or insertion at one or more positions; and
(e) a fragment of the polypeptide of (a), (b), (c), or (d) that has beta-glucanase activity; and
(i) one or more amylases; and/or
(ii) one or more proteases,
preferably said polypeptide having beta-glucanase activity and said one or more amylases and/or one or more proteases have a synergistic effect; further preferably said synergistic effect is a REM synergistic effect, further most preferably said REM synergistic effect is of more than about 6.5 at about 40° C. for about 30 minutes at pH of about 7.5, further most preferably said REM synergistic effect is of more than about 6.1 at about 40° C. for about 30 minutes at pH of about 10, further most preferably said REM synergistic effect is of more than about 6.2 at about 40° C. for about 30 minutes at pH of about 10, further most preferably said beta-glucanase activity is not an endo-cellulase activity on β-1,4 linkages between D-glucose units of cellulose;
said cleaning or detergent composition is a dish washing composition.

57. The cleaning or detergent composition of paragraph 56, wherein said polypeptide has at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% sequence identity to the mature polypeptide of the sequence selected from the group of: SEQ ID NO: 2, SEQ ID NO: 3, SEQ ID NO: 5, SEQ ID NO: 7, SEQ ID NO: 9.

58. The cleaning or detergent composition of paragraph 57 or 58, wherein said polypeptide is encoded by a polynucleotide that hybridizes under low stringency conditions, low-medium stringency conditions, medium stringency conditions, medium-high stringency conditions, high stringency conditions, or very high stringency conditions with (i) the mature polypeptide coding sequence of the sequence selected from the group of: SEQ ID NO: 1, SEQ ID NO: 4, SEQ ID NO: 6, SEQ ID NO: 8; or (ii) the full-length complement of (i).

59. The cleaning or detergent composition of any of paragraphs 56-58, wherein said polypeptide is encoded by a polynucleotide having at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% sequence identity to the mature polypeptide coding sequence of the sequence selected from the group of: SEQ ID NO: 1, SEQ ID NO: 4, SEQ ID NO: 6, SEQ ID NO: 8.

60. The cleaning or detergent composition of any of paragraphs 56-59, wherein said polypeptide comprises or consists of: i) the sequence selected from the group of: SEQ ID NO: 2, SEQ ID NO: 3, SEQ ID NO: 5, SEQ ID NO: 7, SEQ ID NO: 9; or ii) the mature polypeptide of the sequence selected from the group of: SEQ ID NO: 2, SEQ ID NO: 3, SEQ ID NO: 5, SEQ ID NO: 7, SEQ ID NO: 9.

61. The cleaning or detergent composition of paragraph 60, wherein the mature polypeptide is selected from the group of: i) amino acids 1 to 351 of SEQ ID NO: 2, ii) amino acids 1 to 351 of SEQ ID NO: 3, iii) amino acids 1 to 245 of SEQ ID NO: 5, iv) amino acids 1 to 222 of SEQ ID NO: 7, v) amino acids 1 to 214 of SEQ ID NO: 9.

62. The cleaning or detergent composition of any of paragraphs 56-59, wherein said polypeptide is a variant of the mature polypeptide of the sequence selected from the group of: i) SEQ ID NO: 2, ii) SEQ ID NO: 3, iii) SEQ ID NO: 5, iv) SEQ ID NO: 7, v) SEQ ID NO: 9; wherein said variant comprising a substitution, deletion, and/or insertion at one or more positions.

63. The cleaning or detergent composition of paragraph 56, wherein said polypeptide is a fragment of the sequence selected from the group of: SEQ ID NO: 2, SEQ ID NO: 3, SEQ ID NO: 5, SEQ ID NO: 7, SEQ ID NO: 9, wherein the fragment has beta-glucanase activity.

64. The cleaning or detergent composition of any of paragraphs 56-63, wherein said polypeptide is capable of having beta-glucanase activity in an aqueous solution with a pH in the range from about 7.5 to about 13.5, wherein said aqueous solution optionally comprises a bleaching agent, preferably said pH is in the range from about 7.5 to about 12.5, further preferably said pH is in the range from about 8.5 to about 11.5, most preferably said pH is in the range from about 9.5 to about 10.5.

65. The cleaning or detergent composition of any of paragraphs 56-64, wherein said polypeptide is capable of showing beta-glucanase activity in an aqueous solution at a temperature selected in the range from about 20° C. to about 75° C., and/or in the range from about 40° C. to about 60° C., wherein said aqueous solution optionally comprises a bleaching agent.

66. The cleaning or detergent composition of any of paragraphs 64-65, wherein said polypeptide is capable of having beta-glucanase activity for at least about 15 minutes, preferably for at least about 30 minutes.

67. The cleaning or detergent composition of any of paragraphs 56-66, wherein said beta-glucanase activity comprises alkaline beta-glucanase activity, wherein said alkaline beta-glucanase activity is beta-glucanase activity at pH of about 7.5 or above.

68. The cleaning or detergent composition of any of paragraphs 56-67, wherein said beta-glucanase activity comprises licheninase EC 3.2.1.73 activity, preferably said beta-glucanase activity is licheninase EC 3.2.1.73 activity.

69. The cleaning or detergent composition of any of paragraphs 56-68, wherein said amylase is an alpha-amylase.

70. The cleaning or detergent composition of any of paragraphs 56-69, further comprising one or more detergent components.

71. The cleaning or detergent composition of paragraph 70, wherein the detergent component is selected from the group of: surfactants, hydrotropes, builders, co-builders, chelators, bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors, enzyme stabilizers, enzyme activators, antioxidants, and solubilizers.

72. The cleaning or detergent composition of any of paragraphs 56-71, further comprising one or more additional enzymes.

73. The cleaning or detergent composition of any of paragraphs 56-72, further comprising an enzyme selected from the group of: DNases, perhydrolases, amylases, proteases, peroxidases, cellulases, betaglucanases, xyloglucanases, hemicellulases, xanthanases, xanthan lyases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-beta-mannanases, exo-beta-mannanases, pectin methylesterases, cellobiohydrolases, transglutaminases, and combinations thereof.

74. The cleaning or detergent composition of any of paragraphs 56-73, wherein said composition has pH of about 7.5 or above and optionally, comprises a bleaching agent; preferably said pH is selected in the range from about 7.5 to about 13.5, further preferably said pH is selected in the range from about 7.5 to about 12.5, most preferably said pH is selected in the range from about 8.5 to about 11.5, further most preferably said pH is selected in the range from about 9.5 to about 10.5.

75. The cleaning or detergent composition of any of paragraphs 69-74, wherein said alpha-amylase is selected from the group of:

(a) a polypeptide having at least about 90% sequence identity to SEQ ID NO: 13 (corresponding to SEQ ID NO: 2 of WO 95/10603);

(b) a polypeptide having at least about 90% sequence identity to SEQ ID NO: 13 (corresponding to SEQ ID NO: 2 in WO 95/10603) wherein the polypeptide comprises a substitution in one or more of positions: 15, 23, 105, 106, 124, 128, 133, 154, 156, 178, 179, 181, 188, 190, 197, 201, 202, 207, 208, 209, 211, 243, 264, 304, 305, 391, 408, and/or 444;

(c) a polypeptide having at least about 90% sequence identity to SEQ ID NO: 14 (corresponding to SEQ ID NO: 6 in WO 02/010355);

(d) a polypeptide having at least about 90% sequence identity to the hybrid polypeptide of SEQ ID NO: 15 (comprising residues 1-33 of SEQ ID NO: 6 of WO 2006/066594 and residues 36-483 of SEQ ID NO: 4 of WO 2006/066594);

(e) a polypeptide having at least about 90% sequence identity to the hybrid polypeptide of SEQ ID NO: 15 (comprising residues 1-33 of SEQ ID NO: 6 of WO 2006/066594 and residues 36-483 of SEQ ID NO: 4 of WO 2006/066594), wherein the hybrid polypeptide comprises a substitution, a deletion or an insertion in one of more of positions: 48, 49, 107, 156, 181, 190, 197, 201, 209 and/or 264;

(f) a polypeptide having at least about 90% sequence identity to SEQ ID NO: 16 (corresponding to SEQ ID NO: 6 of WO 02/019467);

(g) a polypeptide having at least about 90% sequence identity to SEQ ID NO: 16 (corresponding to SEQ ID NO: 6 of WO 02/019467), wherein the polypeptide comprises a substitution, a deletion or an insertion in one of more of positions: 181, 182, 183, 184, 195, 206, 212, 216 and/or 269;

(h) a polypeptide having at least about 90% sequence identity to SEQ ID NO: 17, SEQ ID NO: 18 or SEQ ID NO: 19 (corresponding to SEQ ID NO: 1, SEQ ID NO: 2 or SEQ ID NO: 7 of WO 96/023873)

(i) a polypeptide having at least about 90% sequence identity to SEQ ID NO: 17, SEQ ID NO: 18 or SEQ ID NO: 19 (corresponding to SEQ ID NO: 1, SEQ ID NO: 2 or SEQ ID NO: 7 of WO 96/023873), wherein the polypeptide comprises a substitution, a deletion or an insertion in one of more of positions: 140, 183, 184 195, 206, 243, 260, 304 and/or 476;

(j) a polypeptide having at least about 90% sequence identity to SEQ ID NO: 20 (corresponding to SEQ ID NO: 2 of WO 08/153815);

(k) a polypeptide having at least about 90% sequence identity to SEQ ID NO: 21 (corresponding to SEQ ID NO: 10 of WO 01/66712);

(l) a polypeptide having at least about 90% sequence identity to SEQ ID NO: 21 (corresponding to SEQ ID NO: 10 of WO 01/66712), wherein the polypeptide comprises a substitution, a deletion or an insertion in one of more of positions: 176, 177, 178, 179, 190, 201, 207, 211 and/or 264;

(m) a polypeptide having at least about 90% sequence identity to SEQ ID NO: 22 (corresponding to SEQ ID NO: 2 of WO 09/061380);

(n) a polypeptide having at least about 90% sequence identity to SEQ ID NO: 22 (corresponding to SEQ ID NO: 2 of WO 09/061380), wherein the polypeptide comprises a substitution, a deletion or an insertion in one of more of positions: 87, 98, 125, 128, 131, 165, 178, 180, 181, 182, 183, 201, 202, 225, 243, 272, 282, 305, 309, 319, 320, 359, 444 and/or 475;

(o) a polypeptide having at least about 90% sequence identity to SEQ ID NO: 21, wherein the polypeptide comprises a substitution, a deletion or an insertion in one or more of positions: 28, 118, 174; 181, 182, 183, 184, 186, 189, 195, 202, 298, 299, 302, 303, 306, 310, 314; 320, 324, 345, 396, 400, 439, 444, 445, 446, 449, 458, 471 and/or 484; and (p) a polypeptide having at least about 90% sequence identity to SEQ ID NO: 12;

(q) a variant of SEQ ID NO:23 having alterations G182*+ D183*;

(r) a variant of SEQ ID NO:24 having alterations H183*+ G184*+I405L+A421H+A422P+A428T;

(s) a variant of SEQ ID NO:24 having alterations M9L+ R118K+G149A+G182T+G186A+D183*+G184*+N195F+ M202L+T257I+Y295F+N299Y+R320K+M323T+A339S+ E345R+R458K;

(t) a variant of SEQ ID NO: 24 having alterations R178*+ G179*+E187P+I203Y+R458N+T459S+D460T+G476K (u) a variant of SEQ ID NO: 27 having alteration M202L;

(v) a variant of SEQ ID NO: 28 having alterations R180*+ S181*+S243Q+G475K;

(w) a variant of SEQ ID NO: 29 having alterations D183*+ G184*+W140Y+N195F+I206Y+Y243F+E260G+G304R+ G476K;

(x) a variant of SEQ ID NO: 30 having alterations H1*+ N54S+V56T+K72R+G109A+F113Q+R116Q+W167F+ Q172G+A174S+G184T+N195F+V206L+K391A+P473R+ G476K;

(y) a variant of SEQ ID NO: 31 having alterations M9L+ R118K+G149A+G182T+G186A+D183*+G184*+N195F+ T246V+T257I+Y295F+N299Y+R320K+M323T+A339S+ E345R+R458K.

76. The cleaning or detergent composition of any of paragraphs 56-75, wherein said protease is selected from the group of:

1) a polypeptide having protease activity, which has at least about 60% sequence identity (e.g., at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% sequence identity) to SEQ ID NO: 34;

2) a polypeptide having protease activity, which has at least about 60% sequence identity (e.g., at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% sequence identity) to SEQ ID NO: 35;

3) a polypeptide having protease activity, which has at least about 60% sequence identity (e.g., at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% sequence identity) to SEQ ID NO: 36.

77. The cleaning or detergent composition of any of paragraphs 56-76, wherein said composition has improved stability and/or performance under alkaline conditions, preferably said alkaline conditions have pH of about 7.5 or above.

78. The cleaning or detergent composition of any of paragraphs 56-77, wherein said composition is in form selected from a group of: a bar, a homogenous tablet, a tablet having two or more layers, a pouch having one or more compartments, a regular or compact powder, a granule, a paste, a gel, or a regular, compact or concentrated liquid.

79. The cleaning or detergent composition of any of paragraphs 56-78, having an enzyme detergency benefit in cleaning or detergent applications.

80. The cleaning or detergent composition of any of paragraphs 56-79 having improved stability and/or performance, preferably said improved stability and/or performance is under alkaline conditions having pH of about 7.5 or above.

81. A method for removing a stain from a surface which comprises contacting the surface with a composition according to any of paragraphs 56-80.

82. Use of the cleaning or detergent composition of any of paragraphs 56-80 for degrading a beta-glucan, preferably said beta-glucan is a beta-D-glucan, further preferably said beta-glucan is a beta-1,3-1,4 glucan, most preferably said beta-glucan is a mix-linkage beta-glucan, further most preferably said beta-glucan is a barley beta-glucan or oatmeal beta-glucan (e.g., from cooked oats and/or from cooked and burned-in oats and/or from uncooked oats); optionally said use is carried out under alkaline conditions having pH of about 7.5 or above.

83. Use of the cleaning or detergent composition of any of paragraphs 56-80 for washing or cleaning a textile and/or a hard surface such as dish wash including Automatic Dish Wash (ADW), preferably said washing or cleaning is washing or cleaning of cooked oats and/or cooked and burned-in oats and/or uncooked oats; optionally said use is carried out under alkaline conditions having pH of about 7.5 or above.

84. Use of the cleaning or detergent composition of any of paragraphs 56-80 in a cleaning process such as laundry or hard surface cleaning including dish wash including Automatic Dish Wash (ADW) and industrial cleaning; optionally said use is carried out under alkaline conditions having pH of about 7.5 or above.

85. Use of the cleaning or detergent composition of any of paragraphs 56-80 for laundering and/or hard surface cleaning including dish wash including Automatic Dish Wash (ADW), wherein said composition has an enzyme detergency benefit; optionally said use is carried out under alkaline conditions having pH of about 7.5 or above.

86. Use of the cleaning or detergent composition of any of paragraphs 56-80 for at least one of the following: preventing, reducing or removing a biofilm from an item, preferably a malodor is reduced or removed from said item; optionally said use is carried out under alkaline conditions having pH of about 7.5 or above.

87. A process of degrading a beta-glucan comprising applying the cleaning or detergent composition of any of paragraphs 56-80 to said beta-glucan, preferably said beta-glucan is a beta-D-glucan, further preferably said beta-glucan is a beta-1,3-1,4 glucan, most preferably said beta-glucan is a mix-linkage beta-glucan, further most preferably said beta-glucan is a barley beta-glucan or oatmeal beta-glucan (e.g., from cooked oats and/or from cooked and burned-in oats and/or from uncooked oats); optionally, said process is carried out under alkaline conditions having pH of about 7.5 or above.

88. The process of paragraph 87, wherein said beta-glucan is on the surface of a textile or hard surface, such as dish wash.

89. A method for reducing or preventing soil redeposition using a polypeptide or detergent composition of any of preceding paragraphs, preferably said detergent composition is a dish washing composition.

90. The method of paragraph 89, wherein the detergent composition also comprises one or more further enzymes.

91. The method of any of paragraphs 89-90, wherein the further enzymes are selected from the group comprising proteases, amylases, lipases, cutinases, cellulases, endoglucanases, xyloglucanases, pectinases, pectin lyases, xanthanases, peroxidaes, haloperoxygenases, catalases and mannanases, or any mixture thereof.

92. The method of any of paragraphs 89-91, wherein the detergent composition also comprises one or more detergent components.

93. The method of any of paragraphs 89-92, wherein the detergent components are selected from the group comprising surfactants, builders, hydrotopes, bleaching systems, polymers, fabric hueing agents, adjunct materials, dispersants, dye transfer inhibiting agents, fluorescent whitening agents and soil release polymers, or any mixture thereof.

94. The method of any of paragraphs 89-93, wherein the detergent composition is in the form of a bar, a homogenous tablet, a tablet having two or more layers, a pouch having one or more compartments, a regular or compact powder, a granulate, a paste, a gel, or a regular, compact or concentrated liquid.

95. The method of any of paragraphs 89-94, for dish wash or laundering.

96. Use of one or more polypeptide(s) or cleaning or detergent composition of any of preceding paragraphs for one or more of the following:
a) reducing or preventing soil redeposition, preferably said use is in a cleaning process or during a cleaning process, further preferably said cleaning or detergent composition is a dish wash composition, further preferably said cleaning process is a dish washing process;
b) removal of cereal containing soil, especially dried-on cereal containing soil, preferably oat flakes containing soil, especially dried-on oat flakes containing soil and/or cooked oats containing soil, and/or cooked and burned-in oats containing soil, and/or uncooked oats containing soil, further preferably said use is in a cleaning process or during a cleaning process, further most preferably said cleaning process is a dish washing process;
c) facilitating removal of starch-containing soil in the presence of one or more amylases (e.g., according to any of the preceding paragraphs) and/or for enhancing amylase related cleaning performance, preferably said use is in a cleaning process or during a cleaning process, further preferably said cleaning process is t a dish washing process
d) facilitating removal of protein-containing soil in the presence of one or more proteases (e.g., according to any of the preceding paragraphs) and/or for enhancing protease related cleaning performance, preferably said use is in a cleaning process or during a cleaning process, further preferably said cleaning process is a dish washing process.

97. The cleaning or detergent composition of any of preceding paragraphs, wherein said composition has pH of about 6 or above, preferably about 7 or above, more preferably about 7.5 or above and optionally comprises a bleaching agent; preferably said pH is in the range from about 7.5 to about 13.5, further preferably said pH is in the range from about 7.5 to about 12.5, most preferably said pH is in the range from about 8.5 to about 11.5, further most preferably said pH is in the range from about 9.5 to about 10.5; preferably said cleaning or detergent composition is a dish washing composition.

98. The cleaning or detergent composition of any of preceding paragraphs, further comprising a copolymer that contains at least one sulfonic acid containing monomer, preferably in an amount from about 0.1 to about 20% by weight, in particular from about 0.5 to about 18% by weight, particularly preferably from about 1.0 to about 15% by weight, in particular from about 4 to about 14% by weight, particularly from about 6 to about 12% by weight, preferably said cleaning or detergent composition is a dish washing composition.

99. The cleaning or detergent composition of any of preceding paragraphs, wherein said composition comprises said polypeptide in concentrations of from about 0.00001 mg enzyme protein/g composition to about 100 mg enzyme protein/g composition, preferred from about 0.0001 mg enzyme protein/g composition to about 50 mg enzyme protein/g composition, more preferred from about 0.001 mg enzyme protein/g composition to about 20 mg enzyme protein/g composition, especially preferred from about 0.01 mg enzyme protein/g composition to about 10 mg enzyme protein/g composition; preferably said cleaning or detergent composition is a dish washing composition.

The present disclosure is further described by the following examples that should not be construed as limiting the scope of the present disclosure.

EXAMPLES

Detergent compositions used in the example sections as described herein included the following:

TABLE A

| Model detergent A: | | |
|---|---|---|
| Compound | Content of compound (% w/w) | Active component (% w/w) |
| LAS | 12.0 | 97 |
| AEOS, SLES | 17.6 | 28 |
| Soy fatty acid | 2.8 | 90 |
| Coco fatty acid | 2.8 | 99 |
| AEO | 11.0 | 100 |

TABLE A-continued

Model detergent A:

| Compound | Content of compound (% w/w) | Active component (% w/w) |
|---|---|---|
| Sodium hydroxide | 1.8 | 99 |
| Ethanol/Propan-2-ol | 3.0 | 90/10 |
| MPG | 6.0 | 98 |
| Glycerol | 1.7 | 99.5 |
| TEA | 3.3 | 100 |
| Sodium formate | 1.0 | 95 |
| Sodium citrate | 2.0 | 100 |
| DTMPA (as Na7-salt) | 0.5 | 42 |
| PCA (as Na-salt) | 0.5 | 40 |
| Phenoxy ethanol | 0.5 | 99 |
| Ion exchanged water | 33.6 | — |

Water hardness was adjusted to 15° dH by addition of $CaCl_2$, $MgCl_2$, and $NaHCO_3$ ($Ca^{2+}:Mg^{2+}:HCO_{3-}$ = 4:1:7.5) to the test system.

TABLE B

Model detergent X:

| Compound | Content of compound (% w/w) | Active component (% w/w) |
|---|---|---|
| LAS | 16.5 | 91 |
| AEO* | 2 | 99.5 |
| Sodium carbonate | 20 | 100 |
| Sodium (di)silicate | 12 | 82.5 |
| Zeolite A | 15 | 80 |
| Sodium sulfate | 33.5 | 100 |
| PCA | 1 | 100 |

*Model detergent X was mixed without AEO. AEO was added separately before wash.
Water hardness was adjusted to 12° dH by addition of $CaCl_2$, $MgCl_2$, and $NaHCO_3$ ($Ca^{2+}:Mg^{2+}:HCO_{3-}$ = 2:1:4.5) to the test system.

TABLE C

Model detergent Z without bleach:

| Compound | Content of compound (% w/w) | % active component (% w/w) |
|---|---|---|
| LAS | 7.0 | 85.3 |
| Soap | 1.1 | 93 |
| AEO* | 1.5 | 99.5 |
| Soda ash | 20.1 | 99.5 |
| Hydrous sodium silicate | 10.0 | 80.1 |
| Zeolite A | 5.0 | 80 |
| Sodium citrate | 2.0 | 100 |
| HEDP-Na4 | 0.2 | 84 |
| Polyaerylate | 1.1 | 92 |
| Sodium sulfate | 52.0 | 100 |

*Model detergent Z without bleach was mixed without AEO. AEO was added separately before wash.
Water hardness was adjusted to 15° dH by addition of $CaCl_2$, $MgCl_2$, and $NaHCO_3$ ($Ca^{2+}:Mg^{2+}:HCO_{3-}$ = 4:1:7.5) to the test system. pH was used as is (10.6) or adjusted to 11.3 with 4M NaOH.

TABLE D

Model detergent Z with bleach:

| Compound | Content of compound (%w/w) | % active component (% w/w) |
|---|---|---|
| LAS | 7.0 | 85.3 |
| Soap | 1.1 | 93 |
| AEO* | 1.5 | 99.5 |
| Soda ash | 20.1 | 99.5 |
| Hydrous sodium silicate | 10.0 | 80.1 |
| Zeolite A | 5.0 | 80 |
| Sodium citrate | 2.0 | 100 |
| HEDP-Na4 | 0.2 | 84 |

TABLE D-continued

Model detergent Z with bleach:

| Compound | Content of compound (%w/w) | % active component (% w/w) |
|---|---|---|
| Polyaerylate | 1.1 | 92 |
| Sodium percarbonate | 9.3 | 86 |
| TEAD | 1.1 | 91.8 |
| Sodium sulfate | 41.6 | 100 |

*Model detergent Z with bleach was mixed without AEO. AEO was added separately before wash.
Water hardness was adjusted to 15° dH by addition of $CaCl_2$, $MgCl_2$, and $NaHCO_3$ ($Ca^{2+}:Mg^{2+}:HCO_{3-}$ = 4:1:7.5) to the test system. pH was either as is (10.5) or adjusted to 11.1 with 4M NaOH.

TABLE E

ADW model detergent A:

| Compound | Content of compound (% w/w) | Active component (% w/w) |
|---|---|---|
| MGDA (Trilon M Granules SG) | 20 | 59 |
| Sodium citrate | 20 | 100 |
| Sodium carbonate | 20 | 100 |
| Sodium percarbonate | 10 | 88 |
| Sodium Silicate | 5 | 80 |
| Sodium sulfate | 12 | 100 |
| Acusol 588G | 5 | 92 |
| TAED | 3 | 92 |
| Surfac 23-6.5 (liq) | 5 | 100 |

Water hardness was adjusted to 21° dH by addition of $CaCl_2$, $MgCl_2$, and $NaHCO_3$ ($Ca^{2+}:Mg^{2+}:HCO_{3-}$ = 4:1:10) to the test system.

Example 1: Determination of Beta-Glucanase (Lichenase) Activity

An AZCL-Barley beta-glucan (azurine dye covalently cross-linked beta-glucan) assay was used for detection of endo-glucanase activity (Lichenase activity).

AZCL-Barley beta-glucan (75 mg) was suspended in 15 mL detergent (Model detergents A, X, Z with and without bleach and pH adjusted, ADW Model A). To 1 mL of this solution in Eppendorf tubes was added 10 μL enzyme (0.33 mg enzyme protein/Liter), incubated for 15 min at 40° C. while shaking at 1250 rpm in a pre-heated thermo mixer and spun down for 2 min at 13200 rpm, diluted 5 times with a 5% Triton-X-100 including 10 μM $CaCl_2$ and 250 μL of the solution was transferred to a micro-titer plate and the sample absorbance was measured at 590 nm.

Example 2: Cloning, Expression and Purification of GH16 Endo-β-1,3-1,4-Glucanase from the Genus *Bacillus*

The beta-glucanases were derived from bacterial strains obtain either from the German collection of Microorganisms and Cell Cultures (DSMZ) or by isolation from environmental samples by classical microbiological techniques according to Table 1.

TABLE 1

Source and Source country of GH16 endo-β-1,3-1,4-glucanase from the genus *Bacillus*:

| Strain name | Source | Source Country |
|---|---|---|
| *Bacillus* sp-62449 | Environmental sample | United States |
| *Bacillus akibai* | Soil | Greece |

TABLE 1-continued

Source and Source country of GH16 endo-β-1,3-
1,4-glucanase from the genus *Bacillus*:

| Strain name | Source | Source Country |
|---|---|---|
| *Bacillus agaradhaerens* | Soil | United States |
| *Bacillus mojavensis* | DSMZ (DSM9205) | United States |

Chromosomal DNA from pure cultures of the individual strains was purified and subjected to full genome sequencing using Illumina technology. The assembled genome sequence and subsequent analysis of the 16S ribosomal subunit gene sequences confirmed the identity of the strains.

The individual genes encoding β-1,3-1,4-glucanases were amplified by PCR and fused with regulatory elements and homology regions for recombination into the *B. subtilis* genome.

The linear integration construct was a SOE-PCR fusion product (Horton, R. M., Hunt, H. D., Ho, S. N., Pullen, J. K. and Pease, L. R. (1989) Engineering hybrid genes without the use of restriction enzymes, gene splicing by overlap extension Gene 77: 61-68) made by fusion of the gene between two *Bacillus subtilis* chromosomal regions along with strong promoters and a chloramphenicol resistance marker. The SOE PCR method is also described in patent application WO 2003095658.

The gene was expressed under the control of a triple promoter system (as described in WO 99/43835), of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence.

The gene was expressed with a *Bacillus clausii* secretion signal (encoding the following amino acid sequence: MKKPLGKIVASTALLISVAFSSSIASA (SEQ ID NO: 10) replacing the native secretion signal. Furthermore the expression construct results in the addition of a N-terminal poly histidine affinity purification tag of the sequence HHHHHHPR (SEQ ID NO: 11) to the expressed mature protein.

The SOE-PCR product was transformed into *Bacillus subtilis* and integrated in the chromosome by homologous recombination into the pectate lyase locus. Subsequently, a recombinant *Bacillus subtilis* clone containing the integrated expression construct was grown in rich liquid culture. The culture broth was centrifuged (20000×g, 20 min) and the supernatant was carefully decanted from the precipitate and used for purification of the enzyme.

Purification of Recombinant Enzymes by Nickel Affinity Chromatography

The pH of the cleared supernatant was adjusted to pH 8, filtrated through a 0.2 μM filter, and the supernatant applied to a 5 ml HisTrap™ excel column. Prior to loading, the column had been equilibrated in 5 column volumes (CV) of 50 mM Tris/HCl pH 8. In order to remove unbound material, the column was washed with 8 CV of 50 mM Tris/HCl pH 8, and elution of the target was obtained with 50 mM HEPES pH 7+10 mM imidazole. The eluted protein was desalted on a HiPrep™ 26/10 desalting column, equilibrated using 3 CV of 50 mM HEPES pH 7+100 mM NaCl. This buffer was also used for elution of the target, and the flow rate was 10 ml/min. Relevant fractions were selected and pooled based on the chromatogram and SDS-PAGE analysis.

Example 3: AZCL-Assay with Beta-Glucanase Enzymes

In this example enzymatic activity were measured on AZCL-Barely beta-glucan substrate under various pH's, temperature and detergent thus modeling various laundry conditions. Measurements of enzymatic activity were carried out as described in example 1, but without the 5 times dilution with 5% Triton-X-100 including 10 μM $CaCl_2$). Comparisons were made with beta-glucanase from *Bacillus amyloliquefaciens* and beta-glucanase from *Bacillus subtilis* in Model detergent A, Model detergent X, Model detergent Z with bleach, Model detergent Z without bleach, Model detergent Z with bleach pH-adjusted and Model Z without bleach pH-adjusted detergent compositions.

TABLE 2

Beta-glucanase activity measured under various pH's, temperatures and laundry detergents using the AZCL-Barley beta-glucan assay (Absorbance):

| Enzyme | pH 7.7 Model A | | pH 10.1 Model X | | pH 10.5 Model Z with bleach | | pH 10.6 Model Z without bleach | | pH 11.1 Model Z with bleach pH-adjusted | | pH 11.3 Model Z without bleach pH-adjusted | |
|---|---|---|---|---|---|---|---|---|---|---|---|---|
| | 40° C. | 60° C. | 40° C. | 60° C. | 40° C. | 60° C. | 40° C. | 60° C. | 40° C. | 60° C. | 40° C. | 60° C. |
| *B. amyloliquefaciens* beta-glucanase/lichenase | 2.44 | 0.71 | 2.83 | 0.83 | 0.05 | 0.04 | 0.10 | 0.01 | 0.01 | 0.03 | 0.07 | 0.01 |
| *B. subtilis* beta-glucanase/lichenase | 2.45 | 0.62 | 3.41 | 0.30 | 0.05 | 0.01 | 0.08 | 0.01 | 0.00 | 0.04 | 0.07 | 0.02 |
| *B. akibai* Beta-glucanase/lichenase | 0.18 | 0.10 | 3.41 | 1.55 | 0.03 | 0.37 | 0.05 | 0.27 | 0.03 | 0.15 | 0.04 | 0.05 |
| *B. agaradhaerens* beta-glucanase/lichenase | 0.36 | 0.70 | 3.41 | 2.50 | 0.58 | 0.16 | 0.47 | 0.04 | 0.17 | 0.03 | 0.01 | 0.02 |

TABLE 2-continued

Beta-glucanase activity measured under various pH's, temperatures and laundry detergents using the AZCL-Barley beta-glucan assay (Absorbance):

| Enzyme | pH 7.7 Model A | | pH 10.1 Model X | | pH 10.5 Model Z with bleach | | pH 10.6 Model Z without bleach | | pH 11.1 Model Z with bleach pH-adjusted | | pH 11.3 Model Z without bleach pH-adjusted | |
|---|---|---|---|---|---|---|---|---|---|---|---|---|
| | 40° C. | 60° C. | 40° C. | 60° C. | 40° C. | 60° C. | 40° C. | 60° C. | 40° C. | 60° C. | 40° C. | 60° C. |
| B. sp-62449 beta-glucanase/lichenase | 1.22 | 1.15 | 3.25 | 0.08 | 0.22 | 0.10 | 0.30 | 0.11 | 0.05 | 0.04 | 0.04 | 0.01 |
| B. mojavensis beta-glucanase/lichenase | 1.65 | 0.20 | 3.41 | 2.36 | 0.17 | 0.11 | 0.18 | 0.01 | 0.03 | 0.03 | 0.01 | 0.02 |

For details of the model detergent compositions see Tables A-D above.

Example 4: AZCL-Assay of Enzyme Activity on AZCL-Beta-Barley Substrate in Automated Dish Wash Model Detergent Measurements of enzymatic activity were carried out as described in example 1. In this example enzymatic activities of novel beta-glucanases were compared to enzymatic activities of beta-glucanases from *Bacillus amyloliquefaciens* and *Bacillus subtilis* in the automated dish wash detergent ADW model A. The obtained data are shown in Table 3 below:

TABLE 3

Beta-glucanase activity measured under various temperatures in ADW Model A detergent using the AZCL-Barley beta-glucan assay (Absorbance), pH of the ADW model detergent A was 10.2:

| Enzyme | ADW model detergent A | |
|---|---|---|
| | 40° C. | 60° C. |
| Blank | 0.07 | 0.11 |
| *Bacillus amyloliquefaciens* beta-glucanase (lichenase) | 0.46 | 0.34 |
| *Bacillus subtilis* beta-glucanase (lichenase) | 0.42 | 0.21 |
| *Bacillus akibai* beta-glucanase (lichenase) | 0.15 | 2.07 |
| *Bacillus agaradhaerens* beta-glucanase (lichenase) | 0.85 | 1.77 |
| *Bacillus mojavensis* beta-glucanase (lichenase) | 0.85 | 1.06 |
| *Bacillus sp-62449* beta-glucanase (lichenase) | 1.60 | 0.49 |

Example 5: Beta-Glucanase Stability Measured by TSA

In this example stability of novel beta-glucanases were compared to stabilities of beta-glucanases from *Bacillus amyloliquefaciens* and *Bacillus subtilis*. Thermal shift assays (TSA) were performed with enzyme samples diluted to 0.3 mg/ml in assay buffers: 0.1 M succinic acid, 0.1 M HEPES, 0.1 M CHES, 0.1 M CAPS, 0.15 M KCl, 1 mM CaCl2, 0.01% Triton X100, pH adjusted to 5, 7.5 and 10 respectively. SYPRO Orange dye (Life Technologies S6650) diluted 101× in mQ water. 10 µl diluted enzyme sample+10 µl assay buffer+10 µl dye were mixed in wells of TSA assay plates (LightCycler 480 Multiwell plate 96, white (Roche) and covered with optic seal (LightCycler 480 Sealing foil, Roche). Protein melting analysis was conducted at 25-99° C. at 200° C./h in a Roche Lightcycler 480 II machine running Roche LightCycler 480 software (release 1.5.0 SP4). All samples were analyzed in duplicate. The reported readout is Tm, defined as the midpoint value of the protein melting curves. The obtained data are shown in Table 4 below.

TABLE 4

Stability measured by TSA:

| Enzyme | Buffer pH | TSA |
|---|---|---|
| *Bacillus akibai* beta-glucanase (lichenase) | 5 | 70.9 |
| | 7.5 | 71.8 |
| | 10 | 71.6 |
| *Bacillus agaradhaerens* beta-glucanase (lichenase) | 5 | 58.2 |
| | 7.5 | 64.0 |
| | 10 | 58.6 |
| *Bacillus mojavensis* beta-glucanase (lichenase) | 5 | 72.8 |
| | 7.5 | 71.2 |
| | 10 | 72.2 |
| *Bacillus sp-62449* beta-glucanase (lichenase) | 5 | 43.2 |
| | 7.5 | 53.9 |
| | 10 | 49.4 |
| *Bacillus amyloliquefaciens* beta-glucanase (lichenase) | 5 | 72.8 |
| | 7.5 | 70.1 |
| | 10 | 73.2 |
| *Bacillus subtilis* beta-glucanase (lichenase) | 5 | 64.2 |
| | 7.5 | 64.7 |
| | 10 | 64.8 |

Example 6: Beta-Glucanase Substrate Specificity

The substrate specificities of beta-glucanases were further tested using various AZCL-assays from Megazymes (AZCL-Barely beta-glucan, AZCL-HE-cellulose, AZCL-pachyman and AZCL-curdlan (azurine dye covalently cross-linked beta-glucan). The AZCL-substrate (75 mg) was suspended in 15 mL model detergent X. To 1 mL of this solution in Eppendorf tubes was added 10 µL enzyme (0.33 mg enzyme protein/Liter), incubated for 15 min at 40° C. while shaking at 1250 rpm in a pre-heated thermo mixer and spun down for 2 min at 13200 rpm, diluted 5 times with a 5% Triton-X-100 including 10 µM CaCl$_2$) and 250 µL of the solution was transferred to a micro-titer plate and the sample absorbance was measured at 590 nm.

In this example substrate specificity of all 6 beta-glucanases (i.e. from *Bacillus akibai*, *Bacillus agaradhaerens*, *Bacillus mojavensis*, *Bacillus* sp-62449, *Bacillus amyloliquefaciens* and *Bacillus subtilis*) were tested on AZCL-Barley beta-glucan, AZCL-HE-Cellulose AZCL-pachyman and AZCL-curdlan substrates. The obtained results have further confirmed that all 6 tested beta-glucanases have activity on AZCL-Barley beta-glucan substrate only (i.e. positive reaction on AZCL-Barley beta-glucan as a substrate and negative reactions on AZCL-HE-Cellulose AZCL-pachyman and AZCL-curdlan as substrates, Table 5 below). The data shows that tested beta-glucanases only showed activity on beta-glucans containing both beta-1,3 and beta-1,4 linkages and not beta-glucans of pure beta-1,4-glucans or beta-1,3 glucans only or a mixture of beta-1,3- and beta-1,6 linkages. Based on the above results, beta-glucanases of the present disclosure can be further distinguished from endo-cellulases within beta-glucanase definition as used herein, said endo-cellulases having activity on β-1,4 linkages between D-glucose units of cellulose. Based on the above it is concluded that beta-glucanases of the present disclosure have licheninase (EC 3.2.1.73) enzymatic activity.

TABLE 5

Substrate specificity of 6 beta-glucanases measured by AZCL-substrates:

| Substrate | Reaction | Substrate for the assay of: | Polymer description |
|---|---|---|---|
| AZCL-Barley beta-glucan | Yes | Lichenase, endo-glucanase and cellulase | β-1,4; β-1,3 linkages between D-glucose units |
| AZCL-HE-cellulose | No | Endo-cellulase | β-1,4 linkages between D-glucose units |
| AZCL-curdlan | No | Endo-1,3-beta-D-glucanase | β-1,3 linkages between D-glucose |
| AZCL-pachyman | No | Endo-1,3-beta-D-glucanase | β-1,3 linkages between D-glucose units (branched with β-1,6 glucose units average on every 4) |

Example 7: Synergistic Effect of Beta-Glucanases (Lichenases) of the Present Disclosure when Combined with an Alpha-Amylase I. Wascator Bottle Wash Method Description:
A Wascator bottle wash method was used to detect the performance of the enzymes. In a Wascator washing machine (FOM 71 Lab) bottles (60 mL, DSE PP 70X35 Aseptisk, material No.: 216-2620, from VWR) with 25 mL detergent solution including enzyme(s) and four stains (035KC Chocolate porridge oat from Equest, 2 cm in diameter) were added. Two kg ballast (tea towels, cotton) was included in the washing machine. Washed in 25 L water for 30 min at 40° C. in liquid and powder model detergents for laundry (model detergent A1 and model detergent X1, respectively) and in ADW model detergent (ADW model detergent A1). After wash the stains were rinsed with tap water twice (3 L) and dried ON at rt (room temperature) in drying cabinet (Electrolux, Intuition, EDD2400). The remission was measured on a spectrophotometer (Macbeth Color-Eye 7000 Remissions) at 460 nm.

II. Results:
In this example the results of combining the individual lichenases with an alpha-amylase (Stainzyme) (SEQ ID NO: 12) were studied in order to investigate a potential synergistic effect between the two enzymes in various detergents with various pHs using the Wascator bottle wash method. Comparisons were made with lichenase from *Bacillus amyloliquefaciens* and lichenase from *Bacillus subtilis* in Model detergent A1, Model detergent X1 and ADW model detergent A1 using 0.01 mg enzyme protein per liter of lichenase and 0.05 mg enzyme protein per liter of Stainzyme at 40° C. The detailed conditions used in this example are described in Tables F-K and the results are shown in Tables 6-8 below.

TABLE F

Experimental condition:

| | |
|---|---|
| Detergent | Model detergent A1 (see Table G below) |
| Detergent dosage | 3.33 g/L |
| Test solution volume | 25 mL |
| pH | As is |
| Wash time | 30 minutes |
| Temperature | 40° C. |
| Water hardness | 15° dH |
| Amylase concentration in test | 0.05 mg/L |
| Beta-glucanase (Lichenase) concentration in test | 0.01 mg/L |
| Test material | O35 KC Chocolate porridge oats |

TABLE G

Model detergent A1:

| Compound | Content of compound (% w/w) | Active component (% w/w) |
|---|---|---|
| LAS | 12.0 | 97 |
| AEOS, SLES | 17.6 | 28 |
| Soy fatty acid | 2.8 | 90 |
| Coco fatty acid | 2.8 | 99 |
| AEO | 11.0 | 100 |
| Sodium hydroxide | 1.8 | 99 |
| Ethanol/Propan-2-ol | 3.0 | 90/10 |
| MPG | 6.0 | 98 |
| Glycerol | 1.7 | 99.5 |
| TEA | 3.3 | 100 |
| Sodium formate | 1.0 | 95 |
| Sodium citrate | 2.0 | 100 |
| DTMPA (as $Na_7$-salt) | 0.5 | 42 |
| PCA (as Na-salt) | 0.5 | 40 |
| Phenoxy ethanol | 0.5 | 99 |
| Ion exchanged water | 33.6 | — |

Water hardness was adjusted to 15° dH by addition of CaCl2, MgCl2, and NaHCO3 (Ca2+:Mg2+:HCO3— = 4:1:7.5) to the test system.

TABLE H

Experimental condition:

| | |
|---|---|
| Detergent | Model detergent X1 (see Table I below) |
| Detergent dosage | 1.75 g/L |
| Test solution volume | 25 mL |
| pH | As is |
| Wash time | 30 minutes |
| Temperature | 40° C. |
| Water hardness | 12° dH |
| Amylase concentration in test | 0.05 mg/L |
| Beta-glucanase (Lichenase) concentration in test | 0.01 mg/L |
| Test material | O35 KC Chocolate porridge oats |

TABLE I

Model detergent X1:

| Compound | Content of compound (% w/w) | Active component (% w/w) |
|---|---|---|
| LAS | 16.5 | 91 |
| AEO* | 2 | 99.5 |
| Sodium carbonate | 20 | 100 |
| Sodium (di)silicate | 12 | 82.5 |
| Zeolite A | 15 | 80 |
| Sodium sulfate | 33.5 | 100 |
| PCA | 1 | 100 |

*Model detergent X1 is mixed without AEO. AEO is added separately before wash.

Water hardness was adjusted to 12° dH by addition of CaCl2, MgCl2, and NaHCO3 (Ca2+:Mg2+:HCO3— = 2:1:4.5) to the test system.

TABLE J

| Experimental condition: | |
|---|---|
| Detergent | ADW model detergent A1 (see Table K below) |
| Detergent dosage | 3.77 g/L |
| Test solution volume | 25 mL |
| pH | As is |
| Wash time | 30 minutes |
| Temperature | 40° C. |
| Water hardness | 15° dH |
| Amylase concentration in test | 0.05 mg/L |

TABLE J-continued

| Experimental condition: | |
|---|---|
| Beta-glucanase (Lichenase) concentration in test | 0.01 mg/L |
| Test material | O35 KC Chocolate porridge oats |

TABLE K

ADW model detergent A1:

| Compound | Content of compound (% w/w) | Active component (% w/w) |
|---|---|---|
| MGDA (Trilon M Granules SG) | 20 | 59 |
| Sodium citrate | 20 | 100 |
| Sodium carbonate | 20 | 100 |
| Sodium percarbonate | 10 | 88 |
| Sodium Silicate | 5 | 80 |
| Sodium sulfate | 12 | 100 |
| Acusol 588G | 5 | 92 |
| TAED | 3 | 92 |
| Surfac 23-6.5 (liq) | 5 | 100 |

Water hardness was adjusted to 21° dH by addition of CaCl2, MgCl2, and NaHCO3 (Ca2+:Mg2+:HCO3— = 4:1:10) to the test system.

Abbreviations as used herein:
REM=Measured value
ΔREM=REM−Blank
REM combined=Measured value
ΔREM combined=REM combined−Blank
ΔREM theoretic=ΔREM (Amylase)+ΔREM (Lichenase)
REM Synergistic effect=ΔREM combined−ΔREM theoretic

TABLE 6

Wascator bottle wash in Model detergent A1 at 40° C., 30 min (pH 7.7):

| | Enzymes solo | | REM combined | ΔREM combined | ΔREM theoretic | REM Synergistic effect |
|---|---|---|---|---|---|---|
| | REM | ΔREM | | | | |
| Beta-glucanase (Lichenase) in combination with the amylase (Stainzyme) | | | | | | |
| B. agaradhaerens beta-glucanase (lichenase) | 66.0 | 0.4 | 80.1 | 14.5 | 6.7 | 7.8 |
| B. akibai beta-glucanase (lichenase) | 65.3 | −0.2 | 79.1 | 13.6 | 6.1 | 7.5 |
| B. mojavensis beta-glucanase (lichenase) | 65.8 | 0.2 | 79.3 | 13.7 | 6.5 | 7.2 |
| B. SP-62449 beta-glucanase (lichenase) | 64.9 | −0.7 | 80.0 | 14.4 | 5.6 | 8.8 |
| B. amyloliquefaciens beta-glucanase (lichenase) | 67.3 | 1.8 | 79.5 | 13.9 | 8.1 | 5.9 |
| B. subtilis beta-glucanase (lichenase) | 67.3 | 1.7 | 80.1 | 14.5 | 8.0 | 6.5 |
| Stainzyme | 71.8 | 6.3 | — | — | — | — |
| Blank | 65.5 | 0.0 | — | — | — | — |

TABLE 7

Wascator bottle wash in Model detergent X1 at 40° C., 30 min (pH 10.1):

| | Enzymes solo | | REM combined | ΔREM combined | ΔREM theoretic | REM Synergistic effect |
|---|---|---|---|---|---|---|
| | REM | ΔREM | | | | |
| *B. agaradhaerens* beta-glucanase (lichenase) | 61.4 | −0.4 | 74.5 | 12.7 | 4.4 | 8.2 |
| *B. akibai* beta-glucanase (lichenase) | 62.2 | 0.3 | 74.9 | 13.1 | 5.2 | 7.9 |
| *B. mojavensis* beta-glucanase (lichenase) | 61.8 | −0.1 | 74.3 | 12.4 | 4.8 | 7.6 |
| B. SP-62449 beta-glucanase (lichenase) | 61.9 | 0.1 | 73.0 | 11.1 | 5.0 | 6.1 |
| *B. amyloliquefaciens* beta-glucanase (lichenase) | 59.9 | −1.9 | 72.0 | 10.2 | 2.9 | 7.3 |
| *B. subtilis* beta-glucanase (lichenase) | 60.8 | −1.0 | 71.8 | 10.0 | 3.8 | 6.1 |
| Stainzyme | 66.7 | 4.9 | — | — | — | — |
| Blank | 61.8 | 0.0 | — | — | — | — |

TABLE 8

Wascator bottle wash in ADW Model detergent A1 at 40° C., 30 min (pH 10.2):

| | Enzymes solo | | REM combined | ΔREM combined | ΔREM theoretic | REM Synergistic effect |
|---|---|---|---|---|---|---|
| | REM | ΔREM | | | | |
| *B. agaradhaerens* beta-glucanase (lichenase) | 60.5 | −2.1 | 75.1 | 12.5 | 6.1 | 6.4 |
| *B. akibai* beta-glucanase (lichenase) | 60.7 | −1.9 | 73.9 | 11.3 | 6.3 | 5.0 |
| *B. mojavensis* beta-glucanase (lichenase) | 63.0 | 0.3 | 73.3 | 10.7 | 8.5 | 2.1 |
| B. SP-62449 beta-glucanase (lichenase) | 60.8 | −1.8 | 74.5 | 11.9 | 6.4 | 5.5 |
| *B. amyloliquefaciens* beta-glucanase (lichenase) | 61.6 | −1.0 | 71.3 | 8.6 | 7.2 | 1.4 |
| *B. subtilis* beta-glucanase (lichenase) | 58.1 | −4.5 | 72.5 | 9.9 | 3.7 | 6.2 |
| Stainzyme | 70.8 | 8.2 | — | — | — | — |
| Blank | 62.6 | 0.0 | — | — | — | — |

Example 8: Determination of the pH Optimum

Subsequently, the pH optimum of all 6 beta-glucanases was determined on 0.4% w/v AZCL-glucan(barley) substrate in Britton Robinson buffer (100 mM phosphoric acid, 100 mM acetic acid, 100 mM boric acid, 0.01% Trinton X-100, 100 mM KCl, 2 mM CaCl$_2$) adjusted to pH 2-12 with NaOH. An enzyme dilution expected to be in the high end of the linear assay range was selected for all pH values under investigation. The pH optimum was investigated in the pH 2-10 range, and for a few samples both lower and higher pH values were included to positively identify the optimum. The results are shown in this Table 9.

TABLE 9 pH optimum of beta-glucanases (lichenases):

| Organism | Mw, kDa | pI | A595/ mg | pH optimum | pH 10/ pH opt |
|---|---|---|---|---|---|
| Bacillus amyloliquefaciens | 24 | 5.2 | 765 | 6 | 0.01 |
| Bacillus subtilis | 24 | 6.1 | 242 | 6 | 0.11 |
| Bacillus sp-62449 | 40 | 4.4 | 763 | 8 | 0.73 |
| Bacillus akibai | 29 | 5.2 | 5 | 6-9 | 0.9 |
| Bacillus agaradhaerens | 27 | 4.5 | 106 | 9 | 0.68 |
| Bacillus mojavensis | 25 | 7.4 | 313 | 8 | 0.23 |

Based on the above a number of observations were made:
The beta-glucanase from *Bacillus amyloliquefaciens* and *Bacillus subtilis* was found to have a pH optimum of 6.0, and relative to this activity only between 1-11% percent activity at pH 10.0. The new bacterial beta-glucanases were found to have pH optimum ranging from pH 6-9, but with a significantly higher relative activity at pH 10 ranging from 23-90% compared to the enzymes from *Bacillus subtilis* and *Bacillus amyloliquefaciens*. The GH16 beta-glucanase from *B. akibai* had a very broad pH optimum.

Example 9: Synergistic Effect of Lichenases Combined with Alpha-Amylases

I. Wascator Bottle Wash Method Description:
A Wascator bottle wash method was used to detect the performance of the enzymes. In a Wascator washing machine (FOM 71 Lab) was added bottles (60 mL, DSE PP 70X35 Aseptisk, material #: 216-2620, from VWR) with 25 mL detergent solution including enzyme(s) and four stains (035KC Chocolate porridge oat from Warwick Equest Ltd, Unit 55, Consett Business Park, Consett, County Durham, DH8 6BN, United Kingdom, 2 cm in diameter). Two kg ballast (tea towels, cotton) was included in the washing machine. Washed in 25 L water for 20 or 30 min at 40° C. in liquid and powder model detergents for laundry (model detergent A and model detergent X, respectively) and in ADW model detergent (ADW model detergent A). After wash the stains were rinsed with tap water twice (3 L) and dried overnight at room temperature in drying cabinet (Electrolux, Intuition, EDD2400). The remission was measured on a spectrophotometer (Macbeth Color-Eye 7000 Remissions) at 460 nm.

II. Results:
In this example the results of combining the individual mature lichenases of *Bacillus agaradhaerens* Lichenase (SEQ ID NO: 39, His-tagged, recombinant), *Bacillus* akibai Lichenase (SEQ ID NO: 38, His-tagged, recombinant), *Bacillus mojavensis* Lichenase (SEQ ID NO: 40, His-tagged, recombinant), *Bacillus* sp-62449 Lichenase (SEQ ID NO: 37, His-tagged, recombinant), *Bacillus amyloliquefaciens* Lichenase (SEQ ID NO: 32) and *Bacillus subtilis* Lichenase (SEQ ID NO: 33) with different amylases as outlined below were studied in order to investigate a potential synergy effect between the two enzymes in various detergents with various pHs using the Wascator bottle wash method. Comparisons were made with lichenase from *Bacillus amyloliquefaciens* and lichenase from *Bacillus subtilis* in Model detergent A, Model detergent X and ADW model detergent A using lichenase concentration of 0.01 mg enzyme protein per liter and amylase concentration of 0.05 mg enzyme protein per liter at 40° C. The detailed conditions are described in Tables 10-15 and the results are shown in Tables 16-47 below.

TABLE 10

| Experimental condition | |
|---|---|
| Detergent | Model detergent A (see Table 11) |
| Detergent dosage | 3.33 g/L |
| Test solution volume | 25 mL |
| pH | As is |
| Wash time | 20 or 30 minutes |
| Temperature | 40° C. |
| Water hardness | 15° dH |
| Amylase concentration in test | 0.05 mg/L |
| Lichenase concentration in test | 0.01 mg/L |
| Test material | O35 KC Chocolate porridge oats |

TABLE 11

Model detergent A

| Compound | Content of compound (% w/w) | Active component (% w/w) |
|---|---|---|
| LAS | 12.0 | 97 |
| AEOS, SLES | 17.6 | 28 |
| Soy fatty acid | 2.8 | 90 |
| Coco fatty acid | 2.8 | 99 |
| AEO | 11.0 | 100 |
| Sodium hydroxide | 1.8 | 99 |
| Ethanol/Propan-2-ol | 3.0 | 90/10 |
| MPG | 6.0 | 98 |
| Glycerol | 1.7 | 99.5 |
| TEA | 3.3 | 100 |
| Sodium formate | 1.0 | 95 |
| Sodium citrate | 2.0 | 100 |
| DTMPA (as $Na_7$-salt) | 0.5 | 42 |
| PCA (as Na-salt) | 0.5 | 40 |
| Phenoxy ethanol | 0.5 | 99 |
| Ion exchanged water | 33.6 | — |

Water hardness was adjusted to 15° dH by addition of $CaCl_2$, $MgCl_2$, and $NaHCO_3$ ($Ca^{2+}:Mg^{2+}:HCO_3^- = 4:1:7.5$) to the test system.

TABLE 12

| Experimental condition | |
|---|---|
| Detergent | Model detergent X (see Table 13) |
| Detergent dosage | 1.75 g/L |
| Test solution volume | 25 mL |
| pH | As is |
| Wash time | 20 or 30 minutes |
| Temperature | 40° C. |
| Water hardness | 12° dH |
| Amylase concentration in test | 0.05 mg/L |
| Lichenase concentration in test | 0.01 mg/L |
| Test material | O35 KC Chocolate porridge oats |

TABLE 13

Model detergent X

| Compound | Content of compound (% w/w) | Active component (% w/w) |
|---|---|---|
| LAS | 16.5 | 91 |
| AEO* | 2 | 99.5 |
| Sodium carbonate | 20 | 100 |
| Sodium (di)silicate | 12 | 82.5 |
| Zeolite A | 15 | 80 |
| Sodium sulfate | 33.5 | 100 |
| PCA | 1 | 100 |

*Model detergent X is mixed without AEO. AEO is added separately before wash.
Water hardness was adjusted to 12° dH by addition of $CaCl_2$, $MgCl_2$, and $NaHCO_3$ ($Ca^{2+}:Mg^{2+}:HCO_3^- = 2:1:4.5$) to the test system.

TABLE 14

| Experimental condition | |
|---|---|
| Detergent | ADW model detergent A (see Table 15) |
| Detergent dosage | 3.77 g/L |
| Test solution volume | 25 mL |
| pH | As is |
| Wash time | 20 or 30 minutes |
| Temperature | 40° C. |
| Water hardness | 21° dH |
| Amylase concentration in test | 0.05 mg/L |
| Lichenase concentration in test | 0.01 mg/L |
| Test material | O35 KC Chocolate porridge oats |

TABLE 15

ADW model detergent A

| Compound | Content of compound (% w/w) | Active component (% w/w) |
|---|---|---|
| MGDA (Trilon M Granules SG) | 20 | 59 |
| Sodium citrate | 20 | 100 |
| Sodium carbonate | 20 | 100 |
| Sodium percarbonate | 10 | 88 |
| Sodium Silicate | 5 | 80 |
| Sodium sulfate | 12 | 100 |
| Acusol 588G | 5 | 92 |
| TAED | 3 | 92 |
| Surfac 23-6.5 (liq) | 5 | 100 |

Water hardness was adjusted to 21° dH by addition of CaCl2, MgCl2, and NaHCO3 ($Ca^{2+}:Mg^{2+}:HCO3^- = 4:1:10$) to the test system.

Abbreviations

REM=Measured value

ΔREM=REM−Blank

REM combined=Measured value

ΔREM combined=REM combined−Blank

ΔREM theoretic=ΔREM (Amylase)+ΔREM (Lichenase)

REM Synergy effect=ΔREM combined−ΔREM theoretic

TABLE 16

Wascator bottle wash in Model detergent A at 40° C., 30 min (pH 7.7)

| | Enzymes solo | | REM combined | ΔREM combined | ΔREM theoretic | REM Synergy effect |
|---|---|---|---|---|---|---|
| | REM | ΔREM | | | | |
| *Bacillus agaradhaerens* lichenase | 65.1 | −0.4 | 80.1 | 14.6 | 5.9 | 8.7 |
| *Bacillus Akibai* Lichenase | 66.3 | 0.9 | 79.1 | 13.6 | 7.2 | 6.4 |
| *Bacillus Mojavensis* Lichenase | 65.8 | 0.3 | 79.3 | 13.8 | 6.7 | 7.1 |
| *Bacillus* SP-62449 Lichenase | 64.9 | −0.6 | 78.7 | 13.2 | 5.8 | 7.5 |
| *Bacillus amyloliquefaciens* lichenase | 66.1 | 0.7 | 79.5 | 14.0 | 7.0 | 7.0 |
| *Bacillus Subtillis* Lichenase | 67.3 | 1.8 | 80.1 | 14.6 | 8.2 | 6.4 |
| Amylase having SEQ ID NO: 12 | 71.8 | 6.3 | — | — | — | — |
| Blank | 65.5 | 0.0 | — | — | — | — |

TABLE 17

Wascator bottle wash in Model detergent A at 40° C., 30 min (pH 7.7)

Lichenase in combination with the amylase, which is the variant of SEQ ID NO: 23 having alterations G182* + D183*

| | Enzymes solo | | REM combined | ΔREM combined | ΔREM theoretic | REM Synergy effect |
|---|---|---|---|---|---|---|
| | REM | ΔREM | | | | |
| *Bacillus agaradhaerens* lichenase | 63.9 | 0.4 | 76.2 | 12.7 | 6.1 | 6.6 |

TABLE 17-continued

Wascator bottle wash in Model detergent A at 40° C., 30 min (pH 7.7)

|  | Enzymes solo | | Lichenase in combination with the amylase, which is the variant of SEQ ID NO: 23 having alterations G182* + D183* | | | |
| --- | --- | --- | --- | --- | --- | --- |
|  | REM | ΔREM | REM combined | ΔREM combined | ΔREM theoretic | REM Synergy effect |
| *Bacillus Akibai* Lichenase | 63.5 | 0.1 | 75.3 | 11.9 | 5.8 | 6.1 |
| *Bacillus Mojavensis* Lichenase | 65.0 | 1.6 | 74.5 | 11.1 | 7.3 | 3.8 |
| *Bacillus* SP-62449 Lichenase | 64.6 | 1.1 | 75.0 | 11.6 | 6.9 | 4.7 |
| *Bacillus amyloliquefaciens* lichenase | 65.7 | 2.3 | 75.6 | 12.2 | 8.0 | 4.2 |
| Amylase, which is the variant of SEQ ID NO: 23 having alterations G182* + D183* | 69.2 | 5.7 | — | — | — | — |
| Blank | 63.4 | 0.0 | — | — | — | — |

TABLE 18

Wascator bottle wash in Model detergent A at 40° C., 30 min (pH 7.7)

|  | Enzymes solo | | Lichenase in combination with the amylase, which is the variant of SEQ ID NO: 24 having alterations H183* + G184* + I405L + A421H + A422P + A428T | | | |
| --- | --- | --- | --- | --- | --- | --- |
|  | REM | ΔREM | REM combined | ΔREM combined | ΔREM theoretic | REM Synergy effect |
| *Bacillus agaradhaerens* lichenase | 63.9 | 0.4 | 77.5 | 14.1 | 8.6 | 5.5 |
| *Bacillus Akibai* Lichenase | 63.5 | 0.1 | 78.1 | 14.7 | 8.3 | 6.4 |
| *Bacillus Mojavensis* Lichenase | 65.0 | 1.6 | 77.9 | 14.5 | 9.7 | 4.7 |
| *Bacillus* SP-62449 Lichenase | 64.6 | 1.1 | 77.1 | 13.6 | 9.3 | 4.3 |
| Amylase, which is the variant of SEQ ID NO: 24 having alterations H183* + G184* + I405L + A421H + A422P + A428T | 71.6 | 8.1 | — | — | — | — |
| Blank | 63.4 | 0.0 | — | — | — | — |

TABLE 19

Wascator bottle wash in Model detergent A at 40° C., 30 min (pH 7.7)

| | Enzymes solo | | REM combined | ΔREM combined | ΔREM theoretic | REM Synergy effect |
|---|---|---|---|---|---|---|
| | REM | ΔREM | | | | |
| *Bacillus agaradhaerens* lichenase | 65.1 | −0.4 | 75.9 | 10.4 | 6.4 | 4.0 |
| *Bacillus Akibai* Lichenase | 66.3 | 0.9 | 75.8 | 10.4 | 7.7 | 2.7 |
| *Bacillus Mojavensis* Lichenase | 65.8 | 0.3 | 76.9 | 11.4 | 7.1 | 4.3 |
| *Bacillus* SP-62449 Lichenase | 64.9 | −0.6 | 75.9 | 10.4 | 6.2 | 4.2 |
| *Bacillus amyloliquefaciens* lichenase | 66.1 | 0.7 | 76.7 | 11.2 | 7.5 | 3.7 |
| *Bacillus Subtillis* Lichenase | 67.3 | 1.8 | 76.9 | 11.4 | 8.6 | 2.8 |
| Amylase, which is the variant of SEQ ID NO: 24 having alterations M9L + R118K + G149A + G182T + G186A + D183* + G184* + N195F + M202L + T257I + Y295F + N299Y + R320K + M323T + A339S + E345R + R458K | 72.3 | 6.8 | — | — | — | — |
| Blank | 65.5 | 0.0 | — | — | — | — |

Lichenase in combination with the amylase, which is the variant of SEQ ID NO: 24 having alterations M9L + R118K + G149A + G182T + G186A + D183* + G184* + N195F + M202L + T257I + Y295F + N299Y + R320K + M323T + A339S + E345R + R458K

TABLE 20

Wascator bottle wash in Model detergent A at 40° C., 20 min (pH 7.7)

| | Enzymes solo | | REM combined | ΔREM combined | ΔREM theoretic | REM Synergy effect |
|---|---|---|---|---|---|---|
| | REM | ΔREM | | | | |
| *Bacillus agaradhaerens* lichenase | 64.0 | −0.8 | 77.7 | 13.0 | 10.6 | 2.3 |
| *Bacillus Akibai* Lichenase | 64.7 | −0.1 | 77.6 | 12.8 | 11.3 | 1.5 |
| *Bacillus* SP-62449 Lichenase | 64.0 | −0.8 | 77.4 | 12.6 | 10.6 | 2.0 |
| Amylase, which is the variant of SEQ ID NO: 24 having alterations | 76.2 | 11.4 | — | — | — | — |

Lichenase in combination with the amylase, which is the variant of SEQ ID NO: 24 having alterations R178* + G179* + E187P + I203Y + R458N + T459S + D460T + G476K

TABLE 20-continued

Wascator bottle wash in Model detergent A at 40° C., 20 min (pH 7.7)

|  | Enzymes solo | | REM | ΔREM | ΔREM | REM Synergy |
|---|---|---|---|---|---|---|
|  | REM | ΔREM | combined | combined | theoretic | effect |
| R178* + G179* + E187P + I203Y + R458N + T459S + D460T + G476K |  |  |  |  |  |  |
| Blank | 64.8 | 0.0 | — | — | — | — |

TABLE 21

Wascator bottle wash in Model detergent A at 40° C., 30 min (pH 7.7)

Lichenase in combination with the amylase, which is the variant of SEQ ID NO: 27 having alteration M202L

|  | Enzymes solo | | REM | ΔREM | ΔREM | REM Synergy |
|---|---|---|---|---|---|---|
|  | REM | ΔREM | combined | combined | theoretic | effect |
| *Bacillus agaradhaerens* lichenase | 65.1 | −0.4 | 72.2 | 6.7 | 3.7 | 3.0 |
| *Bacillus Mojavensis* Lichenase | 65.8 | 0.3 | 73.4 | 7.9 | 4.5 | 3.5 |
| *Bacillus* SP-62449 Lichenase | 64.9 | −0.6 | 71.5 | 6.1 | 3.6 | 2.5 |
| *Bacillus amyloliquefaciens* lichenase | 66.1 | 0.7 | 72.1 | 6.6 | 4.8 | 1.8 |
| Amylase, which is the variant of SEQ ID NO: 27 having alteration M202L | 69.6 | 4.2 | — | — | — | — |
| Blank | 65.5 | 0.0 | — | — | — | — |

TABLE 22

Wascator bottle wash in Model detergent A at 40° C., 30 min (pH 7.7)

Lichenase in combination with the amylase, which the variant of SEQ ID NO: 28 having alterations R180* + S181* + S243Q + G475K

|  | Enzymes solo | | REM | ΔREM | ΔREM | REM Synergy |
|---|---|---|---|---|---|---|
|  | REM | ΔREM | combined | combined | theoretic | effect |
| *Bacillus agaradhaerens* lichenase | 65.1 | −0.4 | 79.2 | 13.7 | 6.0 | 7.7 |
| *Bacillus Akibai* Lichenase | 66.3 | 0.9 | 75.9 | 10.4 | 7.3 | 3.1 |
| *Bacillus Mojavensis* Lichenase | 65.8 | 0.3 | 79.0 | 13.5 | 6.8 | 6.7 |

TABLE 22-continued

Wascator bottle wash in Model detergent A at 40° C., 30 min (pH 7.7)

|  | Enzymes solo | | REM combined | ΔREM combined | ΔREM theoretic | REM Synergy effect |
|---|---|---|---|---|---|---|
|  | REM | ΔREM | | | | |
| Bacillus SP-62449 Lichenase | 64.9 | −0.6 | 78.9 | 13.5 | 5.8 | 7.6 |
| Bacillus amyloliquefaciens lichenase | 66.1 | 0.7 | 77.9 | 12.5 | 7.1 | 5.4 |
| Bacillus Subtillis Lichenase | 67.3 | 1.8 | 78.2 | 12.7 | 8.2 | 4.5 |
| Amylase, which the variant of SEQ ID NO: 28 having alterations R180* + S181* + S243Q + G475K | 71.9 | 6.4 | — | — | — | — |
| Blank | 65.5 | 0.0 | — | — | — | — |

Lichenase in combination with the amylase, which the variant of SEQ ID NO: 28 having alterations R180* + S181* + S243Q + G475K

TABLE 23

Wascator bottle wash in Model detergent A at 40° C., 30 min (pH 7.7)

Lichenase in combination with the amylase of SEQ ID NO: 29 having alterations D183* + G184* + W140Y + N195F + I206Y + Y243F + E260G + G304R + G476K

|  | Enzymes solo | | REM combined | ΔREM combined | ΔREM theoretic | REM Synergy effect |
|---|---|---|---|---|---|---|
|  | REM | ΔREM | | | | |
| Bacillus agaradhaerens lichenase | 65.1 | −0.4 | 77.4 | 11.9 | 7.9 | 4.0 |
| Bacillus Akibai Lichenase | 66.3 | 0.9 | 77.9 | 12.4 | 9.2 | 3.2 |
| Bacillus Mojavensis Lichenase | 65.8 | 0.3 | 79.1 | 13.6 | 8.7 | 5.0 |
| Bacillus SP-62449 Lichenase | 64.9 | −0.6 | 79.6 | 14.1 | 7.8 | 6.3 |
| Bacillus amyloliquefaciens lichenase | 66.1 | 0.7 | 77.7 | 12.3 | 9.0 | 3.3 |
| Bacillus Subtillis Lichenase | 67.3 | 1.8 | 77.2 | 11.8 | 10.2 | 1.6 |
| Amylase of SEQ ID NO: 29 having alterations D183* + G184* + W140Y + N195F + I206Y + Y243F + E260G + G304R + G476K | 73.8 | 8.4 | — | — | — | — |
| Blank | 65.5 | 0.0 | — | — | — | — |

TABLE 24

Wascator bottle wash in Model detergent A at 40° C., 30 min (pH 7.7)

|  | Enzymes solo | | REM combined | ΔREM combined | ΔREM theoretic | REM Synergy effect |
|---|---|---|---|---|---|---|
|  | REM | ΔREM | | | | |

Lichenase in combination with the amylase, which is the variant of SEQ ID NO: 30 having alterations H1* + N54S + V56T + K72R + G109A + F113Q + R116Q + W167F + Q172G + A174S + G184T + N195F + V206L + K391A + P473R + G476K

| | | | | | | |
|---|---|---|---|---|---|---|
| *Bacillus agaradhaerens* lichenase | 65.1 | −0.4 | 80.6 | 15.1 | 5.9 | 9.2 |
| *Bacillus Akibai* Lichenase | 66.3 | 0.9 | 79.4 | 13.9 | 7.2 | 6.8 |
| *Bacillus Mojavensis* Lichenase | 65.8 | 0.3 | 79.4 | 14.0 | 6.6 | 7.3 |
| *Bacillus* SP-62449 Lichenase | 64.9 | −0.6 | 80.2 | 14.7 | 5.7 | 9.0 |
| *Bacillus amyloliquefaciens* lichenase | 66.1 | 0.7 | 79.5 | 14.1 | 7.0 | 7.1 |
| *Bacillus Subtillis* Lichenase | 67.3 | 1.8 | 80.2 | 14.7 | 8.1 | 6.6 |
| Amylase, which is the variant of SEQ ID NO: 30 having alterations H1* + N54S + V56T + K72R + G109A + F113Q + R116Q + W167F + Q172G + A174S + G184T + N195F + V206L + K391A + P473R + G476K | 71.8 | 6.3 | — | — | — | — |
| Blank | 65.5 | 0.0 | — | — | — | — |

TABLE 25

Wascator bottle wash in Model detergent A at 40° C., 30 min (pH 7.7)

Lichenase in combination with the amylase, which is the variant of SEQ ID NO: 31 having alterations M9L + R118K + G149A + G182T + G186A + D183* + G184* + N195F + T246V + T257I + Y295F + N299Y + R320K + M323T + A339S + E345R + R458K

|  | Enzymes solo | | REM combined | ΔREM combined | ΔREM theoretic | REM Synergy effect |
|---|---|---|---|---|---|---|
|  | REM | ΔREM | | | | |
| *Bacillus agaradhaerens* lichenase | 65.5 | 0.8 | 76.2 | 11.4 | 6.8 | 4.7 |
| *Bacillus Akibai* Lichenase | 66.1 | 1.3 | 76.7 | 12.0 | 7.3 | 4.6 |
| *Bacillus Mojavensis* Lichenase | 65.8 | 1.0 | 77.5 | 12.7 | 7.0 | 5.7 |
| *Bacillus* SP-62449 Lichenase | 64.6 | −0.2 | 76.6 | 11.8 | 5.8 | 6.0 |
| *Bacillus Subtillis* Lichenase | 67.4 | 2.7 | 76.1 | 11.4 | 8.7 | 2.7 |
| Amylase, which is the variant of SEQ ID NO: 31 having alterations M9L + R118K + G149A + G182T + G186A + D183* + G184* + N195F + T246V + T257I + Y295F + N299Y + R320K + M323T + A339S + E345R + R458K | 70.8 | 6.0 | — | — | — | — |
| Blank | 64.8 | 0.0 | — | — | — | — |

TABLE 26

Wascator bottle wash in Model detergent X at 40° C., 30 min (pH 10.1)

Lichenase in combination with the amylase having SEQ ID NO: 12

|  | Enzymes solo | | REM combined | ΔREM combined | ΔREM theoretic | REM Synergy effect |
|---|---|---|---|---|---|---|
|  | REM | ΔREM | | | | |
| *Bacillus agaradhaerens* lichenase | 62.0 | 0.2 | 74.5 | 12.7 | 5.0 | 7.6 |
| *Bacillus Akibai* Lichenase | 62.2 | 0.3 | 74.9 | 13.1 | 5.2 | 7.9 |
| *Bacillus Mojavensis* Lichenase | 61.8 | −0.1 | 74.3 | 12.4 | 4.8 | 7.6 |
| *Bacillus* SP-62449 Lichenase | 61.9 | 0.1 | 73.0 | 11.1 | 5.0 | 6.1 |
| amylase having SEQ ID NO: 12 | 66.7 | 4.9 | — | — | — | — |
| Blank | 61.8 | 0.0 | — | — | — | — |

TABLE 27

Wascator bottle wash in Model detergent X at 40° C., 30 min (pH 10.1)

|  | Enzymes solo | | REM combined | ΔREM combined | ΔREM theoretic | REM Synergy effect |
|---|---|---|---|---|---|---|
|  | REM | ΔREM | | | | |
| *Bacillus agaradhaerens* lichenase | 59.4 | −0.1 | 72.8 | 13.3 | 6.4 | 6.8 |
| *Bacillus Akibai* Lichenase | 59.8 | 0.3 | 73.1 | 13.6 | 6.8 | 6.8 |
| *Bacillus Mojavensis* Lichenase | 59.5 | −0.1 | 73.2 | 13.6 | 6.5 | 7.2 |
| *Bacillus* SP-62449 Lichenase | 60.9 | 1.3 | 72.1 | 12.6 | 7.9 | 4.7 |
| *Bacillus amyloliquefaciens* lichenase | 59.9 | 0.4 | 69.6 | 10.0 | 6.9 | 3.1 |
| Amylase, which is the variant of SEQ ID NO: 23 having alterations G182* + D183* | 66.1 | 6.5 | — | — | — | — |
| Blank | 59.5 | 0.0 | — | — | — | — |

Lichenase in combination with the amylase, which is the variant of SEQ ID NO: 23 having alterations G182* + D183*

TABLE 28

Wascator bottle wash in Model detergent X at 40° C., 30 min (pH 10.1)

Lichenase in combination with the amylase, which is the variant of SEQ ID NO: 24 having alterations H183* + G184* + I405L + A421H + A422P + A428T

|  | Enzymes solo | | REM combined | ΔREM combined | ΔREM theoretic | REM Synergy effect |
|---|---|---|---|---|---|---|
|  | REM | ΔREM | | | | |
| *Bacillus agaradhaerens* lichenase | 59.4 | −0.1 | 70.4 | 10.9 | 5.0 | 5.8 |
| *Bacillus Akibai* Lichenase | 59.8 | 0.3 | 70.1 | 10.5 | 5.4 | 5.1 |
| *Bacillus Mojavensis* Lichenase | 59.5 | −0.1 | 70.5 | 10.9 | 5.1 | 5.9 |
| *Bacillus* SP-62449 Lichenase | 60.9 | 1.3 | 69.9 | 10.4 | 6.5 | 3.9 |
| *Bacillus amyloliquefaciens* lichenase | 59.9 | 0.4 | 68.4 | 8.9 | 5.5 | 3.4 |
| Amylase, which is the variant of SEQ ID NO: 24 having alterations H183* + G184* + I405L + A421H + A422P + A428T | 64.7 | 5.1 | — | — | — | — |
| Blank | 59.5 | 0.0 | — | — | — | — |

TABLE 29

Wascator bottle wash in Model detergent X at 40° C., 30 min (pH 10.1)

Lichenase in combination with the amylase, which is the variant of SEQ ID NO: 24 having alterations M9L + R118K + G149A + G182T + G186A + D183* + G184* + N195F + M202L + T257I + Y295F + N299Y + R320K + M323T + A339S + E345R + R458K

|  | Enzymes solo | | REM combined | ΔREM combined | ΔREM theoretic | REM Synergy effect |
|---|---|---|---|---|---|---|
|  | REM | ΔREM | | | | |
| *Bacillus agaradhaerens* lichenase | 62.5 | 1.6 | 74.9 | 13.9 | 7.8 | 6.1 |
| *Bacillus Akibai* Lichenase | 61.6 | 0.7 | 73.6 | 12.6 | 6.9 | 5.7 |
| *Bacillus Mojavensis* Lichenase | 61.7 | 0.7 | 71.4 | 10.4 | 6.9 | 3.5 |
| *Bacillus* SP-62449 Lichenase | 59.2 | −1.8 | 73.1 | 12.1 | 4.5 | 7.6 |
| *Bacillus amyloliquefaciens* lichenase | 61.2 | 0.2 | 68.9 | 7.9 | 6.4 | 1.5 |
| *Bacillus Subtillis* Lichenase | 60.8 | −0.2 | 71.5 | 10.5 | 6.1 | 4.4 |
| Amylase, which is the variant of SEQ ID NO: 24 having alterations M9L + R118K + G149A + G182T + G186A + D183* + G184* + N195F + M202L + T257I + Y295F + N299Y + R320K + M323T + A339S + E345R + R458K | 67.2 | 6.2 | — | — | — | — |
| Blank | 61.0 | 0.0 | — | — | — | — |

TABLE 30

Wascator bottle wash in Model detergent X at 40° C., 30 min (pH 10.1)

| | Enzymes solo | | Lichenase in combination with the amylase, which is the variant of SEQ ID NO: 24 having alterations R178* + G179* + E187P + I203Y + R458N + T459S + D460T + G476K | | | |
|---|---|---|---|---|---|---|
| | REM | ΔREM | REM combined | ΔREM combined | ΔREM theoretic | REM Synergy effect |
| *Bacillus agaradhaerens* lichenase | 62.3 | 0.4 | 73.7 | 11.7 | 6.4 | 5.3 |
| *Bacillus Akibai* Lichenase | 61.6 | −0.4 | 72.4 | 10.4 | 5.7 | 4.7 |
| *Bacillus Mojavensis* Lichenase | 61.4 | −0.6 | 73.0 | 11.1 | 5.5 | 5.6 |
| *Bacillus* SP-62449 Lichenase | 61.0 | −1.0 | 72.0 | 10.0 | 5.1 | 4.9 |
| *Bacillus amyloliquefaciens* lichenase | 62.1 | 0.1 | 71.5 | 9.5 | 6.2 | 3.3 |
| *Bacillus Subtillis* Lichenase | 62.2 | 0.2 | 72.8 | 10.8 | 6.3 | 4.6 |
| amylase, which is the variant of SEQ ID NO: 24 having alterations R178* + G179* + E187P + I203Y + R458N + T459S + D460T + G476K | 68.0 | 6.1 | — | — | — | — |
| Blank | 62.0 | 0.0 | — | — | — | — |

TABLE 31

Wascator bottle wash in Model detergent X at 40° C., 30 min (pH 10.1)

| | Enzymes solo | | Lichenase in combination with the amylase, which is the variant of SEQ ID NO: 27 having alteration M202L | | | |
|---|---|---|---|---|---|---|
| | REM | ΔREM | REM combined | ΔREM combined | ΔREM theoretic | REM Synergy effect |
| *Bacillus agaradhaerens* lichenase | 62.3 | 0.4 | 72.0 | 10.1 | 5.4 | 4.7 |
| *Bacillus Akibai* Lichenase | 61.6 | −0.4 | 71.3 | 9.3 | 4.6 | 4.7 |
| *Bacillus Mojavensis* Lichenase | 61.4 | −0.6 | 71.6 | 9.6 | 4.4 | 5.2 |
| *Bacillus* SP-62449 Lichenase | 61.0 | −1.0 | 70.6 | 8.6 | 4.0 | 4.6 |
| *Bacillus amyloliquefaciens* lichenase | 62.1 | 0.1 | 68.5 | 6.6 | 5.1 | 1.4 |
| *Bacillus Subtillis* Lichenase | 62.2 | 0.2 | 71.2 | 9.2 | 5.2 | 4.0 |
| Amylase, which is the variant of SEQ ID NO: 27 having alteration M202L | 67.0 | 5.0 | — | — | — | — |
| Blank | 62.0 | 0.0 | — | — | — | — |

TABLE 32

Wascator bottle wash in Model detergent X at 40° C., 20 min (pH 10.1)

| | Enzymes solo | | Lichenase in combination with the amylase, which the variant of SEQ ID NO: 28 having alterations R180* + S181* + S243Q + G475K | | | |
|---|---|---|---|---|---|---|
| | REM | ΔREM | REM combined | ΔREM combined | ΔREM theoretic | REM Synergy effect |
| *Bacillus Akibai* Lichenase | 61.8 | −0.4 | 63.3 | 1.1 | −0.3 | 1.4 |
| *Bacillus Mojavensis* Lichenase | 60.4 | −1.8 | 65.9 | 3.7 | −1.7 | 5.3 |
| *Bacillus* SP-62449 Lichenase | 62.1 | −0.1 | 64.2 | 2.0 | 0.0 | 2.0 |
| amylase, which the variant of SEQ ID NO: 28 having alterations R180* + S181* + S243Q + G475K | 62.3 | 0.1 | — | — | — | — |
| Blank | 62.2 | 0.0 | — | — | — | — |

TABLE 33

Wascator bottle wash in Model detergent X at 40° C., 30 min (pH 10.1)

| | Enzymes solo | | REM combined | ΔREM combined | ΔREM theoretic | REM Synergy effect |
|---|---|---|---|---|---|---|
| | REM | ΔREM | | | | |
| *Bacillus agaradhaerens* lichenase | 62.0 | 0.2 | 66.4 | 4.5 | 2.1 | 2.4 |
| *Bacillus Akibai* Lichenase | 62.2 | 0.3 | 66.4 | 4.6 | 2.3 | 2.3 |
| *Bacillus Mojavensis* Lichenase | 61.8 | −0.1 | 68.5 | 6.7 | 1.9 | 4.8 |
| *Bacillus* SP-62449 Lichenase | 61.9 | 0.1 | 66.9 | 5.1 | 2.1 | 3.0 |
| Amylase of SEQ ID NO: 29 having alterations D183* + G184* + W140Y + N195F + I206Y + Y243F + E260G + G304R + G476K | 63.8 | 2.0 | — | — | — | — |
| Blank | 61.8 | 0.0 | — | — | — | — |

Lichenase in combination with the amylase of SEQ ID NO: 29 having alterations D183* + G184* + W140Y + N195F + I206Y + Y243F + E260G + G304R + G476K

TABLE 34

Wascator bottle wash in Model detergent X at 40° C., 20 min (pH 10.1)

Lichenase in combination with the amylase, which is the variant of SEQ ID NO: 30 having alterations H1* + N54S + V56T + K72R + G109A + F113Q + R116Q + W167F + Q172G + A174S + G184T + N195F + V206L + K391A + P473R + G476K

| | Enzymes solo | | REM combined | ΔREM combined | ΔREM theoretic | REM Synergy effect |
|---|---|---|---|---|---|---|
| | REM | ΔREM | | | | |
| *Bacillus agaradhaerens* lichenase | 60.1 | −0.3 | 65.8 | 5.5 | 3.1 | 2.4 |
| *Bacillus Akibai* Lichenase | 58.9 | −1.4 | 63.1 | 2.8 | −0.1 | 2.9 |
| *Bacillus Mojavensis* Lichenase | 59.2 | −1.1 | 62.3 | 1.9 | 0.2 | 1.7 |
| *Bacillus* SP-62449 Lichenase | 59.8 | −0.6 | 62.6 | 2.3 | 0.8 | 1.5 |
| *Bacillus amyloliquefaciens* lichenase | 59.7 | −0.7 | 64.3 | 4.0 | 3.1 | 0.9 |
| *Bacillus Subtillis* Lichenase | 59.9 | −0.5 | 61.9 | 1.6 | 0.9 | 0.7 |
| Amylase, which is the variant of SEQ ID NO: 30 having alterations H1* + N54S + V56T + K72R + G109A + F113Q + R116Q + W167F + Q172G + A174S + G184T + N195F + V206L + K391A + P473R + G476K | 61.7 | 1.3 | — | — | — | — |
| Blank | 60.4 | 0.0 | — | — | — | — |

TABLE 35

Wascator bottle wash in Model detergent X at 40° C., 30 min (pH 10.1)

Lichenase in combination with the amylase, which is the variant of SEQ ID NO: 31 having alterations M9L + R118K + G149A + G182T + G186A + D183* + G184* + N195F + T246V + T257I + Y295F + N299Y + R320K + M323T + A339S + E345R + R458K

| | Enzymes solo | | REM combined | ΔREM combined | ΔREM theoretic | REM Synergy effect |
|---|---|---|---|---|---|---|
| | REM | ΔREM | | | | |
| *Bacillus agaradhaerens* lichenase | 62.3 | 0.4 | 76.1 | 14.2 | 6.2 | 7.9 |
| *Bacillus Akibai* Lichenase | 61.6 | −0.4 | 75.1 | 13.2 | 5.5 | 7.7 |
| *Bacillus Mojavensis* Lichenase | 61.4 | −0.6 | 74.2 | 12.2 | 5.3 | 7.0 |
| *Bacillus* SP-62449 Lichenase | 61.0 | −1.0 | 74.0 | 12.1 | 4.9 | 7.2 |
| *Bacillus amyloliquefaciens* lichenase | 62.1 | 0.1 | 73.3 | 11.3 | 6.0 | 5.3 |
| *Bacillus Subtillis* Lichenase | 62.2 | 0.2 | 73.9 | 11.9 | 6.1 | 5.8 |
| Amylase, which is the variant of SEQ ID NO: 31 having alterations M9L + R118K + G149A + G182T + G186A + D183* + G184* + N195F + T246V + T257I + Y295F + N299Y + R320K + M323T + A339S + E345R + R458K | 67.8 | 5.9 | — | — | — | — |
| Blank | 62.0 | 0.0 | — | — | — | — |

TABLE 36

Wascator bottle wash in ADW Model detergent A at 40° C., 30 min (pH 10.2)

| | Enzymes solo | | Lichenase in combination with the amylase having SEQ ID NO: 12 | | | |
|---|---|---|---|---|---|---|
| | REM | ΔREM | REM combined | ΔREM combined | ΔREM theoretic | REM Synergy effect |
| *Bacillus agaradhaerens* lichenase | 60.5 | −2.1 | 75.1 | 12.5 | 5.4 | 7.1 |
| *Bacillus Akibai* Lichenase | 60.7 | −1.9 | 73.9 | 11.3 | 5.6 | 5.7 |
| *Bacillus Mojavensis* Lichenase | 63.0 | 0.3 | 73.3 | 10.7 | 7.8 | 2.8 |
| *Bacillus* SP-62449 Lichenase | 60.8 | −1.8 | 74.5 | 11.9 | 5.7 | 6.2 |
| *Bacillus amyloliquefaciens* lichenase | 61.6 | −1.0 | 70.4 | 7.8 | 6.5 | 1.2 |
| amylase having SEQ ID NO: 12 | 70.1 | 7.5 | — | — | — | — |
| Blank | 62.6 | 0.0 | — | — | — | — |

TABLE 37

Wascator bottle wash in ADW Model detergent A at 40° C., 30 min (pH 10.2)

| | Enzymes solo | | Lichenase in combination with the amylase, which is the variant of SEQ ID NO: 23 having alterations G182* + D183* | | | |
|---|---|---|---|---|---|---|
| | REM | ΔREM | REM combined | ΔREM combined | ΔREM theoretic | REM Synergy effect |
| *Bacillus agaradhaerens* lichenase | 60.9 | 1.3 | 71.8 | 12.1 | 8.0 | 4.2 |
| *Bacillus Akibai* Lichenase | 60.9 | 1.2 | 71.5 | 11.8 | 7.9 | 3.9 |
| *Bacillus Mojavensis* Lichenase | 61.3 | 1.6 | 71.3 | 11.6 | 8.3 | 3.3 |
| *Bacillus* SP-62449 Lichenase | 60.9 | 1.2 | 71.7 | 12.0 | 7.9 | 4.1 |
| *Bacillus amyloliquefaciens* lichenase | 60.9 | 1.3 | 68.5 | 8.8 | 8.0 | 0.9 |
| *Bacillus Subtillis* Lichenase | 60.3 | 0.6 | 68.4 | 8.8 | 7.3 | 1.5 |
| amylase, which is the variant of SEQ ID NO: 23 having alterations G182* + D183* | 66.4 | 6.7 | — | — | — | — |
| Blank | 59.7 | 0.0 | — | — | — | — |

TABLE 38

Wascator bottle wash in ADW Model detergent A at 40° C., 30 min (pH 10.2)

| | Enzymes solo | | Lichenase in combination with the amylase, which is the variant of SEQ ID NO: 24 having alterations H183* + G184* + I405L + A421H + A422P + A428T | | | |
|---|---|---|---|---|---|---|
| | REM | ΔREM | REM combined | ΔREM combined | ΔREM theoretic | REM Synergy effect |
| *Bacillus agaradhaerens* lichenase | 60.9 | 1.3 | 73.3 | 13.7 | 8.0 | 5.6 |

TABLE 38-continued

Wascator bottle wash in ADW Model detergent A at 40° C., 30 min (pH 10.2)

|  | Lichenase in combination with the amylase, which is the variant of SEQ ID NO: 24 having alterations H183* + G184* + I405L + A421H + A422P + A428T | | | | | |
|---|---|---|---|---|---|---|
|  | Enzymes solo | | REM | ΔREM | ΔREM | REM Synergy |
|  | REM | ΔREM | combined | combined | theoretic | effect |
| *Bacillus Akibai* Lichenase | 60.9 | 1.2 | 71.7 | 12.1 | 8.0 | 4.0 |
| *Bacillus Mojavensis* Lichenase | 61.3 | 1.6 | 72.2 | 12.5 | 8.4 | 4.2 |
| *Bacillus* SP-62449 Lichenase | 60.9 | 1.2 | 72.5 | 12.8 | 8.0 | 4.8 |
| *Bacillus amyloliquefaciens* lichenase | 60.9 | 1.3 | 68.9 | 9.2 | 8.1 | 1.2 |
| *Bacillus Subtillis* Lichenase | 60.3 | 0.6 | 68.6 | 8.9 | 7.4 | 1.5 |
| Amylase, which is the variant of SEQ ID NO: 24 having alterations H183* + G184* + I405L + A421H + A422P + A428T | 66.5 | 6.8 | — | — | — | — |
| Blank | 59.7 | 0.0 | — | — | — | — |

TABLE 39

Wascator bottle wash in ADW Model detergent A at 40° C., 30 min (pH 10.2)

|  | Lichenase in combination with the amylase, which is the variant of SEQ ID NO: 24 having alterations M9L + R118K + G149A + G182T + G186A + D183* + G184* + N195F + M202L + T257I + Y295F + N299Y + R320K + M323T + A339S + E345R + R458K | | | | | |
|---|---|---|---|---|---|---|
|  | Enzymes solo | | REM | ΔREM | ΔREM | REM Synergy |
|  | REM | ΔREM | combined | combined | theoretic | effect |
| *Bacillus agaradhaerens* lichenase | 60.5 | −2.1 | 73.1 | 10.9 | 2.3 | 8.2 |
| *Bacillus Akibai* Lichenase | 60.7 | −1.9 | 73.2 | 10.6 | 2.5 | 8.1 |
| *Bacillus Mojavensis* Lichenase | 63.0 | 0.3 | 74.0 | 11.4 | 4.7 | 6.6 |
| *Bacillus* SP-62449 Lichenase | 60.8 | −1.8 | 75.1 | 12.4 | 2.6 | 9.9 |
| *Bacillus amyloliquefaciens* lichenase | 61.6 | −1.0 | 70.8 | 8.2 | 3.4 | 4.8 |
| Amylase, which is the variant of SEQ ID NO: 24 having alterations M9L + R118K + G149A + G182T + G186A + D183* + G184* + N195F + M202L + | 67.0 | 4.4 | — | — | — | — |

TABLE 39-continued

Wascator bottle wash in ADW Model detergent A at 40° C., 30 min (pH 10.2)

|  | Enzymes solo | | REM combined | ΔREM combined | ΔREM theoretic | REM Synergy effect |
|---|---|---|---|---|---|---|
|  | REM | ΔREM | | | | |

Lichenase in combination with the amylase, which is the variant of SEQ ID NO: 24 having alterations M9L + R118K + G149A + G182T + G186A + D183* + G184* + N195F + M202L + T257I + Y295F + N299Y + R320K + M323T + A339S + E345R + R458K

| | REM | ΔREM | REM combined | ΔREM combined | ΔREM theoretic | REM Synergy effect |
|---|---|---|---|---|---|---|
| T257I + Y295F + N299Y + R320K + M323T + A339S + E345R + R458K | | | | | | |
| Blank | 62.6 | 0.0 | — | — | — | — |

TABLE 40

Wascator bottle wash in ADW Model detergent A at 40° C., 30 min (pH 10.2)

Lichenase in combination with the amylase, which is the variant of SEQ ID NO: 24 having alterations R178* + G179* + E187P + I203Y + R458N + T459S + D460T + G476K

| | Enzymes solo | | REM combined | ΔREM combined | ΔREM theoretic | REM Synergy effect |
|---|---|---|---|---|---|---|
| | REM | ΔREM | | | | |
| Bacillus Mojavensis Lichenase | 62.4 | 1.0 | 69.8 | 8.4 | 7.1 | 1.3 |
| Bacillus SP-62449 Lichenase | 60.8 | −0.6 | 69.8 | 8.4 | 5.5 | 2.9 |
| amylase, which is the variant of SEQ ID NO: 24 having alterations R178* + G179* + E187P + I203Y + R458N + T459S + D460T + G476K | 67.5 | 6.1 | — | — | — | — |
| Blank | 61.4 | 0.0 | — | — | — | — |

TABLE 41

Wascator bottle wash in ADW Model detergent A at 40° C., 30 min (pH 10.2)

Lichenase in combination with the amylase, which is the variant of SEQ ID NO: 27 having alteration M202L

| | Enzymes solo | | REM combined | ΔREM combined | ΔREM theoretic | REM Synergy effect |
|---|---|---|---|---|---|---|
| | REM | ΔREM | | | | |
| Bacillus agaradhaerens lichenase | 62.2 | 0.8 | 69.4 | 8.0 | 5.3 | 2.8 |
| Bacillus Akibai Lichenase | 62.0 | 0.6 | 69.5 | 8.1 | 5.1 | 3.0 |
| Bacillus Mojavensis Lichenase | 62.4 | 1.0 | 68.9 | 7.5 | 5.5 | 2.0 |

TABLE 41-continued

Wascator bottle wash in ADW Model detergent A at 40° C., 30 min (pH 10.2)

|  | Enzymes solo | | REM combined | ΔREM combined | ΔREM theoretic | REM Synergy effect |
|---|---|---|---|---|---|---|
|  | REM | ΔREM | | | | |
| *Bacillus* SP-62449 Lichenase | 60.8 | −0.6 | 69.3 | 7.9 | 3.9 | 4.0 |
| Amylase, which is the variant of SEQ ID NO: 27 having alteration M202L | 65.9 | 4.5 | — | — | — | — |
| Blank | 61.4 | 0.0 | — | — | — | — |

Lichenase in combination with the amylase, which is the variant of SEQ ID NO: 27 having alteration M202L

TABLE 42

Wascator bottle wash in ADW Model detergent A at 40° C., 30 min (pH 10.2)

Lichenase in combination with the amylase, which the variant of SEQ ID NO: 28 having alterations R180* + S181* + S243Q + G475K

|  | Enzymes solo | | REM combined | ΔREM combined | ΔREM theoretic | REM Synergy effect |
|---|---|---|---|---|---|---|
|  | REM | ΔREM | | | | |
| *Bacillus Akibai* Lichenase | 62.0 | 0.7 | 67.5 | 6.2 | 3.9 | 2.3 |
| *Bacillus* SP-62449 Lichenase | 61.2 | −0.1 | 68.4 | 7.1 | 3.1 | 4.1 |
| *Bacillus amyloliquefaciens* lichenase | 62.3 | 1.0 | 67.4 | 6.1 | 4.2 | 2.0 |
| *Bacillus Subtillis* Lichenase | 61.9 | 0.6 | 66.5 | 5.2 | 3.8 | 1.3 |
| Amylase, which the variant of SEQ ID NO: 28 having alterations R180* + S181* + S243Q + G475K | 64.5 | 3.2 | — | — | — | — |
| Blank | 61.3 | 0.0 | — | — | — | — |

TABLE 43

Wascator bottle wash in ADW Model detergent A at 40° C., 30 min (pH 10.2)

Lichenase in combination with the amylase of SEQ ID NO: 29 having alterations D183* + G184* + W140Y + N195F + I206Y + Y243F + E260G + G304R + G476K

|  | Enzymes solo | | REM combined | ΔREM combined | ΔREM theoretic | REM Synergy effect |
|---|---|---|---|---|---|---|
|  | REM | ΔREM | | | | |
| *Bacillus Akibai* Lichenase | 60.0 | −1.8 | 65.7 | 3.9 | 1.3 | 2.6 |
| *Bacillus Mojavensis* Lichenase | 62.1 | 0.4 | 66.9 | 5.2 | 3.5 | 1.7 |

TABLE 43-continued

Wascator bottle wash in ADW Model detergent A at 40° C., 30 min (pH 10.2)

Lichenase in combination with the amylase of SEQ ID NO: 29 having alterations D183* + G184* + W140Y + N195F + I206Y + Y243F + E260G + G304R + G476K

|  | Enzymes solo | | REM combined | ΔREM combined | ΔREM theoretic | REM Synergy effect |
|---|---|---|---|---|---|---|
|  | REM | ΔREM |  |  |  |  |
| *Bacillus amyloliquefaciens* lichenase | 62.0 | 0.3 | 65.9 | 4.2 | 3.4 | 0.8 |
| *Bacillus Subtillis* Lichenase | 61.6 | −0.2 | 65.7 | 3.9 | 2.9 | 1.0 |
| Amylase of SEQ ID NO: 29 having alterations D183* + G184* + W140Y + N195F + I206Y + Y243F + E260G + G304R + G476K | 64.8 | 3.1 | — | — | — | — |
| Blank | 61.7 | 0.0 | — | — | — | — |

TABLE 44

Wascator bottle wash in ADW Model detergent A at 40° C., 20 min (pH 10.2)

Lichenase in combination with the amylase, which is the variant of SEQ ID NO: 30 having alterations H1* + N54S + V56T + K72R + G109A + F113Q + R116Q + W167F + Q172G + A174S + G184T + N195F + V206L + K391A + P473R + G476K

|  | Enzymes solo | | REM combined | ΔREM combined | ΔREM theoretic | REM Synergy effect |
|---|---|---|---|---|---|---|
|  | REM | ΔREM |  |  |  |  |
| *Bacillus Akibai* Lichenase | 59.4 | −0.8 | 61.6 | 1.4 | −0.5 | 1.9 |
| *Bacillus amyloliquefaciens* lichenase | 60.5 | 0.4 | 61.8 | 1.6 | 0.7 | 1.0 |
| *Bacillus Subtillis* Lichenase | 60.1 | −0.1 | 61.5 | 1.3 | 0.3 | 1.0 |
| Amylase, which is the variant of SEQ ID NO: 30 having alterations H1* + N54S + V56T + K72R + G109A + F113Q + R116Q + W167F + Q172G + A174S + G184T + N195F + V206L + K391A + P473R + G476K | 60.5 | 0.3 | — | — | — | — |
| Blank | 60.2 | 0.0 | — | — | — | — |

TABLE 45

Wascator bottle wash in ADW Model detergent A at 40° C., 30 min (pH 10.2)

|  | Enzymes solo | | Lichenase in combination with the amylase, which is the variant of SEQ ID NO: 31 having alterations M9L + R118K + G149A + G182T + G186A + D183* + G184* + N195F +P0 T246V + T257I + Y295F + N299Y + R320K + M323T + A339S + E345R + R458K | | | |
|---|---|---|---|---|---|---|
|  | REM | ΔREM | REM combined | ΔREM combined | ΔREM theoretic | REM Synergy effect |
| *Bacillus agaradhaerens* lichenase | 61.4 | −0.4 | 72.9 | 11.1 | 7.0 | 4.1 |
| *Bacillus Akibai* Lichenase | 60.0 | −1.8 | 74.1 | 12.4 | 5.7 | 6.7 |
| *Bacillus Mojavensis* Lichenase | 62.1 | 0.4 | 73.2 | 11.5 | 7.8 | 3.7 |
| *Bacillus* SP-62449 Lichenase | 61.4 | −0.3 | 75.1 | 13.4 | 7.1 | 6.3 |
| *Bacillus amyloliquefaciens* lichenase | 62.0 | 0.3 | 72.6 | 10.8 | 7.7 | 3.1 |
| *Bacillus Subtillis* Lichenase | 61.6 | −0.2 | 71.1 | 9.3 | 7.3 | 2.1 |
| amylase, which is the variant of SEQ ID NO: 31 having alterations M9L + R118K + G149A + G182T + G186A + D183* + G184* + N195F + T246V + T257I + Y295F + N299Y + R320K + M323T + A339S + E345R + R458K | 69.2 | 7.4 | — | — | — | — |
| Blank | 61.7 | 0.0 | — | — | — | — |

TABLE 46

Wascator bottle wash in ADW Model detergent A at 40° C., 20 min (pH 10.2)

|  | Enzymes solo | | Lichenase in combination with the amylase, which the variant of SEQ ID NO: 28 having alterations R180* + S181* + S243Q + G475K | | | |
|---|---|---|---|---|---|---|
|  | REM | ΔREM | REM combined | ΔREM combined | ΔREM theoretic | REM Synergy effect |
| *Bacillus agaradhaerens* lichenase | 60.2 | −0.9 | 63.9 | 2.9 | 1.0 | 1.9 |
| *Bacillus Akibai* Lichenase | 60.4 | −0.6 | 65.5 | 4.5 | 1.2 | 3.3 |
| *Bacillus Mojavensis* Lichenase | 60.9 | −0.2 | 65.0 | 4.0 | 1.7 | 2.3 |
| *Bacillus amyloliquefaciens* lichenase | 60.9 | −0.1 | 63.9 | 2.9 | 1.7 | 1.1 |

TABLE 46-continued

Wascator bottle wash in ADW Model detergent A at 40° C., 20 min (pH 10.2)

|  | Enzymes solo | | REM combined | ΔREM combined | ΔREM theoretic | REM Synergy effect |
|---|---|---|---|---|---|---|
|  | REM | ΔREM |  |  |  |  |
| Bacillus Subtillis Lichenase | 60.7 | −0.4 | 63.5 | 2.5 | 1.5 | 1.0 |
| amylase, which the variant of SEQ ID NO: 28 having alterations R180* + S181* + S243Q + G475K | 62.9 | 1.9 | — | — | — | — |
| Blank | 61.0 | 0.0 | — | — | — | — |

TABLE 47

Wascator bottle wash in ADW Model detergent A at 40° C., 20 min (pH 10.2)

Lichenase in combination with the amylase of SEQ ID NO: 29 having alterations D183* + G184* + W140Y + N195F + I206Y + Y243F + E260G + G304R + G476K

|  | Enzymes solo | | REM combined | ΔREM combined | ΔREM theoretic | REM Synergy effect |
|---|---|---|---|---|---|---|
|  | REM | ΔREM |  |  |  |  |
| Bacillus agaradhaerens lichenase | 60.2 | −0.9 | 65.0 | 4.0 | 1.8 | 2.2 |
| Bacillus amyloliquefaciens lichenase | 60.9 | −0.1 | 62.8 | 1.8 | 2.5 | −0.7 |
| amylase of SEQ ID NO: 29 having alterations D183* + G184* + W140Y + N195F + I206Y + Y243F + E260G + G304R + G476K | 63.7 | 2.6 | — | — | — | — |
| Blank | 61.0 | 0.0 | — | — | — | — |

Example 10: Synergistic Effect of Lichenases Combined with Proteases

I. Wascator Bottle Wash Method Description:
A Wascator bottle wash method was used to detect the performance of the enzymes. In a Wascator washing machine (FOM 71 Lab) was added bottles (60 mL, DSE PP 70X35 Aseptisk, material #: 216-2620, from VWR) with 25 mL detergent solution including enzyme(s) and four stains (C-H097—Cocoa/oatflakes, from Center for Testmaterials BV, P.O. Box 120, 3133 KT Vlaardingen, the Netherlands, 2 cm in diameter). Two kg ballast (tea towels, cotton) was included in the washing machine. Washed in 25 L water for 15 min at 40° C. in model detergent for laundry (model X) and in ADW model detergent A for automated dish wash. After wash the stains were rinsed with tap water twice (3 L) and dried overnight at room temperature in drying cabinet (Electrolux, Intuition, EDD2400). The remission was measured on a spectrophotometer (Macbeth Color-Eye 7000 Remissions) at 460 nm.

II. Results:
In this example the results of combining the individual mature lichenases of Bacillus agaradhaerens Lichenase (SEQ ID NO: 39, His-tagged, recombinant), Bacillus akibai Lichenase (SEQ ID NO: 38, His-tagged, recombinant), Bacillus mojavensis Lichenase (SEQ ID NO: 40, His-tagged, recombinant), Bacillus sp-62449 Lichenase (SEQ ID NO: 37, His-tagged, recombinant), Bacillus amyloliquefaciens Lichenase (SEQ ID NO: 32) and Bacillus subtilis Lichenase (SEQ ID NO: 33) with a protease (Savinase, SEQ ID NO: 34) was studied in order to investigate a potential synergy effect between the two enzyme classes in various detergents using the Wascator bottle wash method is shown. Comparisons were made with lichenase from Bacillus amyloliquefaciens and lichenase from Bacillus subtilis in Model detergent X and ADW model detergent A using lichenase concentration of 0.01 mg enzyme protein per liter and protease concentration of 0.23 mg enzyme protein per liter at 40° C. The detailed conditions are described in Table 48 and 49 and the results are shown in Table 50 and 51.

TABLE 48

| Experimental condition | |
|---|---|
| Detergent | Model detergent X (see Table 13) |
| Detergent dosage | 1.75 g/L |
| Test solution volume | 25 mL |
| pH | As is |
| Wash time | 15 minutes |
| Temperature | 40° C. |
| Water hardness | 12° dH |
| Protease concentration in test | 0.23 mg/L |
| Lichenase concentration in test | 0.01 mg/L |
| Test material | C-H097 Cocoa/oatflakes |

TABLE 49

| Experimental condition | |
|---|---|
| Detergent | ADW model detergent A (see Table 15) |
| Detergent dosage | 3.77 g/L |
| Test solution volume | 25 mL |
| pH | As is |
| Wash time | 15 minutes |
| Temperature | 40° C. |
| Water hardness | 21° dH |
| Protease concentration in test | 0.23 mg/L |
| Lichenase concentration in test | 0.01 mg/L |
| Test material | C-H097 Cocoa/oatflakes |

TABLE 50

Wascator bottle wash in Model detergent X at 40° C., 15 min (pH 10.1)

| | Enzymes solo | | REM combined | ΔREM combined | ΔREM theoretic | REM Synergy effect |
|---|---|---|---|---|---|---|
| | REM | ΔREM | | | | |
| *Bacillus agaradhaerens* lichenase | 40.0 | 6.1 | 54.5 | 20.6 | 10.6 | 10.0 |
| *Bacillus Akibai* Lichenase | 37.6 | 3.8 | 45.4 | 11.5 | 8.2 | 3.3 |
| *Bacillus Mojavensis* Lichenase | 37.6 | 3.7 | 50.9 | 17.0 | 8.2 | 8.7 |
| *Bacillus* SP-62449 Lichenase | 37.7 | 3.8 | 48.4 | 14.5 | 8.3 | 6.2 |
| *Bacillus amyloliquefaciens* lichenase | 34.6 | 0.7 | 42.8 | 8.9 | 5.2 | 3.6 |
| *Bacillus Subtillis* Lichenase | 35.8 | 1.9 | 42.8 | 8.9 | 6.4 | 2.5 |
| Savinase (SEQ ID NO: 34) | 38.4 | 4.5 | — | — | — | — |
| Blank | 33.9 | 0.0 | — | — | — | — |

TABLE 51

Wascator bottle wash in ADW Model detergent A at 40° C., 15 min (pH 10.2)

| | Enzymes solo | | REM combined | ΔREM combined | ΔREM theoretic | REM Synergy effect |
|---|---|---|---|---|---|---|
| | REM | ΔREM | | | | |
| *Bacillus agaradhaerens* lichenase | 40.0 | 4.6 | 53.0 | 17.6 | 10.3 | 7.4 |
| *Bacillus Akibai* Lichenase | 36.8 | 1.4 | 52.2 | 16.8 | 7.1 | 9.7 |
| *Bacillus Mojavensis* Lichenase | 39.0 | 3.6 | 51.1 | 15.7 | 9.3 | 6.4 |
| *Bacillus* SP-62449 Lichenase | 42.7 | 7.3 | 59.6 | 24.2 | 12.9 | 11.3 |
| *Bacillus amyloliquefaciens* lichenase | 36.6 | 1.2 | 47.2 | 11.8 | 6.8 | 5.0 |

TABLE 51-continued

Wascator bottle wash in ADW Model detergent A at 40° C., 15 min (pH 10.2)

| | Enzymes solo | | REM | ΔREM | ΔREM | REM Synergy |
|---|---|---|---|---|---|---|
| | REM | ΔREM | combined | combined | theoretic | effect |
| Bacillus Subtillis Lichenase | 37.1 | 1.7 | 48.3 | 12.9 | 7.4 | 5.5 |
| Savinase (SEQ ID NO: 34) | 41.1 | 5.7 | — | — | — | — |
| Blank | 35.4 | 0.0 | — | — | — | — |

Example 11: Automated Dish Wash Cleaning of Cooked Oats with Lichenases

I. Automated Dish Washing Machine

Automated dish washing machines (Miele, G 1223, GSL-2) were used to show lichenase performance on cooked oats.

II. Results:

Full scale dish wash performance on cooked oats was tested in ADW model detergent A under the experimental conditions given in Table 52.

TABLE 52

| Experimental conditions: | |
|---|---|
| | ADW Model detergent A (See Table 15) |
| Detergent dosage | 3.77 g/L |
| Lichenase concentration | 0 or 0.3 mg enzyme protein/L |
| Amylase concentration | 0.5 mg enzyme protein/L |
| Water hardness | As is |
| Protease concentration | SEQ ID NO: 35: 3.7 mg enzyme protein/L |
| | SEQ ID NO: 36: 5.9 mg enzyme protein/L |
| Test solution volume | 5.4 L |
| Miele machine | G 1223, GSL-2, program: 45° C./3'/8'/55 |
| Soiling (Oat:Milk:Sugar) | 150 g:300 mL:50 g |
| Soiling per plate | 35 g |
| Ballast | 50 g IKW ballast slurry |

The soiling was prepared by mixing grinded oats (150 g AXA Finvalsede Havregryn in an immersion blender "chopper), milk (300 mL) and sugar (50 g) in a beaker. The mixture was heated to boiling point and cooked for 2 minutes. The soiling was added on porcelain plates (35 g) and dried overnight at 40° C. in an oven (Heraeus Instruments, Typ UT6200). The plates were cooled to room temperature, weighted, and washed in Miele dish washing machines (G 1223, GSL-2) for 8 min (main wash) at 45° C. with 50 g IKW ballast slurry in ADW Model detergent A, amylase (which is the variant of SEQ ID NO:24 having alterations M9L+R118K+G149A+G182T+G186A+D183*+G184*+N195F+M202L+T257I+Y295F+N299Y+R320K+M323T+A339S+E345R+R458K; 0.5 mg enzyme protein/L) and proteases (SEQ ID NO: 35; 3.7 mg enzyme protein/L, SEQ ID NO: 36; 5.9 mg enzyme protein/L) or ADW Model detergent A, amylase (which is the variant of SEQ ID NO:24 having alterations M9L+R118K+G149A+G182T+G186A+D183*+G184*+N195F+M202L+T257I+Y295F+N299Y+R320K+M323T+A339S+E345R+R458K; 0.5 mg enzyme protein/L), proteases (SEQ ID NO: 35; 3.7 mg enzyme protein/L, SEQ ID NO: 36; 5.9 mg enzyme protein/L) and lichenase (Bacillus agaradhaerens (SEQ ID NO: 39, His-tagged, recombinant; 0.3 mg enzyme protein/L).

An effect of the lichenase on cooked oats is clearly visual seen as well as weighted. The measured numbers are shown in Table 53 as well as the calculated number for soiling left on the plates after wash.

Calculations:

Weight of soiling left on plates before wash=Weight of plate and soiling before wash−Weight of plate with no soiling before wash.

Weight of soiling left on plates after wash=Weight of plate and soiling after wash−Weight of plate with no soiling before wash.

TABLE 53

Wash performance on cooked oats:

| | Weight of plate and soiling before wash (g)* | Weight of plate and soiling after wash (g)* | Weight of plate with no soiling before wash (g)* | Weight of soiling left on plates before wash (g)* | Weight of soiling left on plates after wash (g)* |
|---|---|---|---|---|---|
| No lichenase | 530.6 | 515.9 | 514.5 | 16.1 | 1.4 |
| With lichenase | 549.0 | 533.0 | 532.8 | 16.2 | 0.2 |

*Average of 4 replicates.

Example 12: Automated Dish Wash Cleaning of Cooked and Burned-in Oats with Lichenases I. Automated Dish Washing Machine Automated dish washing machines (Miele, G 1223, GSL-2) were used to show lichenase performance on cooked and burned-in oats.

II. Results:

Full scale dish wash performance on cooked and burned-in oats was tested in ADW model detergent A under the experimental conditions given in Table 54.

TABLE 54

| Experimental conditions: | |
|---|---|
| | ADW Model detergent A (See Table 15) |
| Detergent dosage | 3.77 g/L |
| Lichenase concentration | 0 or 0.3 mg enzyme protein/L |
| Amylase concentration | 0.5 mg enzyme protein/L |

TABLE 54-continued

| Experimental conditions: | |
|---|---|
| | ADW Model detergent A (See Table 15) |
| Water hardness | As is |
| Protease concentration | SEQ ID NO: 35: 3.7 mg enzyme protein/L |
| | SEQ ID NO: 36: 5.9 mg enzyme protein/L |
| Test solution volume | 5.4 L |
| Miele machine | G 1223, GSL-2, program: 45° C./3'/8'/55 |
| Soiling (Oat:Milk:Sugar) | 150 g:300 mL:50 g |
| Soiling per plate | 15 g |
| Ballast | 50 g IKW ballast slurry |

The soiling was prepared by mixing grinded oats (150 g AXA Finvalsede Havregryn in an immersion blender "chopper), milk (300 mL) and sugar (50 g) in a beaker. The mixture was heated to boiling point and cooked for 2 minutes. The soiling was added on steel plates (15 g) and dried in an oven (Heraeus Instruments, Typ UT6200) for 40 minutes at 140° C. The plates were cooled down, weighted, and washed in Miele dish washing machines (G 1223, GSL-2) for 8 min (main wash) at 45° C. with 50 g IKW ballast slurry in ADW Model detergent A, amylase (which is the variant of SEQ ID NO:24 having alterations M9L+R118K+G149A+G182T+G186A+D183*+G184*+N195F+M202L+T257I+Y295F+N299Y+R320K+M323T+A339S+E345R+R458K, 0.5 mg enzyme protein/L) and proteases (SEQ ID NO: 35; 3.7 mg enzyme protein/L, SEQ ID NO: 36; 5.9 mg enzyme protein/L) or ADW Model detergent A, amylase (which is the variant of SEQ ID NO:24 having alterations M9L+R118K+G149A+G182T+G186A+D183*+G184*+N195F+M202L+T257I+Y295F+N299Y+R320K+M323T+A339S+E345R+R458K; 0.5 mg enzyme protein/L), proteases (SEQ ID NO: 35; 3.7 mg enzyme protein/L, SEQ ID NO: 36; 5.9 mg enzyme protein/L) and lichenase (*Bacillus agaradhaerens*, SEQ ID NO: 39, His-tagged, recombinant; 0.3 mg enzyme protein/L). After wash the plates were dried at room temperature and weighted.

Calculations:

Weight of soiling left on plates before wash=Weight of plate and soiling before wash−Weight of plate with no soiling before wash.

Weight of soiling left on plates after wash=Weight of plate and soiling after wash−Weight of plate with no soiling before wash.

A clear effect of the lichenase is seen on cooked and burned-in oats and the measured numbers are shown in Table 55 as well as the calculated number for soiling left on the plates after wash.

TABLE 55

Wash performance on cooked and burned-in oats:

| | Weight of plate and soiling before wash (g)* | Weight of plate and soiling after wash (g)* | Weight of plate with no soiling wash (g)* | Weight of soiling left on plates before wash (g)* | Weight of soiling left on plates after wash (g)* |
|---|---|---|---|---|---|
| No lichenase | 210.1 | 205.8 | 203.6 | 6.5 | 2.2 |
| With lichenase | 205.9 | 200.5 | 199.4 | 6.5 | 1.2 |

*Average of 6 replicates.

Example 13: Automated Dish Wash Cleaning of Uncooked Oats with Lichenases

I. Automated Dish Washing Machine

Automated dish washing machines (Miele, G 1223, GSL-2) were used to show lichenase performance on uncooked oats.

II. Results:

Full scale dish wash performance on uncooked oats was tested in ADW model detergent A under the experimental conditions given in Table 56.

TABLE 56

| Experimental conditions: | |
|---|---|
| | ADW Model detergent A (see Table 15) |
| Detergent dosage | 3.77 g/L |
| Lichenase concentration | 0 or 0.3 mg enzyme protein/L |
| Amylase concentration | 0.5 mg enzyme protein/L |
| Water hardness | As is |
| Protease concentration | SEQ ID NO: 35: 3.7 mg enzyme protein/L |
| | SEQ ID NO: 36: 5.9 mg enzyme protein/L |
| Test solution volume | 5.4 L |
| Miele machine | G 1223, GSL-2, program: 45° C./3'/8'/55 |
| Soiling (Oat:Milk:Sugar) | 150 g:300 mL:50 g |
| Soiling per plate | 35 g |
| Ballast | 50 g IKW ballast slurry |

The soiling was prepared by mixing grinded oats (150 g AXA Finvalsede Havregryn in an immersion blender "chopper), milk (300 mL) and sugar (50 g) in a beaker. The soiling was added on porcelain plates (35 g) and dried overnight at 40° C. in an oven (Heraeus Instruments, Typ UT6200). The plates were cooled to room temperature, weighted, and washed in Miele dish washing machines (G 1223, GSL-2) for 8 min (main wash) at 45° C. with 50 g IKW ballast slurry in ADW Model detergent A, amylase (which is the variant of SEQ ID NO:24 having alterations M9L+R118K+G149A+G182T+G186A+D183*+G184*+N195F+M202L+T257I+Y295F+N299Y+R320K+M323T+A339S+E345R+R458K, 0.5 mg enzyme protein/L) and proteases (SEQ ID NO: 35; 3.7 mg enzyme protein/L, SEQ ID NO: 36; 5.9 mg enzyme protein/L) or ADW Model detergent A, amylase (which is the variant of SEQ ID NO:24 having alterations M9L+R118K+G149A+G182T+G186A+D183*+G184*+N195F+M202L+T257I+Y295F+N299Y+R320K+M323T+A339S+E345R+R458K; 0.5 mg enzyme protein/L), proteases (SEQ ID NO: 35; 3.7 mg enzyme protein/L, SEQ ID NO: 36; 5.9 mg enzyme protein/L) and lichenase (*Bacillus agaradhaerens*; SEQ ID NO: 39, His-tagged, recombinant; 0.3 mg enzyme protein/L). After wash the plates were dried at room temperature and weighted.

An effect of the lichenase on uncooked oats is clearly visual seen as well as weighted. The measured numbers are shown in Table 57 as well as the calculated number for soiling left on the plates after wash.

Calculations:

Weight of soiling left on plates before wash=Weight of plate and soiling before wash−Weight of plate with no soiling before wash.

Weight of soiling left on plates after wash=Weight of plate and soiling after wash−Weight of plate with no soiling before wash.

TABLE 57

Wash performance on uncooked oats:

| | Weight of plate and soiling before wash (g)* | Weight of plate and soiling after wash (g)* | Weight of plate with no soiling before wash (g)* | Weight of soiling left on plates before wash (g)* | Weight of soiling left on plates after wash (g)* |
|---|---|---|---|---|---|
| No lichenase | 530.5 | 515.2 | 514.5 | 16.0 | 0.7 |
| With lichenase | 548.8 | 532.8 | 532.8 | 16.0 | 0.0 |

*Average of 4 replicates.

Example 14: Wash Performance and Anti-Redeposition Effect of Lichenases

I. Mini Terg-O-Tometer (MiniTOM) Wash Assay

The Mini Tergo-To-Meter (MiniTOM) is a medium scale model wash system that can be applied to test 16 different wash conditions simultaneously. A MiniTOM is basically a large temperature controlled water bath with up to 16 open metal beakers (300 mL) submerged into it. Each beaker constitutes one small top loader style washing machine and during an experiment, each of them will contain a solution of a specific detergent/enzyme system and the soiled and unsoiled fabrics its performance is tested on. Mechanical stress is achieved by a rotating stirring arm, which stirs the liquid within each beaker. Because the MiniTOM beakers have no lid, it is possible to withdraw samples during a MiniTOM experiment and assay for information on-line during wash.

The MiniTOM model wash system is mainly used in medium scale testing of detergents and enzymes at US or LA/AP wash conditions. In a MiniTOM experiment, factors such as the ballast to soil ratio and the fabric to wash liquor ratio can be varied. Therefore, the MiniTOM provides the link between small scale experiments, such as AMSA and mini-wash, and the more time consuming full scale experiments in top loader washing machines.

II. Results:

MiniTergotometer (MiniTOM) anti-redeposition by the lichenase, Bacillus agaradhaerens (SEQ ID NO: 7), was tested in model detergent A under the experimental conditions given in Table 58.

TABLE 58

Experimental conditions:

Model A (See Table 11)

| | |
|---|---|
| Detergent dosage | 3.33 g/L |
| Lichenase concentration | 0 or 0.3 mg enzyme protein/L |
| Amylase concentration | 0.2 mg enzyme protein/L |
| Water hardness | 15° dH ($Ca^{2+}$:$Mg^{2+}$:$HCO_3^-$ = 4:1:7.5) |
| Test solution volume | 100 ml |
| Wash time | 20 minutes |
| Rotation | 120 rpm |
| pH | as is |
| Temperature | 20° C. |
| Test material | Textile sample C-H097 (Cocoa/oatflakes) was obtained from Center for Testmaterials BV, P.O. Box 120, 3133 KT Vlaardingen, the Netherlands. |

TABLE 58-continued

Experimental conditions:

Model A (See Table 11)

Swatches with no initial soiling: Prewashed Knitted cotton was obtained from Warwick Equest Ltd, Unit 55, Consett Business Park, Consett, County Durham, DH8 6BN, United Kingdom.

The anti-redeposition (and wash performance) of the lichenase, Bacillus agaradhaserens (SEQ ID NO: 7), was tested as described below.

The wash solutions were prepared by adjusting the water hardness to 15° dH ($Ca^{2+}$:$Mg^{2+}$:$HCO_3^-$=4:1:7.5) by addition of $CaCl_2$, $MgCl_2$ and $NAHCO_3$, adding the desired amount of detergent (3.33 g/L of Model detergent A) and adjusting the temperature to 40° C. in the buckets. The detergent was dissolved during magnet stirring for 10 minutes (wash solution was used within 30 to 60 min after preparation). The temperature and rotation in the water bath in the MiniTOM were set to 40° C. and 120 rpm, respectively. When the temperature was adjusted according to settings (tolerance is +/−0.5° C.), 100 mL of the wash solution was added to the MiniTOM beakers (300 mL).

Swatches (1 knitted cotton swatches (circular, 2 cm in diameter) and 12 C-H097 (circular, 2 cm in diameter), lichenase (Bacillus agaradhaerens (SEQ ID NO: 39, His-tagged, recombinant), 0 or 0.3 mg enzyme protein/L) and amylase (SEQ ID NO: 12, 0.2 mg enzyme protein/L) were added to the beakers and washed for 20 minutes. Swatches were rinsed in cold tap water for 5 minutes. The swatches were sorted and dried between filter paper in a drying cupboard without heat overnight.

The anti-redeposition (and wash performance) was measured as the brightness of the color of the textile washed expressed in remission values (REM). Remission measurements were made using a Macbeth 7000 Color Eye spectrophotometer. Each of the dry swatches was measured. As there is a risk of interference from the back-ground, the swatches were placed on top of 2 layers of fabric during the measurement of the remission. The remission was measured at 460 nm. The UV filter was not included. An average result for remission for the swatches was calculated.

The anti-redeposition effect due to the presence of the lichenase is shown in Table 59. In the beakers without the lichenase present, the released soil from the soiled swatch (C-H097) is redeposit to the swatch with no initial soiling on. When the lichenase is present in the wash liquor, an anti-redeposition effect is clearly seen.

TABLE 59

Anti-redeposition effect and wash performance of lichenases:

| | REM before wash | REM after wash without Lichenase | REM after wash with Lichenase |
|---|---|---|---|
| Swatch with no initial soiling (Anti-redeposition) | 92.1 | 65.3 | 88.2 |
| Swatch with soiling (C-H097) (Wash performance) | 18.8 | 38.1 | 42.2 |

Example 15

Cleaning Performance on Oat Flakes:

500 g oat flakes, 167 g sugar and 1 l semi-skimmed milk (1.5% fat) are intensely mixed. The mixture is let unstirred for at least 2 hours at room temperature. Afterwards, 15 g (+/−0.2 g) of this preparation is spread evenly on a plate (china) in form of a circle using a metal ring (radius 11 cm) and left to dry over night at 40° C.

Cleaning performance is tested in an automatic dishwashing machine Miele GSL, 21° dH, 45° C., 8 min holding time, and 55° C. rinse temperature, with soiled dish ware/cutlery placed inside (according to IKW method, Söfwjournal, 142, (06) 2016, S. 33-48) with additional 4 plates as prepared above placed therein. Pasta and starch-mix cleaning performance was measured according to IKW. The results, also for oatflakes, are documented as arithmetic averages, evaluation according to IKW. Higher values indicated a better cleaning performance, differences above 1.0 are considered to be significant.

Cleaning Performance:

A two component liquid automatic dishwashing product (15 ml of each composition A and B, Table 60, 61) was dosed at the same time into the dosing chamber of the dishwashing machine.

TABLE 60

| Enzymphase (EP) | A |
| --- | --- |
| Amylase (wt. % enzyme protein) | 0.02 |
| Protease (wt. % enzyme protein) | 0.20 |
| Glycerol | 8.0 |
| Copolymer comprising sulfonic acid group containing monomer | 7.5 |
| MGDA Na4 | 10.00 |
| Nonionic surfactant(s) | 2.8 |
| Polypeptide according to present disclosure* (Mature polypeptide according to SEQID No: 7) | s. below |
| Misc (perfume, colorant, stabilizers for enzymes and UV, glass corrosion inhibitors, thickener, water) | Ad 100 |
| pH-Wert (not diluted, 25° C.) | 7.5 |

TABLE 61

| Alkaline Phase (AP) | B |
| --- | --- |
| HEDP | 2.5 |
| MGDA (Tetranatriumsalz) | 3.5 |
| KOH | 3.2 |
| Sodium Carbonate | 8.5 |
| Kationic copolymer | 0.5 |
| Sodium citrate × 2H$_2$O | 14.0 |
| Misc (perfume, colorant, stabilizers for enzymes and UV, glass corrosion inhibitors, thickener, water) | Ad 100 |
| pH-Wert (not diluted, 25° C.) adjusted (KOH/Citric Acid) | 10.5 |

TABLE 62

| Cleaning performance | Oat flakes | Starch Mix |
| --- | --- | --- |
| No Licheninase, prepared directly before testing | 6.5 | 7.3 |
| 1.5 mg Licheninase* in A, prepared directly before testing | 8.0 | 8.3 |

*(Mature polypeptide according to SEQID No: 7)

TABLE 63

| Cleaning performance | Spaghetti |
| --- | --- |
| No Licheninase, prepared directly before testing | 5.8 |
| 1 mg Licheninase* in A, prepared directly before testing | 7.5 |

*(Mature polypeptide according to SEQID No: 7)

TABLE 64

| Liquid automatic dishwashing product | Cleaning performance on Oat flakes |
| --- | --- |
| No Licheninase, storage conditions: 4 weeks at T = 22° C. | 5.9 |
| 1 mg Licheninase* in A, prepared directly before testing | 7.5 |
| 1 mg Licheninase* in A, storage conditions: 4 weeks at T = 22° C. | 7.3 |
| 1 mg Licheninase* in A, storage conditions: 4 weeks at T = 30° C. | 7.6 |
| 1 mg Licheninase* in A, storage conditions: 4 weeks at T = 40° C. | 7.1 |

*(Mature polypeptide according to SEQID No: 7)

Surprisingly, it has been found that the cleaning performance of a dishwash composition, preferably an automatic dishwash composition is enhanced on pasta (spaghetti) and/or starch-containing soils (Table 62, 63). Therefore the licheninases of the present disclosure facilitate the removal of starch-containing soil in the presence of one or more amylases and enhance amylase related cleaning performance.

The cleaning performance of the dishwash composition on Oatflakes is not significantly altered after 4 weeks storage at different temperatures (Table 64). Comparable results were found for automatic dishwash compositions containing 1.5 or 2.0 mg active enzyme protein/job Licheninase, storage conditions: 8 weeks at T=40° C. or 2 weeks at T=50° C.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cleaning or detergent composition, wherein said cleaning or detergent composition is a dish washing composition, said composition comprising a detergent ingredient and a polypeptide having beta-glucanase activity and selected from the group of:
   (a) a polypeptide having at least 87% sequence identity to the mature polypeptide of SEQ ID NO: 7, SEQ ID NO: 2, or SEQ ID NO: 3 or at least 99% sequence identity to the mature polypeptide of SEQ ID NO: 5 or at least 98% sequence identity to the mature polypeptide of SEQ ID NO: 9;
   (b) a polypeptide encoded by a polynucleotide that hybridizes with (i) the mature polypeptide coding sequence of SEQ ID NO: 6, SEQ ID NO: 1, SEQ ID NO: 4, or SEQ ID NO: 8, or (ii) the full-length complement of (i), wherein the polypeptide has at least 87% sequence identity to the mature polypeptide of SEQ ID NO: 7, SEQ ID NO: 2, or SEQ ID NO: 3 or at least 99% sequence identity to the mature polypeptide of SEQ ID NO: 5 or at least 98% sequence identity to the mature polypeptide of SEQ ID NO: 9;
   (c) a polypeptide encoded by a polynucleotide having at least 87% sequence identity to the mature polypeptide coding sequence of SEQ ID NO: 6 or SEQ ID NO: 1 or at least 99% sequence identity to the mature polypeptide coding sequence of SEQ ID NO: 4 or at least 98% sequence identity to the mature polypeptide coding sequence of SEQ ID NO: 8;
   (d) a variant of the mature polypeptide of SEQ ID NO: 7, SEQ ID NO: 2, SEQ ID NO: 3, SEQ ID NO: 5, or SEQ ID NO: 9, wherein the variant comprises a substitution, deletion, and/or insertion at one or more positions, and wherein the variant has at least 87% sequence identity to the mature polypeptide of the sequence selected from the group of: SEQ ID NO: 7, SEQ ID NO: 2, or SEQ ID NO: 3 or at least 99% sequence identity to the mature polypeptide of SEQ ID NO: 5 or at least 98% sequence identity to the mature polypeptide of SEQ ID NO: 9; and
   (e) a fragment of the polypeptide of (a), (b), (c), or (d) that has beta-glucanase activity, wherein the fragment has at least 87% sequence identity to the mature polypeptide of SEQ ID NO: 7, SEQ ID NO: 2, or SEQ ID NO: 3 or at least 99% sequence identity to the mature polypeptide of SEQ ID NO: 5 or at least 98% sequence identity to the mature polypeptide of SEQ ID NO: 9.

2. The cleaning or detergent composition of claim 1, wherein the polypeptide has at least 90% sequence identity to the mature polypeptide of SEQ ID NO: 7, SEQ ID NO: 2, or SEQ ID NO: 3.

3. The cleaning or detergent composition of claim 1, wherein the mature polypeptide is selected from the group of: amino acids 1 to 222 of SEQ ID NO: 7, amino acids 1 to 351 of SEQ ID NO: 2, amino acids 1 to 351 of SEQ ID NO: 3, amino acids 1 to 245 of SEQ ID NO: 5, and amino acids 1 to 214 of SEQ ID NO: 9.

4. The cleaning or detergent composition of claim 1, wherein the beta-glucanase activity is licheninase EC 3.2.1.73 activity.

5. The cleaning or detergent composition of claim 1, wherein the cleaning or detergent composition has a pH of about 6.5 or above, and optionally comprises a bleaching agent.

6. The cleaning or detergent composition of claim 1, further comprising:
   i) one or more detergent components; and/or
   ii) one or more additional enzymes.

7. The cleaning or detergent composition of claim 1, further comprising a copolymer that comprises at least one sulfonic acid comprising monomers.

8. The cleaning or detergent composition of claim 1, wherein the cleaning or detergent composition comprises the polypeptide in a concentration of from about 0.00001 mg enzyme protein/g composition to about 100 mg enzyme protein/g composition.

9. The cleaning or detergent composition of claim 1, wherein the cleaning or detergent composition further comprises:
   (i) one or more amylases; and/or
   (ii) one or more proteases.

10. The cleaning or detergent composition of claim 9, wherein the polypeptide has at least 90% sequence identity to the mature polypeptide of SEQ ID NO: 7, SEQ ID NO: 2, or SEQ ID NO: 3, wherein the mature polypeptide is selected from the group of: amino acids 1 to 222 of SEQ ID NO: 7, amino acids 1 to 351 of SEQ ID NO: 2, and amino acids 1 to 351 of SEQ ID NO: 3, and wherein the beta-glucanase activity is licheninase EC 3.2.1.73 activity.

11. The cleaning or detergent composition of claim 9, wherein the one or more amylases includes an alpha-amylase.

12. The cleaning or detergent composition of claim 11, wherein the alpha-amylase is selected from the group of:
   (a) a polypeptide having at least about 90% sequence identity to SEQ ID NO: 13;
   (b) a polypeptide having at least about 90% sequence identity to SEQ ID NO: 13, wherein the polypeptide comprises a substitution in one or more of positions: 15, 23, 105, 106, 124, 128, 133, 154, 156, 178, 179, 181, 188, 190, 197, 201, 202, 207, 208, 209, 211, 243, 264, 304, 305, 391, 408, and/or 444;
   (c) a polypeptide having at least about 90% sequence identity to SEQ ID NO: 14;
   (d) a polypeptide having at least about 90% sequence identity to the hybrid polypeptide of SEQ ID NO: 15;
   (e) a polypeptide having at least about 90% sequence identity to the hybrid polypeptide of SEQ ID NO: 15, wherein the hybrid polypeptide comprises a substitution, a deletion or an insertion in one of more of positions: 48, 49, 107, 156, 181, 190, 197, 201, 209 and/or 264;
   (f) a polypeptide having at least about 90% sequence identity to SEQ ID NO: 16;

(g) a polypeptide having at least about 90% sequence identity to SEQ ID NO: 16, wherein the polypeptide comprises a substitution, a deletion or an insertion in one of more of positions: 181, 182, 183, 184, 195, 206, 212, 216 and/or 269;

(h) a polypeptide having at least about 90% sequence identity to SEQ ID NO: 17, SEQ ID NO: 18 or SEQ ID NO: 19;

(i) a polypeptide having at least about 90% sequence identity to SEQ ID NO: 17, SEQ ID NO: 18 or SEQ ID NO: 19, wherein the polypeptide comprises a substitution, a deletion or an insertion in one of more of positions: 140, 183, 184 195, 206, 243, 260, 304 and/or 476;

(j) a polypeptide having at least about 90% sequence identity to SEQ ID NO: 20;

(k) a polypeptide having at least about 90% sequence identity to SEQ ID NO: 21;

(l) a polypeptide having at least about 90% sequence identity to SEQ ID NO: 21, wherein the polypeptide comprises a substitution, a deletion or an insertion in one of more of positions: 176, 177, 178, 179, 190, 201, 207, 211 and/or 264;

(m) a polypeptide having at least about 90% sequence identity to SEQ ID NO: 22;

(n) a polypeptide having at least about 90% sequence identity to SEQ ID NO: 22, wherein the polypeptide comprises a substitution, a deletion or an insertion in one of more of positions: 87, 98, 125, 128, 131, 165, 178, 180, 181, 182, 183, 201, 202, 225, 243, 272, 282, 305, 309, 319, 320, 359, 444 and/or 475;

(o) a polypeptide having at least about 90% sequence identity to SEQ ID NO: 21, wherein the polypeptide comprises a substitution, a deletion or an insertion in one of more of positions: 28, 118, 174; 181, 182, 183, 184, 186, 189, 195, 202, 298, 299, 302, 303, 306, 310, 314; 320, 324, 345, 396, 400, 439, 444, 445, 446, 449, 458, 471 and/or 484; and (p) a polypeptide having at least about 90% sequence identity to SEQ ID NO: 12

(q) a variant of SEQ ID NO:23 having alterations G182*+D183*;

(r) a variant of SEQ ID NO:24 having alterations H183*+G184*+I405L+A421H+A422P+A428T;

(s) a variant of SEQ ID NO:24 having alterations M9L+R118K+G149A+G182T+G186A+D183*+G184*+N195F+M202L+T257I+Y295F+N299Y+R320K+M323T+A339S+E345R+R458K;

(t) a variant of SEQ ID NO: 24 having alterations R178*+G179*+E187P+I203Y+R458N+T459S+D460T+G476K (u) a variant of SEQ ID NO: 27 having alteration M202L;

(v) a variant of SEQ ID NO: 28 having alterations R180*+S181*+S243Q+G475K;

(w) a variant of SEQ ID NO: 29 having alterations D183*+G184*+W140Y+N195F+I206Y+Y243F+E260G+G304R+G476K;

(x) a variant of SEQ ID NO: 30 having alterations H1*+N54S+V56T+K72R+G109A+F113Q+R116Q+W167F+Q172G+A174S+G184T+N195F+V206L+K391A+P473R+G476K;

(y) a variant of SEQ ID NO: 31 having alterations M9L+R118K+G149A+G182T+G186A+D183*+G184*+N195F+T246V+T257I+Y295F+N299Y+R320K+M323T+A339S+E345R+R458K.

13. The cleaning or detergent composition of claim 9, wherein the one or more proteases are selected from the group of:
   a) a polypeptide having at least about 60% sequence identity to SEQ ID NO: 34, wherein the polypeptide has protease activity;
   b) a polypeptide having at least about 60% sequence identity to SEQ ID NO: 35, wherein the polypeptide has protease activity; and
   c) a polypeptide having at least about 60% sequence identity to SEQ ID NO: 36, wherein the polypeptide has protease activity.

14. The cleaning or detergent composition of claim 1, wherein the cleaning or detergent composition has improved stability and/or wash performance under alkaline conditions.

15. The cleaning or detergent composition of claim 1, wherein the polypeptide has at least 99% sequence identity to the mature polypeptide of SEQ ID NO: 7, SEQ ID NO: 2, SEQ ID NO: 3, or SEQ ID NO: 9.

16. The cleaning or detergent composition of claim 1, wherein the polypeptide has at least 99% sequence identity to the mature polypeptide of SEQ ID NO: 7, SEQ ID NO: 2, SEQ ID NO: 3, or SEQ ID NO: 9; wherein the mature polypeptide is selected from the group of: amino acids 1 to 222 of SEQ ID NO: 7, amino acids 1 to 351 of SEQ ID NO: 2, amino acids 1 to 351 of SEQ ID NO: 3, or amino acids 1 to 214 of SEQ ID NO: 9; wherein the beta-glucanase activity is licheninase EC 3.2.1.73 activity; wherein the cleaning or detergent composition has a pH of from about 9.5 to about 10.5; wherein the cleaning or detergent composition further comprises one or more detergent components, and/or one or more additional enzymes, and a copolymer that comprises at least one sulfonic acid comprising monomers in an amount of from 6 to 12% by weight; and wherein the cleaning or detergent composition further comprises the polypeptide in a concentration of from about 0.01 mg enzyme protein/g composition to 10 mg enzyme protein/g composition.

17. The cleaning or detergent composition of claim 9, wherein the polypeptide has at least 99% sequence identity to the mature polypeptide of SEQ ID NO: 7, SEQ ID NO: 2, SEQ ID NO: 3, or SEQ ID NO: 9 wherein the mature polypeptide is selected from the group of: amino acids 1 to 222 of SEQ ID NO: 7, amino acids 1 to 351 of SEQ ID NO: 2, amino acids 1 to 351 of SEQ ID NO: 3, and amino acids 1 to 214 of SEQ ID NO: 9, and wherein the beta-glucanase activity is licheninase EC 3.2.1.73 activity.

* * * * *

SEQUENCE LISTING

<160> NUMBER OF SEQ ID NOS: 40

<210> SEQ ID NO 1
<211> LENGTH: 1140
<212> TYPE: DNA
<213> ORGANISM: Bacillus sp-62449

```
<220> FEATURE:
<221> NAME/KEY: CDS
<222> LOCATION: (1)..(1137)
<220> FEATURE:
<221> NAME/KEY: misc_feature
<222> LOCATION: (1)..(3)
<223> OTHER INFORMATION: The first amino acid (position -28) in the
      polypeptide shown in SEQ ID NO: 2 and encoded by the
      polynucleotide shown in SEQ ID NO:1 should be Met, not Val. When
      the first codon is gtg a Met is inserted though gtg normally codes
      for V
<220> FEATURE:
<221> NAME/KEY: sig_peptide
<222> LOCATION: (1)..(84)
<220> FEATURE:
<221> NAME/KEY: mat_peptide
<222> LOCATION: (85)..(1137)

<400> SEQUENCE: 1 gtg gtt aaa att aaa att aac aat agt att aga att gta atg ctg acg       48
Val Val Lys Ile Lys Ile Asn Asn Ser Ile Arg Ile Val Met Leu Thr
            -25                 -20                 -15 cta ata atg atg tcc gtt tca gtg gtg gct tat gcg tac aac cca gta       96
Leu Ile Met Met Ser Val Ser Val Val Ala Tyr Ala Tyr Asn Pro Val
        -10                  -5                  -1  1 aca gag gac gaa cta tat cat tcg ttc gat agt cat gat gct cgg aac      144
Thr Glu Asp Glu Leu Tyr His Ser Phe Asp Ser His Asp Ala Arg Asn
  5                  10                  15                  20 tgg cag att tct gat ggt tgg aga aat ggc gat gat ttt ttc ggt tgc      192
Trp Gln Ile Ser Asp Gly Trp Arg Asn Gly Asp Asp Phe Phe Gly Cys
                 25                  30                  35 cat tgg agt caa aac agg gtt aat ttt aat cgt ggt gaa atg gaa cta      240
His Trp Ser Gln Asn Arg Val Asn Phe Asn Arg Gly Glu Met Glu Leu
             40                  45                  50 tct ctt cgt aca aat tat tca tac tca gct ccg tat aat tat gag tgt      288
Ser Leu Arg Thr Asn Tyr Ser Tyr Ser Ala Pro Tyr Asn Tyr Glu Cys
         55                  60                  65 gca gag tat gcg acg agt aat ttc tat gga tat ggt ttg tac gaa gta      336
Ala Glu Tyr Ala Thr Ser Asn Phe Tyr Gly Tyr Gly Leu Tyr Glu Val
     70                  75                  80 tct atg aaa cca gcc aat gta tca gga gtg att tct tct ttc ttc acg      384
Ser Met Lys Pro Ala Asn Val Ser Gly Val Ile Ser Ser Phe Phe Thr
 85                  90                  95                 100 tat aca ggt cct tca tat aat gga gca cct tgg gat gag att gat att      432
Tyr Thr Gly Pro Ser Tyr Asn Gly Ala Pro Trp Asp Glu Ile Asp Ile
                105                 110                 115 gaa ttt cta gga aac gac acg aca aaa gtt caa ttc aat tat tac acg      480
Glu Phe Leu Gly Asn Asp Thr Thr Lys Val Gln Phe Asn Tyr Tyr Thr
            120                 125                 130 aac ggt gta gga gga aat gaa ata att tac gat tta gga ttt gat gct      528
Asn Gly Val Gly Gly Asn Glu Ile Ile Tyr Asp Leu Gly Phe Asp Ala
        135                 140                 145 gca aat agt ttt aat acg tat gcg ttt gat tgg caa gag aat tat att      576
Ala Asn Ser Phe Asn Thr Tyr Ala Phe Asp Trp Gln Glu Asn Tyr Ile
    150                 155                 160 agc tgg tat gtt aat ggg aac ttg gta gct aca gca aca gaa aat att      624
Ser Trp Tyr Val Asn Gly Asn Leu Val Ala Thr Ala Thr Glu Asn Ile
165                 170                 175                 180 cca agt aac ccg agt aaa atc atg atg aat gtg tgg aat acg tac gga      672
Pro Ser Asn Pro Ser Lys Ile Met Met Asn Val Trp Asn Thr Tyr Gly
                185                 190                 195 att gat gaa tgg gca ggg gca tat gga gga gaa gcc gct aat gcc acc      720
Ile Asp Glu Trp Ala Gly Ala Tyr Gly Gly Glu Ala Ala Asn Ala Thr
            200                 205                 210
```

```
tat gaa tgg gta cgg tat aca ccg aat aat gga aac aca act cct tcc     768
Tyr Glu Trp Val Arg Tyr Thr Pro Asn Asn Gly Asn Thr Thr Pro Ser
        215                 220                 225 act gct cct gac ttt caa ttg caa gcg tgt gat tac tca gat tca agt     816
Thr Ala Pro Asp Phe Gln Leu Gln Ala Cys Asp Tyr Ser Asp Ser Ser
230                 235                 240 ggg atc aca tct tgg tct tgt ggg gta ggg acc ttt cat tct agt aat     864
Gly Ile Thr Ser Trp Ser Cys Gly Val Gly Thr Phe His Ser Ser Asn
245                 250                 255                 260 tgg att aaa ttt gat agc gtt gat tta tct aca ggg tat aat gca ttt     912
Trp Ile Lys Phe Asp Ser Val Asp Leu Ser Thr Gly Tyr Asn Ala Phe
                265                 270                 275 gct gtc agc tat act tct ccg gga agt ggt agt ttt gat att aga cta     960
Ala Val Ser Tyr Thr Ser Pro Gly Ser Gly Ser Phe Asp Ile Arg Leu
            280                 285                 290 ggt agt cct cat ggt caa aga att ggt act gta aac tat ggt gca act    1008
Gly Ser Pro His Gly Gln Arg Ile Gly Thr Val Asn Tyr Gly Ala Thr
        295                 300                 305 ggt ggt tgg tct aac tac gag tgg agt ggt acc ccg tca tta gat gtg    1056
Gly Gly Trp Ser Asn Tyr Glu Trp Ser Gly Thr Pro Ser Leu Asp Val
310                 315                 320 acc gta aga gga gca cat gat ata tac att gta gct acg agc gga gcg    1104
Thr Val Arg Gly Ala His Asp Ile Tyr Ile Val Ala Thr Ser Gly Ala
325                 330                 335                 340 gct aat cta agg gaa ttt tgg ttt aaa aat gaa taa                    1140
Ala Asn Leu Arg Glu Phe Trp Phe Lys Asn Glu
                345                 350
```

<210> SEQ ID NO 2
<211> LENGTH: 379
<212> TYPE: PRT
<213> ORGANISM: Bacillus sp-62449

<400> SEQUENCE: 2

Val Val Lys Ile Lys Ile Asn Asn Ser Ile Arg Ile Val Met Leu Thr
        -25                 -20                 -15

Leu Ile Met Met Ser Val Ser Val Val Ala Tyr Ala Tyr Asn Pro Val
        -10                  -5                  -1  1

Thr Glu Asp Glu Leu Tyr His Ser Phe Asp Ser His Asp Ala Arg Asn
5                   10                  15                  20

Trp Gln Ile Ser Asp Gly Trp Arg Asn Gly Asp Phe Phe Gly Cys
                25                  30                  35

His Trp Ser Gln Asn Arg Val Asn Phe Asn Arg Gly Glu Met Glu Leu
            40                  45                  50

Ser Leu Arg Thr Asn Tyr Ser Tyr Ser Ala Pro Tyr Asn Tyr Glu Cys
        55                  60                  65

Ala Glu Tyr Ala Thr Ser Asn Phe Tyr Gly Tyr Gly Leu Tyr Glu Val
70                  75                  80

Ser Met Lys Pro Ala Asn Val Ser Gly Val Ile Ser Phe Phe Thr
85                  90                  95                  100

Tyr Thr Gly Pro Ser Tyr Asn Gly Ala Pro Trp Asp Glu Ile Asp Ile
                105                 110                 115

Glu Phe Leu Gly Asn Asp Thr Thr Lys Val Gln Phe Asn Tyr Tyr Thr
            120                 125                 130

Asn Gly Val Gly Gly Asn Glu Ile Ile Tyr Asp Leu Gly Phe Asp Ala
        135                 140                 145

Ala Asn Ser Phe Asn Thr Tyr Ala Phe Asp Trp Gln Glu Asn Tyr Ile

```
            150                 155                 160
Ser Trp Tyr Val Asn Gly Asn Leu Val Ala Thr Ala Thr Glu Asn Ile
165                 170                 175                 180

Pro Ser Asn Pro Ser Lys Ile Met Met Asn Val Trp Asn Thr Tyr Gly
                185                 190                 195

Ile Asp Glu Trp Ala Gly Ala Tyr Gly Gly Ala Ala Asn Ala Thr
                200                 205                 210

Tyr Glu Trp Val Arg Tyr Thr Pro Asn Asn Gly Asn Thr Thr Pro Ser
                215                 220                 225

Thr Ala Pro Asp Phe Gln Leu Gln Ala Cys Asp Tyr Ser Asp Ser Ser
230                 235                 240

Gly Ile Thr Ser Trp Ser Cys Gly Val Gly Thr Phe His Ser Ser Asn
245                 250                 255                 260

Trp Ile Lys Phe Asp Ser Val Asp Leu Ser Thr Gly Tyr Asn Ala Phe
                265                 270                 275

Ala Val Ser Tyr Thr Ser Pro Gly Ser Gly Ser Phe Asp Ile Arg Leu
                280                 285                 290

Gly Ser Pro His Gly Gln Arg Ile Gly Thr Val Asn Tyr Gly Ala Thr
                295                 300                 305

Gly Gly Trp Ser Asn Tyr Glu Trp Ser Gly Thr Pro Ser Leu Asp Val
                310                 315                 320

Thr Val Arg Gly Ala His Asp Ile Tyr Ile Val Ala Thr Ser Gly Ala
325                 330                 335                 340

Ala Asn Leu Arg Glu Phe Trp Phe Lys Asn Glu
                345                 350

<210> SEQ ID NO 3
<211> LENGTH: 379
<212> TYPE: PRT
<213> ORGANISM: Bacillus sp-62449
<220> FEATURE:
<221> NAME/KEY: SIGNAL
<222> LOCATION: (1)..(28)
<220> FEATURE:
<221> NAME/KEY: mat_peptide
<222> LOCATION: (29)..(379)

<400> SEQUENCE: 3

Met Val Lys Ile Lys Ile Asn Asn Ser Ile Arg Ile Val Met Leu Thr
            -25                 -20                 -15

Leu Ile Met Met Ser Val Ser Val Val Ala Tyr Ala Tyr Asn Pro Val
            -10                 -5                  -1  1

Thr Glu Asp Glu Leu Tyr His Ser Phe Asp Ser His Asp Ala Arg Asn
5                   10                  15                  20

Trp Gln Ile Ser Asp Gly Trp Arg Asn Gly Asp Asp Phe Phe Gly Cys
                25                  30                  35

His Trp Ser Gln Asn Arg Val Asn Phe Asn Arg Gly Glu Met Glu Leu
            40                  45                  50

Ser Leu Arg Thr Asn Tyr Ser Tyr Ser Ala Pro Tyr Asn Tyr Glu Cys
            55                  60                  65

Ala Glu Tyr Ala Thr Ser Asn Phe Tyr Gly Tyr Gly Leu Tyr Glu Val
70                  75                  80

Ser Met Lys Pro Ala Asn Val Ser Gly Val Ile Ser Ser Phe Phe Thr
85                  90                  95                  100

Tyr Thr Gly Pro Ser Tyr Asn Gly Ala Pro Trp Asp Glu Ile Asp Ile
                105                 110                 115
```

```
Glu Phe Leu Gly Asn Asp Thr Thr Lys Val Gln Phe Asn Tyr Tyr Thr
            120                 125                 130

Asn Gly Val Gly Gly Asn Glu Ile Ile Tyr Asp Leu Gly Phe Asp Ala
            135                 140                 145

Ala Asn Ser Phe Asn Thr Tyr Ala Phe Asp Trp Gln Glu Asn Tyr Ile
150                 155                 160

Ser Trp Tyr Val Asn Gly Asn Leu Val Ala Thr Ala Thr Glu Asn Ile
165                 170                 175                 180

Pro Ser Asn Pro Ser Lys Ile Met Met Asn Val Trp Asn Thr Tyr Gly
                185                 190                 195

Ile Asp Glu Trp Ala Gly Ala Tyr Gly Gly Glu Ala Ala Asn Ala Thr
                200                 205                 210

Tyr Glu Trp Val Arg Tyr Thr Pro Asn Asn Gly Asn Thr Thr Pro Ser
            215                 220                 225

Thr Ala Pro Asp Phe Gln Leu Gln Ala Cys Asp Tyr Ser Asp Ser Ser
    230                 235                 240

Gly Ile Thr Ser Trp Ser Cys Gly Val Gly Thr Phe His Ser Ser Asn
245                 250                 255                 260

Trp Ile Lys Phe Asp Ser Val Asp Leu Ser Thr Gly Tyr Asn Ala Phe
                265                 270                 275

Ala Val Ser Tyr Thr Ser Pro Gly Ser Gly Ser Phe Asp Ile Arg Leu
            280                 285                 290

Gly Ser Pro His Gly Gln Arg Ile Gly Thr Val Asn Tyr Gly Ala Thr
            295                 300                 305

Gly Gly Trp Ser Asn Tyr Glu Trp Ser Gly Thr Pro Ser Leu Asp Val
310                 315                 320

Thr Val Arg Gly Ala His Asp Ile Tyr Ile Val Ala Thr Ser Gly Ala
325                 330                 335                 340

Ala Asn Leu Arg Glu Phe Trp Phe Lys Asn Glu
                345                 350
```

```
<210> SEQ ID NO 4
<211> LENGTH: 831
<212> TYPE: DNA
<213> ORGANISM: Bacillus akibai
<220> FEATURE:
<221> NAME/KEY: CDS
<222> LOCATION: (1)..(828)
<220> FEATURE:
<221> NAME/KEY: sig_peptide
<222> LOCATION: (1)..(93)
<220> FEATURE:
<221> NAME/KEY: mat_peptide
<222> LOCATION: (94)..(828)

<400> SEQUENCE: 4 atg aaa aag aaa ttt gtt tta ttt tct atg tgt tta tta ttg ttt agc     48
Met Lys Lys Lys Phe Val Leu Phe Ser Met Cys Leu Leu Leu Phe Ser
-30             -25                 -20 ggc ctc ata act gga tta gtt caa agt cca caa gtt gct gaa gca gca     96
Gly Leu Ile Thr Gly Leu Val Gln Ser Pro Gln Val Ala Glu Ala Ala
-15             -10                 -5              -1   1 gaa aga cca att ggg act aca ttt gtt gaa aca ttt gaa tca tat gac    144
Glu Arg Pro Ile Gly Thr Thr Phe Val Glu Thr Phe Glu Ser Tyr Asp
            5                   10                  15 tca gaa cgt tgg tcg aaa gcg gga gtt tgg aca aat gga caa atg ttt    192
Ser Glu Arg Trp Ser Lys Ala Gly Val Trp Thr Asn Gly Gln Met Phe
            20                  25                  30 aat gca aca tgg tat cca gaa caa gtt act ttt tct gat ggt aag atg    240
```

```
Asn Ala Thr Trp Tyr Pro Glu Gln Val Thr Phe Ser Asp Gly Lys Met
     35              40                  45 aag ttg caa att gat aaa gaa gac aat gaa act gcg agc ccg cca tac      288
Lys Leu Gln Ile Asp Lys Glu Asp Asn Glu Thr Ala Ser Pro Pro Tyr
 50              55                  60                  65 aaa gct gga gaa ctt cgt aca aac gat ttt tat cac tac ggg ttg ttt      336
Lys Ala Gly Glu Leu Arg Thr Asn Asp Phe Tyr His Tyr Gly Leu Phe
                 70                  75                  80 gaa gtg agt atg aaa cct gca aaa tca acg gga aca gtc tct tca ttt      384
Glu Val Ser Met Lys Pro Ala Lys Ser Thr Gly Thr Val Ser Ser Phe
                     85                  90                  95 ttc acc tat act gga cct tgg gat tgg gat aat gat cca tgg gat gaa      432
Phe Thr Tyr Thr Gly Pro Trp Asp Trp Asp Asn Asp Pro Trp Asp Glu
                         100                 105                 110 att gat atc gaa ttt tta ggt aag gat act act aaa ata caa ttt aat      480
Ile Asp Ile Glu Phe Leu Gly Lys Asp Thr Thr Lys Ile Gln Phe Asn
                             115                 120                 125 tat ttt aca aac gga gta ggc gga aat gag cat tac cat gaa tta gga      528
Tyr Phe Thr Asn Gly Val Gly Gly Asn Glu His Tyr His Glu Leu Gly
130                 135                 140                 145 ttt gat gca gca gat gat ttt aat acg tat gct ttt gag tgg aga cca      576
Phe Asp Ala Ala Asp Asp Phe Asn Thr Tyr Ala Phe Glu Trp Arg Pro
                    150                 155                 160 gaa tct att cgt tgg ttt gta aat ggt gaa ctg gtt cat aca gca aca      624
Glu Ser Ile Arg Trp Phe Val Asn Gly Glu Leu Val His Thr Ala Thr
                        165                 170                 175 gaa aat ata cca caa aca cca caa aaa ata atg atg aac tta tgg cct      672
Glu Asn Ile Pro Gln Thr Pro Gln Lys Ile Met Met Asn Leu Trp Pro
                            180                 185                 190 ggt att gga gta gac ggg tgg act ggt aga ttt aat gga gaa gat act      720
Gly Ile Gly Val Asp Gly Trp Thr Gly Arg Phe Asn Gly Glu Asp Thr
                                195                 200                 205 cct gta gtt aca cag tac gat tgg gtg aag tat aca cca ctt gag gaa      768
Pro Val Val Thr Gln Tyr Asp Trp Val Lys Tyr Thr Pro Leu Glu Glu
210                 215                 220                 225 ctg ggc tgt tac aat gag aaa aat aat aaa tac aag aaa tgt aag aaa      816
Leu Gly Cys Tyr Asn Glu Lys Asn Asn Lys Tyr Lys Lys Cys Lys Lys
                    230                 235                 240 acg aag gta aaa tag                                                  831
Thr Lys Val Lys
             245

<210> SEQ ID NO 5
<211> LENGTH: 276
<212> TYPE: PRT
<213> ORGANISM: Bacillus akibai

<400> SEQUENCE: 5

Met Lys Lys Lys Phe Val Leu Phe Ser Met Cys Leu Leu Leu Phe Ser
    -30                 -25                 -20

Gly Leu Ile Thr Gly Leu Val Gln Ser Pro Gln Val Ala Glu Ala Ala
-15                 -10                  -5                  -1   1

Glu Arg Pro Ile Gly Thr Thr Phe Val Glu Thr Phe Glu Ser Tyr Asp
                 5                  10                  15

Ser Glu Arg Trp Ser Lys Ala Gly Val Trp Thr Asn Gly Gln Met Phe
                     20                  25                  30

Asn Ala Thr Trp Tyr Pro Glu Gln Val Thr Phe Ser Asp Gly Lys Met
                         35                  40                  45

Lys Leu Gln Ile Asp Lys Glu Asp Asn Glu Thr Ala Ser Pro Pro Tyr
```

```
                50                  55                  60                  65
           Lys Ala Gly Glu Leu Arg Thr Asn Asp Phe Tyr His Tyr Gly Leu Phe
                            70                  75                  80

Glu Val Ser Met Lys Pro Ala Lys Ser Thr Gly Thr Val Ser Ser Phe
                        85                  90                  95

Phe Thr Tyr Thr Gly Pro Trp Asp Trp Asn Asp Pro Trp Asp Glu
                    100                 105                 110

Ile Asp Ile Glu Phe Leu Gly Lys Asp Thr Thr Lys Ile Gln Phe Asn
                    115                 120                 125

Tyr Phe Thr Asn Gly Val Gly Gly Asn Glu His Tyr His Glu Leu Gly
           130                 135                 140                 145

Phe Asp Ala Ala Asp Asp Phe Asn Thr Tyr Ala Phe Glu Trp Arg Pro
                            150                 155                 160

Glu Ser Ile Arg Trp Phe Val Asn Gly Glu Leu Val His Thr Ala Thr
                        165                 170                 175

Glu Asn Ile Pro Gln Thr Pro Gln Lys Ile Met Met Asn Leu Trp Pro
                    180                 185                 190

Gly Ile Gly Val Asp Gly Trp Thr Gly Arg Phe Asn Gly Glu Asp Thr
                    195                 200                 205

Pro Val Val Thr Gln Tyr Asp Trp Val Lys Tyr Thr Pro Leu Glu Glu
           210                 215                 220                 225

Leu Gly Cys Tyr Asn Glu Lys Asn Asn Lys Tyr Lys Lys Cys Lys Lys
                            230                 235                 240

Thr Lys Val Lys
                    245

<210> SEQ ID NO 6
<211> LENGTH: 714
<212> TYPE: DNA
<213> ORGANISM: Bacillus agaradhaerens
<220> FEATURE:
<221> NAME/KEY: CDS
<222> LOCATION: (1)..(711)
<220> FEATURE:
<221> NAME/KEY: sig_peptide
<222> LOCATION: (1)..(45)
<220> FEATURE:
<221> NAME/KEY: mat_peptide
<222> LOCATION: (46)..(711)

<400> SEQUENCE: 6 atg ttg acg tta cta atg atg tct ttc gcg ggt gcg gca tat gca cat    48
Met Leu Thr Leu Leu Met Met Ser Phe Ala Gly Ala Ala Tyr Ala His
-15                 -10                  -5                  -1  1 aat cca gta aca gat gaa gaa gtc tat cat tcg ttt aac agt cat gat    96
Asn Pro Val Thr Asp Glu Glu Val Tyr His Ser Phe Asn Ser His Asp
            5                   10                  15 tgg caa aac tgg aat atg tct gac ggt tgg aaa aat gat gat tac ttt   144
Trp Gln Asn Trp Asn Met Ser Asp Gly Trp Lys Asn Asp Asp Tyr Phe
        20                  25                  30 ttc ggg tgt cat tgg agt cag aac aga gtt aac ttt tat ggt ggg caa   192
Phe Gly Cys His Trp Ser Gln Asn Arg Val Asn Phe Tyr Gly Gly Gln
    35                  40                  45 atg gag ttg tca ctg cgt aca aac tat tca tac gca cct cct tac aac   240
Met Glu Leu Ser Leu Arg Thr Asn Tyr Ser Tyr Ala Pro Pro Tyr Asn
50                  55                  60                  65 tat gag tgt gcg gag tat acg acc aat aat ttt tat gga tat gga tta   288
Tyr Glu Cys Ala Glu Tyr Thr Thr Asn Asn Phe Tyr Gly Tyr Gly Leu
                70                  75                  80
```

-continued

| | | | | | | | | | | | | | | | |
|---|---|---|---|---|---|---|---|---|---|---|---|---|---|---|---|
| tac | gag | gta | tct | atg | aaa | cca | gca | aag | gta | tca | ggg | gtc | att | tct | tct |
| Tyr | Glu | Val | Ser | Met | Lys | Pro | Ala | Lys | Val | Ser | Gly | Val | Ile | Ser | Ser |
| | | | 85 | | | | 90 | | | | | 95 | | | |

336

| | | | | | | | | | | | | | |
|---|---|---|---|---|---|---|---|---|---|---|---|---|---|
| ttc | ttc | acg | tat | aca | ggg | cct | tcc | tat | aat | gga | gcc | cct | tgg | gat | gaa |
| Phe | Phe | Thr | Tyr | Thr | Gly | Pro | Ser | Tyr | Asn | Gly | Ala | Pro | Trp | Asp | Glu |
| | | | 100 | | | | | 105 | | | | 110 | | | |

384

| att | gac | att | gaa | ttt | tta | gga | aac | gac | acg | act | aag | gtt | caa | ttc | aat |
|---|---|---|---|---|---|---|---|---|---|---|---|---|---|---|---|
| Ile | Asp | Ile | Glu | Phe | Leu | Gly | Asn | Asp | Thr | Thr | Lys | Val | Gln | Phe | Asn |
| 115 | | | | | 120 | | | | | 125 | | | | | |

432

| tat | tac | aca | gat | ggc | gta | gga | ggg | aat | gaa | ata | ctt | tat | gac | tta | gga |
|---|---|---|---|---|---|---|---|---|---|---|---|---|---|---|---|
| Tyr | Tyr | Thr | Asp | Gly | Val | Gly | Gly | Asn | Glu | Ile | Leu | Tyr | Asp | Leu | Gly |
| 130 | | | | | 135 | | | | | 140 | | | | | 145 |

480

| ttc | gat | gca | gcg | gat | agt | tat | aat | acg | tat | gca | ttc | gat | tgg | caa | gaa |
|---|---|---|---|---|---|---|---|---|---|---|---|---|---|---|---|
| Phe | Asp | Ala | Ala | Asp | Ser | Tyr | Asn | Thr | Tyr | Ala | Phe | Asp | Trp | Gln | Glu |
| | | | | | 150 | | | | | 155 | | | | | 160 |

528

| aat | tat | att | aat | tgg | tat | gtt | aat | ggc | caa | ctt | gtt | gca | aca | gca | acg |
|---|---|---|---|---|---|---|---|---|---|---|---|---|---|---|---|
| Asn | Tyr | Ile | Asn | Trp | Tyr | Val | Asn | Gly | Gln | Leu | Val | Ala | Thr | Ala | Thr |
| | | | 165 | | | | | 170 | | | | | 175 | | |

576

| gaa | aac | ata | cct | agt | aat | cct | agt | aaa | att | atg | atg | aac | att | tgg | aat |
|---|---|---|---|---|---|---|---|---|---|---|---|---|---|---|---|
| Glu | Asn | Ile | Pro | Ser | Asn | Pro | Ser | Lys | Ile | Met | Met | Asn | Ile | Trp | Asn |
| | | | 180 | | | | | 185 | | | | | 190 | | |

624

| acg | tat | ggt | att | gac | gag | tgg | gca | gga | agg | tat | tat | gga | gag | gat | gcc |
|---|---|---|---|---|---|---|---|---|---|---|---|---|---|---|---|
| Thr | Tyr | Gly | Ile | Asp | Glu | Trp | Ala | Gly | Arg | Tyr | Tyr | Gly | Glu | Asp | Ala |
| 195 | | | | | 200 | | | | | 205 | | | | | |

672

| aat | gct | tca | tat | aat | tgg | gtt | cgc | tat | aca | cct | aac | cgt | taa |
|---|---|---|---|---|---|---|---|---|---|---|---|---|---|
| Asn | Ala | Ser | Tyr | Asn | Trp | Val | Arg | Tyr | Thr | Pro | Asn | Arg | |
| 210 | | | | 215 | | | | | 220 | | | | |

714

<210> SEQ ID NO 7
<211> LENGTH: 237
<212> TYPE: PRT
<213> ORGANISM: Bacillus agaradhaerens

<400> SEQUENCE: 7

| Met | Leu | Thr | Leu | Leu | Met | Met | Ser | Phe | Ala | Gly | Ala | Ala | Tyr | Ala | His |
|---|---|---|---|---|---|---|---|---|---|---|---|---|---|---|---|
| -15 | | | | -10 | | | | | -5 | | | | | -1 | 1 |

| Asn | Pro | Val | Thr | Asp | Glu | Glu | Val | Tyr | His | Ser | Phe | Asn | Ser | His | Asp |
|---|---|---|---|---|---|---|---|---|---|---|---|---|---|---|---|
| | | | 5 | | | | | 10 | | | | | 15 | | |

| Trp | Gln | Asn | Trp | Asn | Met | Ser | Asp | Gly | Trp | Lys | Asn | Asp | Asp | Tyr | Phe |
|---|---|---|---|---|---|---|---|---|---|---|---|---|---|---|---|
| | | | 20 | | | | | 25 | | | | | 30 | | |

| Phe | Gly | Cys | His | Trp | Ser | Gln | Asn | Arg | Val | Asn | Phe | Tyr | Gly | Gly | Gln |
|---|---|---|---|---|---|---|---|---|---|---|---|---|---|---|---|
| | | | 35 | | | | | 40 | | | | | 45 | | |

| Met | Glu | Leu | Ser | Leu | Arg | Thr | Asn | Tyr | Ser | Tyr | Ala | Pro | Pro | Tyr | Asn |
|---|---|---|---|---|---|---|---|---|---|---|---|---|---|---|---|
| 50 | | | | | 55 | | | | | 60 | | | | | 65 |

| Tyr | Glu | Cys | Ala | Glu | Tyr | Thr | Thr | Asn | Asn | Phe | Tyr | Gly | Tyr | Gly | Leu |
|---|---|---|---|---|---|---|---|---|---|---|---|---|---|---|---|
| | | | | 70 | | | | | 75 | | | | | 80 | |

| Tyr | Glu | Val | Ser | Met | Lys | Pro | Ala | Lys | Val | Ser | Gly | Val | Ile | Ser | Ser |
|---|---|---|---|---|---|---|---|---|---|---|---|---|---|---|---|
| | | | | 85 | | | | | 90 | | | | | 95 | |

| Phe | Phe | Thr | Tyr | Thr | Gly | Pro | Ser | Tyr | Asn | Gly | Ala | Pro | Trp | Asp | Glu |
|---|---|---|---|---|---|---|---|---|---|---|---|---|---|---|---|
| | | | 100 | | | | | 105 | | | | | 110 | | |

| Ile | Asp | Ile | Glu | Phe | Leu | Gly | Asn | Asp | Thr | Thr | Lys | Val | Gln | Phe | Asn |
|---|---|---|---|---|---|---|---|---|---|---|---|---|---|---|---|
| 115 | | | | | 120 | | | | | 125 | | | | | |

| Tyr | Tyr | Thr | Asp | Gly | Val | Gly | Gly | Asn | Glu | Ile | Leu | Tyr | Asp | Leu | Gly |
|---|---|---|---|---|---|---|---|---|---|---|---|---|---|---|---|
| 130 | | | | | 135 | | | | | 140 | | | | | 145 |

| Phe | Asp | Ala | Ala | Asp | Ser | Tyr | Asn | Thr | Tyr | Ala | Phe | Asp | Trp | Gln | Glu |
|---|---|---|---|---|---|---|---|---|---|---|---|---|---|---|---|
| | | | | | 150 | | | | | 155 | | | | | 160 |

| Asn | Tyr | Ile | Asn | Trp | Tyr | Val | Asn | Gly | Gln | Leu | Val | Ala | Thr | Ala | Thr |
|---|---|---|---|---|---|---|---|---|---|---|---|---|---|---|---|
| | | | 165 | | | | | 170 | | | | | 175 | | |

```
Glu Asn Ile Pro Ser Asn Pro Ser Lys Ile Met Met Asn Ile Trp Asn
        180                 185                 190

Thr Tyr Gly Ile Asp Glu Trp Ala Gly Arg Tyr Tyr Gly Glu Asp Ala
    195                 200                 205

Asn Ala Ser Tyr Asn Trp Val Arg Tyr Thr Pro Asn Arg
210                 215                 220

<210> SEQ ID NO 8
<211> LENGTH: 732
<212> TYPE: DNA
<213> ORGANISM: Bacillus mojavensis
<220> FEATURE:
<221> NAME/KEY: CDS
<222> LOCATION: (1)..(729)
<220> FEATURE:
<221> NAME/KEY: sig_peptide
<222> LOCATION: (1)..(87)
<220> FEATURE:
<221> NAME/KEY: mat_peptide
<222> LOCATION: (88)..(729)

<400> SEQUENCE: 8
```

| | | | | | | | | | | | | | | | | |
|---|---|---|---|---|---|---|---|---|---|---|---|---|---|---|---|---|
| atg | tct | tat | cgt | atg | aaa | cga | gta | ttg | ttg | ctt | ctt | gtt | act | ggg | ttg | 48 |
| Met | Ser | Tyr | Arg | Met | Lys | Arg | Val | Leu | Leu | Leu | Leu | Val | Thr | Gly | Leu | |
| | | | -25 | | | | -20 | | | | | -15 | | | | |
| ttt | atg | agt | ttg | tct | gca | ttc | act | tct | act | gcc | tcg | gct | caa | aca | ggt | 96 |
| Phe | Met | Ser | Leu | Ser | Ala | Phe | Thr | Ser | Thr | Ala | Ser | Ala | Gln | Thr | Gly | |
| | | -10 | | | | | -5 | | | | | -1 | 1 | | | |
| gga | tcg | ttt | ttt | gac | ccc | ttt | aat | ggc | tac | aac | tcc | ggt | ttt | tgg | caa | 144 |
| Gly | Ser | Phe | Phe | Asp | Pro | Phe | Asn | Gly | Tyr | Asn | Ser | Gly | Phe | Trp | Gln | |
| | 5 | | | | | 10 | | | | | 15 | | | | | |
| aag | gca | aat | ggc | tat | tcg | aat | gga | aat | atg | ttt | aac | tgt | acc | tgg | cgt | 192 |
| Lys | Ala | Asn | Gly | Tyr | Ser | Asn | Gly | Asn | Met | Phe | Asn | Cys | Thr | Trp | Arg | |
| 20 | | | | | 25 | | | | | 30 | | | | | 35 | |
| gca | aat | aac | gta | tca | atg | acg | tca | tta | ggg | gaa | atg | cgt | ttg | gcg | cta | 240 |
| Ala | Asn | Asn | Val | Ser | Met | Thr | Ser | Leu | Gly | Glu | Met | Arg | Leu | Ala | Leu | |
| | | | | 40 | | | | | 45 | | | | | 50 | | |
| aca | agt | cca | tct | tat | aac | aag | ttt | gac | tgc | ggg | gaa | aac | cgc | tct | gtt | 288 |
| Thr | Ser | Pro | Ser | Tyr | Asn | Lys | Phe | Asp | Cys | Gly | Glu | Asn | Arg | Ser | Val | |
| | | | 55 | | | | | 60 | | | | | 65 | | | |
| caa | aca | tat | ggc | tat | gga | ctt | tat | gaa | gtc | agg | atg | aaa | cca | gct | aaa | 336 |
| Gln | Thr | Tyr | Gly | Tyr | Gly | Leu | Tyr | Glu | Val | Arg | Met | Lys | Pro | Ala | Lys | |
| | | | 70 | | | | | 75 | | | | | 80 | | | |
| aac | gta | gga | att | gtt | tca | tcg | ttc | ttc | act | tac | aca | ggt | cca | aca | gat | 384 |
| Asn | Val | Gly | Ile | Val | Ser | Ser | Phe | Phe | Thr | Tyr | Thr | Gly | Pro | Thr | Asp | |
| | 85 | | | | | 90 | | | | | 95 | | | | | |
| gga | act | cct | tgg | gat | gag | att | gat | atc | gaa | ttt | tta | gga | aaa | gac | aca | 432 |
| Gly | Thr | Pro | Trp | Asp | Glu | Ile | Asp | Ile | Glu | Phe | Leu | Gly | Lys | Asp | Thr | |
| 100 | | | | | 105 | | | | | 110 | | | | | 115 | |
| aca | aag | gtt | caa | ttt | aac | tat | tat | aca | aat | ggt | gta | gga | aac | cat | gag | 480 |
| Thr | Lys | Val | Gln | Phe | Asn | Tyr | Tyr | Thr | Asn | Gly | Val | Gly | Asn | His | Glu | |
| | | | 120 | | | | | 125 | | | | | 130 | | | |
| aag | ctc | gtg | gat | ctc | gga | ttt | gat | gct | gcc | aac | gcc | tat | cat | acg | tat | 528 |
| Lys | Leu | Val | Asp | Leu | Gly | Phe | Asp | Ala | Ala | Asn | Ala | Tyr | His | Thr | Tyr | |
| | | | 135 | | | | | 140 | | | | | 145 | | | |
| gcg | ttc | gat | tgg | cag | cca | aac | tct | att | aaa | tgg | tat | gtc | gat | ggg | caa | 576 |
| Ala | Phe | Asp | Trp | Gln | Pro | Asn | Ser | Ile | Lys | Trp | Tyr | Val | Asp | Gly | Gln | |
| | | | 150 | | | | | 155 | | | | | 160 | | | |
| tta | aaa | cat | act | gcg | aca | agc | caa | att | ccg | aca | aca | cca | ggt | aag | atc | 624 |
| Leu | Lys | His | Thr | Ala | Thr | Ser | Gln | Ile | Pro | Thr | Thr | Pro | Gly | Lys | Ile | |
| | 165 | | | | | 170 | | | | | 175 | | | | | |

| | | | | | | | | | | | | | | |
|---|---|---|---|---|---|---|---|---|---|---|---|---|---|---|
| atg | atg | aac | ttg | tgg | aat | ggt | acg | ggt | gta | gat | gaa | tgg | ctc | ggt | tcc | 672 |
| Met | Met | Asn | Leu | Trp | Asn | Gly | Thr | Gly | Val | Asp | Glu | Trp | Leu | Gly | Ser |
| 180 | | | | 185 | | | | | 190 | | | | | 195 | |

| tac | aat | ggt | gtg | aca | ccg | cta | tac | gct | cat | tac | gac | tgg | gtg | cgc | tat | 720 |
| Tyr | Asn | Gly | Val | Thr | Pro | Leu | Tyr | Ala | His | Tyr | Asp | Trp | Val | Arg | Tyr |
| | | | | 200 | | | | | 205 | | | | | 210 | |

| aca | aaa | aaa | taa | | | | | | | | | | | | | 732 |
| Thr | Lys | Lys | | | | | | | | | | | | | |

<210> SEQ ID NO 9
<211> LENGTH: 243
<212> TYPE: PRT
<213> ORGANISM: Bacillus mojavensis

<400> SEQUENCE: 9

Met Ser Tyr Arg Met Lys Arg Val Leu Leu Leu Val Thr Gly Leu
                 -25                 -20                 -15

Phe Met Ser Leu Ser Ala Phe Thr Ser Thr Ala Ser Ala Gln Thr Gly
            -10                  -5                  -1   1

Gly Ser Phe Phe Asp Pro Phe Asn Gly Tyr Asn Ser Gly Phe Trp Gln
         5                  10                  15

Lys Ala Asn Gly Tyr Ser Asn Gly Asn Met Phe Asn Cys Thr Trp Arg
 20                  25                  30                  35

Ala Asn Asn Val Ser Met Thr Ser Leu Gly Glu Met Arg Leu Ala Leu
                 40                  45                  50

Thr Ser Pro Ser Tyr Asn Lys Phe Asp Cys Gly Glu Asn Arg Ser Val
             55                  60                  65

Gln Thr Tyr Gly Tyr Gly Leu Tyr Glu Val Arg Met Lys Pro Ala Lys
             70                  75                  80

Asn Val Gly Ile Val Ser Ser Phe Phe Thr Tyr Thr Gly Pro Thr Asp
             85                  90                  95

Gly Thr Pro Trp Asp Glu Ile Asp Ile Glu Phe Leu Gly Lys Asp Thr
100                 105                 110                 115

Thr Lys Val Gln Phe Asn Tyr Tyr Thr Asn Gly Val Gly Asn His Glu
                120                 125                 130

Lys Leu Val Asp Leu Gly Phe Asp Ala Ala Asn Ala Tyr His Thr Tyr
            135                 140                 145

Ala Phe Asp Trp Gln Pro Asn Ser Ile Lys Trp Tyr Val Asp Gly Gln
            150                 155                 160

Leu Lys His Thr Ala Thr Ser Gln Ile Pro Thr Thr Pro Gly Lys Ile
            165                 170                 175

Met Met Asn Leu Trp Asn Gly Thr Gly Val Asp Glu Trp Leu Gly Ser
180                 185                 190                 195

Tyr Asn Gly Val Thr Pro Leu Tyr Ala His Tyr Asp Trp Val Arg Tyr
                200                 205                 210

Thr Lys Lys

<210> SEQ ID NO 10
<211> LENGTH: 27
<212> TYPE: PRT
<213> ORGANISM: Bacillus clausii
<220> FEATURE:
<221> NAME/KEY: SIGNAL
<222> LOCATION: (1)..(27)
<223> OTHER INFORMATION: Secretion signal

<400> SEQUENCE: 10

Met Lys Lys Pro Leu Gly Lys Ile Val Ala Ser Thr Ala Leu Leu Ile

```
1               5                   10                  15
Ser Val Ala Phe Ser Ser Ser Ile Ala Ser Ala
            20                  25
```

<210> SEQ ID NO 11
<211> LENGTH: 8
<212> TYPE: PRT
<213> ORGANISM: Artificial Sequence
<220> FEATURE:
<223> OTHER INFORMATION: N-terminal poly histidine affinity purification tag

<400> SEQUENCE: 11

```
His His His His His His Pro Arg
1               5
```

<210> SEQ ID NO 12
<211> LENGTH: 483
<212> TYPE: PRT
<213> ORGANISM: Bacillus sp.

<400> SEQUENCE: 12

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Lys Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Lys Gly Trp Asp Trp Glu Val Asp Thr Glu
            180                 185                 190

Phe Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Asn Lys Thr Asn Trp Asn His Ser Val Phe Asp
        275                 280                 285
```

```
Val Pro Leu His Tyr Asn Leu Tyr Asn Ala Ser Lys Ser Gly Gly Asn
    290                 295                 300

Tyr Asp Met Arg Gln Ile Phe Asn Gly Thr Val Gln Lys His Pro
305                 310                 315                 320

Met His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
                340                 345                 350

Leu Thr Leu Thr Arg Glu Gln Gly Tyr Pro Ser Val Phe Tyr Gly Asp
    355                 360                 365

Tyr Tyr Gly Ile Pro Thr His Gly Val Pro Ala Met Lys Ser Lys Ile
    370                 375                 380

Asp Pro Ile Leu Glu Ala Arg Gln Lys Tyr Ala Tyr Gly Arg Gln Asn
385                 390                 395                 400

Asp Tyr Leu Asp His His Asn Ile Ile Gly Trp Thr Arg Glu Gly Asn
                405                 410                 415

Thr Ala His Pro Asn Ser Gly Leu Ala Thr Ile Met Ser Asp Gly Ala
                420                 425                 430

Gly Gly Asn Lys Trp Met Phe Val Gly Arg Asn Lys Ala Gly Gln Val
                435                 440                 445

Trp Thr Asp Ile Thr Gly Asn Lys Ala Gly Thr Val Thr Ile Asn Ala
450                 455                 460

Asp Gly Trp Gly Asn Phe Ser Val Asn Gly Gly Ser Val Ser Ile Trp
465                 470                 475                 480

Val Asn Lys

<210> SEQ ID NO 13
<211> LENGTH: 483
<212> TYPE: PRT
<213> ORGANISM: Bacillus licheniformis
<220> FEATURE:
<221> NAME/KEY: MISC_FEATURE
<223> OTHER INFORMATION: corresponding to SEQ ID NO: 2 in WO 95/10603

<400> SEQUENCE: 13

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
                20                  25                  30

Ala Glu His Gly Ile Thr Ala Val Trp Ile Pro Pro Ala Tyr Lys Gly
            35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160
```

Asp Gly Thr Asp Trp Asp Glu Ser Arg Lys Leu Asn Arg Ile Tyr Lys
            165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
            195                 200                 205

Ala Ala Glu Ile Lys Arg Trp Gly Thr Trp Tyr Ala Asn Glu Leu Gln
210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
            275                 280                 285

His Tyr Gln Phe His Ala Ala Ser Thr Gln Gly Gly Gly Tyr Asp Met
290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
            355                 360                 365

Thr Lys Gly Asp Ser Gln Arg Glu Ile Pro Ala Leu Lys His Lys Ile
            370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
            435                 440                 445

Trp His Asp Ile Thr Gly Asn Arg Ser Glu Pro Val Val Ile Asn Ser
450                 455                 460

Glu Gly Trp Gly Glu Phe His Val Asn Gly Gly Ser Val Ser Ile Tyr
465                 470                 475                 480

Val Gln Arg

<210> SEQ ID NO 14
<211> LENGTH: 515
<212> TYPE: PRT
<213> ORGANISM: Bacillus stearothermophilus
<220> FEATURE:
<221> NAME/KEY: MISC_FEATURE
<223> OTHER INFORMATION: corresponding to SEQ ID NO: 6 in WO 2002/010355

<400> SEQUENCE: 14

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

```
Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
        50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
                100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
        130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
                195                 200                 205

Pro Glu Val Val Thr Glu Leu Lys Asn Trp Gly Lys Trp Tyr Val Asn
        210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
                260                 265                 270

Leu His Asn Tyr Ile Thr Lys Thr Asp Gly Thr Met Ser Leu Phe Asp
        275                 280                 285

Ala Pro Leu His Asn Lys Phe Tyr Thr Ala Ser Lys Ser Gly Gly Ala
        290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
        370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Gly
                405                 410                 415

Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
                435                 440                 445
```

```
Phe Tyr Asp Leu Thr Gly Asn Arg Ser Asp Thr Val Thr Ile Asn Ser
            450                 455                 460

Asp Gly Trp Gly Glu Phe Lys Val Asn Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
                500                 505                 510

Ala Trp Pro
        515

<210> SEQ ID NO 15
<211> LENGTH: 481
<212> TYPE: PRT
<213> ORGANISM: Artificial Sequence
<220> FEATURE:
<223> OTHER INFORMATION: Residues 1-33 of SEQ ID NO: 6 of WO 2006/066594
      and residues 36-483 of SEQ ID NO: 4 of WO 2006/066594
<220> FEATURE:
<221> NAME/KEY: MISC_FEATURE
<223> OTHER INFORMATION: corresponding to the hybrid polypeptide
      comprising residues 1-33 of SEQ ID NO: 6 of WO 2006/066594 and
      residues 36-483 of SEQ ID NO: 4 of WO 2006/066594

<400> SEQUENCE: 15

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
                20                  25                  30

Ile Gly Ile Thr Ala Val Trp Ile Pro Pro Ala Tyr Lys Gly Thr Ser
            35                  40                  45

Gln Ala Asp Val Gly Tyr Gly Ala Tyr Asp Leu Tyr Asp Leu Gly Glu
        50                  55                  60

Phe His Gln Lys Gly Thr Val Arg Thr Lys Tyr Gly Thr Lys Gly Glu
65                  70                  75                  80

Leu Gln Ser Ala Ile Lys Ser Leu His Ser Arg Asp Ile Asn Val Tyr
                85                  90                  95

Gly Asp Val Val Ile Asn His Lys Gly Ala Asp Ala Thr Glu Asp
                100                 105                 110

Val Thr Ala Val Glu Val Asp Pro Ala Asp Arg Asn Arg Val Ile Ser
            115                 120                 125

Gly Glu His Leu Ile Lys Ala Trp Thr His Phe His Phe Pro Gly Arg
130                 135                 140

Gly Ser Thr Tyr Ser Asp Phe Lys Trp His Trp Tyr His Phe Asp Gly
145                 150                 155                 160

Thr Asp Trp Asp Glu Ser Arg Lys Leu Asn Arg Ile Tyr Lys Phe Gln
                165                 170                 175

Gly Lys Ala Trp Asp Trp Glu Val Ser Asn Glu Asn Gly Asn Tyr Asp
            180                 185                 190

Tyr Leu Met Tyr Ala Asp Ile Asp Tyr Asp His Pro Asp Val Ala Ala
        195                 200                 205

Glu Ile Lys Arg Trp Gly Thr Trp Tyr Ala Asn Glu Leu Gln Leu Asp
    210                 215                 220

Gly Phe Arg Leu Asp Ala Val Lys His Ile Lys Phe Ser Phe Leu Arg
225                 230                 235                 240

Asp Trp Val Asn His Val Arg Glu Lys Thr Gly Lys Glu Met Phe Thr
                245                 250                 255
```

Val Ala Glu Tyr Trp Gln Asn Asp Leu Gly Ala Leu Glu Asn Tyr Leu
            260                 265                 270

Asn Lys Thr Asn Phe Asn His Ser Val Phe Asp Val Pro Leu His Tyr
        275                 280                 285

Gln Phe His Ala Ala Ser Thr Gln Gly Gly Tyr Asp Met Arg Lys
    290                 295                 300

Leu Leu Asn Gly Thr Val Val Ser Lys His Pro Leu Lys Ser Val Thr
305                 310                 315                 320

Phe Val Asp Asn His Asp Thr Gln Pro Gly Gln Ser Leu Glu Ser Thr
                325                 330                 335

Val Gln Thr Trp Phe Lys Pro Leu Ala Tyr Ala Phe Ile Leu Thr Arg
            340                 345                 350

Glu Ser Gly Tyr Pro Gln Val Phe Tyr Gly Asp Met Tyr Gly Thr Lys
        355                 360                 365

Gly Asp Ser Gln Arg Glu Ile Pro Ala Leu Lys His Lys Ile Glu Pro
    370                 375                 380

Ile Leu Lys Ala Arg Lys Gln Tyr Ala Tyr Gly Ala Gln His Asp Tyr
385                 390                 395                 400

Phe Asp His His Asp Ile Val Gly Trp Thr Arg Glu Gly Asp Ser Ser
                405                 410                 415

Val Ala Asn Ser Gly Leu Ala Ala Leu Ile Thr Asp Gly Pro Gly Gly
            420                 425                 430

Ala Lys Arg Met Tyr Val Gly Arg Gln Asn Ala Gly Glu Thr Trp His
        435                 440                 445

Asp Ile Thr Gly Asn Arg Ser Glu Pro Val Val Ile Asn Ser Glu Gly
    450                 455                 460

Trp Gly Glu Phe His Val Asn Gly Gly Ser Val Ser Ile Tyr Val Gln
465                 470                 475                 480

Arg

<210> SEQ ID NO 16
<211> LENGTH: 485
<212> TYPE: PRT
<213> ORGANISM: Bacillus sp.
<220> FEATURE:
<221> NAME/KEY: MISC_FEATURE
<223> OTHER INFORMATION: corresponding to SEQ ID NO: 6 of WO 2002/019467

<400> SEQUENCE: 16

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

```
Gln Glu Val Thr Gly Glu Tyr Thr Ile Glu Ala Trp Thr Arg Phe Asp
130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Lys
                485
```

<210> SEQ ID NO 17
<211> LENGTH: 485
<212> TYPE: PRT
<213> ORGANISM: Bacillus sp. NCIB 12512
<220> FEATURE:
<221> NAME/KEY: MISC_FEATURE
<223> OTHER INFORMATION: corresponding to SEQ ID NO: 1 of WO 1996/023873

<400> SEQUENCE: 17

-continued

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
            35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Ile Val Asn Ala Val Glu Val Asn Arg Ser Asn Arg Asn
            115                 120                 125

Gln Glu Thr Ser Gly Glu Tyr Ala Ile Glu Ala Trp Thr Lys Phe Asp
            130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Tyr Ala Asp Val Asp Met
            195                 200                 205

Asp His Pro Glu Val Ile His Glu Leu Arg Asn Trp Gly Val Trp Tyr
            210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Pro Met Phe Ala Val Ala Glu Phe Trp Lys Asn Asp Leu
            260                 265                 270

Gly Ala Ile Glu Asn Tyr Leu Asn Lys Thr Ser Trp Asn His Ser Val
            275                 280                 285

Phe Asp Val Pro Leu His Tyr Asn Leu Tyr Asn Ala Ser Asn Ser Gly
            290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                325                 330                 335

Gly Glu Ala Leu Glu Ser Phe Val Gln Gln Trp Phe Lys Pro Leu Ala
            340                 345                 350

Tyr Ala Leu Val Leu Thr Arg Glu Gln Gly Tyr Pro Ser Val Phe Tyr
            355                 360                 365

Gly Asp Tyr Tyr Gly Ile Pro Thr His Gly Val Pro Ala Met Lys Ser
            370                 375                 380

Lys Ile Asp Pro Leu Leu Gln Ala Arg Gln Thr Phe Ala Tyr Gly Thr
385                 390                 395                 400

Gln His Asp Tyr Phe Asp His His Asp Ile Ile Gly Trp Thr Arg Glu
                405                 410                 415

```
Gly Asn Ser Ser His Pro Asn Ser Gly Leu Ala Thr Ile Met Ser Asp
            420                 425                 430

Gly Pro Gly Gly Asn Lys Trp Met Tyr Val Gly Lys Asn Lys Ala Gly
            435                 440                 445

Gln Val Trp Arg Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Val Trp Val Lys Gln
            485

<210> SEQ ID NO 18
<211> LENGTH: 485
<212> TYPE: PRT
<213> ORGANISM: Bacillus sp. NCIB 12513
<220> FEATURE:
<221> NAME/KEY: MISC_FEATURE
<223> OTHER INFORMATION: corresponding to SEQ ID NO: 2 of WO 1996/023873

<400> SEQUENCE: 18

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
    130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285
```

```
Phe Asp Val Pro Leu His Tyr Asn Leu Tyr Asn Ala Ser Asn Ser Gly
    290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
    370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile
    450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 19
<211> LENGTH: 485
<212> TYPE: PRT
<213> ORGANISM: Bacillus sp. #707
<220> FEATURE:
<221> NAME/KEY: MISC_FEATURE
<223> OTHER INFORMATION: corresponding to SEQ ID NO: 7 of WO 1996/023873

<400> SEQUENCE: 19

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
                20                  25                  30

Asn Leu Lys Ser Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
                100                 105                 110

Ala Thr Glu Met Val Arg Ala Val Glu Val Asn Pro Asn Asn Arg Asn
            115                 120                 125

Gln Glu Val Thr Gly Glu Tyr Thr Ile Glu Ala Trp Thr Arg Phe Asp
        130                 135                 140

Phe Pro Gly Arg Gly Asn Thr His Ser Ser Phe Lys Trp Arg Trp Tyr
```

```
145                 150                 155                 160
His Phe Asp Gly Val Asp Trp Asp Gln Ser Arg Arg Leu Asn Asn Arg
                165                 170                 175
Ile Tyr Lys Phe Arg Gly His Gly Lys Ala Trp Asp Trp Glu Val Asp
                180                 185                 190
Thr Glu Asn Gly Asn Tyr Asp Tyr Leu Met Tyr Ala Asp Ile Asp Met
                195                 200                 205
Asp His Pro Glu Val Val Asn Glu Leu Arg Asn Trp Gly Val Trp Tyr
210                 215                 220
Thr Asn Thr Leu Gly Leu Asp Gly Phe Arg Ile Asp Ala Val Lys His
225                 230                 235                 240
Ile Lys Tyr Ser Phe Thr Arg Asp Trp Ile Asn His Val Arg Ser Ala
                245                 250                 255
Thr Gly Lys Asn Met Phe Ala Val Ala Glu Phe Trp Lys Asn Asp Leu
                260                 265                 270
Gly Ala Ile Glu Asn Tyr Leu Gln Lys Thr Asn Trp Asn His Ser Val
                275                 280                 285
Phe Asp Val Pro Leu His Tyr Asn Leu Tyr Asn Ala Ser Lys Ser Gly
                290                 295                 300
Gly Asn Tyr Asp Met Arg Asn Ile Phe Asn Gly Thr Val Val Gln Arg
305                 310                 315                 320
His Pro Ser His Ala Val Thr Phe Val Asp Asn His Asp Ser Gln Pro
                325                 330                 335
Glu Glu Ala Leu Glu Ser Phe Val Glu Trp Phe Lys Pro Leu Ala
                340                 345                 350
Tyr Ala Leu Thr Leu Thr Arg Glu Gln Gly Tyr Pro Ser Val Phe Tyr
                355                 360                 365
Gly Asp Tyr Tyr Gly Ile Pro Thr His Gly Val Pro Ala Met Arg Ser
                370                 375                 380
Lys Ile Asp Pro Ile Leu Glu Ala Arg Gln Lys Tyr Ala Tyr Gly Lys
385                 390                 395                 400
Gln Asn Asp Tyr Leu Asp His His Asn Ile Ile Gly Trp Thr Arg Glu
                405                 410                 415
Gly Asn Thr Ala His Pro Asn Ser Gly Leu Ala Thr Ile Met Ser Asp
                420                 425                 430
Gly Ala Gly Gly Ser Lys Trp Met Phe Val Gly Arg Asn Lys Ala Gly
                435                 440                 445
Gln Val Trp Ser Asp Ile Thr Gly Asn Arg Thr Gly Thr Val Thr Ile
                450                 455                 460
Asn Ala Asp Gly Trp Gly Asn Phe Ser Val Asn Gly Gly Ser Val Ser
465                 470                 475                 480
Ile Trp Val Asn Lys
                485

<210> SEQ ID NO 20
<211> LENGTH: 485
<212> TYPE: PRT
<213> ORGANISM: Bacillus sp. A 7-7 (DSM 12368)
<220> FEATURE:
<221> NAME/KEY: MISC_FEATURE
<223> OTHER INFORMATION: corresponding to SEQ ID NO: 2 of WO 2008/153815

<400> SEQUENCE: 20

His His Asn Gly Thr Asn Gly Thr Met Met Gln Tyr Phe Glu Trp Tyr
1               5                   10                  15
```

-continued

```
Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
        275                 280                 285

Phe Asp Val Pro Leu His Tyr Asn Leu Tyr Asn Ala Ser Arg Ser Gly
    290                 295                 300

Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Asp Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Met Ile Gly Trp Thr Arg Glu
                405                 410                 415

Gly Asn Thr Ala His Pro Asn Ser Gly Leu Ala Thr Ile Met Ser Asp
            420                 425                 430

Gly Pro Gly Gly Asn Lys Trp Met Tyr Val Gly Arg Asn Lys Ala Gly
```

```
                     435                 440                 445
Gln Val Trp Arg Asp Ile Thr Gly Asn Arg Ser Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Asn
                485

<210> SEQ ID NO 21
<211> LENGTH: 483
<212> TYPE: PRT
<213> ORGANISM: Bacillus amyloliquefaciens
<220> FEATURE:
<221> NAME/KEY: MISC_FEATURE
<223> OTHER INFORMATION: corresponding to SEQ ID NO: 10 of WO
      2001/066712

<400> SEQUENCE: 21

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
                20                  25                  30

Ile Gly Ile Thr Ala Val Trp Ile Pro Pro Ala Tyr Lys Gly Leu Ser
            35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
                100                 105                 110

Val Thr Ala Val Glu Val Asn Pro Ala Asn Arg Asn Gln Glu Thr Ser
            115                 120                 125

Glu Glu Tyr Gln Ile Lys Ala Trp Thr Asp Phe Arg Phe Pro Gly Arg
    130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
                180                 185                 190

Tyr Asp Tyr Leu Met Tyr Ala Asp Val Asp Tyr Asp His Pro Asp Val
            195                 200                 205

Val Ala Glu Thr Lys Lys Trp Gly Ile Trp Tyr Ala Asn Glu Leu Ser
    210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
                260                 265                 270

Tyr Leu Asn Lys Thr Ser Phe Asn Gln Ser Val Phe Asp Val Pro Leu
            275                 280                 285

His Phe Asn Leu Gln Ala Ala Ser Ser Gln Gly Gly Gly Tyr Asp Met
    290                 295                 300
```

```
Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Thr Ser Pro Lys Glu Ile Pro Ser Leu Lys Asp Asn Ile
    370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

Val Gln Lys

<210> SEQ ID NO 22
<211> LENGTH: 484
<212> TYPE: PRT
<213> ORGANISM: Bacillus sp. TS-23
<220> FEATURE:
<221> NAME/KEY: MISC_FEATURE
<223> OTHER INFORMATION: corresponding to SEQ ID NO: 2 of WO 2009/061380

<400> SEQUENCE: 22

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
                20                  25                  30

Asn Leu Ser Ser Leu Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175
```

```
Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Thr Glu Leu Lys Asn Trp Gly Thr Trp Tyr Val
210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
    290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Gly Leu Lys Ser Lys
    370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
            420                 425                 430

Pro Gly Gly Ser Lys Trp Met Tyr Val Gly Lys His Ala Gly Lys
        435                 440                 445

Val Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
465                 470                 475                 480

Trp Val Ala Lys

<210> SEQ ID NO 23
<211> LENGTH: 485
<212> TYPE: PRT
<213> ORGANISM: Bacillus sp.

<400> SEQUENCE: 23

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
            20                  25                  30

Asn Leu Lys Asn Ala Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60
```

```
Asp Leu Gly Glu Phe Asn Gln Lys Gly Thr Val Arg Thr Lys Tyr Gly
 65                  70                  75                  80

Thr Lys Ala Glu Leu Glu Arg Ala Ile Arg Ser Leu Lys Ala Asn Gly
                 85                  90                  95

Ile Gln Val Tyr Gly Asp Val Val Met Asn His Lys Gly Gly Ala Asp
            100                 105                 110

Phe Thr Glu Arg Val Gln Ala Val Glu Val Asn Pro Gln Asn Arg Asn
        115                 120                 125

Gln Glu Val Ser Gly Thr Tyr Gln Ile Glu Ala Trp Thr Gly Phe Asn
    130                 135                 140

Phe Pro Gly Arg Gly Asn Gln His Ser Ser Phe Lys Trp Arg Trp Tyr
145                 150                 155                 160

His Phe Asp Gly Thr Asp Trp Asp Gln Ser Arg Gln Leu Ala Asn Arg
                165                 170                 175

Ile Tyr Lys Phe Arg Gly Asp Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile Asn Glu Leu Asn Arg Trp Gly Val Trp Tyr
    210                 215                 220

Ala Asn Thr Leu Asn Leu Asp Gly Phe Arg Leu Asp Ala Val Lys His
225                 230                 235                 240

Ile Lys Phe Ser Phe Met Arg Asp Trp Leu Gly His Val Arg Gly Gln
                245                 250                 255

Thr Gly Lys Asn Leu Phe Ala Val Ala Glu Tyr Trp Lys Asn Asp Leu
            260                 265                 270

Gly Ala Leu Glu Asn Tyr Leu Ser Lys Thr Asn Trp Thr Met Ser Ala
        275                 280                 285

Phe Asp Val Pro Leu His Tyr Asn Leu Tyr Gln Ala Ser Asn Ser Ser
    290                 295                 300

Gly Asn Tyr Asp Met Arg Asn Leu Leu Asn Gly Thr Leu Val Gln Arg
305                 310                 315                 320

His Pro Ser His Ala Val Thr Phe Val Asp Asn His Asp Thr Gln Pro
                325                 330                 335

Gly Glu Ala Leu Glu Ser Phe Val Gln Gly Trp Phe Lys Pro Leu Ala
            340                 345                 350

Tyr Ala Thr Ile Leu Thr Arg Glu Gln Gly Tyr Pro Gln Val Phe Tyr
        355                 360                 365

Gly Asp Tyr Tyr Gly Ile Pro Ser Asp Gly Val Pro Ser Tyr Arg Gln
    370                 375                 380

Gln Ile Asp Pro Leu Leu Lys Ala Arg Gln Gln Tyr Ala Tyr Gly Arg
385                 390                 395                 400

Gln His Asp Tyr Phe Asp His Trp Asp Val Ile Gly Trp Thr Arg Glu
                405                 410                 415

Gly Asn Ala Ser His Pro Asn Ser Gly Leu Ala Thr Ile Met Ser Asp
            420                 425                 430

Gly Pro Gly Gly Ser Lys Trp Met Tyr Val Gly Arg Gln Lys Ala Gly
        435                 440                 445

Glu Val Trp His Asp Met Thr Gly Asn Arg Ser Gly Thr Val Thr Ile
    450                 455                 460

Asn Gln Asp Gly Trp Gly His Phe Phe Val Asn Gly Gly Ser Val Ser
465                 470                 475                 480
```

```
Val Trp Val Lys Arg
            485
```

```
<210> SEQ ID NO 24
<211> LENGTH: 483
<212> TYPE: PRT
<213> ORGANISM: Bacillus sp.

<400> SEQUENCE: 24
```

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly Lys Ala Trp Asp Trp Glu Val Asp Thr Glu
            180                 185                 190

Asn Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Gln Lys Thr Asn Trp Asn His Ser Val Phe Asp
        275                 280                 285

Val Pro Leu His Tyr Asn Leu Tyr Asn Ala Ser Lys Ser Gly Gly Asn
290                 295                 300

Tyr Asp Met Arg Asn Ile Phe Asn Gly Thr Val Val Gln Arg His Pro
305                 310                 315                 320

Ser His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
            340                 345                 350

Leu Thr Leu Thr Arg Glu Gln Gly Tyr Pro Ser Val Phe Tyr Gly Asp
        355                 360                 365
```

```
Tyr Tyr Gly Ile Pro Thr His Gly Val Pro Ala Met Arg Ser Lys Ile
            370                 375                 380

Asp Pro Ile Leu Glu Ala Arg Gln Lys Tyr Ala Tyr Gly Pro Gln His
385                 390                 395                 400

Asp Tyr Leu Asp His Pro Asp Val Ile Gly Trp Thr Arg Glu Gly Asp
                405                 410                 415

Ser Ser His Pro Lys Ser Gly Leu Ala Thr Leu Ile Thr Asp Gly Pro
            420                 425                 430

Gly Gly Ser Lys Arg Met Tyr Ala Gly Leu Lys Asn Ala Gly Glu Thr
            435                 440                 445

Trp Tyr Asp Ile Thr Gly Asn Arg Ser Asp Thr Val Lys Ile Gly Ser
            450                 455                 460

Asp Gly Trp Gly Glu Phe His Val Asn Asp Gly Ser Val Ser Ile Tyr
465                 470                 475                 480

Val Gln Lys

<210> SEQ ID NO 25
<211> LENGTH: 485
<212> TYPE: PRT
<213> ORGANISM: Bacillus sp.

<400> SEQUENCE: 25

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
                20                  25                  30

Asn Leu Lys Asp Lys Gly Ile Ser Ala Val Trp Ile Pro Pro Ala Trp
            35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255
```

```
Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
            275                 280                 285

Phe Asp Val Pro Leu His Tyr Asn Leu Tyr Asn Ala Ser Lys Ser Gly
290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
            355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Asn Lys Trp Met Phe Val Gly Arg Asn Lys Ala Gly
            435                 440                 445

Gln Val Trp Thr Asp Ile Thr Gly Asn Arg Ala Gly Thr Val Thr Ile
            450                 455                 460

Asn Ala Asp Gly Trp Gly Asn Phe Ser Val Asn Gly Ser Val Ser
465                 470                 475                 480

Ile Trp Val Asn Lys
            485

<210> SEQ ID NO 26
<211> LENGTH: 485
<212> TYPE: PRT
<213> ORGANISM: Cytophaga sp.

<400> SEQUENCE: 26

Ala Ala Thr Asn Gly Thr Met Met Gln Tyr Phe Glu Trp Tyr Val Pro
1               5                   10                  15

Asn Asp Gly Gln Gln Trp Asn Arg Leu Arg Thr Asp Ala Pro Tyr Leu
            20                  25                  30

Ser Ser Val Gly Ile Thr Ala Val Trp Thr Pro Pro Ala Tyr Lys Gly
        35                  40                  45

Thr Ser Gln Ala Asp Val Gly Tyr Gly Pro Tyr Asp Leu Tyr Asp Leu
50                  55                  60

Gly Glu Phe Asn Gln Lys Gly Thr Val Arg Thr Lys Tyr Gly Thr Lys
65                  70                  75                  80

Gly Glu Leu Lys Ser Ala Val Asn Thr Leu His Ser Asn Gly Ile Gln
            85                  90                  95

Val Tyr Gly Asp Val Val Met Asn His Lys Ala Gly Ala Asp Tyr Thr
            100                 105                 110

Glu Asn Val Thr Ala Val Glu Val Asn Pro Ser Asn Arg Asn Gln Glu
        115                 120                 125

Thr Ser Gly Glu Tyr Asn Ile Gln Ala Trp Thr Gly Phe Asn Phe Pro
```

```
            130                 135                 140
Gly Arg Gly Thr Thr Tyr Ser Asn Phe Lys Trp Gln Trp Phe His Phe
145                 150                 155                 160

Asp Gly Thr Asp Trp Asp Gln Ser Arg Ser Leu Ser Arg Ile Phe Lys
                165                 170                 175

Phe Arg Gly Thr Gly Lys Ala Trp Asp Trp Glu Val Ser Ser Glu Asn
            180                 185                 190

Gly Asn Tyr Asp Tyr Leu Met Tyr Ala Asp Ile Asp Tyr Asp His Pro
        195                 200                 205

Asp Val Val Asn Glu Met Lys Lys Trp Gly Val Trp Tyr Ala Asn Glu
    210                 215                 220

Val Gly Leu Asp Gly Tyr Arg Leu Asp Ala Val Lys His Ile Lys Phe
225                 230                 235                 240

Ser Phe Leu Lys Asp Trp Val Asp Asn Ala Arg Ala Ala Thr Gly Lys
                245                 250                 255

Glu Met Phe Thr Val Gly Glu Tyr Trp Gln Asn Asp Leu Gly Ala Leu
            260                 265                 270

Asn Asn Tyr Leu Ala Lys Val Asn Tyr Asn Gln Ser Leu Phe Asp Ala
        275                 280                 285

Pro Leu His Tyr Asn Phe Tyr Ala Ala Ser Thr Gly Gly Gly Tyr Tyr
    290                 295                 300

Asp Met Arg Asn Ile Leu Asn Asn Thr Leu Val Ala Ser Asn Pro Thr
305                 310                 315                 320

Lys Ala Val Thr Leu Val Glu Asn His Asp Thr Gln Pro Gly Gln Ser
                325                 330                 335

Leu Glu Ser Thr Val Gln Pro Trp Phe Lys Pro Leu Ala Tyr Ala Phe
            340                 345                 350

Ile Leu Thr Arg Ser Gly Gly Tyr Pro Ser Val Phe Tyr Gly Asp Met
        355                 360                 365

Tyr Gly Thr Lys Gly Thr Thr Thr Arg Glu Ile Pro Ala Leu Lys Ser
    370                 375                 380

Lys Ile Glu Pro Leu Leu Lys Ala Arg Lys Asp Tyr Ala Tyr Gly Thr
385                 390                 395                 400

Gln Arg Asp Tyr Ile Asp Asn Pro Asp Val Ile Gly Trp Thr Arg Glu
                405                 410                 415

Gly Asp Ser Thr Lys Ala Lys Ser Gly Leu Ala Thr Val Ile Thr Asp
            420                 425                 430

Gly Pro Gly Gly Ser Lys Arg Met Tyr Val Gly Thr Ser Asn Ala Gly
        435                 440                 445

Glu Ile Trp Tyr Asp Leu Thr Gly Asn Arg Thr Asp Lys Ile Thr Ile
    450                 455                 460

Gly Ser Asp Gly Tyr Ala Thr Phe Pro Val Asn Gly Gly Ser Val Ser
465                 470                 475                 480

Val Trp Val Gln Gln
                485

<210> SEQ ID NO 27
<211> LENGTH: 485
<212> TYPE: PRT
<213> ORGANISM: Bacillus sp.

<400> SEQUENCE: 27

His His Asn Gly Thr Asn Gly Thr Met Met Gln Tyr Phe Glu Trp Tyr
1               5                   10                  15
```

-continued

```
Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
```

```
                    435                 440                 445
Gln Val Trp Ser Asp Ile Thr Gly Asn Arg Thr Gly Thr Val Thr Ile
            450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 28
<211> LENGTH: 484
<212> TYPE: PRT
<213> ORGANISM: Bacillus sp.

<400> SEQUENCE: 28

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Thr Glu Leu Lys Asn Trp Gly Thr Trp Tyr Val
    210                 215                 220

Asn Thr Thr Asn Ile Asp Gly Phe Arg Leu Asp Ala Val Lys His Ile
225                 230                 235                 240

Lys Tyr Thr Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
    290                 295                 300

Tyr Phe Asp Met Arg Tyr Leu Leu Asn Asn Thr Leu Met Lys Asp Gln
305                 310                 315                 320
```

```
Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
            355                 360                 365

Asp Tyr Tyr Gly Ile Pro Lys Tyr Asn Ile Pro Gly Leu Lys Ser Lys
        370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
                420                 425                 430

Pro Gly Gly Ser Lys Trp Met Tyr Val Gly Lys Lys His Ala Gly Lys
                435                 440                 445

Val Phe Tyr Asp Leu Thr Gly Asn Arg Ser Asp Thr Val Thr Ile Asn
            450                 455                 460

Ala Asp Gly Trp Gly Glu Phe Lys Val Asn Gly Gly Ser Val Ser Ile
465                 470                 475                 480

Trp Val Ala Lys

<210> SEQ ID NO 29
<211> LENGTH: 485
<212> TYPE: PRT
<213> ORGANISM: Bacillus halmapalus

<400> SEQUENCE: 29

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
                20                  25                  30

Asn Leu Arg Asn Arg Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
                100                 105                 110

Ala Thr Glu Asn Val Leu Ala Val Glu Val Asn Pro Asn Asn Arg Asn
            115                 120                 125

Gln Glu Ile Ser Gly Asp Tyr Thr Ile Glu Ala Trp Thr Lys Phe Asp
        130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205
```

Asp His Pro Glu Val Val Asn Glu Leu Arg Arg Trp Gly Glu Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
            245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
            275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
            355                 360                 365

Gly Asp Tyr Tyr Gly Ile Pro Thr His Ser Val Pro Ala Met Lys Ala
370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
            435                 440                 445

Gln Val Trp His Asp Ile Thr Gly Asn Lys Pro Gly Thr Val Thr Ile
            450                 455                 460

Asn Ala Asp Gly Trp Ala Asn Phe Ser Val Asn Gly Gly Ser Val Ser
465                 470                 475                 480

Ile Trp Val Lys Arg
            485

<210> SEQ ID NO 30
<211> LENGTH: 485
<212> TYPE: PRT
<213> ORGANISM: Artificial Sequence
<220> FEATURE:
<223> OTHER INFORMATION: Artificial Amylase Protein Sequence

<400> SEQUENCE: 30

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
                20                  25                  30

Asn Leu Lys Asn Ala Gly Ile Thr Ala Ile Trp Ile Pro Pro Ala Trp
            35                  40                  45

Lys Gly Thr Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

```
Thr Lys Ala Glu Leu Glu Arg Ala Ile Arg Ser Leu Lys Ala Asn Gly
                85                  90                  95
Ile Gln Val Tyr Gly Asp Val Val Met Asn His Lys Gly Gly Ala Asp
            100                 105                 110
Phe Thr Glu Arg Val Gln Ala Val Glu Val Asn Pro Gln Asn Arg Asn
        115                 120                 125
Gln Glu Val Ser Gly Thr Tyr Gln Ile Glu Ala Trp Thr Gly Phe Asn
    130                 135                 140
Phe Pro Gly Arg Gly Asn Gln His Ser Ser Phe Lys Trp Arg Trp Tyr
145                 150                 155                 160
His Phe Asp Gly Thr Asp Trp Asp Gln Ser Arg Gln Leu Ala Asn Arg
                165                 170                 175
Ile Tyr Lys Phe Arg Gly Asp Gly Lys Ala Trp Asp Trp Glu Val Asp
            180                 185                 190
Thr Glu Asn Gly Asn Tyr Asp Tyr Leu Met Tyr Ala Asp Val Asp Met
        195                 200                 205
Asp His Pro Glu Val Ile Asn Glu Leu Asn Arg Trp Gly Val Trp Tyr
    210                 215                 220
Ala Asn Thr Leu Asn Leu Asp Gly Phe Arg Leu Asp Ala Val Lys His
225                 230                 235                 240
Ile Lys Phe Ser Phe Met Arg Asp Trp Leu His Val Arg Gly Gln
                245                 250                 255
Thr Gly Lys Asn Leu Phe Ala Val Ala Glu Tyr Trp Lys Asn Asp Leu
            260                 265                 270
Gly Ala Leu Glu Asn Tyr Leu Ser Lys Thr Asn Trp Thr Met Ser Ala
        275                 280                 285
Phe Asp Val Pro Leu His Tyr Asn Leu Tyr Gln Ala Ser Asn Ser Ser
    290                 295                 300
Gly Asn Tyr Asp Met Arg Asn Leu Leu Asn Gly Thr Leu Val Gln Arg
305                 310                 315                 320
His Pro Ser His Ala Val Thr Phe Val Asp Asn His Asp Thr Gln Pro
                325                 330                 335
Gly Glu Ala Leu Glu Ser Phe Val Gln Gly Trp Phe Lys Pro Leu Ala
            340                 345                 350
Tyr Ala Thr Ile Leu Thr Arg Glu Gln Gly Tyr Pro Gln Val Phe Tyr
        355                 360                 365
Gly Asp Tyr Tyr Gly Ile Pro Ser Asp Gly Val Pro Ser Tyr Arg Gln
    370                 375                 380
Gln Ile Asp Pro Leu Leu Lys Ala Arg Gln Gln Tyr Ala Tyr Gly Thr
385                 390                 395                 400
Gln His Asp Tyr Leu Asp Asn Gln Asp Val Ile Gly Trp Thr Arg Glu
                405                 410                 415
Gly Asp Ser Ala His Ala Gly Ser Gly Leu Ala Thr Val Met Ser Asp
            420                 425                 430
Gly Pro Gly Gly Ser Lys Thr Met Tyr Val Gly Thr Ala His Ala Gly
        435                 440                 445
Gln Val Phe Lys Asp Ile Thr Gly Asn Arg Thr Asp Thr Val Thr Ile
    450                 455                 460
Asn Ser Ala Gly Asn Gly Thr Phe Pro Cys Asn Gly Gly Ser Val Ser
465                 470                 475                 480
Ile Trp Val Lys Gln
                485
```

```
<210> SEQ ID NO 31
<211> LENGTH: 485
<212> TYPE: PRT
<213> ORGANISM: Bacillus sp.
<223> OTHER INFORMATION: Amylase Protein Sequence from Bacillus sp.

<400> SEQUENCE: 31

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380
```

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
            405                 410                 415

Gly Asn Thr Ala His Pro Asn Ser Gly Leu Ala Thr Ile Met Ser Asp
        420                 425                 430

Gly Ala Gly Gly Asn Lys Trp Met Phe Val Gly Arg Asn Lys Ala Gly
    435                 440                 445

Gln Val Trp Thr Asp Ile Thr Gly Asn Arg Ala Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Lys
            485

<210> SEQ ID NO 32
<211> LENGTH: 214
<212> TYPE: PRT
<213> ORGANISM: Bacillus amyloliquefaciens
<223> OTHER INFORMATION: Beta-Glucanase Protein Sequence from Bacillus
      amyloliquefaciens

<400> SEQUENCE: 32

Gln Thr Gly Gly Ser Phe Phe Glu Pro Phe Asn Ser Tyr Asn Ser Gly
1               5                   10                  15

Leu Trp Gln Lys Ala Asn Gly Tyr Ser Asn Gly Asp Met Phe Asn Cys
            20                  25                  30

Thr Trp Arg Ala Asn Asn Val Ser Met Thr Ser Ser Gly Glu Met Arg
        35                  40                  45

Leu Ala Leu Thr Ser Pro Ser Tyr Asn Lys Phe Asp Cys Gly Glu Asn
    50                  55                  60

Arg Ser Val Gln Thr Tyr Gly Tyr Gly Leu Tyr Glu Val Arg Met Lys
65                  70                  75                  80

Pro Ala Lys Asn Thr Gly Ile Val Ser Ser Phe Phe Thr Tyr Thr Gly
                85                  90                  95

Pro Thr Asp Gly Thr Pro Trp Asp Glu Ile Asp Ile Glu Phe Leu Gly
            100                 105                 110

Lys Asp Thr Thr Lys Val Gln Phe Asn Tyr Tyr Thr Asn Gly Ala Gly
        115                 120                 125

Asn His Glu Lys Val Ala Asp Leu Gly Phe Asp Ala Thr Asn Ala Tyr
    130                 135                 140

His Thr Tyr Ala Phe Asp Trp Gln Pro Asn Ser Ile Lys Trp Tyr Val
145                 150                 155                 160

Asp Gly Gln Leu Lys His Thr Ala Thr Ser Gln Ile Pro Thr Asn Pro
                165                 170                 175

Gly Lys Ile Met Met Asn Leu Trp Asn Gly Ile Gly Val Asp Asp Trp
            180                 185                 190

Leu Gly Ser Tyr Asn Gly Val Asn Pro Leu Tyr Ala His Tyr Asp Trp
        195                 200                 205

Val Arg Tyr Thr Lys Lys
    210

<210> SEQ ID NO 33
<211> LENGTH: 214
<212> TYPE: PRT
<213> ORGANISM: Bacillus subtilis
<223> OTHER INFORMATION: Beta-Glucanase Protein Sequence from Bacillus
      subtilis

<400> SEQUENCE: 33

Gln Thr Gly Gly Ser Phe Phe Asp Pro Phe Asn Gly Tyr Asn Ser Gly
1               5                   10                  15

Phe Trp Gln Lys Ala Asp Gly Tyr Ser Asn Gly Asn Met Phe Asn Cys
                20                  25                  30

Thr Trp Arg Ala Asn Asn Val Ser Met Thr Ser Leu Gly Glu Met Arg
            35                  40                  45

Leu Ala Leu Thr Ser Pro Ala Tyr Asn Lys Phe Asp Cys Gly Glu Asn
        50                  55                  60

Arg Ser Val Gln Thr Tyr Gly Tyr Gly Leu Tyr Glu Val Arg Met Lys
65                  70                  75                  80

Pro Ala Lys Asn Thr Gly Ile Val Ser Ser Phe Phe Thr Tyr Thr Gly
                85                  90                  95

Pro Thr Asp Gly Thr Pro Trp Asp Glu Ile Asp Ile Glu Phe Leu Gly
                100                 105                 110

Lys Asp Thr Thr Lys Val Gln Phe Asn Tyr Tyr Thr Asn Gly Ala Gly
            115                 120                 125

Asn His Glu Lys Ile Val Asp Leu Gly Phe Asp Ala Ala Asn Ala Tyr
        130                 135                 140

His Thr Tyr Ala Phe Asp Trp Gln Pro Asn Ser Ile Lys Trp Tyr Val
145                 150                 155                 160

Asp Gly Gln Leu Lys His Thr Ala Thr Asn Gln Ile Pro Thr Thr Pro
                165                 170                 175

Gly Lys Ile Met Met Asn Leu Trp Asn Gly Thr Gly Val Asp Glu Trp
                180                 185                 190

Leu Gly Ser Tyr Asn Gly Val Asn Pro Leu Tyr Ala His Tyr Asp Trp
            195                 200                 205

Val Arg Tyr Thr Lys Lys
                210

<210> SEQ ID NO 34
<211> LENGTH: 269
<212> TYPE: PRT
<213> ORGANISM: Bacillus Lentus
<223> OTHER INFORMATION: Protease Protein Sequence from Bacillus Lentus

<400> SEQUENCE: 34

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
                195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

<210> SEQ ID NO 35
<211> LENGTH: 270
<212> TYPE: PRT
<213> ORGANISM: Artificial Sequence
<220> FEATURE:
<223> OTHER INFORMATION: Artificial Protease Protein Sequence

<400> SEQUENCE: 35

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ala Asp Gly Ser Gly Ser Val Ser Ser Ile Ala Gln Gly Leu Glu Trp
                100                 105                 110

Ala Gly Asn Asn Gly Met His Val Ala Asn Leu Ser Leu Gly Ser Pro
            115                 120                 125

Ser Pro Ser Ala Thr Leu Glu Gln Ala Val Asn Ser Ala Thr Ser Arg
                130                 135                 140

Gly Val Leu Val Val Ala Ala Ser Gly Asn Ser Gly Ala Gly Ser Ile
145                 150                 155                 160

Ser Tyr Pro Ala Arg Tyr Ala Asn Ala Met Ala Val Gly Ala Thr Asp
                165                 170                 175

Gln Asn Asn Asn Arg Ala Ser Phe Ser Gln Tyr Gly Ala Gly Leu Asp
                180                 185                 190

Ile Val Ala Pro Gly Val Asn Val Gln Ser Thr Tyr Pro Gly Ser Thr
                195                 200                 205

Tyr Ala Ser Leu Asn Gly Thr Ser Met Ala Thr Pro His Val Ala Gly
            210                 215                 220

```
Ala Ala Ala Leu Val Lys Gln Lys Asn Pro Ser Trp Ser Asn Val Gln
225                 230                 235                 240

Ile Arg Asn His Leu Lys Asn Thr Ala Thr Ser Leu Gly Ser Thr Asn
            245                 250                 255

Leu Tyr Gly Ser Gly Leu Val Asn Ala Glu Ala Ala Thr Arg
260                 265                 270
```

<210> SEQ ID NO 36
<211> LENGTH: 269
<212> TYPE: PRT
<213> ORGANISM: Artificial Sequence
<220> FEATURE:
<223> OTHER INFORMATION: Artificial Protease Protein Sequence

<400> SEQUENCE: 36

```
Ala Gln Ser Val Pro Trp Gly Ile Arg Arg Val Gln Ala Pro Thr Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Ala Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asp Gly Thr Ser Met Ala Thr Pro His Val Ala Gly Ala
    210                 215                 220

Ala Ala Leu Val Lys Gln Lys Asn Pro Ser Trp Ser Asn Val Arg Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 37
<211> LENGTH: 359
<212> TYPE: PRT
<213> ORGANISM: Artificial Sequence
<220> FEATURE:
<223> OTHER INFORMATION: His-tagged recombinant mature beta-glucanacase
      protein sequence from Bacillus sp-62449

```
<400> SEQUENCE: 37

His His His His His His Pro Arg Tyr Asn Pro Val Thr Glu Asp Glu
1               5                   10                  15

Leu Tyr His Ser Phe Asp Ser His Asp Ala Arg Asn Trp Gln Ile Ser
            20                  25                  30

Asp Gly Trp Arg Asn Gly Asp Asp Phe Phe Gly Cys His Trp Ser Gln
        35                  40                  45

Asn Arg Val Asn Phe Asn Arg Gly Glu Met Glu Leu Ser Leu Arg Thr
    50                  55                  60

Asn Tyr Ser Tyr Ser Ala Pro Tyr Asn Tyr Glu Cys Ala Glu Tyr Ala
65                  70                  75                  80

Thr Ser Asn Phe Tyr Gly Tyr Gly Leu Tyr Glu Val Ser Met Lys Pro
                85                  90                  95

Ala Asn Val Ser Gly Val Ile Ser Ser Phe Phe Thr Tyr Thr Gly Pro
            100                 105                 110

Ser Tyr Asn Gly Ala Pro Trp Asp Glu Ile Asp Ile Glu Phe Leu Gly
        115                 120                 125

Asn Asp Thr Thr Lys Val Gln Phe Asn Tyr Tyr Thr Asn Gly Val Gly
130                 135                 140

Gly Asn Glu Ile Ile Tyr Asp Leu Gly Phe Asp Ala Ala Asn Ser Phe
145                 150                 155                 160

Asn Thr Tyr Ala Phe Asp Trp Gln Glu Asn Tyr Ile Ser Trp Tyr Val
                165                 170                 175

Asn Gly Asn Leu Val Ala Thr Ala Thr Glu Asn Ile Pro Ser Asn Pro
            180                 185                 190

Ser Lys Ile Met Met Asn Val Trp Asn Thr Tyr Gly Ile Asp Glu Trp
        195                 200                 205

Ala Gly Ala Tyr Gly Gly Glu Ala Ala Asn Ala Thr Tyr Glu Trp Val
    210                 215                 220

Arg Tyr Thr Pro Asn Asn Gly Asn Thr Thr Pro Ser Thr Ala Pro Asp
225                 230                 235                 240

Phe Gln Leu Gln Ala Cys Asp Tyr Ser Asp Ser Ser Gly Ile Thr Ser
                245                 250                 255

Trp Ser Cys Gly Val Gly Thr Phe His Ser Ser Asn Trp Ile Lys Phe
            260                 265                 270

Asp Ser Val Asp Leu Ser Thr Gly Tyr Asn Ala Phe Ala Val Ser Tyr
        275                 280                 285

Thr Ser Pro Gly Ser Gly Ser Phe Asp Ile Arg Leu Gly Ser Pro His
    290                 295                 300

Gly Gln Arg Ile Gly Thr Val Asn Tyr Gly Ala Thr Gly Gly Trp Ser
305                 310                 315                 320

Asn Tyr Glu Trp Ser Gly Thr Pro Ser Leu Asp Val Thr Val Arg Gly
                325                 330                 335

Ala His Asp Ile Tyr Ile Val Ala Thr Ser Gly Ala Ala Asn Leu Arg
            340                 345                 350

Glu Phe Trp Phe Lys Asn Glu
            355

<210> SEQ ID NO 38
<211> LENGTH: 253
<212> TYPE: PRT
<213> ORGANISM: Artificial Sequence
<220> FEATURE:
<223> OTHER INFORMATION: His-tagged recombinant mature beta-glucanase
``` protein sequence from Bacillus akibai

<400> SEQUENCE: 38

```
His His His His His Pro Arg Ala Glu Arg Pro Ile Gly Thr Thr
 1               5                  10                  15

Phe Val Glu Thr Phe Glu Ser Tyr Asp Ser Glu Arg Trp Ser Lys Ala
                20                  25                  30

Gly Val Trp Thr Asn Gly Gln Met Phe Asn Ala Thr Trp Tyr Pro Glu
            35                  40                  45

Gln Val Thr Phe Ser Asp Gly Lys Met Lys Leu Gln Ile Asp Lys Glu
        50                  55                  60

Asp Asn Glu Thr Ala Ser Pro Pro Tyr Lys Ala Gly Glu Leu Arg Thr
 65                  70                  75                  80

Asn Asp Phe Tyr His Tyr Gly Leu Phe Glu Val Ser Met Lys Pro Ala
                85                  90                  95

Lys Ser Thr Gly Thr Val Ser Ser Phe Phe Thr Tyr Thr Gly Pro Trp
               100                 105                 110

Asp Trp Asp Asn Asp Pro Trp Asp Glu Ile Asp Ile Glu Phe Leu Gly
            115                 120                 125

Lys Asp Thr Thr Lys Ile Gln Phe Asn Tyr Phe Thr Asn Gly Val Gly
        130                 135                 140

Gly Asn Glu His Tyr His Glu Leu Gly Phe Asp Ala Ala Asp Asp Phe
145                 150                 155                 160

Asn Thr Tyr Ala Phe Glu Trp Arg Pro Glu Ser Ile Arg Trp Phe Val
                165                 170                 175

Asn Gly Glu Leu Val His Thr Ala Thr Glu Asn Ile Pro Gln Thr Pro
            180                 185                 190

Gln Lys Ile Met Met Asn Leu Trp Pro Gly Ile Gly Val Asp Gly Trp
        195                 200                 205

Thr Gly Arg Phe Asn Gly Glu Asp Thr Pro Val Val Thr Gln Tyr Asp
    210                 215                 220

Trp Val Lys Tyr Thr Pro Leu Glu Glu Leu Gly Cys Tyr Asn Glu Lys
225                 230                 235                 240

Asn Asn Lys Tyr Lys Lys Cys Lys Lys Thr Lys Val Lys
                245                 250
```

<210> SEQ ID NO 39
<211> LENGTH: 230
<212> TYPE: PRT
<213> ORGANISM: Artificial Sequence
<220> FEATURE:
<223> OTHER INFORMATION: His-tagged recominant mature beta-glucanase
      protein sequence from Bacillus agaradhaerens

<400> SEQUENCE: 39

```
His His His His His His Pro Arg His Asn Pro Val Thr Asp Glu Glu
 1               5                  10                  15

Val Tyr His Ser Phe Asn Ser His Asp Trp Gln Asn Trp Asn Met Ser
                20                  25                  30

Asp Gly Trp Lys Asn Asp Asp Tyr Phe Phe Gly Cys His Trp Ser Gln
            35                  40                  45

Asn Arg Val Asn Phe Tyr Gly Gly Gln Met Glu Leu Ser Leu Arg Thr
        50                  55                  60

Asn Tyr Ser Tyr Ala Pro Pro Tyr Asn Tyr Glu Cys Ala Glu Tyr Thr
 65                  70                  75                  80

Thr Asn Asn Phe Tyr Gly Tyr Gly Leu Tyr Glu Val Ser Met Lys Pro
```

-continued

```
                85                  90                  95
Ala Lys Val Ser Gly Val Ile Ser Ser Phe Phe Thr Tyr Thr Gly Pro
            100                 105                 110

Ser Tyr Asn Gly Ala Pro Trp Asp Glu Ile Asp Ile Glu Phe Leu Gly
            115                 120                 125

Asn Asp Thr Thr Lys Val Gln Phe Asn Tyr Tyr Thr Asp Gly Val Gly
            130                 135                 140

Gly Asn Glu Ile Leu Tyr Asp Leu Gly Phe Asp Ala Ala Asp Ser Tyr
145                 150                 155                 160

Asn Thr Tyr Ala Phe Asp Trp Gln Glu Asn Tyr Ile Asn Trp Tyr Val
                165                 170                 175

Asn Gly Gln Leu Val Ala Thr Ala Thr Glu Asn Ile Pro Ser Asn Pro
            180                 185                 190

Ser Lys Ile Met Met Asn Ile Trp Asn Thr Tyr Gly Ile Asp Glu Trp
            195                 200                 205

Ala Gly Arg Tyr Tyr Gly Glu Asp Ala Asn Ala Ser Tyr Asn Trp Val
            210                 215                 220

Arg Tyr Thr Pro Asn Arg
225                 230

<210> SEQ ID NO 40
<211> LENGTH: 222
<212> TYPE: PRT
<213> ORGANISM: Artificial Sequence
<220> FEATURE:
<223> OTHER INFORMATION: His-tagged recombinant mature beta-glucanase
      protein sequence from Bacillus mojavensis

<400> SEQUENCE: 40

His His His His His His Pro Arg Gln Thr Gly Gly Ser Phe Phe Asp
1               5                   10                  15

Pro Phe Asn Gly Tyr Asn Ser Gly Phe Trp Gln Lys Ala Asn Gly Tyr
            20                  25                  30

Ser Asn Gly Asn Met Phe Asn Cys Thr Trp Arg Ala Asn Asn Val Ser
        35                  40                  45

Met Thr Ser Leu Gly Glu Met Arg Leu Ala Leu Thr Ser Pro Ser Tyr
50                  55                  60

Asn Lys Phe Asp Cys Gly Glu Asn Arg Ser Val Gln Thr Tyr Gly Tyr
65                  70                  75                  80

Gly Leu Tyr Glu Val Arg Met Lys Pro Ala Lys Asn Val Gly Ile Val
            85                  90                  95

Ser Ser Phe Phe Thr Tyr Thr Gly Pro Thr Asp Gly Thr Pro Trp Asp
            100                 105                 110

Glu Ile Asp Ile Glu Phe Leu Gly Lys Asp Thr Thr Lys Val Gln Phe
            115                 120                 125

Asn Tyr Tyr Thr Asn Gly Val Gly Asn His Glu Lys Leu Val Asp Leu
            130                 135                 140

Gly Phe Asp Ala Ala Asn Ala Tyr His Thr Tyr Ala Phe Asp Trp Gln
145                 150                 155                 160

Pro Asn Ser Ile Lys Trp Tyr Val Asp Gly Gln Leu Lys His Thr Ala
                165                 170                 175

Thr Ser Gln Ile Pro Thr Thr Pro Gly Lys Ile Met Met Asn Leu Trp
            180                 185                 190
```

```
Asn Gly Thr Gly Val Asp Glu Trp Leu Gly Ser Tyr Asn Gly Val Thr
        195                 200                 205

Pro Leu Tyr Ala His Tyr Asp Trp Val Arg Tyr Thr Lys Lys
    210                 215                 220
```